US009951107B2

(12) United States Patent
Rome et al.

(10) Patent No.: US 9,951,107 B2
(45) Date of Patent: *Apr. 24, 2018

(54) VAULT COMPLEXES

(71) Applicants: The Regents of the University of California, Oakland, CA (US); The Scripps Research Institute, La Jolla, CA (US)

(72) Inventors: Leonard H. Rome, Los Angeles, CA (US); Valerie A. Kickhoefer, Sherman Oaks, CA (US); Glen Nemerow, La Jolla, CA (US); Cheng-Yu Lai, La Jolla, CA (US); Christopher Wiethoff, Downers Grove, IL (US); Mu Han, Los Angeles, CA (US)

(73) Assignees: The Regets of the University of California, Oakland, CA (US); The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/863,750

(22) Filed: Sep. 24, 2015

(65) Prior Publication Data

US 2016/0068576 A1 Mar. 10, 2016

Related U.S. Application Data

(60) Continuation of application No. 14/018,325, filed on Sep. 4, 2013, now Pat. No. 9,181,312, which is a division of application No. 12/950,994, filed on Nov. 19, 2010, now Pat. No. 8,551,781.

(60) Provisional application No. 61/291,081, filed on Dec. 30, 2009, provisional application No. 61/262,667, filed on Nov. 19, 2009.

(51) Int. Cl.
*C07K 14/005* (2006.01)
*C12N 15/87* (2006.01)
*C12N 15/88* (2006.01)
*C07K 14/435* (2006.01)
*C12N 9/10* (2006.01)
*C07K 14/485* (2006.01)

(52) U.S. Cl.
CPC .......... *C07K 14/005* (2013.01); *C07K 14/435* (2013.01); *C07K 14/485* (2013.01); *C12N 9/1077* (2013.01); *C12N 15/87* (2013.01); *C12N 15/88* (2013.01); *C07K 2319/00* (2013.01); *C07K 2319/70* (2013.01); *C07K 2319/75* (2013.01); *C12N 2710/10322* (2013.01); *C12Y 204/0203* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 5,252,479 A | 10/1993 | Srivastava |
| 5,436,146 A | 7/1995 | Shenk et al. |
| 5,665,557 A | 9/1997 | Murray et al. |
| 5,719,197 A | 2/1998 | Kanios et al. |
| 5,981,276 A | 11/1999 | Sodroski et al. |
| 6,110,740 A | 8/2000 | Rome et al. |
| 6,143,520 A | 11/2000 | Marasco et al. |
| 6,156,879 A | 12/2000 | Rome et al. |
| 6,221,383 B1 | 4/2001 | Miranda et al. |
| 6,555,347 B1 | 4/2003 | Rome et al. |
| 7,482,319 B2 | 1/2009 | Rome et al. |
| 8,124,109 B2 * | 2/2012 | Kickhoefer .......... A61K 39/118 424/193.1 |
| 8,318,182 B2 | 11/2012 | Kickhoefer et al. |
| 8,551,781 B2 | 10/2013 | Rome et al. |
| 8,834,896 B2 | 9/2014 | Kickhoefer et al. |
| 8,920,807 B2 | 12/2014 | Rome et al. |
| 9,181,312 B2 * | 11/2015 | Rome .................. C07K 14/005 |
| 2010/0086610 A1 | 4/2010 | Rome et al. |
| 2012/0213809 A1 | 8/2012 | Rome et al. |
| 2013/0122037 A1 | 5/2013 | Kickhoefer et al. |
| 2014/0377301 A1 | 12/2014 | Kickhoefer et al. |

FOREIGN PATENT DOCUMENTS

| | | |
|---|---|---|
| WO | WO-1993/24641 A2 | 12/1993 |
| WO | WO-1994/12649 A2 | 6/1994 |
| WO | WO-1994/13788 A1 | 6/1994 |
| WO | WO-1999/049025 A2 | 9/1999 |
| WO | WO-1999/062547 A1 | 12/1999 |
| WO | WO-2004/081533 A2 | 9/2004 |

OTHER PUBLICATIONS

Lai et al. (ACS Nano., 2009, vol. 3(3), pp. 691-699).*
Lai et al. (Vault Nanoparticles Containing an Adenovirus-Derived Membrane Lytic Protein Facilitate Toxin and Gene Transfer. ACS Nano. 2009 3(3): 691-699).
Kickhoefer et al. (Engineering of vault nanocapsules with enzymatic and fluorescent properties. PNAS (2005) 102(12) 4348-4352).
U.S. Appl. No. 14/565,676, filed Dec. 10, 2014, by Rome et al.
U.S. Appl. No. 14/553,146, filed Nov. 25, 2014, by Rome et al.
U.S. Appl. No. 14/411,982, filed Dec. 30, 2014, by Rome et al.
Anderson, D.H. et al. (Nov. 2007). "Draft Crystal Structure of the Vault Shell at 9-A Resolution," *PLoS Biol.* 5(11): 0318, 10 pages.
Chugani, D.C. et al. (Jan. 1991). "Vault Immunofluorescence in the Brain: New Insights Regarding the Origin of Microglia," *The Journal of Neuroscience* 11:256-268.

(Continued)

*Primary Examiner* — Hope A Robinson
(74) *Attorney, Agent, or Firm* — Suzannah K. Sundby, Esq.; Canady + LLP

(57) ABSTRACT

The invention relates to compositions of vault complexes containing recombinant membrane lytic proteins, such as an adenovirus protein VI lytic domain, and methods of using the vault complexes to facilitate delivery and entry of a biomolecule into a cell or subject.

12 Claims, 18 Drawing Sheets

(56) References Cited

OTHER PUBLICATIONS

Chugani, D.C. et al. (1993). "Evidence that Vault Ribonucleoprotein Particles Localize to the Nuclear Pore Complex," *Journal of Cell Science* 106:23-29.
Goldsmith, L.E. et al. (Oct. 2009, e-pub. Sep. 23, 2009). "Utilization of a Protein 'Shuttle' to Load Vault Nanocapsules with Gold Probes and Proteins," *ACS Nano* 3(10):3175-3183.
Herrmann, C. et al. (Mar. 22, 1999). "Recombinant Major Vault Protein is Targeted to Neuritic Tips of PC12 Cells," *The Journal of Cell Biology* 144(6):1163-1172.
Hu, Y. et al. (2002). "A Very Early Induction of Major Vault Protein Is Accompanied by Increased Drug Resistance in U-937 Cells," *Int. J. Cancer* 97:149-156.
Izquierdo, M.A. et al. (1996). "Relationship of LRP-Human Major Vault Protein to in vitro and Clinical Resistance to Anticancer Drugs," *Cytotechnology* 19:191-197.
Kedersha, N.L. et al. (Apr. 1990). "Vaults. II. Ribonucleoprotein Structures are Highly Conserved Among Higher and Lower Eukaryotes," *J. Cell Biol.* 110:895-901.
Kedersha, N.L. et al. (1990). "Vaults: Large Cytoplasmic RNP's that Associate with Cytoskeletal Elements," *Molecular Biology Reports* 14:121-122.
Kickhoefer, V.A. et al. (Apr. 15, 1993). "Vault Ribonucleoprotein Particles from Rat and Bullfrog Contain a Related Small RNA that is Transcribed by RNA Polymerase III," *J. Biol. Chem.* 268(11):7868-7873.
Kickhoefer, V.A. et al. (1994). "The Sequence of a cDNA Encoding the Major Vault Protein from *Rattus norvegicus*," *Gene* 151:257-260.
Kickhoefer, V.A. et al. (May 1996). "Vaults are the Answer, What is the Question?" *Trends in Cell Biology* 6:174-178.
Kickhoefer, V.A. et al. (Apr. 10, 1998). "Vaults are Up-Regulated in Multidrug Resistant Cancer Cell Lines," *J. Biol. Chem.* 273(15):8971-8974.
Kickhoefer, V.A. et al. (Sep. 6, 1999). "The 193-kD Vault Protein, VPARP, Is a Novel Poly(ADP-ribose) Polymerase," *J. Cell Biol.* 146(5):917-928.
Kickhoefer, V.A. et al. (Nov. 12, 1999). "Vaults and Telomerase Share a Common Subunit, TEP1," *J. Biol. Chem.* 274(46):32712-32717.
Kickhoefer, V.A. et al. (Jan. 8, 2001). "The Telomerase/Vault-Associated Protein TEP1 is Required for Vault RNA Stability and Its Association with the Vault Particle," *J. Cell Biol.* 152:157-164.
Kong, L.B. et al. (2000). "RNA Location and Modeling of a WD40 Repeat Domain within the Vault," *RNA* 6:890-900.
Kong, L.B. at al. (Apr. 1999). "Structure of the Vault, a Ubiquitous Cellular Component," *Structure* 7:371-379.
Liu, Y. et al. (Jun. 2004). "Vault Poly(ADP-Ribose) Polymerase is Associated with Mammalian Telomerase and Is Dispensable for Telomerase Function and Vault Structure In Vivo," *Molecular and Cellular Biology* 24(12):5314-5323.
Ng, B.C. et al. (Oct. 2008, e-pub on Sep. 20, 2008). "Encapsulation of Semiconducting Polymers in Vault Protein Cages," *Nano Letters* 8(10):3503-3509.
Raval-Fernandes, S. et al. (1999). "Cloning of a cDNA Encoding a Sequence-Specific Single-Stranded-DNA-Binding Protein from *Rattus norvegicus*," *Gene* 237:201-207.
Raval-Fernandes, S. et al. (Oct. 1, 2005). "Increased Susceptibility of Vault Poly(ADP- Ribose) Polymerase-Deficient Mice to Carcinogen-Induced Tumorigenesis," *Cancer Res.* 65(19):8846-8852.
Rome, L. et al. (Aug./Sep. 1991). "Unlocking Vaults: Organelles in Search of a Function," *Trends in Cell Biology* 1:47-50.
Rome, L.H. (Jun. 1995). "Multidrug Resistance: Locked in the Vault?" *Nature Medicine* 1(6):527.
Scheper, R.J. et al. (1996). "Role of LRP/Major Vault Protein in Multidrug Resistance," Chapter 7 In *Multidrug Resistance in Cancer Cells: Molecular, Biochemical, Physiological and Biological Aspects*, Gupta, S. et al. eds., John Wiley & Sons, Chichester, England.

Schroeijers, A.B. et al. (Feb. 15, 2000). "The $M_r$ 193,000 Vault Protein is Up-Regulated in Multidrug-Resistant Cancer Cell Lines," *Cancer Research* 60:1104-1110.
Siva, A.C. et al. (2001). "Up-Regulation of Vaults May Be Necessary But Not Sufficient for Multidrug Resistance," *Int. J. Cancer* 92:195-202.
Slesina, M. et al. (2005, e-pub. May 18, 2005). "Nuclear Localization of the Major Vault Protein in U373 Cells," *Cell Tissue Res.* 321:97-104.
Slesina, M. et al. (2006, e-pub. Feb. 28, 2006). "Movement of Vault Particles Visualized by GFP-Tagged Major Vault Protein," *Cell Tissue Res.* 324:403-410.
Tanaka, H. et al. (Jan. 16, 2009). "The Structure of Rat Liver Vault at 3.5 Angstrom Resolution," *Science* 323:384-388.
Vasu, S.K. et al. (Jul. 25, 1993). "cDNA Cloning and Disruption of the Major Vault Protein α Gene (mvpA) in *Dictyostelium discoideum*," *J. Biol. Chem.* 268(21):15356-15360.
Vilalta, A. et al. (Nov. 25, 1994). "The Rat Vault RNA Gene Contains a Unique RNA Polymerase III Promoter Composed of Both External and Internal Elements that Function Synergistically," *J. Biol. Chem.* 269(47):29752-29759.
Xia, T. et al. (Jul. 2008). "Nanobiology: Particles Slip Cell Security," *Nature Materials* 7:519-520.
Xia, Y. et al. (2010, e-pub. Feb. 10, 2010). "Immobilization of Recombinant Vault Nanoparticles on Solid Substrates," *ACS Nano* 4(3):1417-1424.
Yang, J. et al. (2010, e-pub. Dec. 1, 2010). "Vaults Are Dynamically Unconstrained Cytoplasmic Nanoparticles Capable of Half Vault Exchange," *ACS Nano* 4(12):7229-7240.
Yu, M. et al. (Oct. 2008, e-pub. Sep. 20, 2008). "Reversible pH Lability of Cross-Linked Vault Nanocapsules," *Nano Letters* 8(10):3510-3515.
Non-Final Office Action dated Mar. 21, 2013 for U.S. Appl. No. 13,737,963, filed Jan. 10, 2013, eleven pages.
Final Office Action dated Aug. 6, 2013 for U.S. Appl. No. 13,737,963, filed Jan. 10, 2013, twelve pages.
Notice of Allowance dated Apr. 1, 2014 for U.S. Appl. No. 13,737,963, filed Jan. 10, 2013, ten pages.
Allen, T.M. et al. (Mar. 19, 2004). "Drug Delivery Systems: Entering the Mainstream," *Science* 303:1818-1822.
Altschul, S.F. et al. (Oct. 5, 1990). "Basic Local Alignment Search Tool," *J. Mol. Biol.* 215(3):403-410.
Barbiei, L. et al. (1993). "Ribosome-Inactivating Proteins from Plants," *Biochima et Biophysica Acta* 1154:237-282.
Berger, W. et al. (2009, e-pub. Sep. 19, 2008). "Vaults and the Major Vault Protein: Novel Roles in Signal Pathway Regulation and Immunity," *Cell Mol. Life Sci.* 66(1):43-61.
Blumenthal, R. et al. (1986). "pH Dependent Lysis of Liposomes by Adenovirus," *Biochemistry* 25:2231-2237.
Boesen, J.J. et al. (1994). "Circumvention of Chemotherapy-Induced Myelosuppression by Transfer of the Mdr1 Gene," *Biotherapy* 6(4):291-302.
Bout, A. et al. (1994). "Lung Gene Therapy: In Vivo Adenovirus-Mediated Gene Transfer to Rhesus Monkey Airway Epithelium," *Human Gene Therapy* 5:3-10.
Champion, C.I. et al. (Apr. 2009). "A Vault Nanoparticle Vaccine Induces Protective Mucosal Immunity," *PLoS ONE* 4(4):e5409, 12 pages.
Clowes, M.M. et al. (Feb. 1994). "Long-Term Biological Response of Injured Rat Carotid Artery Seeded with Smooth Muscle Cells Expressing Retrovirally Introduced Human Genes," *J. Clin. Invest.* 93:644-651.
Esfandiary, R. et al. (Apr. 2009, e-pub. Aug. 6, 2008). "Structural Stability of Vault Particles," *Journal of Pharmaceutical Sciences* 98(4):1376-1386.
Fisher, K.J. et al. (Jan. 1996). "Transduction with Recombinant Adeno-Associated Virus for Gene Therapy Is Limited by Leading-Strand Synthesis," *Journal of Virology* 70(1):520-532.
Goldsmith, L.E. et al. (Mar. 13, 2007, e-pub. Feb. 16, 2007). "Vault Nanocapsule Dissociation into Halves Triggered at Low pH," *Biochemistry* 46(10):2865-2875.

(56) References Cited

OTHER PUBLICATIONS

Goodman, R. M. et al. (1976). "Assembly of Flexuous Plant Viruses and Their Proteins," *Philosophical Transactions of the Royal Society of London* 276:173-179.

Greish, K. (Aug.-Sep. 2007). "Enhanced Permeability and Retention of Macromolecular Drugs in Solid Tumors: A Royal Gate for Targeted Anticancer Nanomedicines," *Journal of Drug Targeting* 15(7-8):457-464.

Grossman, M. et al. (1993). "Retroviruses: Delivery Vehicle to the Liver," *Current Opinion in Genetics and Development* 3:110-114.

Haidar, M.A. (1976). "Tobacco Rattle Virus RNA-Protein Interactions," *Philosophical Transactions of the Royal Society of London* 276:165-172.

Hed, J. et al. (1987). "The Use of Fluorescence Quenching in Flow Cytofluorometry to Measure the Attachment and Ingestion Phases in Phagocytosis in Peripheral Blood Without Prior Cell Separation," *Journal of Immunological Methods* 101:119-125.

Izquierdo, M.A. et al. (Mar. 1996). "Broad Distribution of the Multidrug Resistance-Related Vault Lung Resistance Protein in Normal Human Tissues and Tumors," *American Journal of Pathology* 148(3):877-887.

Kaddis, C.S. et al. (2007, e-pub. Apr. 16, 2007). "Sizing Large Proteins and Protein Complexes by Electrospray Ionization Mass Spectrometry and Ion Mobility," *J. Am. Soc. Mass Spectrom* 18:1206-1216.

Kedersha, N.L. et al. (Sep. 1986). "Isolation and Characterization of a Novel Ribonucleoprotein Particle: Large Structures Contain a Single Species of Small RNA," *J. Cell Biol.* 103:699-709.

Kedersha, N.L. et al. (Jan. 1991). "Vaults. III. Vault Ribonucleoprotein Particles Open into Flower-like Structures with Octagonal Symmetry," *J. Cell Biol.* 112:225-235.

Kickhoefer, V.A. et al. (Mar. 22, 2005). "Engineering of Vault Nanocapsules with Enzymatic and Fluorescent Properties," *PNAS* 102(12):.4348-4352.

Kickhoefer, V.A. et al. (2009, e-pub. Dec. 19, 2008). "Targeting Vault Nanoparticles to Specific Cell Surface Receptors," *ACS Nano* 3(1):27-36.

Kiem, H.-P. et al. (Mar. 15, 1994). "Retrovirus-Mediated Gene Transduction Into Canine Peripheral Blood Repopulating Cells," *Blood* 83(6):1467-1473.

Kingdon, G. C. et al. (1970). "Effects of Listeria Monocytogenes Hemolysin on Phagocytic Cells and Lysosomes," *Infection and Immunity* 1(4):356-62.

Kong, L.B. et al. (Apr. 1999). "Structure of the Vault, a Ubiquitous Cellular Component," *Structure* 7:371-379.

Kozarsky, K.F. et al. (1993). "Gene Therapy: Adenovirus Vectors," *Current Opinion in Genetics and Development* 3:499-503.

Lee, J. H. et al. (Mar. 1, 1999). "Delivery of an Adenovirus Vector in a Calcium Phosphate Coprecipitate Enhances the Therapeutic Index of Gene Transfer to Airway Epithelia," *Human Gene Therapy* 10:603-613.

Maeda, H. et al. (2000). "Tumor Vascular Permeability and the EPR Effect in Macromolecular Therapeutics: A Review," *Journal of Controlled Release* 65:271-284.

Mastrangeli, A. et al. (1993). "Diversity of Airway Epithelial Cell Targets for In Vivo Recombinant Adenovirus-Mediated Gene Transfer," J. Clin. Invest. 91:225-234.

Mikyas, Y. et al. (2004). "Cryoelectron Microscopy Imaging of Recombinant and Tissue Derived Vaults: Localization of the MVP N Termini and VPARP," *J. Mol. Biol.* 344:91-105.

Miller, A.D. et al. (1993). "Use of Retroviral Vectors for Gene Transfer and Expression," *Methods Enzymol.* 217:581-599.

Needleman, S.B. et al. (Mar. 1970). "A General Method Applicable to the Search for Similarities in the Amino Acid Sequence of Two Proteins," *J. Mol. Biol.* 48(3):443-453.

Pearson, W.R. et al. (Apr. 1988). "Improved tools for biological sequence comparison," *PNAS* 85(8):2444-2448.

Poderycki, M.J. et al. (2005). "The p80 Homology Region of TEP1 is Sufficient for its Association with the Telomerase and Vault RNAs, and the Vault Particle," *Nucleic Acids Research* 33(3):893-902.

Poderycki, M.J. et al. (Oct. 3, 2006, a-pub. Sep. 7, 2006). "The Vault Exterior Shell is a Dynamic Structure that Allows Incorporation of Vault-Associated Proteins into Its Interior," *Biochemistry* 45(39):12184-12193.

Rosenfeld, M.A. et al. (Apr. 19, 1991). "Adenovirus-Mediated Transfer of a Recombinant α1-Antitrypsin Gene to the Lung Epithelium in Vivo," *Science* 252:431-434.

Rosenfeld, M.A. et al. (Jan. 10, 1992). "In Vivo Transfer of the Human Cystic Fibrosis Transmembrane Conductance Regulator Gene to the Airway Epithelium," *Cell* 68:143-155.

Salmons, B. et al. (1993). "Targeting of Retroviral Vectors for Gene Therapy," *Human Gene Therapy* 4:129-141.

Samulski, R.J. et al. (Oct. 1987). "A Recombinant Plasmid from Which an Infectious Adeno-Associated Virus Genome Can Be Excised in Vitro and Its Use to Study Viral Replication," *Journal of Virology* 61(10):3096-3101.

Samulski, R.J. et al. (Sep. 1989). "Helper-Free Stocks of Recombinant Adeno-Associated Viruses: Normal Integration Does Not Require Viral Gene Expression," *Journal of Virology* 63(9):3822-3828.

Seiler, M. P. et al. (Feb. 2007). "Dendritic Cell Function After Gene Transfer with Adenovirus-Calcium Phosphate Co-precipitates," *Molecular Therapy* 15(2):386-392.

Shaughnessy, L. M. et al. (2006). "Membrane Perforations Inhibit Lysosome Fusion by Altering pH and Calcium in *Listeria Monocytogenes* Vacuoles," *Cellular Microbiology* 8(5): 81-92.

Smith, T.F. et al. (Dec. 1981). "Comparison of Biosequences," *Advances in Applied Mathematics* 2(4):482-489.

Stephen, A.G. et al. (Jun. 29, 2001). "Assembly of Vault-Like Particles in Insect Cells Expressing Only the Major Vault Protein," *J. Biol. Chem.* 276(26):23217-23220.

Suprenant, K.A. (Dec. 10, 2002, a-pub. Oct. 23, 2002). "Vault Ribonucleoprotein Particles: Sarcophagi, Gondolas, or Safety Deposit Boxes?" *Biochemistry* 41(49):14447-14454.

Toyoda, K. et al. (2000). "Calcium Phosphate Precipitates Augment Adenovirus-Mediated Gene Transfer to Blood Vessels in Vitro and in Vivo," *Gene Therapy* 7:1284-1291.

Walsh, C.E. et al. (1993). "Gene Therapy for Human Hemoglobinopathies," *Exp. Biol. Med.* 204:289-300.

Walters, R. et al. (1999). "Mechanism by Which Calcium Phosphate Coprecipitation Enhances Adenovirus-Mediated Gene Transfer," *Gene Therapy* 6:1845-1850.

Wang, Q. et al. (1995). "A Packaging Cell Line far Propagation of Recombinant Adenovirus Vectors Containing Two Lethal Gene-Region Deletions," *Gene Therapy* 2:775-783.

Wells, A. (1999). "EGF Receptor," *The International Journal of Biochemistry & Cell Biology* 31(6):637-643.

Weyergang, A. et al. (2006). "Photochemically Stimulated Drug Delivery Increases the Cytotoxicity and Specificity of EGF-Saporin," *Journal of Controlled Release* 111:165-173.

Wiethoff, C. M. et al. (Feb. 2005). "Adenovirus Protein VI Mediates Membrane Disruption Following Capsid Disassembly," *Journal of Virology* 79(4):1992-2000.

Xia, H. et al. (Oct. 2002, e-pub. Sep. 16, 2002). "sIRNA-Mediated Gene Silencing in vitro and in vivo," *Nature Biotechnology* 20:1006-1010.

Xie, H. et al. (1998). "EGF Receptor Regulation of Cell Motility: EGF Induces Disassembly of Focal Adhesions Independently of the Motility-Associated PLCgamma Signaling Pathway," *J Cell Sci.* 111 (Pt 5):615-624.

Yip, W. L. et al. (2007). "Targeted Delivery and Enhanced Cytotoxicity of Cetuximab-Saporin by Photochemical Internalization in EGFR-Positive Cancer Cells," *Molecular Pharmaceutics* 4:241-251.

\* cited by examiner

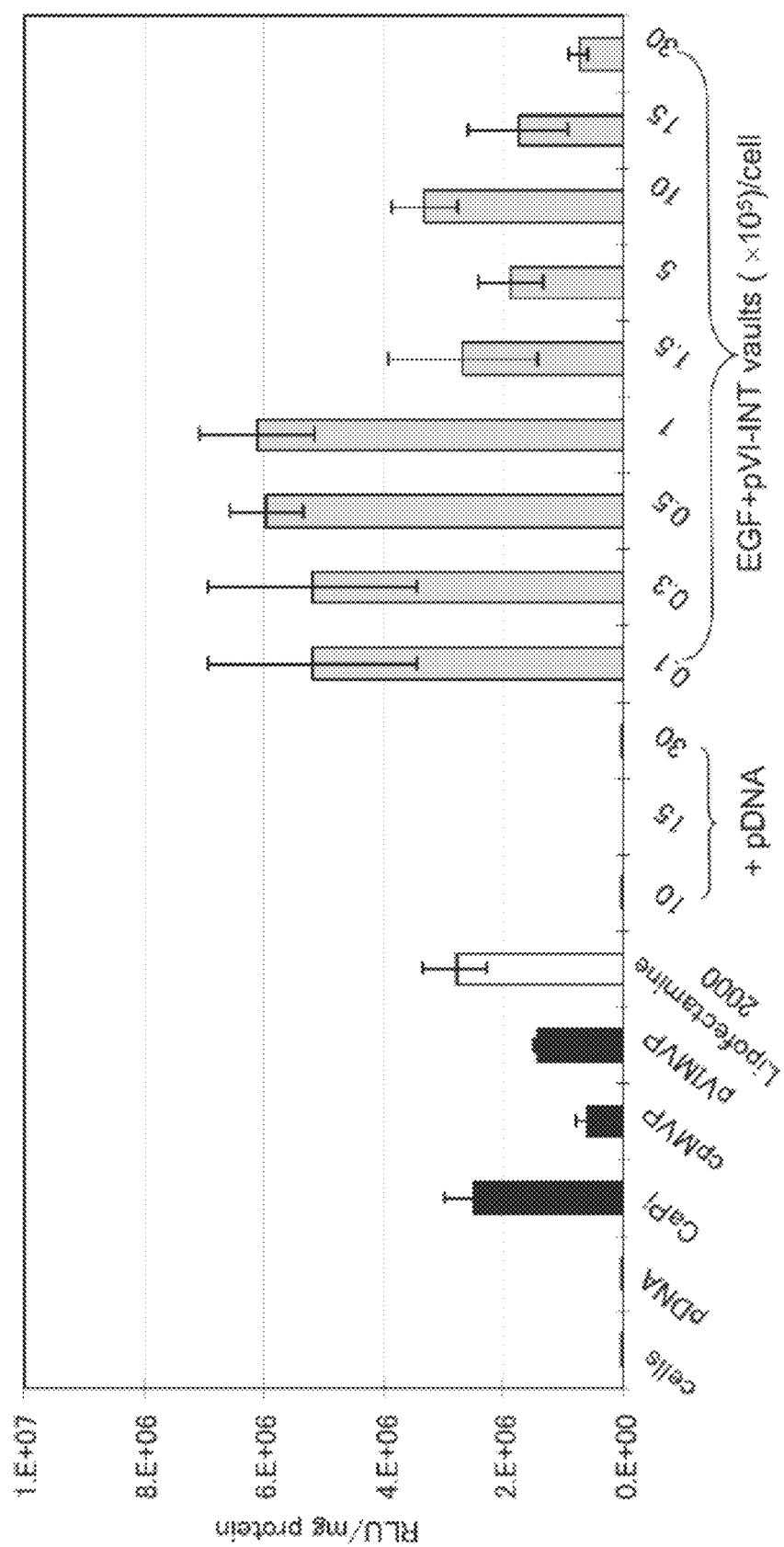
FIG. 8, Panel A

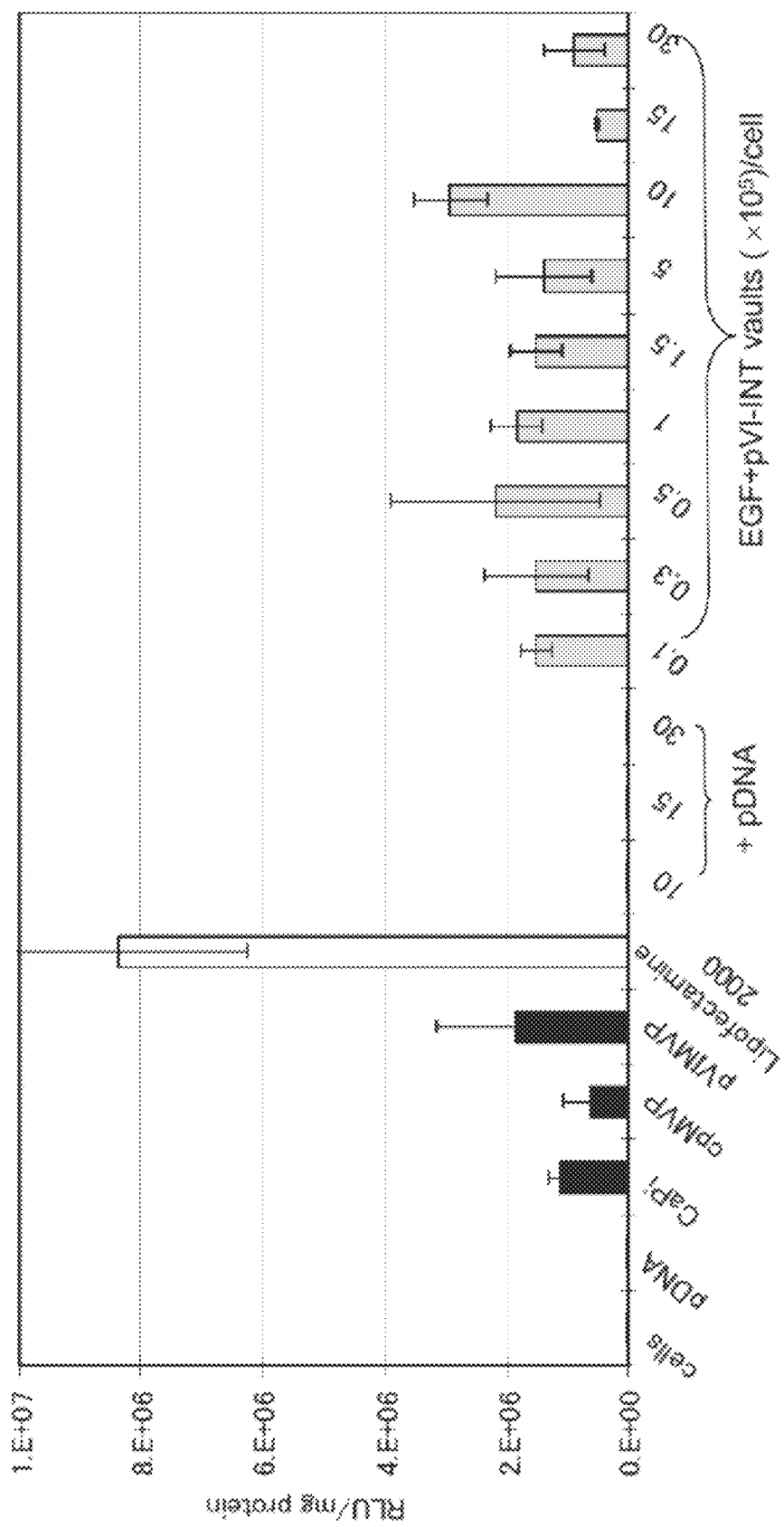
FIG. 8, Panel B

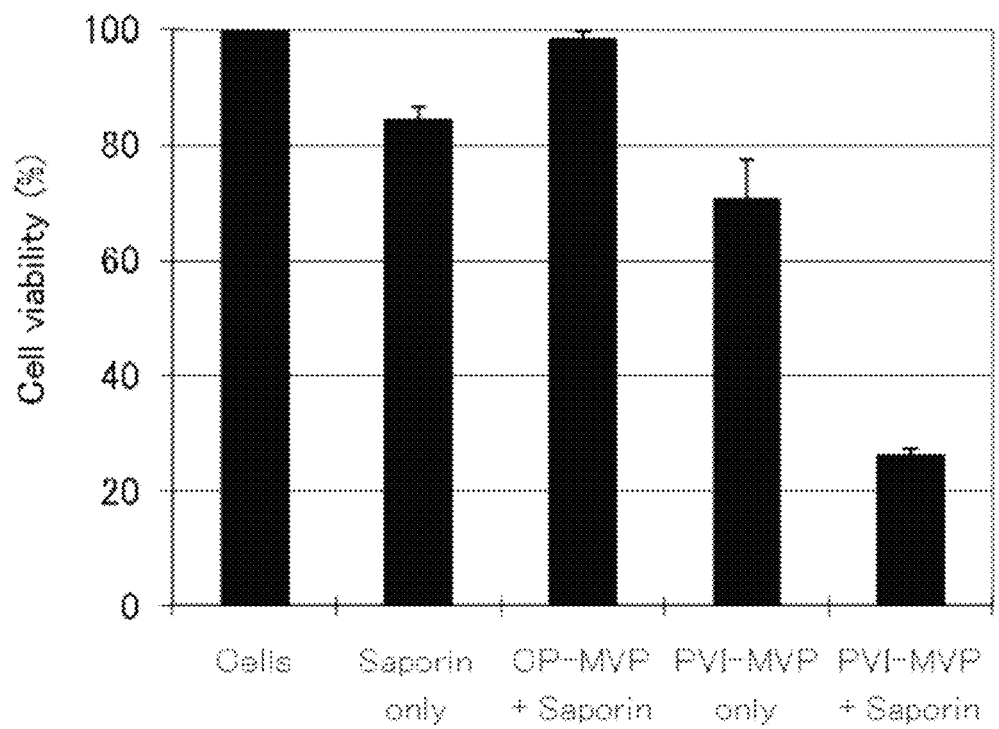
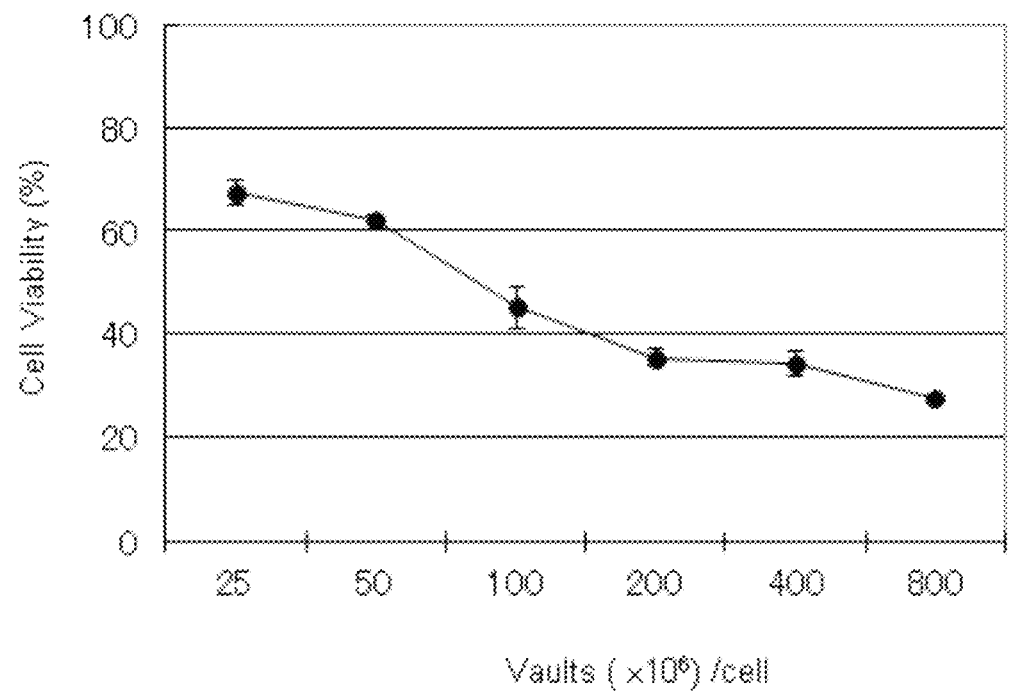
FIG. 10

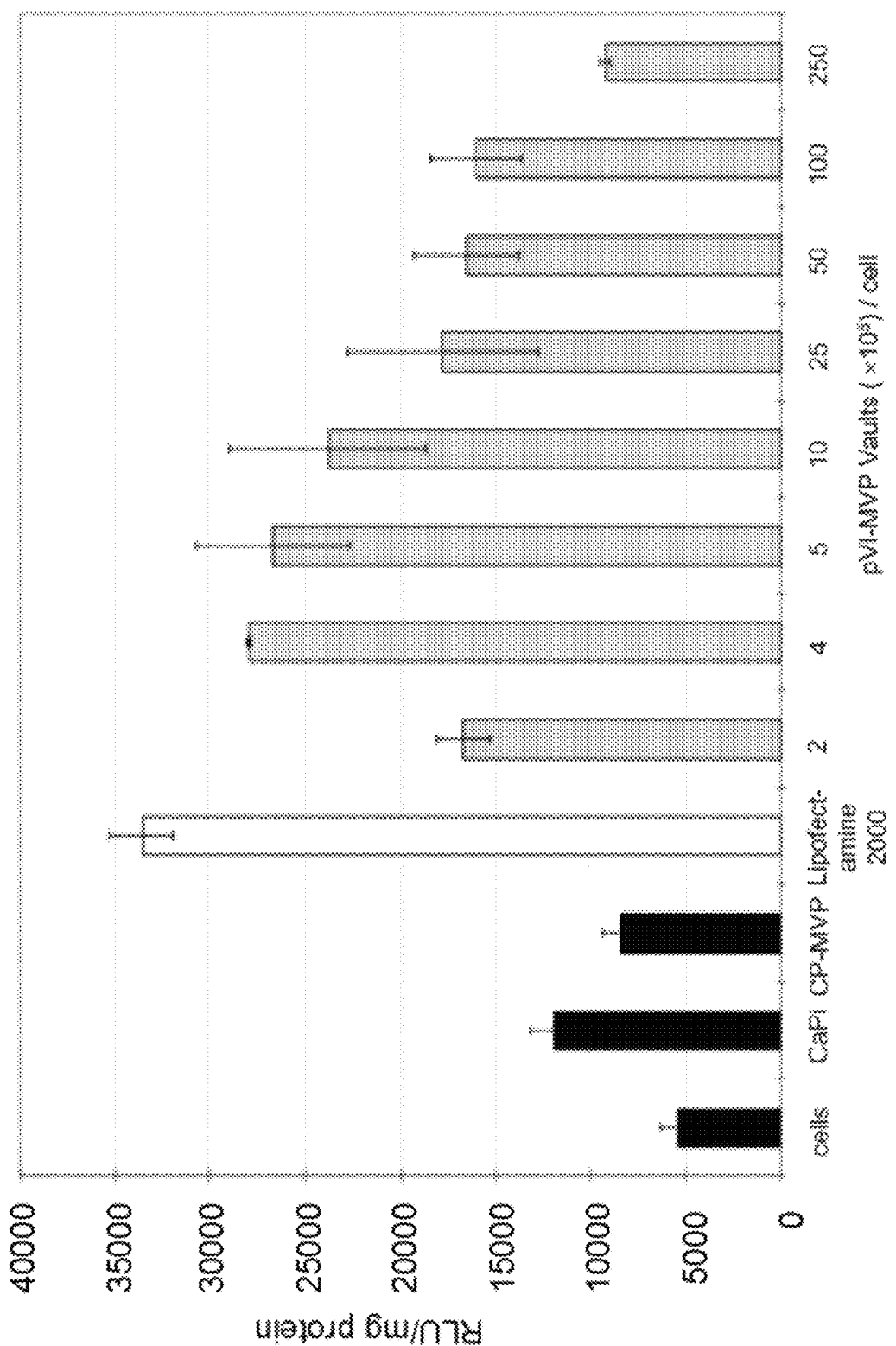
FIG. 11, Panel A

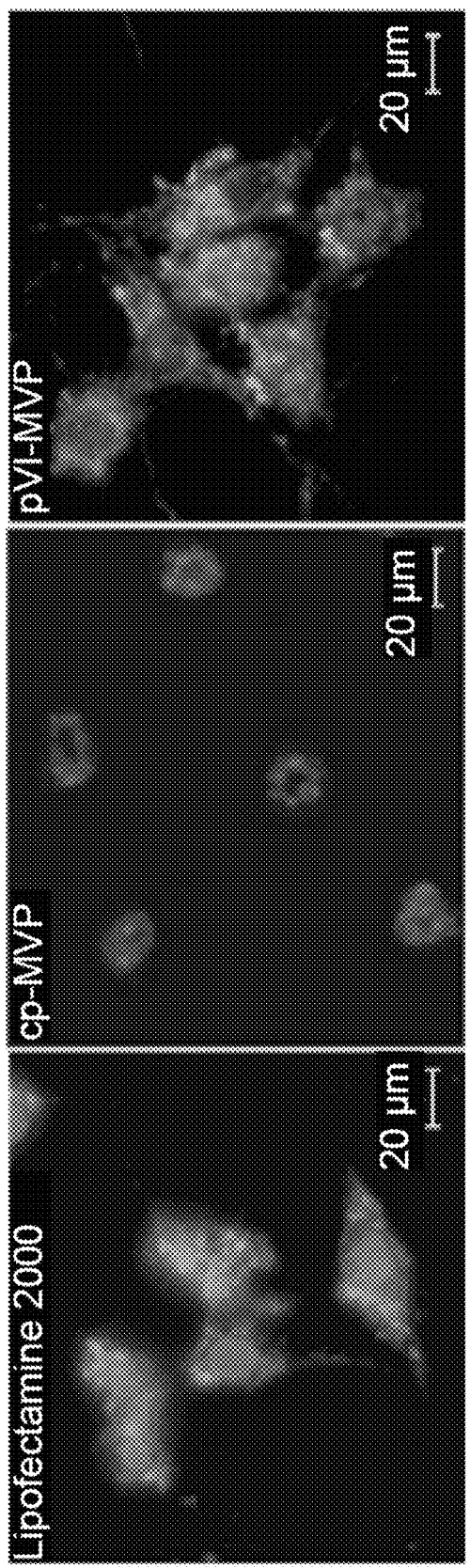
FIG. 11, Panel B

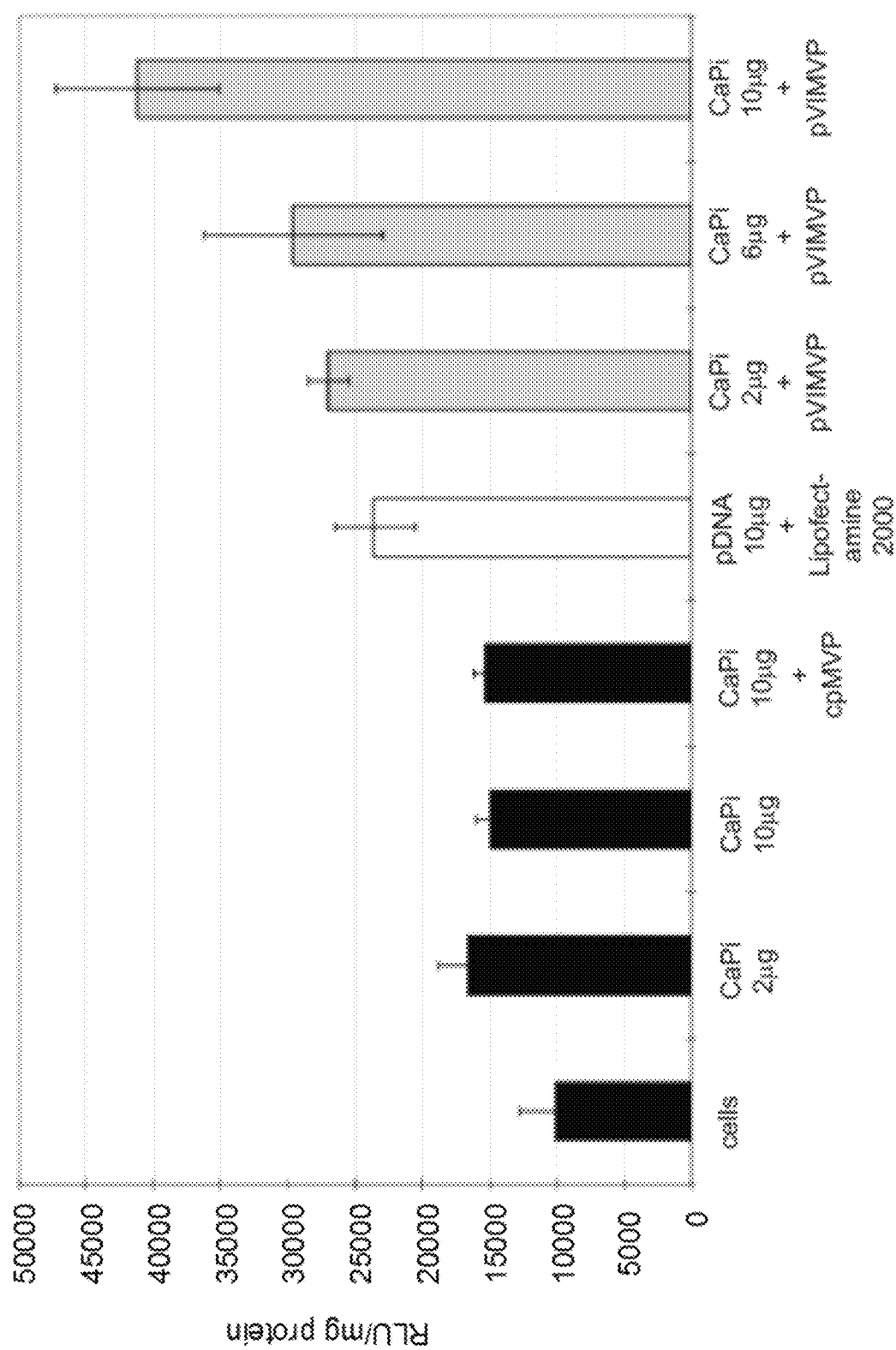
FIG. 11, Panel C

SEQUENCE LISTING

```
<160> NUMBER OF SEQ ID NOS: 55

<210> SEQ ID NO 1
<211> LENGTH: 250
<212> TYPE: PRT
<213> ORGANISM: Human adenovirus 5

<400> SEQUENCE: 1

Met Glu Asp Ile Asn Phe Ala Ser Leu Ala Pro Arg His Gly Ser Arg
1               5                   10                  15

Pro Phe Met Gly Asn Trp Gln Asp Ile Gly Thr Ser Asn Met Ser Gly
            20                  25                  30

Gly Ala Phe Ser Trp Gly Ser Leu Trp Ser Gly Ile Lys Asn Phe Gly
        35                  40                  45

Ser Thr Val Lys Asn Tyr Gly Ser Lys Ala Trp Asn Ser Ser Thr Gly
    50                  55                  60

Gln Met Leu Arg Asp Lys Leu Lys Glu Gln Asn Phe Gln Gln Lys Val
65                  70                  75                  80

Val Asp Gly Leu Ala Ser Gly Ile Ser Gly Val Val Asp Leu Ala Asn
                85                  90                  95

Gln Ala Val Gln Asn Lys Ile Asn Ser Lys Leu Asp Pro Arg Pro Pro
            100                 105                 110

Val Glu Glu Pro Pro Pro Ala Val Glu Thr Val Ser Pro Glu Gly Arg
        115                 120                 125

Gly Glu Lys Arg Pro Arg Pro Asp Arg Glu Glu Thr Leu Val Thr Gln
    130                 135                 140

Ile Asp Glu Pro Pro Ser Tyr Glu Glu Ala Leu Lys Gln Gly Leu Pro
145                 150                 155                 160

Thr Thr Arg Pro Ile Ala Pro Met Ala Thr Gly Val Leu Gly Gln His
                165                 170                 175

Thr Pro Val Thr Leu Asp Leu Pro Pro Pro Ala Asp Thr Gln Gln Lys
            180                 185                 190

Pro Val Leu Pro Gly Pro Thr Ala Val Val Thr Arg Pro Ser Arg
        195                 200                 205

Ala Ser Leu Arg Arg Ala Ala Ser Gly Pro Arg Ser Leu Arg Pro Val
    210                 215                 220

Ala Ser Gly Asn Trp Gln Ser Thr Leu Asn Ser Ile Val Gly Leu Gly
225                 230                 235                 240

Val Gln Ser Leu Lys Arg Arg Arg Cys Phe
                245                 250

<210> SEQ ID NO 2
<211> LENGTH: 60
<212> TYPE: DNA
<213> ORGANISM: Human adenovirus 5

<400> SEQUENCE: 2
gccttcagct ggggctcgct gtggagcggc attaaaaatt tcggttccac cgttaagaac          60

<210> SEQ ID NO 3
```

```
<211> LENGTH: 20
<212> TYPE: PRT
<213> ORGANISM: Human adenovirus 5

<400> SEQUENCE: 3

Ala Phe Ser Trp Gly Ser Leu Trp Ser Gly Ile Lys Asn Phe Gly Ser
1               5                   10                  15

Thr Val Lys Asn
            20

<210> SEQ ID NO 4
<211> LENGTH: 81
<212> TYPE: PRT
<213> ORGANISM: Human adenovirus 5

<400> SEQUENCE: 4

Ala Phe Ser Trp Gly Ser Leu Trp Ser Gly Ile Lys Asn Phe Gly Ser
1               5                   10                  15

Thr Val Lys Asn Tyr Gly Ser Lys Ala Trp Asn Ser Ser Thr Gly Gln
            20                  25                  30

Met Leu Arg Asp Lys Leu Lys Glu Gln Asn Phe Gln Gln Lys Val Val
        35                  40                  45

Asp Gly Leu Ala Ser Gly Ile Ser Gly Val Val Asp Leu Ala Asn Gln
    50                  55                  60

Ala Val Gln Asn Lys Ile Asn Ser Lys Leu Asp Pro Arg Pro Pro Val
65                  70                  75                  80

Glu

<210> SEQ ID NO 5
<211> LENGTH: 489
<212> TYPE: DNA
<213> ORGANISM: Homo sapiens

<400> SEQUENCE: 5
tgcacacaac actggcagga tgctgtgcct tggacagaac tcctcagtct acagacagag      60
gatggcttct ggaaacttac accagaactg ggacttatat aaatcttaa tacaaatggt     120 ttgcacagct ttcttaaaca aaaaggcatt caatctctag gtgtaaaagg aagagaatgt     180
ctcctggacc taattgccac aatgctggta ctacagtttta ttcgcaccag gttggaaaaa    240
gagggaatag tgttcaaatc actgatgaaa atggatgacc cttctatttc caggaatatt     300
ccctgggctt ttgaggcaat aaagcaagca agtgaatggg taagaagaac tgaaggacag     360
tacccatcta tctgcccacg gcttgaactg gggaacgact gggactctgc caccaagcag     420
ttgctgggac tccagcccat aagcactgtg tcccctcttc atagagtcct ccattacagt     480
caaggctaa                                                              489

<210> SEQ ID NO 6
<211> LENGTH: 162
<212> TYPE: PRT
<213> ORGANISM: Homo sapiens

<400> SEQUENCE: 6

Cys Thr Gln His Trp Gln Asp Ala Val Pro Trp Thr Glu Leu Leu Ser
1               5                   10                  15

Leu Gln Thr Glu Asp Gly Phe Trp Lys Leu Thr Pro Glu Leu Gly Leu
            20                  25                  30

Ile Leu Asn Leu Asn Thr Asn Gly Leu His Ser Phe Leu Lys Gln Lys
        35                  40                  45
```

```
Gly Ile Gln Ser Leu Gly Val Lys Gly Arg Glu Cys Leu Leu Asp Leu
            50                  55                  60

Ile Ala Thr Met Leu Val Leu Gln Phe Ile Arg Thr Arg Leu Glu Lys
 65                  70                  75                  80

Glu Gly Ile Val Phe Lys Ser Leu Met Lys Met Asp Asp Pro Ser Ile
                     85                  90                  95

Ser Arg Asn Ile Pro Trp Ala Phe Glu Ala Ile Lys Gln Ala Ser Glu
                100                 105                 110

Trp Val Arg Thr Glu Gly Gln Tyr Pro Ser Ile Cys Pro Arg Leu
                115                 120                 125

Glu Leu Gly Asn Asp Trp Asp Ser Ala Thr Lys Gln Leu Leu Gly Leu
            130                 135                 140

Gln Pro Ile Ser Thr Val Ser Pro Leu His Arg Val Leu His Tyr Ser
145                 150                 155                 160

Gln Gly

<210> SEQ ID NO 7

<400> SEQUENCE: 7

000

<210> SEQ ID NO 8
<211> LENGTH: 2861
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 8
aannngnatt ttactgtttt cgtacagttt tgtaataaaa aaacctataa atattccgga      60
ttattcatac cgtcccacca tcgggcgcgg atcccggtcc gaagcgcgcg gaattcgcgg     120
ccgcgtcgac tgtggcttgc agctgccagc taccctgcta atgtttggt gggaaaagct     180 tgggattcac catggccttc agctgggggct cgctgtggag cggcattaaa aatttcggtt     240
ccaccgttaa gaacggcctg gtgccgcgcg gcagcgccat ggcaactgaa gaggccatca     300
tccgcatccc cccataccac tacatccatg tgctggacca aacagtaat gtgtcccgtg     360 tggaggttgg accaaagacc tacatccggc aggacaatga gagggtactg tttgccccag     420
ttcgcatggt gaccgtcccc ccacgccact actgcatagt ggccaaccct gtgtcccggg     480
acacccagag ttctgtgtta tttgacatca caggacaagt ccgactccgg cacgctgacc     540
aggagatccg actagcccag gaccccttcc ccctgtatcc aggggaggtg ctggaaaagg     600
acatcacccc actgcaggtg gttctgccca acacagcact gcatcttaag gcgttgctgg     660
actttgagga taagaatgga gacaaggtca tggcaggaga cgagtggcta tttgagggac     720
ctggcaccta catcccacag aaggaagtgg aagtcgtgga gatcattcag gccacagtca     780
tcaaacagaa ccaagcactg cggctaaggg cccgaaagga gtgctttgac cgggagggca     840
aggggcgcgt gacaggtgag gagtggctgg tccgatccgt gggggcttac ctcccagctg     900
```

```
tctttgaaga ggtgctggat ctggtggatg ctgtgatcct acagaaaag actgccctgc      960
acctccgggc tctgcagaac ttcaggacc ttcggggagt gctccaccgc accggggagg     1020
aatggttagt gacagtgcag gacacagaag cccatgttcc agatgtctat gaggaggtgc    1080
ttggggtagt acccatcacc accctgggac ctcgacacta ctgtgtcatt cttgacccaa    1140
tgggaccaga cggcaagaac cagctgggac aaaagcgtgt tgtcaaggga gagaagtcct    1200
ttttcctcca gccaggagag aggctggagc gaggcatcca ggatgtgtat gtgctgtcag    1260
agcagcaggg gctgctactg aaggcactgc agcccctgga ggagggagag agcgaggaga    1320
aggtctccca tcaggccgga gactgctggc tcatccgtgg gccccctggag tatgtgccat    1380
ctgcaaaagt ggaggtggtg gaggagcgtc aggctatccc tctggaccaa aatgagggca    1440
tctatgtgca ggatgtcaag acggggaagg tgcgggctgt gattggaagc acctacatgc    1500
tgactcagga tgaagtcctg tgggaaaagg agctgccttc tggggtggag gagctgctga    1560
acttggggca tgaccctctg gcagacaggg gtcagaaggg cacagccaag ccccttcagc    1620
cctcagctcc aaggaacaag acccgagtgg tcagctaccg tgtcccgcac aatgcagcgg    1680
tgcaggtcta tgactacaga gccaagagag cccgtgtggt cttggggccc gagctagtga    1740
cactggatcc tgaggagcag ttcacagtat tgtccctttc tgccgggcga cccaagcgtc    1800
ctcatgcccg ccgtgcactc tgcctactgc tgggacctga tttctttact gatgtcatca    1860
ccatcgaaac tgcagatcat gccaggttgc agctgcagct tgcctacaac tggcactttg    1920
aactgaagaa ccggaatgac cctgcagagg cagccaagct tttctccgtg cctgacttcg    1980
tgggtgacgc ctgcaaggcc attgcatccc gagtccgggg ggctgtagcc tctgtcacct    2040
ttgatgactt ccataaaaac tcagcccgga tcattcgaat ggctgttttt ggctttgaga    2100
tgtctgaaga cacaggtcct gatggcacac tcctgcccaa ggctcgagac caggcagtct    2160
tcccccaaaa cgggctggta gtcagcagtg tggatgtgca gtcagtggag cccgtggacc    2220
agaggacccg ggatgccctt cagcgcagcg ttcagctggc catcgaaatt accaccaact    2280
cccaggaggc agcagccaag cacgaggctc agagactgga acaggaagcc cgtggtcggc    2340
ttgagaggca gaagatcttg gaccagtcag aagctgaaaa agcccgcaag gaactcttgg    2400
agcttgaggc tatgagcatg gctgtggaga gcacgggtaa tgccaaagca gaggctgagt    2460
cccgtgcaga ggcagcgagg atcgaaggag aaggctctgt gctgcaggcc aagctcaagg    2520
cacaggcgct agccattgag acggaggctg agttggagcg agtaaagaaa gtacgagaga    2580
tggaactgat ctatgcccgg gcccagttgg agctggaggt gagcaaggcg cagcagcttg    2640
ccaatgtgga ggcaaagaag ttcaaggaga tgacagaggc actgggcccc ggcaccatca    2700
gggacctggc tgtggccggg ccagagatgc aggtgaaact tctccagtcc ctgggcctga    2760
aatccactct catcaccgat ggctcgtctc ccatcaacct cttcagcaca gccttcgggt    2820
tgctggggct ggggtctgat ggtcagccgc agcacagaa g                         2861
```

<210> SEQ ID NO 9
<211> LENGTH: 890
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Met Ala Phe Ser Trp Gly Ser Leu Trp Ser Gly Ile Lys Asn Phe Gly

-continued

```
1               5                   10                  15
Ser Thr Val Lys Asn Gly Leu Val Pro Arg Gly Ser Ala Met Ala Thr
                20                  25                  30
Glu Glu Ala Ile Ile Arg Ile Pro Tyr His Tyr Ile His Val Leu
                35                  40                  45
Asp Gln Asn Ser Asn Val Ser Arg Val Glu Val Gly Pro Lys Thr Tyr
                50                  55                  60
Ile Arg Gln Asp Asn Glu Arg Val Leu Phe Ala Pro Val Arg Met Val
65                  70                  75                  80
Thr Val Pro Pro Arg His Tyr Cys Ile Val Ala Asn Pro Val Ser Arg
                        85                  90                  95
Asp Thr Gln Ser Ser Val Leu Phe Asp Ile Thr Gly Gln Val Arg Leu
                    100                 105                 110
Arg His Ala Asp Gln Glu Ile Arg Leu Ala Gln Asp Pro Phe Pro Leu
                    115                 120                 125
Tyr Pro Gly Glu Val Leu Glu Lys Asp Ile Thr Pro Leu Gln Val Val
                130                 135                 140
Leu Pro Asn Thr Ala Leu His Leu Lys Ala Leu Leu Asp Phe Glu Asp
145                 150                 155                 160
Lys Asn Gly Asp Lys Val Met Ala Gly Asp Glu Trp Leu Phe Glu Gly
                        165                 170                 175
Pro Gly Thr Tyr Ile Pro Gln Lys Glu Val Glu Val Glu Ile Ile
                    180                 185                 190
Gln Ala Thr Val Ile Lys Gln Asn Gln Ala Leu Arg Leu Arg Ala Arg
                    195                 200                 205
Lys Glu Cys Phe Asp Arg Glu Gly Lys Gly Arg Val Thr Gly Glu Glu
                210                 215                 220
Trp Leu Val Arg Ser Val Gly Ala Tyr Leu Pro Ala Val Phe Glu Glu
225                 230                 235                 240
Val Leu Asp Leu Val Asp Ala Val Ile Leu Thr Glu Lys Thr Ala Leu
                        245                 250                 255
His Leu Arg Ala Leu Gln Asn Phe Arg Asp Leu Arg Gly Val Leu His
                    260                 265                 270
Arg Thr Gly Glu Glu Trp Leu Val Thr Val Gln Asp Thr Glu Ala His
                    275                 280                 285
Val Pro Asp Val Tyr Glu Glu Val Leu Gly Val Pro Ile Thr Thr
                290                 295                 300
Leu Gly Pro Arg His Tyr Cys Val Ile Leu Asp Pro Met Gly Pro Asp
305                 310                 315                 320
Gly Lys Asn Gln Leu Gly Gln Lys Arg Val Val Lys Gly Glu Lys Ser
                        325                 330                 335
Phe Phe Leu Gln Pro Gly Glu Arg Leu Glu Arg Gly Ile Gln Asp Val
                    340                 345                 350
Tyr Val Leu Ser Glu Gln Gly Leu Leu Leu Lys Ala Leu Gln Pro
                    355                 360                 365
Leu Glu Glu Gly Glu Ser Glu Glu Lys Val Ser His Gln Ala Gly Asp
                370                 375                 380
Cys Trp Leu Ile Arg Gly Pro Leu Glu Tyr Val Pro Ser Ala Lys Val
385                 390                 395                 400
Glu Val Val Glu Glu Arg Gln Ala Ile Pro Leu Asp Gln Asn Glu Gly
                        405                 410                 415
Ile Tyr Val Gln Asp Val Lys Thr Gly Lys Val Arg Ala Val Ile Gly
                    420                 425                 430
```

```
Ser Thr Tyr Met Leu Thr Gln Asp Glu Val Leu Trp Glu Lys Glu Leu
        435                 440                 445

Pro Ser Gly Val Glu Glu Leu Leu Asn Leu Gly His Asp Pro Leu Ala
    450                 455                 460

Asp Arg Gly Gln Lys Gly Thr Ala Lys Pro Leu Gln Pro Ser Ala Pro
465                 470                 475                 480

Arg Asn Lys Thr Arg Val Val Ser Tyr Arg Val Pro His Asn Ala Ala
                485                 490                 495

Val Gln Val Tyr Asp Tyr Arg Ala Lys Arg Ala Arg Val Val Phe Gly
            500                 505                 510

Pro Glu Leu Val Thr Leu Asp Pro Glu Glu Gln Phe Thr Val Leu Ser
        515                 520                 525

Leu Ser Ala Gly Arg Pro Lys Arg Pro His Ala Arg Arg Ala Leu Cys
    530                 535                 540

Leu Leu Leu Gly Pro Asp Phe Phe Thr Asp Val Ile Thr Ile Glu Thr
545                 550                 555                 560

Ala Asp His Ala Arg Leu Gln Leu Gln Leu Ala Tyr Asn Trp His Phe
                565                 570                 575

Glu Leu Lys Asn Arg Asn Asp Pro Ala Glu Ala Ala Lys Leu Phe Ser
            580                 585                 590

Val Pro Asp Phe Val Gly Asp Ala Cys Lys Ala Ile Ala Ser Arg Val
        595                 600                 605

Arg Gly Ala Val Ala Ser Val Thr Phe Asp Asp Phe His Lys Asn Ser
    610                 615                 620

Ala Arg Ile Ile Arg Met Ala Val Phe Gly Phe Glu Met Ser Glu Asp
625                 630                 635                 640

Thr Gly Pro Asp Gly Thr Leu Leu Pro Lys Ala Arg Asp Gln Ala Val
                645                 650                 655

Phe Pro Gln Asn Gly Leu Val Val Ser Ser Val Asp Val Gln Ser Val
            660                 665                 670

Glu Pro Val Asp Gln Arg Thr Arg Asp Ala Leu Gln Arg Ser Val Gln
        675                 680                 685

Leu Ala Ile Glu Ile Thr Thr Asn Ser Gln Glu Ala Ala Ala Lys His
    690                 695                 700

Glu Ala Gln Arg Leu Glu Gln Glu Ala Arg Gly Arg Leu Glu Arg Gln
705                 710                 715                 720

Lys Ile Leu Asp Gln Ser Glu Ala Glu Lys Ala Arg Lys Glu Leu Leu
                725                 730                 735

Glu Leu Glu Ala Met Ser Met Ala Val Glu Ser Thr Gly Asn Ala Lys
            740                 745                 750

Ala Glu Ala Glu Ser Arg Ala Glu Ala Arg Ile Glu Gly Glu Gly
        755                 760                 765

Ser Val Leu Gln Ala Lys Leu Lys Ala Gln Ala Leu Ala Ile Glu Thr
    770                 775                 780

Glu Ala Glu Leu Glu Arg Val Lys Lys Val Arg Glu Met Glu Leu Ile
785                 790                 795                 800

Tyr Ala Arg Ala Gln Leu Glu Leu Glu Val Ser Lys Ala Gln Gln Leu
                805                 810                 815

Ala Asn Val Glu Ala Lys Lys Phe Lys Glu Met Thr Glu Ala Leu Gly
            820                 825                 830

Pro Gly Thr Ile Arg Asp Leu Ala Val Ala Gly Pro Glu Met Gln Val
        835                 840                 845
```

```
Lys Leu Leu Gln Ser Leu Gly Leu Lys Ser Thr Leu Ile Thr Asp Gly
    850                 855                 860

Ser Ser Pro Ile Asn Leu Phe Ser Thr Ala Phe Gly Leu Leu Gly Leu
865                 870                 875                 880

Gly Ser Asp Gly Gln Pro Pro Ala Gln Lys
                885                 890

<210> SEQ ID NO 10
<211> LENGTH: 2973
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 10
aannngnatt ttactgtttt cgtacagttt tgtaataaaa aaacctataa atattccgga      60
ttattcatac cgtcccacca tcgggcgcgg atcccggtcc gaagcgcgcg gaattcgcgg     120
ccgcgtcgac tgtggcttgc agctgccagc taccctgcta atgtttggt gggaaaagct     180 tgggattcac catggccttc agctggggct cgctgtggag cggcattaaa aatttcggtt     240
ccaccgttaa gaacggcctg gtgccgcgcg gcagcgccat ggcaactgaa gaggccatca     300
tccgcatccc cccataccac tacatccatg tgctggacca gaacagtaat gtgtcccgtg     360
tggaggttgg accaaagacc tacatccggc aggacaatga gagggtactg tttgccccag     420
ttcgcatggt gaccgtcccc ccacgccact actgcatagt ggccaaccct gtgtcccggg     480
acacccagag ttctgtgtta tttgacatca caggacaagt ccgactccgg cacgctgacc     540
aggagatccg actagcccag gaccccttcc ccctgtatcc aggggaggtg ctggaaaagg     600
acatcacccc actgcaggtg gttctgccca cacagcact gcatcttaag gcgttgctgg     660
actttgagga taagaatgga gacaaggtca tggcaggaga cgagtggcta tttgagggac     720
ctggcaccta catcccacag aaggaagtgg aagtcgtgga gatcattcag gccacagtca     780
tcaaacagaa ccaagcactg cggctaaggg cccgaaagga gtgctttgac cgggagggca     840
aggggcgcgt gacaggtgag gagtggctgg tccgatccgt gggggcttac ctcccagctg     900
tctttgaaga ggtgctggat ctggtggatg ctgtgatcct tacagaaaag actgccctgc     960
acctccgggc tctgcagaac ttcagggacc ttcggggagt gctccaccgc accggggagg    1020
aatggttagt gacagtgcag gacacagaag cccatgttcc agatgtctat gaggaggtgc    1080
ttggggtagt acccatcacc accctgggac ctcgacacta ctgtgtcatt cttgacccaa    1140
tgggaccaga cggcaagaac cagctgggac aaaagcgtgt tgtcaaggga gagaagtcct    1200
ttttcctcca gccaggagag aggctggagc gaggcatcca ggatgtgtat gtgctgtcag    1260
agcagcaggg gctgctactg aaggcactgc agccctggaa ggaggagag agcgaggaga    1320 aggtctccca tcaggccgga gactgctggc tcatccgtgg gcccctggag tatgtgccat    1380
ctgcaaaagt ggaggtggtg gaggagcgtc aggctatccc tctggaccaa aatgagggca    1440
tctatgtgca ggatgtcaag acggggaagg tgcgggctgt gattgaagc acctacatgc    1500 tgactcagga tgaagtcctg tgggaaaagg agctgccttc tggggtggag gagctgctga    1560
```

```
acttggggca tgaccctctg gcagacaggg gtcagaaggg cacagccaag cccttcagc    1620
cctcagctcc aaggaacaag acccgagtgg tcagctaccg tgtcccgcac aatgcagcgg    1680
tgcaggtcta tgactacaga gccaagagag cccgtgtggt ctttgggccc gagctagtga    1740
cactggatcc tgaggagcag ttcacagtat tgtccctttc tgccgggcga cccaagcgtc    1800
ctcatgcccg ccgtgcactc tgcctactgc tgggacctga tttctttact gatgtcatca    1860
ccatcgaaac tgcagatcat gccaggttgc agctgcagct tgcctacaac tggcactttg    1920
aactgaagaa ccggaatgac cctgcagagg cagccaagct tttctccgtg cctgacttcg    1980
tgggtgacgc ctgcaaggcc attgcatccc gagtccgggg ggctgtagcc tctgtcacct    2040
ttgatgactt ccataaaaac tcagcccgga tcattcgaat ggctgttttt ggctttgaga    2100
tgtctgaaga cacaggtcct gatggcacac tcctgcccaa ggctcgagac caggcagtct    2160
ttccccaaaa cgggctggta gtcagcagtg tggatgtgca gtcagtggag cccgtggacc    2220
agaggacccg ggatgccctt cagcgcagcg ttcagctggc catcgaaatt accaccaact    2280
cccaggaggc agcagccaag cacgaggctc agagactgga acaggaagcc cgtggtcggc    2340
ttgagaggca gaagatcttg gaccagtcag aagctgaaaa agcccgcaag gaactcttgg    2400
agcttgaggc tatgagcatg gctgtggaga gcacgggtaa tgccaaagca gaggctgagt    2460
cccgtgcaga ggcagcgagg atcgaaggag aaggctctgt gctgcaggcc aagctcaagg    2520
cacaggcgct agccattgag acggaggctg agttggagcg agtaaagaaa gtacgagaga    2580
tggaactgat ctatgcccgg gcccagttgg agctggaggt gagcaaggcg cagcagcttg    2640
ccaatgtgga ggcaaagaag ttcaaggaga tgacagaggc actgggcccc ggcaccatca    2700
gggacctggc tgtggccggg ccagagatgc aggtgaaact tctccagtcc ctgggcctga    2760
aatccactct catcaccgat ggctcgtctc ccatcaacct cttcagcaca gccttcgggt    2820
tgctggggct ggggtctgat ggtcagccgc cagcacagaa gtttaacatg cagcagcagc    2880
gccgcttta cgaggccctg cacgacccca acctgaacga ggagcagcgc aacgccaaga    2940
ttaagagcat tcgcgacgac tagggtacct cag                                 2973
```

<210> SEQ ID NO 11
<211> LENGTH: 923
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 11

Met Ala Phe Ser Trp Gly Ser Leu Trp Ser Gly Ile Lys Asn Phe Gly
1               5                   10                  15

Ser Thr Val Lys Asn Gly Leu Val Pro Arg Gly Ser Ala Met Ala Thr
            20                  25                  30

Glu Glu Ala Ile Ile Arg Ile Pro Pro Tyr His Tyr Ile His Val Leu
        35                  40                  45

Asp Gln Asn Ser Asn Val Ser Arg Val Glu Val Gly Pro Lys Thr Tyr
    50                  55                  60

Ile Arg Gln Asp Asn Glu Arg Val Leu Phe Ala Pro Val Arg Met Val
65                  70                  75                  80

Thr Val Pro Pro Arg His Tyr Cys Ile Val Ala Asn Pro Val Ser Arg
                85                  90                  95

Asp Thr Gln Ser Ser Val Leu Phe Asp Ile Thr Gly Gln Val Arg Leu

```
                100                 105                 110
Arg His Ala Asp Gln Glu Ile Arg Leu Ala Gln Asp Pro Phe Pro Leu
            115                 120                 125

Tyr Pro Gly Glu Val Leu Glu Lys Asp Ile Thr Pro Leu Gln Val Val
            130                 135                 140

Leu Pro Asn Thr Ala Leu His Leu Lys Ala Leu Leu Asp Phe Glu Asp
145                 150                 155                 160

Lys Asn Gly Asp Lys Val Met Ala Gly Asp Glu Trp Leu Phe Glu Gly
                165                 170                 175

Pro Gly Thr Tyr Ile Pro Gln Lys Glu Val Glu Val Glu Ile Ile
            180                 185                 190

Gln Ala Thr Val Ile Lys Gln Asn Gln Ala Leu Arg Leu Arg Ala Arg
            195                 200                 205

Lys Glu Cys Phe Asp Arg Glu Gly Lys Gly Arg Val Thr Gly Glu Glu
            210                 215                 220

Trp Leu Val Arg Ser Val Gly Ala Tyr Leu Pro Ala Val Phe Glu Glu
225                 230                 235                 240

Val Leu Asp Leu Val Asp Ala Val Ile Leu Thr Glu Lys Thr Ala Leu
                245                 250                 255

His Leu Arg Ala Leu Gln Asn Phe Arg Asp Leu Arg Gly Val Leu His
            260                 265                 270

Arg Thr Gly Glu Glu Trp Leu Val Thr Val Gln Asp Thr Glu Ala His
            275                 280                 285

Val Pro Asp Val Tyr Glu Glu Val Leu Gly Val Pro Ile Thr Thr
            290                 295                 300

Leu Gly Pro Arg His Tyr Cys Val Ile Leu Asp Pro Met Gly Pro Asp
305                 310                 315                 320

Gly Lys Asn Gln Leu Gly Gln Lys Arg Val Val Lys Gly Glu Lys Ser
                325                 330                 335

Phe Phe Leu Gln Pro Gly Glu Arg Leu Glu Arg Gly Ile Gln Asp Val
            340                 345                 350

Tyr Val Leu Ser Glu Gln Gln Gly Leu Leu Leu Lys Ala Leu Gln Pro
            355                 360                 365

Leu Glu Glu Gly Glu Ser Glu Glu Lys Val Ser His Gln Ala Gly Asp
            370                 375                 380

Cys Trp Leu Ile Arg Gly Pro Leu Glu Tyr Val Pro Ser Ala Lys Val
385                 390                 395                 400

Glu Val Val Glu Glu Arg Gln Ala Ile Pro Leu Asp Gln Asn Glu Gly
                405                 410                 415

Ile Tyr Val Gln Asp Val Lys Thr Gly Lys Val Arg Ala Val Ile Gly
            420                 425                 430

Ser Thr Tyr Met Leu Thr Gln Asp Glu Val Leu Trp Glu Lys Glu Leu
            435                 440                 445

Pro Ser Gly Val Glu Glu Leu Leu Asn Leu Gly His Asp Pro Leu Ala
            450                 455                 460

Asp Arg Gly Gln Lys Gly Thr Ala Lys Pro Leu Gln Pro Ser Ala Pro
465                 470                 475                 480

Arg Asn Lys Thr Arg Val Val Ser Tyr Arg Val Pro His Asn Ala Ala
                485                 490                 495

Val Gln Val Tyr Asp Tyr Arg Ala Lys Arg Ala Arg Val Val Phe Gly
            500                 505                 510

Pro Glu Leu Val Thr Leu Asp Pro Glu Glu Gln Phe Thr Val Leu Ser
            515                 520                 525
```

Leu Ser Ala Gly Arg Pro Lys Arg Pro His Ala Arg Arg Ala Leu Cys
          530                 535                 540

Leu Leu Leu Gly Pro Asp Phe Phe Thr Asp Val Ile Thr Ile Glu Thr
545                 550                 555                 560

Ala Asp His Ala Arg Leu Gln Leu Gln Leu Ala Tyr Asn Trp His Phe
                565                 570                 575

Glu Leu Lys Asn Arg Asn Asp Pro Ala Glu Ala Lys Leu Phe Ser
            580                 585                 590

Val Pro Asp Phe Val Gly Asp Ala Cys Lys Ala Ile Ala Ser Arg Val
        595                 600                 605

Arg Gly Ala Val Ala Ser Val Thr Phe Asp Asp Phe His Lys Asn Ser
    610                 615                 620

Ala Arg Ile Ile Arg Met Ala Val Phe Gly Phe Glu Met Ser Glu Asp
625                 630                 635                 640

Thr Gly Pro Asp Gly Thr Leu Leu Pro Lys Ala Arg Asp Gln Ala Val
                645                 650                 655

Phe Pro Gln Asn Gly Leu Val Val Ser Ser Val Asp Val Gln Ser Val
                660                 665                 670

Glu Pro Val Asp Gln Arg Thr Arg Asp Ala Leu Gln Arg Ser Val Gln
            675                 680                 685

Leu Ala Ile Glu Ile Thr Thr Asn Ser Gln Glu Ala Ala Lys His
    690                 695                 700

Glu Ala Gln Arg Leu Glu Gln Glu Ala Arg Gly Arg Leu Glu Arg Gln
705                 710                 715                 720

Lys Ile Leu Asp Gln Ser Glu Ala Glu Lys Ala Arg Lys Glu Leu Leu
                725                 730                 735

Glu Leu Glu Ala Met Ser Met Ala Val Glu Ser Thr Gly Asn Ala Lys
            740                 745                 750

Ala Glu Ala Glu Ser Arg Ala Glu Ala Arg Ile Glu Gly Glu Gly
            755                 760                 765

Ser Val Leu Gln Ala Lys Leu Lys Ala Gln Ala Leu Ala Ile Glu Thr
    770                 775                 780

Glu Ala Glu Leu Glu Arg Val Lys Lys Val Arg Glu Met Glu Leu Ile
785                 790                 795                 800

Tyr Ala Arg Ala Gln Leu Glu Leu Glu Val Ser Lys Ala Gln Gln Leu
                805                 810                 815

Ala Asn Val Glu Ala Lys Lys Phe Lys Glu Met Thr Glu Ala Leu Gly
            820                 825                 830

Pro Gly Thr Ile Arg Asp Leu Ala Val Ala Gly Pro Glu Met Gln Val
            835                 840                 845

Lys Leu Leu Gln Ser Leu Gly Leu Lys Ser Thr Leu Ile Thr Asp Gly
850                 855                 860

Ser Ser Pro Ile Asn Leu Phe Ser Thr Ala Phe Gly Leu Leu Gly Leu
865                 870                 875                 880

Gly Ser Asp Gly Gln Pro Pro Ala Gln Lys Phe Asn Met Gln Gln Gln
                885                 890                 895

Arg Arg Phe Tyr Glu Ala Leu His Asp Pro Asn Leu Asn Glu Glu Gln
                900                 905                 910

Arg Asn Ala Lys Ile Lys Ser Ile Arg Asp Asp
            915                 920

<210> SEQ ID NO 12
<211> LENGTH: 759

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
atggccttca gctggggctc gctgtggagc ggcattaaaa atttcggttc caccgttaag    60
aactatggca gcaaggcctg aacagcagc acaggccaga tgctgaggga taagttgaaa   120
gagcaaaatt tccaacaaaa ggtggtagat ggcctggcct ctggcattag cggggtggtg   180
gacctggcca accaggcagt gcaaaataag attaacagta agcttgatcc ccgccctccc   240
gtagagggat ccgaattcgg cacgaggcgg tgcacacaac actggcagga tgctgtgcct   300
tggacagaac tcctcagtct acagacagag gatggcttct ggaaacttac accagaactg   360
ggacttatat aaatcttaa tacaaatggt ttgcacagct ttcttaaaca aaaaggcatt    420
caatctctag gtgtaaaagg aagagaatgt ctcctggacc taattgccac aatgctggta   480
ctacagttta ttcgcaccag gttggaaaaa gagggaatag tgttcaaatc actgatgaaa   540
atggatgacc cttctatttc caggaatatt ccctgggctt ttgaggcaat aaagcaagca   600
agtgaatggg taagaagaac tgaaggacag tacccatcta tctgcccacg gcttgaactg   660
gggaacgact gggactctgc caccaagcag ttgctgggac tccagcccat aagcactgtg   720
tccctcttc atagagtcct ccattacagt caaggctaa                          759
```

<210> SEQ ID NO 13
<211> LENGTH: 252
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Ala Phe Ser Trp Gly Ser Leu Trp Ser Gly Ile Lys Asn Phe Gly
1               5                   10                  15

Ser Thr Val Lys Asn Tyr Gly Ser Lys Ala Trp Asn Ser Ser Thr Gly
            20                  25                  30

Gln Met Leu Arg Asp Lys Leu Lys Glu Gln Asn Phe Gln Gln Lys Val
        35                  40                  45

Val Asp Gly Leu Ala Ser Gly Ile Ser Gly Val Val Asp Leu Ala Asn
    50                  55                  60

Gln Ala Val Gln Asn Lys Ile Asn Ser Lys Leu Asp Pro Arg Pro Pro
65                  70                  75                  80

Val Glu Gly Ser Glu Phe Gly Thr Arg Arg Cys Thr Gln His Trp Gln
                85                  90                  95

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

Val Lys Gly Arg Glu Cys Leu Leu Asp Leu Ile Ala Thr Met Leu Val
145                 150                 155                 160

Leu Gln Phe Ile Arg Thr Arg Leu Glu Lys Glu Gly Ile Val Phe Lys
                165                 170                 175

Ser Leu Met Lys Met Asp Asp Pro Ser Ile Ser Arg Asn Ile Pro Trp
```

```
              180                 185                 190
Ala Phe Glu Ala Ile Lys Gln Ala Ser Glu Trp Val Arg Arg Thr Glu
            195                 200                 205

Gly Gln Tyr Pro Ser Ile Cys Pro Arg Leu Glu Leu Gly Asn Asp Trp
        210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250

<210> SEQ ID NO 14
<211> LENGTH: 1724
<212> TYPE: PRT
<213> ORGANISM: Homo sapiens

<400> SEQUENCE: 14

Met Val Met Gly Ile Phe Ala Asn Cys Ile Phe Cys Leu Lys Val Lys
1               5                   10                  15

Tyr Leu Pro Gln Gln Lys Lys Leu Gln Thr Asp Ile Lys Glu
            20                  25                  30

Asn Gly Gly Lys Phe Ser Phe Ser Leu Asn Pro Gln Cys Thr His Ile
        35                  40                  45

Ile Leu Asp Asn Ala Asp Val Leu Ser Gln Tyr Gln Leu Asn Ser Ile
50                  55                  60

Gln Lys Asn His Val His Ile Ala Asn Pro Asp Phe Ile Trp Lys Ser
65                  70                  75                  80

Ile Arg Glu Lys Arg Leu Leu Asp Val Lys Asn Tyr Asp Pro Tyr Lys
                85                  90                  95

Pro Leu Asp Ile Thr Pro Pro Asp Gln Lys Ala Ser Ser Ser Glu
            100                 105                 110

Val Lys Thr Glu Gly Leu Cys Pro Asp Ser Ala Thr Glu Glu Glu Asp
        115                 120                 125

Thr Val Glu Leu Thr Glu Phe Gly Met Gln Asn Val Glu Ile Pro His
130                 135                 140

Leu Pro Gln Asp Phe Glu Val Ala Lys Tyr Asn Thr Leu Glu Lys Val
145                 150                 155                 160

Gly Met Glu Gly Gly Gln Glu Ala Val Val Glu Leu Gln Cys Ser
                165                 170                 175

Arg Asp Ser Arg Asp Cys Pro Phe Leu Ile Ser Ser His Phe Leu Leu
            180                 185                 190

Asp Asp Gly Met Glu Thr Arg Arg Gln Phe Ala Ile Lys Lys Thr Ser
        195                 200                 205

Glu Asp Ala Ser Glu Tyr Phe Glu Asn Tyr Ile Glu Glu Leu Lys Lys
        210                 215                 220

Gln Gly Phe Leu Leu Arg Glu His Phe Thr Pro Glu Ala Thr Gln Leu
225                 230                 235                 240

Ala Ser Glu Gln Leu Gln Ala Leu Leu Leu Glu Glu Val Met Asn Ser
                245                 250                 255

Ser Thr Leu Ser Gln Glu Val Ser Asp Leu Val Glu Met Ile Trp Ala
            260                 265                 270

Glu Ala Leu Gly His Leu Glu His Met Leu Leu Lys Pro Val Asn Arg
        275                 280                 285

Ile Ser Leu Asn Asp Val Ser Lys Ala Glu Gly Ile Leu Leu Leu Val
        290                 295                 300
```

```
Lys Ala Ala Leu Lys Asn Gly Glu Thr Ala Glu Gln Leu Gln Lys Met
305                 310                 315                 320

Met Thr Glu Phe Tyr Arg Leu Ile Pro His Lys Gly Thr Met Pro Lys
            325                 330                 335

Glu Val Asn Leu Gly Leu Leu Ala Lys Lys Ala Asp Leu Cys Gln Leu
        340                 345                 350

Ile Arg Asp Met Val Asn Val Cys Glu Thr Asn Leu Ser Lys Pro Asn
            355                 360                 365

Pro Pro Ser Leu Ala Lys Tyr Arg Ala Leu Arg Cys Lys Ile Glu His
    370                 375                 380

Val Glu Gln Asn Thr Glu Glu Phe Leu Arg Val Arg Lys Glu Val Leu
385                 390                 395                 400

Gln Asn His His Ser Lys Ser Pro Val Asp Val Leu Gln Ile Phe Arg
                405                 410                 415

Val Gly Arg Val Asn Glu Thr Thr Glu Phe Leu Ser Lys Leu Gly Asn
            420                 425                 430

Val Arg Pro Leu Leu His Gly Ser Pro Val Gln Asn Ile Val Gly Ile
        435                 440                 445

Leu Cys Arg Gly Leu Leu Leu Pro Lys Val Val Glu Asp Arg Gly Val
    450                 455                 460

Gln Arg Thr Asp Val Gly Asn Leu Gly Ser Gly Ile Tyr Phe Ser Asp
465                 470                 475                 480

Ser Leu Ser Thr Ser Ile Lys Tyr Ser His Pro Gly Glu Thr Asp Gly
                485                 490                 495

Thr Arg Leu Leu Leu Ile Cys Asp Val Ala Leu Gly Lys Cys Met Asp
            500                 505                 510

Leu His Glu Lys Asp Phe Pro Leu Thr Glu Ala Pro Pro Gly Tyr Asp
        515                 520                 525

Ser Val His Gly Val Ser Gln Thr Ala Ser Val Thr Thr Asp Phe Glu
    530                 535                 540

Asp Asp Glu Phe Val Val Tyr Lys Thr Asn Gln Val Lys Met Lys Tyr
545                 550                 555                 560

Ile Ile Lys Phe Ser Met Pro Gly Asp Gln Ile Lys Asp Phe His Pro
                565                 570                 575

Ser Asp His Thr Glu Leu Glu Glu Tyr Arg Pro Glu Phe Ser Asn Phe
            580                 585                 590

Ser Lys Val Glu Asp Tyr Gln Leu Pro Asp Ala Lys Thr Ser Ser Ser
        595                 600                 605

Thr Lys Ala Gly Leu Gln Asp Ala Ser Gly Asn Leu Val Pro Leu Glu
    610                 615                 620

Asp Val His Ile Lys Gly Arg Ile Ile Asp Thr Val Ala Gln Val Ile
625                 630                 635                 640

Val Phe Gln Thr Tyr Thr Asn Lys Ser His Val Pro Ile Glu Ala Lys
                645                 650                 655

Tyr Ile Phe Pro Leu Asp Asp Lys Ala Ala Val Cys Gly Phe Glu Ala
            660                 665                 670

Phe Ile Asn Gly Lys His Ile Val Gly Glu Ile Lys Glu Lys Glu Glu
        675                 680                 685

Ala Gln Gln Glu Tyr Leu Glu Ala Val Thr Gln Gly His Gly Ala Tyr
    690                 695                 700

Leu Met Ser Gln Asp Ala Pro Asp Val Phe Thr Val Ser Val Gly Asn
705                 710                 715                 720

Leu Pro Pro Lys Ala Lys Val Leu Ile Lys Ile Thr Tyr Ile Thr Glu
```

```
                    725                 730                 735
Leu Ser Ile Leu Gly Thr Val Gly Val Phe Met Pro Ala Thr Val
                740                 745                 750
Ala Pro Trp Gln Gln Asp Lys Ala Leu Asn Glu Asn Leu Gln Asp Thr
                755                 760                 765
Val Glu Lys Ile Cys Ile Lys Glu Ile Gly Thr Lys Gln Ser Phe Ser
770                 775                 780
Leu Thr Met Ser Ile Glu Met Pro Tyr Val Ile Glu Phe Ile Phe Ser
785                 790                 795                 800
Asp Thr His Glu Leu Lys Gln Lys Arg Thr Asp Cys Lys Ala Val Ile
                805                 810                 815
Ser Thr Met Glu Gly Ser Ser Leu Asp Ser Ser Gly Phe Ser Leu His
                820                 825                 830
Ile Gly Leu Ser Ala Ala Tyr Leu Pro Arg Met Trp Val Glu Lys His
                835                 840                 845
Pro Glu Lys Glu Ser Glu Ala Cys Met Leu Val Phe Gln Pro Asp Leu
                850                 855                 860
Asp Val Asp Leu Pro Asp Leu Ala Ser Glu Ser Glu Val Ile Ile Cys
865                 870                 875                 880
Leu Asp Cys Ser Ser Ser Met Glu Gly Val Thr Phe Leu Gln Ala Lys
                885                 890                 895
Gln Ile Thr Leu His Ala Leu Ser Leu Val Gly Glu Lys Gln Lys Val
                900                 905                 910
Asn Ile Ile Gln Phe Gly Thr Gly Tyr Lys Glu Leu Phe Ser Tyr Pro
                915                 920                 925
Lys His Ile Thr Ser Asn Thr Ala Ala Glu Phe Ile Met Ser Ala
                930                 935                 940
Thr Pro Thr Met Gly Asn Thr Asp Phe Trp Lys Thr Leu Arg Tyr Leu
945                 950                 955                 960
Ser Leu Leu Tyr Pro Ala Arg Gly Ser Arg Asn Ile Leu Leu Val Ser
                965                 970                 975
Asp Gly His Leu Gln Asp Glu Ser Leu Thr Leu Gln Leu Val Lys Arg
                980                 985                 990
Ser Arg Pro His Thr Arg Leu Phe Ala Cys Gly Ile Gly Ser Thr Ala
                995                 1000                1005
Asn Arg His Val Leu Arg Ile Leu Ser Gln Cys Gly Ala Gly Val
                1010                1015                1020
Phe Glu Tyr Phe Asn Ala Lys Ser Lys His Ser Trp Arg Lys Gln
                1025                1030                1035
Ile Glu Asp Gln Met Thr Arg Leu Cys Ser Pro Ser Cys His Ser
                1040                1045                1050
Val Ser Val Lys Trp Gln Gln Leu Asn Pro Asp Ala Pro Glu Ala
                1055                1060                1065
Leu Gln Ala Pro Ala Gln Val Pro Ser Leu Phe Arg Asn Asp Arg
                1070                1075                1080
Leu Leu Val Tyr Gly Phe Ile Pro His Cys Thr Gln Ala Thr Leu
                1085                1090                1095
Cys Ala Leu Ile Gln Glu Lys Glu Phe Cys Thr Met Val Ser Thr
                1100                1105                1110
Thr Glu Leu Gln Lys Thr Thr Gly Thr Met Ile His Lys Leu Ala
                1115                1120                1125
Ala Arg Ala Leu Ile Arg Asp Tyr Glu Asp Gly Ile Leu His Glu
                1130                1135                1140
```

```
Asn Glu Thr Ser His Glu Met Lys Lys Gln Thr Leu Lys Ser Leu
1145                1150                1155

Ile Ile Lys Leu Ser Lys Glu Asn Ser Leu Ile Thr Gln Phe Thr
1160                1165                1170

Ser Phe Val Ala Val Glu Lys Arg Asp Glu Asn Glu Ser Pro Phe
1175                1180                1185

Pro Asp Ile Pro Lys Val Ser Glu Leu Ile Ala Lys Glu Asp Val
1190                1195                1200

Asp Phe Leu Pro Tyr Met Ser Trp Gln Gly Glu Pro Gln Glu Ala
1205                1210                1215

Val Arg Asn Gln Ser Leu Leu Ala Ser Ser Glu Trp Pro Glu Leu
1220                1225                1230

Arg Leu Ser Lys Arg Lys His Arg Lys Ile Pro Phe Ser Lys Arg
1235                1240                1245

Lys Met Glu Leu Ser Gln Pro Glu Val Ser Glu Asp Phe Glu Glu
1250                1255                1260

Asp Gly Leu Gly Val Leu Pro Ala Phe Thr Ser Asn Leu Glu Arg
1265                1270                1275

Gly Gly Val Glu Lys Leu Leu Asp Leu Ser Trp Thr Glu Ser Cys
1280                1285                1290

Lys Pro Thr Ala Thr Glu Pro Leu Phe Lys Lys Val Ser Pro Trp
1295                1300                1305

Glu Thr Ser Thr Ser Ser Phe Phe Pro Ile Leu Ala Pro Ala Val
1310                1315                1320

Gly Ser Tyr Leu Thr Pro Thr Thr Arg Ala His Ser Pro Ala Ser
1325                1330                1335

Leu Ser Phe Ala Ser Tyr Arg Gln Val Ala Ser Phe Gly Ser Ala
1340                1345                1350

Ala Pro Pro Arg Gln Phe Asp Ala Ser Gln Phe Ser Gln Gly Pro
1355                1360                1365

Val Pro Gly Thr Cys Ala Asp Trp Ile Pro Gln Ser Ala Ser Cys
1370                1375                1380

Pro Thr Gly Pro Pro Gln Asn Pro Pro Ser Ala Pro Tyr Cys Gly
1385                1390                1395

Ile Val Phe Ser Gly Ser Ser Leu Ser Ser Ala Gln Ser Ala Pro
1400                1405                1410

Leu Gln His Pro Gly Gly Phe Thr Thr Arg Pro Ser Ala Gly Thr
1415                1420                1425

Phe Pro Glu Leu Asp Ser Pro Gln Leu His Phe Ser Leu Pro Thr
1430                1435                1440

Asp Pro Asp Pro Ile Arg Gly Phe Gly Ser Tyr His Pro Ser Ala
1445                1450                1455

Tyr Ser Pro Phe His Phe Gln Pro Ser Ala Ala Ser Leu Thr Ala
1460                1465                1470

Asn Leu Arg Leu Pro Met Ala Ser Ala Leu Pro Glu Ala Leu Cys
1475                1480                1485

Ser Gln Ser Arg Thr Thr Pro Val Asp Leu Cys Leu Leu Glu Glu
1490                1495                1500

Ser Val Gly Ser Leu Glu Gly Ser Arg Cys Pro Val Phe Ala Phe
1505                1510                1515

Gln Ser Ser Asp Thr Glu Ser Asp Glu Leu Ser Glu Val Leu Gln
1520                1525                1530
```

| | | | | | | | | | | |
|---|---|---|---|---|---|---|---|---|---|---|
| Asp | Ser | Cys | Phe | Leu | Gln | Ile | Lys | Cys | Asp | Thr | Lys | Asp | Asp | Ser |
| 1535 | | | | 1540 | | | | | 1545 | | | | | |

Asp Ser Cys Phe Leu Gln Ile Lys Cys Asp Thr Lys Asp Asp Ser
   1535                     1540                    1545

Ile Pro Cys Phe Leu Glu Leu Lys Glu Glu Asp Glu Ile Val Cys
   1550                     1555                    1560

Thr Gln His Trp Gln Asp Ala Val Pro Trp Thr Glu Leu Leu Ser
   1565                     1570                    1575

Leu Gln Thr Glu Asp Gly Phe Trp Lys Leu Thr Pro Glu Leu Gly
   1580                     1585                    1590

Leu Ile Leu Asn Leu Asn Thr Asn Gly Leu His Ser Phe Leu Lys
   1595                     1600                    1605

Gln Lys Gly Ile Gln Ser Leu Gly Val Lys Gly Arg Glu Cys Leu
   1610                     1615                    1620

Leu Asp Leu Ile Ala Thr Met Leu Val Leu Gln Phe Ile Arg Thr
   1625                     1630                    1635

Arg Leu Glu Lys Glu Gly Ile Val Phe Lys Ser Leu Met Lys Met
   1640                     1645                    1650

Asp Asp Pro Ser Ile Ser Arg Asn Ile Pro Trp Ala Phe Glu Ala
   1655                     1660                    1665

Ile Lys Gln Ala Ser Glu Trp Val Arg Arg Thr Glu Gly Gln Tyr
   1670                     1675                    1680

Pro Ser Ile Cys Pro Arg Leu Glu Leu Gly Asn Asp Trp Asp Ser
   1685                     1690                    1695

Ala Thr Lys Gln Leu Leu Gly Leu Gln Pro Ile Ser Thr Val Ser
   1700                     1705                    1710

Pro Leu His Arg Val Leu His Tyr Ser Gln Gly
   1715                     1720

<210> SEQ ID NO 15
<211> LENGTH: 5175
<212> TYPE: DNA
<213> ORGANISM: Homo sapiens

<400> SEQUENCE: 15

| | |
|---|---|
| atggtgatgg gaatctttgc aaattgtatc ttctgtttga aagtgaagta cttacctcag | 60 |
| cagcagaaga aaaagctaca aactgacatt aaggaaaatg gcggaaagtt ttccttttcg | 120 |
| ttaaatcctc agtgcacaca tataatctta gataatgctg atgttctgag tcagtaccaa | 180 |
| ctgaattcta tccaaaagaa ccacgttcat attgcaaacc cagattttat atggaaatct | 240 |
| atcagagaaa agagactctt ggatgtaaag aattatgatc cttataagcc cctggacatc | 300 |
| acaccacctc ctgatcagaa ggcgagcagt tctgaagtga aaacagaagg tctatgcccg | 360 |
| gacagtgcca cagaggagga agacactgtg gaactcactg agtttggtat gcagaatgtt | 420 |
| gaaattcctc atcttcctca agattttgaa gttgcaaaat ataacacctt ggagaaagtg | 480 |
| ggaatggagg gaggccagga agctgtggtg gtggagcttc agtgttgcgc ggactccagg | 540 |
| gactgtcctt tcctgatatc ctcacacttc tcctggatg atggcatgga gactagaaga | 600 |
| cagtttgcta taagaaaac ctctgaagat gcaagtgaat actttgaaaa ttacattgaa | 660 |
| gaactgaaga acaaggatt ctactaaga gaacatttca cacctgaagc aacccaatta | 720 |
| gcatctgaac aattgcaagc attgcttttg gaggaagtca tgaattcaag cactctgagc | 780 |
| caagaggtga gcgatttagt agagatgatt tgggcagagg ccctgggcca cctggaacac | 840 |
| atgcttctca agccagtgaa caggattagc ctcaacgatg tgagcaaggc agaggggatt | 900 |
| ctccttctag taaaggcagc actgaaaaat ggagaaacag cagagcaatt gcaaaagatg | 960 |

```
atgacagagt tttacagact gatacctcac aaaggcacaa tgcccaaaga agtgaacctg    1020
ggactattgg ctaagaaagc agacctctgc cagctaataa gagacatggt taatgtctgt    1080
gaaactaatt tgtccaaacc caacccacca tccctggcca ataccgagc tttgaggtgc     1140 aaaattgagc atgttgaaca gaatactgaa gaatttctca gggttagaaa agaggttttg    1200
cagaatcatc acagtaagag cccagtggat gtcttgcaga tatttagagt tggcagagtg    1260
aatgaaacca cagagttttt gagcaaactt ggtaatgtga ggcccttgtt gcatggttct    1320
cctgtacaaa acatcgtggg aatcttgtgt cgagggttgc ttttacccaa agtagtggaa    1380
gatcgtggtg tgcaaagaac agacgtcgga aaccttggaa gtgggattta tttcagtgat    1440
tcgctcagta caagtatcaa gtactcacac ccgggagaga cagatggcac cagactcctg    1500
ctcatttgtg acgtagccct cggaaagtgt atggacttac atgagaagga cttcccctta    1560
actgaagcac caccaggcta cgacagtgtg catggagttt cacaaacagc ctctgtcacc    1620
acagactttg aggatgatga atttgttgtc tataaaacca atcaggttaa aatgaaatat    1680
attattaaat tttccatgcc tggagatcag ataaaggact ttcatcctag tgatcatact    1740
gaattagagg aatacagacc tgagttttca aattttttca aggttgaaga ttaccagtta    1800
ccagatgcca aaacttccag cagcaccaag gccggcctcc aggatgcctc tgggaacttg    1860
gttcctctgg aggatgtcca catcaaaggg agaatcatag acactgtagc ccaggtcatt    1920 gttttcaga catacacaaa taaaagtcac gtgcccattg aggcaaaata tatctttcct    1980
ttggatgaca aggccgctgt gtgtggcttc gaagccttca tcaatgggaa gcacatagtt    2040
ggagagatta agagaagga agaagcccag caagagtacc tagaagccgt gacccagggc    2100
catggcgctt acctgatgag tcaggatgct ccggacgttt ttactgtaag tgttggaaac    2160
ttacccccta aggctaaggt tcttataaaa attacctaca tcacagaact cagcatcctg    2220
ggcactgttg gtgtcttttt catgcccgcc accgtagcac cctggcaaca ggacaaggct    2280
ttgaatgaaa accttcagga tacagtagag aagatttgta taaagaaat aggaacaaag    2340 caaagcttct ctttgactat gtctattgag atgccgtatg tgattgaatt cattttcagt    2400
gatacacatg aactgaaaca aaagcgcaca gactgcaaag ctgtcattag caccatggaa    2460
ggcagctcct tagacagcag tggatttttct ctccacatcg gtttgtctgc tgcctatctc    2520
ccaagaatgt gggttgaaaa acatccagaa aaagaaagcg aggcttgcat gcttgtcttt    2580
caacccgatc tcgatgtcga cctccctgac ctagccagtg agagcgaagt gattatttgt    2640
cttgactgct ccagttccat ggagggtgtg acattcttgc aagccaagca aatcaccttg    2700
catgcgctgt ccttggtggg tgagaagcag aaagtaaata ttatccagtt cggcacaggt    2760
tacaaggagc tattttcgta tcctaagcat atcacaagca ataccacggc agcagagttc    2820
atcatgtctg ccacacctac catggggaac acagacttct ggaaaacact ccgatatctt    2880
agcttattgt accctgctcg agggtcacgg aacatcctcc tggtgtctga tgggcacctc    2940
caggatgaga gcctgacatt acagctcgtg aagaggagcc gcccgcacac caggttattc    3000
gcctgcggta tcggttctac agcaaatcgt cacgtcttaa ggattttgtc ccagtgtggt    3060
gccggagtat ttgaatattt taatgcaaaa tccaagcata gttggagaaa acagatagaa    3120
gaccaaatga ccaggctatg ttctccgagt tgccactctg tctccgtcaa atggcagcaa    3180
ctcaatccag atgcgcccga ggccctgcag gccccagccc aggtgccatc cttgtttcgc    3240
aatgatcgac tccttgtcta tggattcatt cctcactgca cacaagcaac tctgtgtgca    3300
ctaattcaag agaaagaatt ttgtacaatg gtgtcgacta ctgagcttca gaagacaact    3360
```

```
ggaactatga tccacaagct ggcagcccga gctctaatca gagattatga agatggcatt      3420
cttcacgaaa atgaaaccag tcatgagatg aaaaaacaaa ccttgaaatc tctgattatt      3480
aaactcagta agaaaaactc tctcataaca caatttacaa gctttgtggc agttgagaaa      3540
agggatgaga atgagtcgcc ttttcctgat attccaaaag tttctgaact tattgccaaa      3600
gaagatgtag acttcctgcc ctacatgagc tggcaggggg agccccaaga agccgtcagg      3660
aaccagtctc ttttagcatc tctgagtgg ccagaattac gtttatccaa acgaaaacat       3720
aggaaaattc cattttccaa aagaaaaatg gaattatctc agccagaagt ttctgaagat      3780
tttgaagagg atggcttagg tgtactacca gctttcacat caaatttgga acgtggaggt      3840
gtggaaaagc tattggattt aagttggaca gagtcatgta aaccaacagc aactgaacca      3900
ctatttaaga aagtcagtcc atgggaaaca tctacttcta gctttttttcc tatttttggct    3960 ccggccgttg gttcctatct taccccgact acccgcgctc acagtcctgc ttccttgtct      4020
tttgcctcat atcgtcaggt agctagtttc ggttcagctg ctcctcccag acagtttgat     4080
gcatctcaat tcagccaagg ccctgtgcct ggcacttgtg ctgactggat cccacagtcg      4140
gcgtcttgtc ccacaggacc tccccagaac ccaccttctg caccctattg tggcattgtt      4200
ttttcaggga gctcattaag ctctgcacag tctgctccac tgcaacatcc tggaggcttt      4260
actaccaggc cttctgctgg caccttccct gagctggatt ctccccagct tcatttctct     4320
cttcctacag accctgatcc catcagaggt tttgggtctt atcatccctc tgcttactct      4380
ccttttcatt ttcaaccttc cgcagcctct tgactgcca accttaggct gccaatggcc       4440
tctgctttac ctgaggctct ttgcagtcag tcccggacta ccccagtaga tctctgtctt     4500
ctagaagaat cagtaggcag tctcgaagga agtcgatgtc ctgtctttgc ttttcaaagt      4560
tctgacacag aaagtgatga gctatcagaa gtacttcaag acagctgctt tttacaaata     4620
aagtgtgata caaagatgac agtatcccg tgctttctgg aattaaaaga agaggatgaa       4680
atagtgtgca cacaacactg gcaggatgct gtgccttgga cagaactcct cagtctacag      4740
acagaggatg gcttctggaa acttacacca gaactgggac ttatattaaa tcttaataca      4800
aatggtttgc acagctttct taaacaaaaa ggcattcaat ctctaggtgt aaaaggaaga      4860
gaatgtctcc tggacctaat tgccacaatg ctggtactac agtttattcg caccaggttg      4920 gaaaagagg gaatagtgtt caaatcactg atgaaaatgg atgacccttc tatttccagg       4980
aatattccct gggcttttga ggcaataaag caagcaagtg aatgggtaag aagaactgaa      5040
ggacagtacc catctatctg cccacggctt gaactgggga cgactgggga ctctgccacc      5100
aagcagttgc tgggactcca gcccataagc actgtgtccc ctcttcatag agtcctccat      5160
tacagtcaag gctaa                                                      5175
```

<210> SEQ ID NO 16
<211> LENGTH: 893
<212> TYPE: PRT
<213> ORGANISM: Homo sapiens

<400> SEQUENCE: 16

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
            20                  25                  30

Lys Thr Tyr Ile Arg Gln Asp Asn Glu Arg Val Leu Phe Ala Pro Met
        35                  40                  45

```
Arg Met Val Thr Val Pro Pro Arg His Tyr Cys Thr Val Ala Asn Pro
         50              55                  60

Val Ser Arg Asp Ala Gln Gly Leu Val Leu Phe Asp Val Thr Gly Gln
 65              70                  75                      80

Val Arg Leu Arg His Ala Asp Leu Glu Ile Arg Leu Ala Gln Asp Pro
                 85                  90                  95

Phe Pro Leu Tyr Pro Gly Glu Val Leu Glu Lys Asp Ile Thr Pro Leu
             100                 105                 110

Gln Val Val Leu Pro Asn Thr Ala Leu His Leu Lys Ala Leu Leu Asp
         115                 120                 125

Phe Glu Asp Lys Asp Gly Asp Lys Val Val Ala Gly Asp Glu Trp Leu
         130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                 165                 170                 175

Arg Ala Arg Lys Glu Cys Trp Asp Arg Asp Gly Lys Glu Arg Val Thr
             180                 185                 190

Gly Glu Glu Trp Leu Val Thr Thr Val Gly Ala Tyr Leu Pro Ala Val
         195                 200                 205

Phe Glu Glu Val Leu Asp Leu Val Asp Ala Val Ile Leu Thr Glu Lys
210                 215                 220

Thr Ala Leu His Leu Arg Ala Arg Arg Asn Phe Arg Asp Phe Arg Gly
225                 230                 235                 240

Val Ser Arg Arg Thr Gly Glu Glu Trp Leu Val Thr Val Gln Asp Thr
                 245                 250                 255

Glu Ala His Val Pro Asp Val His Glu Glu Val Leu Gly Val Val Pro
             260                 265                 270

Ile Thr Thr Leu Gly Pro His Asn Tyr Cys Val Ile Leu Asp Pro Val
         275                 280                 285

Gly Pro Asp Gly Lys Asn Gln Leu Gly Gln Lys Arg Val Val Lys Gly
290                 295                 300

Glu Lys Ser Phe Phe Leu Gln Pro Gly Glu Gln Leu Glu Gln Gly Ile
305                 310                 315                 320

Gln Asp Val Tyr Val Leu Ser Glu Gln Gln Gly Leu Leu Arg Ala
             325                 330                 335

Leu Gln Pro Leu Glu Glu Gly Glu Asp Glu Glu Lys Val Ser His Gln
             340                 345                 350

Ala Gly Asp His Trp Leu Ile Arg Gly Pro Leu Glu Tyr Val Pro Ser
             355                 360                 365

Ala Lys Val Glu Val Val Glu Glu Arg Gln Ala Ile Pro Leu Asp Glu
370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                 405                 410                 415

Lys Glu Leu Pro Pro Gly Val Glu Glu Leu Leu Asn Lys Gly Gln Asp
             420                 425                 430

Pro Leu Ala Asp Arg Gly Glu Lys Asp Thr Ala Lys Ser Leu Gln Pro
             435                 440                 445

Leu Ala Pro Arg Asn Lys Thr Arg Val Val Ser Tyr Arg Val Pro His
         450                 455                 460
```

```
Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
            485                 490                 495

Val Leu Ser Leu Ser Ala Gly Arg Pro Lys Arg Pro His Ala Arg Arg
        500                 505                 510

Ala Leu Cys Leu Leu Leu Gly Pro Asp Phe Phe Thr Asp Val Ile Thr
        515                 520                 525

Ile Glu Thr Ala Asp His Ala Arg Leu Gln Leu Gln Leu Ala Tyr Asn
    530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Thr Ala Val Phe Gly Phe Glu Thr
        595                 600                 605

Ser Glu Ala Lys Gly Pro Asp Gly Met Ala Leu Pro Arg Pro Arg Asp
    610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
        675                 680                 685

Glu Arg Gln Lys Ile Leu Asp Gln Ser Glu Ala Glu Lys Ala Arg Lys
    690                 695                 700

Glu Leu Leu Glu Leu Glu Ala Leu Ser Met Ala Val Glu Ser Thr Gly
705                 710                 715                 720

Thr Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Gln Arg Val Gln Lys Val Arg Glu Leu
        755                 760                 765

Glu Leu Val Tyr Ala Arg Ala Gln Leu Glu Leu Glu Val Ser Lys Ala
    770                 775                 780

Gln Gln Leu Ala Glu Val Glu Val Lys Lys Phe Lys Gln Met Thr Glu
785                 790                 795                 800

Ala Ile Gly Pro Ser Thr Ile Arg Asp Leu Ala Val Ala Gly Pro Glu
                805                 810                 815

Met Gln Val Lys Leu Leu Gln Ser Leu Gly Leu Lys Ser Thr Leu Ile
            820                 825                 830

Thr Asp Gly Ser Thr Pro Ile Asn Leu Phe Asn Thr Ala Phe Gly Leu
        835                 840                 845

Leu Gly Met Gly Pro Glu Gly Gln Pro Leu Gly Arg Arg Val Ala Ser
    850                 855                 860

Gly Pro Ser Pro Gly Glu Gly Ile Ser Pro Gln Ser Ala Gln Ala Pro
865                 870                 875                 880

Gln Ala Pro Gly Asp Asn His Val Val Pro Val Leu Arg
```

<210> SEQ ID NO 17
<211> LENGTH: 2682
<212> TYPE: DNA
<213> ORGANISM: Homo sapiens

<400> SEQUENCE: 17

| | | | | | |
|---|---|---|---|---|---|
| atggcaactg | aagagttcat | catccgcatc | cccccatacc | actatatcca | tgtgctggac | 60 |
| cagaacagca | acgtgtcccg | tgtggaggtc | gggccaaaga | cctacatccg | gcaggacaat | 120 |
| gagagggtac | tgtttgcccc | catgcgcatg | gtgaccgtcc | ccccacgtca | ctactgcaca | 180 |
| gtggccaacc | ctgtgtctcg | ggatgcccag | ggcttggtgc | tgtttgatgt | cacagggcaa | 240 |
| gttcggcttc | gccacgctga | cctcgagatc | cggctggccc | aggaccccct | tccccctgtac | 300 |
| ccaggggagg | tgctggaaaa | ggacatcaca | ccctgcagg | tggttctgcc | caacactgcc | 360 |
| ctccatctaa | aggcgctgct | tgattttgag | gataaagatg | gagacaaggt | ggtggcagga | 420 |
| gatgagtggc | ttttcgaggg | acctggcacg | tacatccccc | ggaaggaagt | ggaggtcgtg | 480 |
| gagatcattc | aggccaccat | catcaggcag | aaccaggctc | tgcggctcag | ggcccgcaag | 540 |
| gagtgctgga | ccgggacgg | caaggagagg | gtgacaggga | agaatggct | ggtcaccaca | 600 |
| gtagggcgt | acctcccagc | ggtgtttgag | gaggttctgg | atttggtgga | cgccgtcatc | 660 |
| cttacgaaa | agacagccct | gcacctccgg | gctcggcgga | acttccggga | cttcagggga | 720 |
| gtgtcccgcc | gcactgggga | ggagtggctg | gtaacagtgc | aggacacaga | ggcccacgtg | 780 |
| ccagatgtcc | acgaggaggt | gctgggggtt | gtgcccatca | ccaccctggg | cccccacaac | 840 |
| tactgcgtga | ttctcgaccc | tgtcggaccg | gatggcaaga | tcagctggg | gcagaagcgc | 900 |
| gtggtcaagg | gagagaagtc | tttttttcctc | cagccaggag | agcagctgga | caaggcatc | 960 |
| caggatgtgt | atgtgctgtc | ggagcagcag | gggctgctgc | tgagggccct | gcagcccctg | 1020 |
| gaggaggggg | aggatgagga | gaaggtctca | caccaggctg | ggaccactg | gctcatccgc | 1080 |
| ggacccctgg | agtatgtgcc | atctgccaaa | gtggaggtgg | tggaggagcg | ccaggccatc | 1140 |
| cctctagacg | agaacgaggg | catctatgtg | caggatgtca | agaccggaaa | ggtgcgcgct | 1200 |
| gtgattggaa | gcacctacat | gctgacccag | gacgaagtcc | tgtgggagaa | agagctgcct | 1260 |
| cccgggtgg | aggagctgct | gaacaagggg | caggaccctc | tggcagacag | gggtgagaag | 1320 |
| gacacagcta | agagcctcca | gcccttggcg | ccccggaaca | agaccgtgt | ggtcagctac | 1380 |
| cgcgtgcccc | acaacgctgc | ggtgcaggtg | tacgactacc | gagagaagcg | agcccgcgtg | 1440 |
| gtcttcgggc | ctgagctggt | gtcgctgggt | cctgaggagc | agttcacagt | gttgtccctc | 1500 |
| tcagctgggc | ggcccaagcg | tcccatgcc | cgccgtgcgc | tctgcctgct | gctgggggct | 1560 |
| gacttcttca | cagacgtcat | caccatcgaa | acggcggatc | atgccaggct | gcaactgcag | 1620 |
| ctggcctaca | actggcactt | tgaggtgaat | gaccggaagg | accccaaga | gacggccaag | 1680 |
| ctcttttcag | tgccagactt | tgtaggtgat | gcctgcaaag | ccatcgcatc | ccgggtgcgg | 1740 |
| ggggccgtgg | cctctgtcac | tttcgatgac | ttccataaga | actcagcccg | catcattcgc | 1800 |
| actgctgtct | ttggctttga | gacctcgaa | gcgaagggcc | ccgatggcat | ggccctgccc | 1860 |
| aggcccgggg | accaggctgt | cttccccaa | aacgggctgg | tggtcagcag | tgtggacgtg | 1920 |
| cagtcagtgg | agcctgtgga | tcagaggacc | cggacgcccc | tgcaacgcag | cgtccagctg | 1980 |
| gccatcgaga | tcaccaccaa | ctcccaggaa | gcggcggcca | agcatgaggc | tcagagactg | 2040 |
| gagcaggaag | cccgcggccg | gcttgagcgg | cagaagatcc | tggaccagtc | agaagccgag | 2100 |

```
aaagctcgca aggaactttt ggagctggag gctctgagca tggccgtgga gagcaccggg   2160
actgccaagg cggaggccga gtcccgtgcg gaggcagccc ggattgaggg agaagggtcc   2220
gtgctgcagg ccaagctaaa agcacaggcc ttggccattg aaacggaggc tgagctccag   2280
agggtccaga aggtccgaga gctggaactg gtctatgccc gggcccagct ggagctggag   2340
gtgagcaagg ctcagcagct ggctgaggtg gaggtgaaga agttcaagca gatgacagag   2400
gccataggcc ccagcaccat cagggacctt gctgtggctg ggcctgagat gcaggtaaaa   2460
ctgctccagt ccctgggcct gaaatcaacc ctcatcaccg atggctccac tcccatcaac   2520
ctcttcaaca cagcctttgg gctgctgggg atggggcccg agggtcagcc cctgggcaga   2580
agggtggcca gtgggcccag ccctggggag gggatatccc cccagtctgc tcaggcccct   2640
caagctcctg gagacaacca cgtggtgcct gtactgcgct aa                      2682
```

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Ala Gly Cys Gly Cys Pro Cys Gly Cys Gly Ala
1               5                   10

<210> SEQ ID NO 19
<211> LENGTH: 905
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Gly Cys Gly Cys Pro Cys Gly Cys Gly Ala Met Ala Thr Glu
1               5                   10                  15

Glu Phe Ile Ile Arg Ile Pro Pro Tyr His Tyr Ile His Val Leu Asp
                20                  25                  30

Gln Asn Ser Asn Val Ser Arg Val Glu Val Gly Pro Lys Thr Tyr Ile
            35                  40                  45

Arg Gln Asp Asn Glu Arg Val Leu Phe Ala Pro Met Arg Met Val Thr
        50                  55                  60

Val Pro Pro Arg His Tyr Cys Thr Val Ala Asn Pro Val Ser Arg Asp
65                  70                  75                  80

Ala Gln Gly Leu Val Leu Phe Asp Val Thr Gly Gln Val Arg Leu Arg
                85                  90                  95

His Ala Asp Leu Glu Ile Arg Leu Ala Gln Asp Pro Phe Pro Leu Tyr
            100                 105                 110

Pro Gly Glu Val Leu Glu Lys Asp Ile Thr Pro Leu Gln Val Val Leu
        115                 120                 125

Pro Asn Thr Ala Leu His Leu Lys Ala Leu Leu Asp Phe Glu Asp Lys
    130                 135                 140

Asp Gly Asp Lys Val Val Ala Gly Asp Glu Trp Leu Phe Glu Gly Pro
145                 150                 155                 160

Gly Thr Tyr Ile Pro Arg Lys Glu Val Glu Val Val Glu Ile Ile Gln
                165                 170                 175

-continued

```
Ala Thr Ile Ile Arg Gln Asn Gln Ala Leu Arg Leu Arg Ala Arg Lys
            180                 185                 190

Glu Cys Trp Asp Arg Asp Gly Lys Glu Arg Val Thr Gly Glu Glu Trp
        195                 200                 205

Leu Val Thr Thr Val Gly Ala Tyr Leu Pro Ala Val Phe Glu Glu Val
    210                 215                 220

Leu Asp Leu Val Asp Ala Val Ile Leu Thr Glu Lys Thr Ala Leu His
225                 230                 235                 240

Leu Arg Ala Arg Arg Asn Phe Arg Asp Phe Arg Gly Val Ser Arg Arg
                245                 250                 255

Thr Gly Glu Glu Trp Leu Val Thr Val Gln Asp Thr Glu Ala His Val
            260                 265                 270

Pro Asp Val His Glu Glu Val Leu Gly Val Val Pro Ile Thr Thr Leu
        275                 280                 285

Gly Pro His Asn Tyr Cys Val Ile Leu Asp Pro Val Gly Pro Asp Gly
    290                 295                 300

Lys Asn Gln Leu Gly Gln Lys Arg Val Val Lys Gly Glu Lys Ser Phe
305                 310                 315                 320

Phe Leu Gln Pro Gly Glu Gln Leu Glu Gln Gly Ile Gln Asp Val Tyr
                325                 330                 335

Val Leu Ser Glu Gln Gln Gly Leu Leu Leu Arg Ala Leu Gln Pro Leu
            340                 345                 350

Glu Glu Gly Glu Asp Glu Glu Lys Val Ser His Gln Ala Gly Asp His
        355                 360                 365

Trp Leu Ile Arg Gly Pro Leu Glu Tyr Val Pro Ser Ala Lys Val Glu
    370                 375                 380

Val Val Glu Glu Arg Gln Ala Ile Pro Leu Asp Glu Asn Glu Gly Ile
385                 390                 395                 400

Tyr Val Gln Asp Val Lys Thr Gly Lys Val Arg Ala Val Ile Gly Ser
                405                 410                 415

Thr Tyr Met Leu Thr Gln Asp Glu Val Leu Trp Glu Lys Glu Leu Pro
            420                 425                 430

Pro Gly Val Glu Glu Leu Leu Asn Lys Gly Gln Asp Pro Leu Ala Asp
        435                 440                 445

Arg Gly Glu Lys Asp Thr Ala Lys Ser Leu Gln Pro Leu Ala Pro Arg
    450                 455                 460

Asn Lys Thr Arg Val Val Ser Tyr Arg Val Pro His Asn Ala Ala Val
465                 470                 475                 480

Gln Val Tyr Asp Tyr Arg Glu Lys Arg Ala Arg Val Val Phe Gly Pro
                485                 490                 495

Glu Leu Val Ser Leu Gly Pro Glu Glu Gln Phe Thr Val Leu Ser Leu
            500                 505                 510

Ser Ala Gly Arg Pro Lys Arg Pro His Ala Arg Arg Ala Leu Cys Leu
        515                 520                 525

Leu Leu Gly Pro Asp Phe Phe Thr Asp Val Ile Thr Ile Glu Thr Ala
    530                 535                 540

Asp His Ala Arg Leu Gln Leu Gln Leu Ala Tyr Asn Trp His Phe Glu
545                 550                 555                 560

Val Asn Asp Arg Lys Asp Pro Gln Glu Thr Ala Lys Leu Phe Ser Val
                565                 570                 575

Pro Asp Phe Val Gly Asp Ala Cys Lys Ala Ile Ala Ser Arg Val Arg
            580                 585                 590

Gly Ala Val Ala Ser Val Thr Phe Asp Asp Phe His Lys Asn Ser Ala
```

Arg Ile Ile Arg Thr Ala Val Phe Gly Phe Glu Thr Ser Glu Ala Lys
         610                 615                 620

Gly Pro Asp Gly Met Ala Leu Pro Arg Pro Arg Asp Gln Ala Val Phe
625                 630                 635                 640

Pro Gln Asn Gly Leu Val Val Ser Ser Val Asp Gln Ser Val Glu
                645                 650                 655

Pro Val Asp Gln Arg Thr Arg Asp Ala Leu Gln Arg Ser Val Gln Leu
                660                 665                 670

Ala Ile Glu Ile Thr Thr Asn Ser Gln Glu Ala Ala Lys His Glu
            675                 680                 685

Ala Gln Arg Leu Glu Gln Glu Ala Arg Gly Arg Leu Glu Arg Gln Lys
        690                 695                 700

Ile Leu Asp Gln Ser Glu Ala Glu Lys Ala Arg Lys Glu Leu Leu Glu
705                 710                 715                 720

Leu Glu Ala Leu Ser Met Ala Val Glu Ser Thr Gly Thr Ala Lys Ala
                725                 730                 735

Glu Ala Glu Ser Arg Ala Glu Ala Arg Ile Glu Gly Glu Gly Ser
            740                 745                 750

Val Leu Gln Ala Lys Leu Lys Ala Gln Ala Leu Ala Ile Glu Thr Glu
        755                 760                 765

Ala Glu Leu Gln Arg Val Gln Lys Val Arg Glu Leu Glu Leu Val Tyr
770                 775                 780

Ala Arg Ala Gln Leu Glu Leu Glu Val Ser Lys Ala Gln Gln Leu Ala
785                 790                 795                 800

Glu Val Glu Val Lys Lys Phe Lys Gln Met Thr Glu Ala Ile Gly Pro
                805                 810                 815

Ser Thr Ile Arg Asp Leu Ala Val Ala Gly Pro Glu Met Gln Val Lys
                820                 825                 830

Leu Leu Gln Ser Leu Gly Leu Lys Ser Thr Leu Ile Thr Asp Gly Ser
            835                 840                 845

Thr Pro Ile Asn Leu Phe Asn Thr Ala Phe Gly Leu Leu Gly Met Gly
850                 855                 860

Pro Glu Gly Gln Pro Leu Gly Arg Arg Val Ala Ser Gly Pro Ser Pro
865                 870                 875                 880

Gly Glu Gly Ile Ser Pro Gln Ser Ala Gln Ala Pro Gln Ala Pro Gly
                885                 890                 895

Asp Asn His Val Val Pro Val Leu Arg
            900                 905

<210> SEQ ID NO 20
<211> LENGTH: 2718
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggcaggct gcggttgtcc atgcggttgt ggcgccatgg caactgaaga gttcatcatc        60
cgcatccccc cataccacta tatccatgtg ctggaccaga acagcaacgt gtcccgtgtg       120
gaggtcgggc caaagaccta catccggcag acaatgagag ggtactgtt tgccccccatg       180 cgcatggtga ccgtcccccc acgtcactac tgcacagtgg ccaaccctgt gtctcgggat       240
gcccagggct tggtgctgtt tgatgtcaca gggcaagttc ggcttcgcca cgctgacctc       300

```
gagatccggc tggcccagga ccccttcccc ctgtacccag ggaggtgctg ggaaaaggac    360
atcacacccc tgcaggtggt tctgcccaac actgccctcc atctaaaggc gctgcttgat    420
tttgaggata agatggagac aaggtggtg gcaggagatg agtggctttt cgagggacct    480
ggcacgtaca tcccccggaa ggaagtggag gtcgtggaga tcattcaggc caccatcatc    540
aggcagaacc aggctctgcg gctcagggcc cgcaaggagt gctgggaccg ggacggcaag    600
gagagggtga caggggaaga atggctggtc accacagtag gggcgtacct cccagcggtg    660
tttgaggagg ttctggattt ggtggacgcc gtcatcctta cggaaaagac agccctgcac    720
ctccgggctc ggcggaactt ccgggacttc aggggagtgt cccgccgcac tggggaggag    780
tggctggtaa cagtgcagga cacagaggcc cacgtgccag atgtccacga ggaggtgctg    840
ggggttgtgc ccatcaccac cctgggcccc cacaactact gcgtgattct cgaccctgtc    900
ggaccggatg gcaagaatca gctggggcag aagcgcgtgg tcaagggaga gaagtctttt    960
ttcctccagc caggagagca gctggaacaa ggcatccagg atgtgtatgt gctgtcggag   1020
cagcaggggc tgctgctgag ggccctgcag cccctggagg aggggggagga tgaggagaag   1080 gtctcacacc aggctgggga ccactggctc atccgcggac ccctggagta tgtgccatct   1140
gccaaagtgg aggtggtgga ggagcgccag gccatccctc tagacgagaa cgagggcatc   1200
tatgtgcagg atgtcaagac cggaaaggtg cgcgctgtga ttggaagcac ctacatgctg   1260
acccaggacg aagtcctgtg ggagaaagag ctgcctcccg gggtggagga gctgctgaac   1320
aaggggcagg accctctggc agacaggggt gagaaggaca cagctaagag cctccagccc   1380
ttggcgcccc ggaacaagac ccgtgtggtc agctaccgcg tgccccacaa cgctgcggtg   1440
caggtgtacg actaccgaga gaagcgagcc cgcgtggtct cgggcctga gctggtgtcg   1500 ctgggtcctg aggagcagtt cacagtgttg tccctctcag ctgggcggcc caagcgtccc   1560
catgcccgcc gtgcgctctg cctgctgctg gggcctgact tcttcacaga cgtcatcacc   1620
atcgaaacgg cggatcatgc caggctgcaa ctgcagctgg cctacaactg gcactttgag   1680
gtgaatgacc ggaaggaccc ccaagagacg gccaagctct tttcagtgcc agactttgta   1740
ggtgatgcct gcaaagccat cgcatcccgg gtgcgggggg ccgtggcctc tgtcactttc   1800
gatgacttcc ataagaactc agcccgcatc attcgcactg ctgtctttgg ctttgagacc   1860
tcggaagcga agggccccga tggcatggcc ctgcccaggc cccgggacca ggctgtcttc   1920
ccccaaaacg ggctggtggt cagcagtgtg gacgtgcagt cagtggagcc tgtggatcag   1980
aggacccggg acgccctgca acgcagcgtc cagctggcca tcgagatcac caccaactcc   2040
caggaagcgg cggccaagca tgaggctcag agactggagc aggaagcccg cggccggctt   2100
gagcggcaga agatcctgga ccagtcagaa gccgagaaag ctcgcaagga acttttggag   2160
ctggaggctc tgagcatggc cgtggagagc accgggactg ccaaggcgga ggccgagtcc   2220
cgtgcggagc agcccggat tgaggagaa gggtccgtgc tgcaggccaa gctaaaagca   2280
caggccttgg ccattgaaac ggaggctgag ctccagaggg tccagaaggt ccgagagctg   2340
gaactggtct atgcccgggc ccagctggag ctggaggtga gcaaggctca gcagctggct   2400
gaggtggagg tgaagaagtt caagcagatg acagaggcca taggccccag caccatcagg   2460
gaccttgctg tggctgggcc tgagatgcag gtaaaactgc tccagtccct gggcctgaaa   2520
tcaaccctca tcaccgatgg ctccactccc atcaacctct tcaacacagc ctttgggctg   2580
ctggggatgg ggcccgaggg tcagcccctg ggcagaaggg tggccagtgg gcccagccct   2640
```

```
ggggagggga tatcccccca gtctgctcag gcccctcaag ctcctggaga caaccacgtg       2700
gtgcctgtac tgcgctaa                                                    2718
```

<210> SEQ ID NO 21
<211> LENGTH: 2627
<212> TYPE: PRT
<213> ORGANISM: Homo sapiens

<400> SEQUENCE: 21

```
Met Glu Lys Leu His Gly His Val Ser Ala His Pro Asp Ile Leu Ser
1               5                   10                  15

Leu Glu Asn Arg Cys Leu Ala Met Leu Pro Asp Leu Gln Pro Leu Glu
            20                  25                  30

Lys Leu His Gln His Val Ser Thr His Ser Asp Ile Leu Ser Leu Lys
        35                  40                  45

Asn Gln Cys Leu Ala Thr Leu Pro Asp Leu Lys Thr Met Glu Lys Pro
    50                  55                  60

His Gly Tyr Val Ser Ala His Pro Asp Ile Leu Ser Leu Glu Asn Gln
65                  70                  75                  80

Cys Leu Ala Thr Leu Ser Asp Leu Lys Thr Met Glu Lys Pro His Gly
                85                  90                  95

His Val Ser Ala His Pro Asp Ile Leu Ser Leu Glu Asn Arg Cys Leu
            100                 105                 110

Ala Thr Leu Pro Ser Leu Lys Ser Thr Val Ser Ala Ser Pro Leu Phe
        115                 120                 125

Gln Ser Leu Gln Ile Ser His Met Thr Gln Ala Asp Leu Tyr Arg Val
    130                 135                 140

Asn Asn Ser Asn Cys Leu Leu Ser Glu Pro Pro Ser Trp Arg Ala Gln
145                 150                 155                 160

His Phe Ser Lys Gly Leu Asp Leu Ser Thr Cys Pro Ile Ala Leu Lys
                165                 170                 175

Ser Ile Ser Ala Thr Glu Thr Ala Gln Glu Ala Thr Leu Gly Arg Trp
            180                 185                 190

Phe Asp Ser Glu Glu Lys Lys Gly Ala Glu Thr Gln Met Pro Ser Tyr
        195                 200                 205

Ser Leu Ser Leu Gly Glu Glu Glu Val Glu Asp Leu Ala Val Lys
    210                 215                 220

Leu Thr Ser Gly Asp Ser Glu Ser His Pro Glu Pro Thr Asp His Val
225                 230                 235                 240

Leu Gln Glu Lys Lys Met Ala Leu Leu Ser Leu Leu Cys Ser Thr Leu
                245                 250                 255

Val Ser Glu Val Asn Met Asn Asn Thr Ser Asp Pro Thr Leu Ala Ala
            260                 265                 270

Ile Phe Glu Ile Cys Arg Glu Leu Ala Leu Leu Glu Pro Glu Phe Ile
        275                 280                 285

Leu Lys Ala Ser Leu Tyr Ala Arg Gln Gln Leu Asn Val Arg Asn Val
    290                 295                 300

Ala Asn Asn Ile Leu Ala Ile Ala Ala Phe Leu Pro Ala Cys Arg Pro
305                 310                 315                 320

His Leu Arg Arg Tyr Phe Cys Ala Ile Val Gln Leu Pro Ser Asp Trp
                325                 330                 335

Ile Gln Val Ala Glu Leu Tyr Gln Ser Leu Ala Glu Gly Asp Lys Asn
            340                 345                 350

Lys Leu Val Pro Leu Pro Ala Cys Leu Arg Thr Ala Met Thr Asp Lys
```

```
                355                 360                 365
Phe Ala Gln Phe Asp Glu Tyr Gln Leu Ala Lys Tyr Asn Pro Arg Lys
370                 375                 380

His Arg Ala Lys Arg His Pro Arg Arg Pro Arg Ser Pro Gly Met
385                 390                 395                 400

Glu Pro Pro Phe Ser His Arg Cys Phe Pro Arg Tyr Ile Gly Phe Leu
                405                 410                 415

Arg Glu Glu Gln Arg Lys Phe Glu Lys Ala Gly Asp Thr Val Ser Glu
                420                 425                 430

Lys Lys Asn Pro Pro Arg Phe Thr Leu Lys Lys Leu Val Gln Arg Leu
                435                 440                 445

His Ile His Lys Pro Ala Gln His Val Gln Ala Leu Leu Gly Tyr Arg
                450                 455                 460

Tyr Pro Ser Asn Leu Gln Leu Phe Ser Arg Ser Arg Leu Pro Gly Pro
465                 470                 475                 480

Trp Asp Ser Ser Arg Ala Gly Lys Arg Met Lys Leu Ser Arg Pro Glu
                485                 490                 495

Thr Trp Glu Arg Glu Leu Ser Leu Arg Gly Asn Lys Ala Ser Val Trp
                500                 505                 510

Glu Glu Leu Ile Glu Asn Gly Lys Leu Pro Phe Met Ala Met Leu Arg
                515                 520                 525

Asn Leu Cys Asn Leu Leu Arg Val Gly Ile Ser Ser Arg His His Glu
530                 535                 540

Leu Ile Leu Gln Arg Leu Gln His Gly Lys Ser Val Ile His Ser Arg
545                 550                 555                 560

Gln Phe Pro Phe Arg Phe Leu Asn Ala His Asp Ala Ile Asp Ala Leu
                565                 570                 575

Glu Ala Gln Leu Arg Asn Gln Ala Leu Pro Phe Pro Ser Asn Ile Thr
                580                 585                 590

Leu Met Arg Arg Ile Leu Thr Arg Asn Glu Lys Asn Arg Pro Arg Arg
                595                 600                 605

Arg Phe Leu Cys His Leu Ser Arg Gln Gln Leu Arg Met Ala Met Arg
610                 615                 620

Ile Pro Val Leu Tyr Glu Gln Leu Lys Arg Glu Lys Leu Arg Val His
625                 630                 635                 640

Lys Ala Arg Gln Trp Lys Tyr Asp Gly Glu Met Leu Asn Arg Tyr Arg
                645                 650                 655

Gln Ala Leu Glu Thr Ala Val Asn Leu Ser Val Lys His Ser Leu Pro
                660                 665                 670

Leu Leu Pro Gly Arg Thr Val Leu Val Tyr Leu Thr Asp Ala Asn Ala
                675                 680                 685

Asp Arg Leu Cys Pro Lys Ser Asn Pro Gln Gly Pro Pro Leu Asn Tyr
                690                 695                 700

Ala Leu Leu Leu Ile Gly Met Met Ile Thr Arg Ala Glu Gln Val Asp
705                 710                 715                 720

Val Val Leu Cys Gly Gly Asp Thr Leu Lys Thr Ala Val Leu Lys Ala
                725                 730                 735

Glu Glu Gly Ile Leu Lys Thr Ala Ile Lys Leu Gln Ala Gln Val Gln
                740                 745                 750

Glu Phe Asp Glu Asn Asp Gly Trp Ser Leu Asn Thr Phe Gly Lys Tyr
                755                 760                 765

Leu Leu Ser Leu Ala Gly Gln Arg Val Pro Val Asp Arg Val Ile Leu
770                 775                 780
```

```
Leu Gly Gln Ser Met Asp Asp Gly Met Ile Asn Val Ala Lys Gln Leu
785                 790                 795                 800

Tyr Trp Gln Arg Val Asn Ser Lys Cys Leu Phe Val Gly Ile Leu Leu
            805                 810                 815

Arg Arg Val Gln Tyr Leu Ser Thr Asp Leu Asn Pro Asn Asp Val Thr
        820                 825                 830

Leu Ser Gly Cys Thr Asp Ala Ile Leu Lys Phe Ile Ala Glu His Gly
    835                 840                 845

Ala Ser His Leu Leu Glu His Val Gly Gln Met Asp Lys Ile Phe Lys
850                 855                 860

Ile Pro Pro Pro Gly Lys Thr Gly Val Gln Ser Leu Arg Pro Leu
865                 870                 875                 880

Glu Glu Asp Thr Pro Ser Pro Leu Ala Pro Val Ser Gln Gln Gly Trp
                885                 890                 895

Arg Ser Ile Arg Leu Phe Ile Ser Ser Thr Phe Arg Asp Met His Gly
            900                 905                 910

Glu Arg Asp Leu Leu Leu Arg Ser Val Leu Pro Ala Leu Gln Ala Arg
            915                 920                 925

Ala Ala Pro His Arg Ile Ser Leu His Gly Ile Asp Leu Arg Trp Gly
    930                 935                 940

Val Thr Glu Glu Glu Thr Arg Arg Asn Arg Gln Leu Glu Val Cys Leu
945                 950                 955                 960

Gly Glu Val Glu Asn Ala Gln Leu Phe Val Gly Ile Leu Gly Ser Arg
                965                 970                 975

Tyr Gly Tyr Ile Pro Pro Ser Tyr Asn Leu Pro Asp His Pro His Phe
            980                 985                 990

His Trp Ala Gln Gln Tyr Pro Ser Gly Arg Ser Val Thr Glu Met Glu
            995                 1000                1005

Val Met Gln Phe Leu Asn Arg Asn Gln Arg Leu Gln Pro Ser Ala
    1010                1015                1020

Gln Ala Leu Ile Tyr Phe Arg Asp Ser Ser Phe Leu Ser Ser Val
    1025                1030                1035

Pro Asp Ala Trp Lys Ser Asp Phe Val Ser Glu Glu Glu Ala
    1040                1045                1050

Ala Cys Arg Ile Ser Glu Leu Lys Ser Tyr Leu Ser Arg Gln Lys
    1055                1060                1065

Gly Ile Thr Cys Arg Arg Tyr Pro Cys Glu Trp Gly Gly Val Ala
    1070                1075                1080

Ala Gly Arg Pro Tyr Val Gly Gly Leu Glu Glu Phe Gly Gln Leu
    1085                1090                1095

Val Leu Gln Asp Val Trp Asn Met Ile Gln Lys Leu Tyr Leu Gln
    1100                1105                1110

Pro Gly Ala Leu Leu Glu Gln Pro Val Ser Ile Pro Asp Asp Asp
    1115                1120                1125

Leu Val Gln Ala Thr Phe Gln Gln Leu Gln Lys Pro Pro Ser Pro
    1130                1135                1140

Ala Arg Pro Arg Leu Leu Gln Asp Thr Val Gln Gln Leu Met Leu
    1145                1150                1155

Pro His Gly Arg Leu Ser Leu Val Thr Gly Gln Ser Gly Gln Gly
    1160                1165                1170

Lys Thr Ala Phe Leu Ala Ser Leu Val Ser Ala Leu Gln Ala Pro
    1175                1180                1185
```

```
Asp Gly Ala Lys Val Ala Pro Leu Val Phe His Phe Ser Gly
    1190              1195                1200

Ala Arg Pro Asp Gln Gly Leu Ala Leu Thr Leu Leu Arg Arg Leu
    1205              1210                1215

Cys Thr Tyr Leu Arg Gly Gln Leu Lys Glu Pro Gly Ala Leu Pro
    1220              1225                1230

Ser Thr Tyr Arg Ser Leu Val Trp Glu Leu Gln Gln Arg Leu Leu
    1235              1240                1245

Pro Lys Ser Ala Glu Ser Leu His Pro Gly Gln Thr Gln Val Leu
    1250              1255                1260

Ile Ile Asp Gly Ala Asp Arg Leu Val Asp Gln Asn Gly Gln Leu
    1265              1270                1275

Ile Ser Asp Trp Ile Pro Lys Lys Leu Pro Arg Cys Val His Leu
    1280              1285                1290

Val Leu Ser Val Ser Ser Asp Ala Gly Leu Gly Glu Thr Leu Glu
    1295              1300                1305

Gln Ser Gln Gly Ala His Val Leu Ala Leu Gly Pro Leu Glu Ala
    1310              1315                1320

Ser Ala Arg Ala Arg Leu Val Arg Glu Glu Leu Ala Leu Tyr Gly
    1325              1330                1335

Lys Arg Leu Glu Glu Ser Pro Phe Asn Asn Gln Met Arg Leu Leu
    1340              1345                1350

Leu Val Lys Arg Glu Ser Gly Arg Pro Leu Tyr Leu Arg Leu Val
    1355              1360                1365

Thr Asp His Leu Arg Leu Phe Thr Leu Tyr Glu Gln Val Ser Glu
    1370              1375                1380

Arg Leu Arg Thr Leu Pro Ala Thr Val Pro Leu Leu Gln His
    1385              1390                1395

Ile Leu Ser Thr Leu Glu Lys Glu His Gly Pro Asp Val Leu Pro
    1400              1405                1410

Gln Ala Leu Thr Ala Leu Glu Val Thr Arg Ser Gly Leu Thr Val
    1415              1420                1425

Asp Gln Leu His Gly Val Leu Ser Val Trp Arg Thr Leu Pro Lys
    1430              1435                1440

Gly Thr Lys Ser Trp Glu Glu Ala Val Ala Ala Gly Asn Ser Gly
    1445              1450                1455

Asp Pro Tyr Pro Met Gly Pro Phe Ala Cys Leu Val Gln Ser Leu
    1460              1465                1470

Arg Ser Leu Leu Gly Glu Gly Pro Leu Glu Arg Pro Gly Ala Arg
    1475              1480                1485

Leu Cys Leu Pro Asp Gly Pro Leu Arg Thr Ala Ala Lys Arg Cys
    1490              1495                1500

Tyr Gly Lys Arg Pro Gly Leu Glu Asp Thr Ala His Ile Leu Ile
    1505              1510                1515

Ala Ala Gln Leu Trp Lys Thr Cys Asp Ala Asp Ala Ser Gly Thr
    1520              1525                1530

Phe Arg Ser Cys Pro Pro Glu Ala Leu Gly Asp Leu Pro Tyr His
    1535              1540                1545

Leu Leu Gln Ser Gly Asn Arg Gly Leu Leu Ser Lys Phe Leu Thr
    1550              1555                1560

Asn Leu His Val Val Ala Ala His Leu Glu Leu Gly Leu Val Ser
    1565              1570                1575

Arg Leu Leu Glu Ala His Ala Leu Tyr Ala Ser Ser Val Pro Lys
```

```
                1580                1585                1590
Glu Glu Gln Lys Leu Pro Glu Ala Asp Val Ala Val Phe Arg Thr
    1595                1600                1605
Phe Leu Arg Gln Gln Ala Ser Ile Leu Ser Gln Tyr Pro Arg Leu
    1610                1615                1620
Leu Pro Gln Gln Ala Ala Asn Gln Pro Leu Asp Ser Pro Leu Cys
    1625                1630                1635
His Gln Ala Ser Leu Leu Ser Arg Arg Trp His Leu Gln His Thr
    1640                1645                1650
Leu Arg Trp Leu Asn Lys Pro Arg Thr Met Lys Asn Gln Gln Ser
    1655                1660                1665
Ser Ser Leu Ser Leu Ala Val Ser Ser Ser Pro Thr Ala Val Ala
    1670                1675                1680
Phe Ser Thr Asn Gly Gln Arg Ala Ala Val Gly Thr Ala Asn Gly
    1685                1690                1695
Thr Val Tyr Leu Leu Asp Leu Arg Thr Trp Gln Glu Glu Lys Ser
    1700                1705                1710
Val Val Ser Gly Cys Asp Gly Ile Ser Ala Cys Leu Phe Leu Ser
    1715                1720                1725
Asp Asp Thr Leu Phe Leu Thr Ala Phe Asp Gly Leu Leu Glu Leu
    1730                1735                1740
Trp Asp Leu Gln His Gly Cys Arg Val Leu Gln Thr Lys Ala His
    1745                1750                1755
Gln Tyr Gln Ile Thr Gly Cys Cys Leu Ser Pro Asp Cys Arg Leu
    1760                1765                1770
Leu Ala Thr Val Cys Leu Gly Gly Cys Leu Lys Leu Trp Asp Thr
    1775                1780                1785
Val Arg Gly Gln Leu Ala Phe Gln His Thr Tyr Pro Lys Ser Leu
    1790                1795                1800
Asn Cys Val Ala Phe His Pro Glu Gly Gln Val Ile Ala Thr Gly
    1805                1810                1815
Ser Trp Ala Gly Ser Ile Ser Phe Phe Gln Val Asp Gly Leu Lys
    1820                1825                1830
Val Thr Lys Asp Leu Gly Ala Pro Gly Ala Ser Ile Arg Thr Leu
    1835                1840                1845
Ala Phe Asn Val Pro Gly Gly Val Val Ala Val Gly Arg Leu Asp
    1850                1855                1860
Ser Met Val Glu Leu Trp Ala Trp Arg Glu Gly Ala Arg Leu Ala
    1865                1870                1875
Ala Phe Pro Ala His His Gly Phe Val Ala Ala Leu Phe Leu
    1880                1885                1890
His Ala Gly Cys Gln Leu Leu Thr Ala Gly Glu Asp Gly Lys Val
    1895                1900                1905
Gln Val Trp Ser Gly Ser Leu Gly Arg Pro Arg Gly His Leu Gly
    1910                1915                1920
Ser Leu Ser Leu Ser Pro Ala Leu Ser Val Ala Leu Ser Pro Asp
    1925                1930                1935
Gly Asp Arg Val Ala Val Gly Tyr Arg Ala Asp Gly Ile Arg Ile
    1940                1945                1950
Tyr Lys Ile Ser Ser Gly Ser Gln Gly Ala Gln Gly Gln Ala Leu
    1955                1960                1965
Asp Val Ala Val Ser Ala Leu Ala Trp Leu Ser Pro Lys Val Leu
    1970                1975                1980
```

```
Val Ser Gly Ala Glu Asp Gly Ser Leu Gln Gly Trp Ala Leu Lys
1985               1990                    1995

Glu Cys Ser Leu Gln Ser Leu Trp Leu Ser Arg Phe Gln Lys
2000               2005                    2010

Pro Val Leu Gly Leu Ala Thr Ser Gln Glu Leu Leu Ala Ser Ala
2015               2020                    2025

Ser Glu Asp Phe Thr Val Gln Leu Trp Pro Arg Gln Leu Leu Thr
2030               2035                    2040

Arg Pro His Lys Ala Glu Asp Phe Pro Cys Gly Thr Glu Leu Arg
2045               2050                    2055

Gly His Glu Gly Pro Val Ser Cys Cys Ser Phe Ser Thr Asp Gly
2060               2065                    2070

Gly Ser Leu Ala Thr Gly Gly Arg Asp Arg Ser Leu Leu Cys Trp
2075               2080                    2085

Asp Val Arg Thr Pro Lys Thr Pro Val Leu Ile His Ser Phe Pro
2090               2095                    2100

Ala Cys His Arg Asp Trp Val Thr Gly Cys Ala Trp Thr Lys Asp
2105               2110                    2115

Asn Leu Leu Ile Ser Cys Ser Ser Asp Gly Ser Val Gly Leu Trp
2120               2125                    2130

Asp Pro Glu Ser Gly Gln Arg Leu Gly Gln Phe Leu Gly His Gln
2135               2140                    2145

Ser Ala Val Ser Ala Val Ala Val Glu Glu His Val Val Ser
2150               2155                    2160

Val Ser Arg Asp Gly Thr Leu Lys Val Trp Asp His Gln Gly Val
2165               2170                    2175

Glu Leu Thr Ser Ile Pro Ala His Ser Gly Pro Ile Ser His Cys
2180               2185                    2190

Ala Ala Ala Met Glu Pro Arg Ala Ala Gly Gln Pro Gly Ser Glu
2195               2200                    2205

Leu Leu Val Val Thr Val Gly Leu Asp Gly Ala Thr Arg Leu Trp
2210               2215                    2220

His Pro Leu Leu Val Cys Gln Thr His Thr Leu Leu Gly His Ser
2225               2230                    2235

Gly Pro Val Arg Ala Ala Ala Val Ser Glu Thr Ser Gly Leu Met
2240               2245                    2250

Leu Thr Ala Ser Glu Asp Gly Ser Val Arg Leu Trp Gln Val Pro
2255               2260                    2265

Lys Glu Ala Asp Asp Thr Cys Ile Pro Arg Ser Ala Ala Val
2270               2275                    2280

Thr Ala Val Ala Trp Ala Pro Asp Gly Ser Met Ala Val Ser Gly
2285               2290                    2295

Asn Gln Ala Gly Glu Leu Ile Leu Trp Gln Glu Ala Lys Ala Val
2300               2305                    2310

Ala Thr Ala Gln Ala Pro Gly His Ile Gly Ala Leu Ile Trp Ser
2315               2320                    2325

Ser Ala His Thr Phe Phe Val Leu Ser Ala Asp Glu Lys Ile Ser
2330               2335                    2340

Glu Trp Gln Val Lys Leu Arg Lys Gly Ser Ala Pro Gly Asn Leu
2345               2350                    2355

Ser Leu His Leu Asn Arg Ile Leu Gln Glu Asp Leu Gly Val Leu
2360               2365                    2370
```

| | | | | | | | | | | |
|---|---|---|---|---|---|---|---|---|---|---|
| Thr | Ser | Leu | Asp | Trp | Ala | Pro | Asp | Gly | His | Phe | Leu | Ile | Leu | Ala |
| | 2375 | | | | 2380 | | | | 2385 | |
| Lys | Ala | Asp | Leu | Lys | Leu | Leu | Cys | Met | Lys | Pro | Gly | Asp | Ala | Pro |
| 2390 | | | | | 2395 | | | | | 2400 | |

Thr Ser Leu Asp Trp Ala Pro Asp Gly His Phe Leu Ile Leu Ala
            2375                2380                2385

Lys Ala Asp Leu Lys Leu Leu Cys Met Lys Pro Gly Asp Ala Pro
2390                2395                2400

Ser Glu Ile Trp Ser Ser Tyr Thr Glu Asn Pro Met Ile Leu Ser
    2405                2410                2415

Thr His Lys Glu Tyr Gly Ile Phe Val Leu Gln Pro Lys Asp Pro
    2420                2425                2430

Gly Val Leu Ser Phe Leu Arg Gln Lys Glu Ser Gly Glu Phe Glu
    2435                2440                2445

Glu Arg Leu Asn Phe Asp Ile Asn Leu Glu Asn Pro Ser Arg Thr
    2450                2455                2460

Leu Ile Ser Ile Thr Gln Ala Lys Pro Glu Ser Glu Ser Ser Phe
2465                2470                2475

Leu Cys Ala Ser Ser Asp Gly Ile Leu Trp Asn Leu Ala Lys Cys
    2480                2485                2490

Ser Pro Glu Gly Glu Trp Thr Thr Gly Asn Met Trp Gln Lys Lys
    2495                2500                2505

Ala Asn Thr Pro Glu Thr Gln Thr Pro Gly Thr Asp Pro Ser Thr
    2510                2515                2520

Cys Arg Glu Ser Asp Ala Ser Met Asp Ser Asp Ala Ser Met Asp
    2525                2530                2535

Ser Glu Pro Thr Pro His Leu Lys Thr Arg Gln Arg Arg Lys Ile
    2540                2545                2550

His Ser Gly Ser Val Thr Ala Leu His Val Leu Pro Glu Leu Leu
    2555                2560                2565

Val Thr Ala Ser Lys Asp Arg Asp Val Lys Leu Trp Glu Arg Pro
    2570                2575                2580

Ser Met Gln Leu Leu Gly Leu Phe Arg Cys Glu Gly Ser Val Ser
    2585                2590                2595

Cys Leu Glu Pro Trp Leu Gly Ala Asn Ser Thr Leu Gln Leu Ala
    2600                2605                2610

Val Gly Asp Val Gln Gly Asn Val Tyr Phe Leu Asn Trp Glu
    2615                2620                2625

<210> SEQ ID NO 22
<211> LENGTH: 7884
<212> TYPE: DNA
<213> ORGANISM: Homo sapiens

<400> SEQUENCE: 22

```
atggaaaaac tccatgggca tgtgtctgcc catccagaca tcctctcctt ggagaaccgg    60
tgcctggcta tgctccctga cttacagccc ttggagaaac tacatcagca tgtatctacc   120
cactcagata tcctctcctt gaagaaccag tgcctagcca cgcttcctga cctgaagacc   180
atggaaaaac acatggata tgtgtctgcc cacccagaca tcctctcctt ggagaaccag   240
tgcctggcca cactttctga cctgaagacc atggagaaac acatggaca tgtttctgcc   300
cacccagaca tcctctcctt ggagaaccgg tgcctggcca ccctccctag tctaaagagc   360
actgtgtctg ccagcccctt gttccagagt ctacagatat ctcacatgac gcaagctgat   420
ttgtaccgtg tgaacaacag caattgcctg ctctctgagc ctccaagttg gagggctcag   480
catttctcta aggactagac ctttcaacc tgccctatag ccctgaaatc catctctgcc   540
acagagacag ctcaggaagc aactttgggt cgttggtttg attcagaaga gaagaaaggg   600
```

```
gcagagaccc aaatgccttc ttatagtctg agcttgggag aggaggagga ggtggaggat      660
ctggccgtga agctcacctc tggagactct gaatctcatc cagagcctac tgaccatgtc      720
cttcaggaaa agaagatggc tctactgagc ttgctgtgct ctactctggt ctcagaagta      780
aacatgaaca atacatctga ccccacccctg gctgccattt ttgaaatctg tcgtgaactt     840
gccctcctgg agcctgagtt tatcctcaag gcatctttgt atgccaggca gcagctgaac      900
gtccggaatg tggccaataa catcttggcc attgctgctt tcttgccggc gtgtcgcccc      960
cacctgcgac gatatttctg tgccattgtc cagctgcctt ctgactggat ccaggtggct     1020
gagctttacc agagcctggc tgagggagat aagaataagc tggtgcccct gcccgcctgt     1080
ctccgtactg ccatgacgga caaatttgcc cagtttgacg agtaccagct ggctaagtac     1140
aaccctcgga agcaccgggc caagagacac ccccgccggc caccccgctc tccagggatg     1200
gagcctccat tttctcacag atgttttcca aggtacatag ggtttctcag agaagagcag     1260
agaaagtttg agaaggccgg tgatacagtg tcagagaaaa agaatcctcc aaggttcacc     1320
ctgaagaagc tggttcagcg actgcacatc cacaagcctg cccagcacgt tcaagccctg     1380
ctgggttaca gataccccctc caacctacag ctcttttctc gaagtcgcct tcctgggcct     1440
tgggattcta gcagagctgg gaagaggatg aagctgtcta ggccagagac ctgggagcgg     1500
gagctgagcc tacggggggaa caaagcgtcg gtctgggagg aactcattga aaatgggaag     1560
cttcccttca tggccatgct tcggaacctg tgcaacctgc tgcgggttgg aatcagttcc     1620
cgccaccatg agctcattct cagagactca cagcatggga agtcggtgat ccacagtcgg     1680
cagtttccat tcagatttct taacgcccat gatgccattg atgccctcga ggctcaactc     1740
agaaatcaag cattgccctt tccttcgaat ataacactga tgaggcggat actaactaga     1800
aatgaaaaga accgtcccag gcggaggttt ctttgccacc taagccgtca gcagcttcgt     1860
atggcaatga ggatacctgt gttgtatgag cagctcaaga gggagaagct gagagtacac     1920
aaggccagac agtggaaaata tgatggtgag atgctgaaca ggtaccgaca ggccctagag     1980
acagctgtga acctctctgt gaagcacagc ctgcccctgc tgccaggccg cactgtcttg     2040
gtctatctga cagatgctaa tgcagacagg ctctgtccaa agagcaaccc acaagggccc     2100
ccgctgaact atgcactgct gttgattggg atgatgatca cgagggcgga gcaggtggac     2160
gtcgtgctgt gtggaggtga cactctgaag actgcagtgc ttaaggcaga agaaggcatc     2220
ctgaagactg ccatcaagct ccaggctcaa gtccaggagt ttgatgaaaa tgatggatgg     2280
tccctgaata cttttgggaa ataccctgctg tctctggctg gccaaagggt tcctgtggac     2340
agggtcatcc tccttggcca aagcatggat gatggaatga taaatgtggc caaacagctt     2400
tactggcagc gtgtgaattc caagtgcctc tttgttggta tcctcctaag aagggtacaa     2460
tacctgtcaa cagatttgaa tcccaatgat gtgacactct caggctgtac tgatgcgata     2520
ctgaagttca ttgcagagca tgggggcctcc catcttctgg aacatgtggg ccaaatggac     2580
aaaatattca agattccacc acccccagga aagacagggg tccagtctct ccggccactg     2640
gaagaggaca ctccaagccc cttggctcct gtttcccagc aaggatggcg cagcatccgg     2700 cttttcatt catccactt ccgagacatg cacggggagc gggacctgct gctgaggtct     2760
gtgctgccag cactgcaggc ccgagcggcc cctcaccgta tcagccttca cggaatcgac     2820
ctccgctggg gcgtcactga ggaggagacc cgtaggaaca gcaactggaa agtgtgcctt     2880
ggggaggtgg agaacgcaca gctgtttgtg gggattctgg gctcccgtta tggatacatt     2940 ccccccccagct acaaccttcc tgaccatcca cacttccact gggcccagca gtacccttca    3000
```

```
gggcgctctg tgacagagat ggaggtgatg cagttcctga accggaacca acgtctgcag    3060
ccctctgccc aagctctcat ctacttccgg gattccagct tcctcagctc tgtgccagat    3120
gcctggaaat ctgactttgt ttctgagtct gaagaggccg catgtcggat ctcagaactg    3180
aagagctacc taagcagaca gaaagggata acctgccgca gataccsctg tgagtggggg    3240
ggtgtggcag ctggccggcc ctatgttggc gggctggagg agtttgggca gttggttctg    3300
caggatgtat ggaatatgat ccagaagctc tacctgcagc ctggggccct gctggagcag    3360
ccagtgtcca tcccagacga tgacttggtc caggccacct tccagcagct gcagaagcca    3420
ccgagtcctg cccggccacg ccttcttcag gacacagtgc aacagctgat gctgccccac    3480
ggaaggctga gcctggtgac ggggcagtca ggacagggca agacagcctt cctggcatct    3540
cttgtgtcag ccctgcaggc tcctgatggg gccaaggtgg caccattagt cttcttccac    3600
ttttctgggg ctcgtcctga ccagggtctt gccctcactc tgctcagacg cctctgtacc    3660
tatctgcgtg gccaactaaa agagccaggt gccctcccca gcacctaccg aagcctggtg    3720
tgggagctgc agcagaggct gctgcccaag tctgctgagt ccctgcatcc tggccagacc    3780
caggtcctga tcatcgatgg ggctgatagg ttagtggacc agaatgggca gctgattca    3840 gactggatcc caaagaagct tccccggtgt gtacacctgg tgctgagtgt gtctagtgat    3900
gcaggcctag gggagaccct tgagcagagc cagggtgccc acgtgctggc cttgggcct    3960 ctggaggcct ctgctcgggc ccggctggtg agagaggagc tggccctgta cgggaagcgg    4020
ctggaggagt caccatttaa caaccagatg cgactgctgc tggtgaagcg ggaatcaggc    4080
cggccgctct acctgcgctt ggtcaccgat cacctgaggc tcttcacgct gtatgagcag    4140
gtgtctgaga gactccggac cctgcctgcc actgtccccc tgctgctgca gcacatcctg    4200
agcacactgg agaaggagca cgggcctgat gtccttcccc aggccttgac tgccctagaa    4260
gtcacacgga gtggtttgac tgtgaccag ctgcacggag tgctgagtgt gtggcggaca    4320
ctaccgaagg ggactaagag ctgggaagaa gcagtggctg ctggtaacag tggagaccc    4380 taccccatgg gccgtttgc ctgcctcgtc cagagtctgc gcagtttgct aggggagggc    4440
cctctggagc gccctggtgc ccggctgtgc ctccctgatg ggccctgag aacagcagct    4500 aaacgttgct atgggaagag gccagggcta gagqacacgg cacacatcct cattgcagct    4560
cagctctgga agacatgtga cgctgatgcc tcaggcacct tccgaagttg ccctcctgag    4620
gctctgggag acctgcctta ccacctgctc cagagcggga accgtggact tctttcgaag    4680
ttccttacca acctccatgt ggtggctgca cacttggaat tgggtctggt ctctcggctc    4740
ttggaggccc atgccctcta tgcttcttca gtccccaaag aggaacaaaa gctccccgag    4800
gctgacgttg cagtgtttcg caccttcctg aggcagcagg cttcaatcct cagccagtac    4860
ccccggctcc tgccccagca ggcagccaac cagcccctgg actcacctct ttgccaccaa    4920
gcctcgctgc tctcccggag atggcacctc caacacacac tacgatggct taataaaccc    4980
cggaccatga aaaatcagca aagctccagc ctgtctctgg cagtttcctc atcccctact    5040
gctgtggcct tctccaccaa tgggcaaaga gcagctgtgg gcactgccaa tgggacagtt    5100
tacctgttgg acctgagaac ttggcaggag gagaagtctg tggtgagtgg ctgtgatgga    5160
atctctgctt gtttgttcct ctccgatgat acactctttc ttactgcctt cgacgggctc    5220
ctggagctct gggacctgca gcatggttgt cgggtgctgc agactaaggc tcaccagtac    5280
caaatcactg gctgctgcct gagcccagac tgccggctgc tagccaccgt gtgcttggga    5340
```

```
ggatgcctaa agctgtggga cacagtccgt gggcagctgg ccttccagca cacctacccc    5400
aagtccctga actgtgttgc cttccaccca gaggggcagg taatagccac aggcagctgg    5460
gctggcagca tcagcttctt ccaggtggat gggctcaaag tcaccaagga cctgggggca    5520
cccggagcct ctatccgtac cttggccttc aatgtgcctg ggggggttgt ggctgtgggc    5580
cggctggaca gtatggtgga gctgtgggcc tggcgagaag gggcacggct ggctgccttc    5640
cctgcccacc atggctttgt tgctgctgcg cttttcctgc atgcgggttg ccagttactg    5700
acggctggag aggatggcaa ggttcaggtg tggtcagggt ctctgggtcg gccccgtggg    5760
cacctgggtt ccctttctct ctctcctgcc ctctctgtgg cactcagccc agatggtgat    5820
cgggtggctg ttggatatcg agcggatggc attaggatct acaaaatctc ttcaggttcc    5880 caggggctc agggtcaggc actgatgtg gcagtgtccg ccctggcctg gctaagcccc    5940
aaggtattgg tgagtggtgc agaagatggg tccttgcagg gctgggcact caaggaatgc    6000
tcccttcagt ccctctggct cctgtccaga ttcagaagc ctgtgctagg actggccact    6060
tcccaggagc tcttggcttc tgcctcagag gatttcacag tgcagctgtg gccaaggcag    6120
ctgctgacgc ggccacacaa ggcagaagac tttccctgtg gcactgagct gcggggacat    6180
gagggccctg tgagctgctg tagtttcagc actgatggag gcagcctggc caccgggggc    6240
cgggatcgga gtctcctctg ctgggacgtg aggacaccca aaaccctgt tttgatccac    6300 tccttccctg cctgtcaccg tgactgggtc actggctgtg cctggaccaa agataaccta    6360
ctgatatcct gctccagtga tggctctgtg gggctctggg acccagagtc aggacagcgg    6420
cttggtcagt tcctgggtca tcagagtgct gtgagcgctg tggcagctgt ggaggagcac    6480
gtggtgtctg tgagccggga tgggaccttg aaagtgtggg accatcaagg cgtggagctg    6540
accagcatcc ctgctcactc aggacccatt agccactgtg cagctgccat ggagcccgt    6600 gcagctggac agcctgggtc agagcttctg gtggtaaccg tcgggctaga tggggccaca    6660
cggttatggc atccactctt ggtgtgccaa acccacaccc tcctgggaca cagcggccca    6720
gtccgtgctg ctgctgtttc agaaacctca ggcctcatgc tgaccgcctc tgaggatggt    6780
tctgtacggc tctggcaggt tcctaaggaa gcagatgaca catgtatacc aaggagttct    6840
gcagccgtca ctgctgtggc ttgggcacca gatggttcca tggcagtatc tggaaatcaa    6900
gctggggaac taatcttgtg gcaggaagct aaggctgtgg ccacagcaca ggctccaggc    6960
cacattggtg ctctgatctg gtcctcggca cacaccttt ttgtcctcag tgctgatgag    7020
aaaatcagcg agtggcaagt gaaactgcgg aagggttcgg caccgggaaa tttgagtctt    7080
cacctgaacc gaattctaca ggaggactta ggggtgctga caagtctgga ttgggctcct    7140
gatggtcact ttctcatctt ggccaaagca gatttgaagt tactttgcat gaagccaggg    7200
gatgctccat ctgaaatctg gagcagctat acagaaaatc ctatgatatt gtccacccac    7260
aaggagtatg gcatatttgt cctgcagccc aaggatcctg gagttctttc tttcttgagg    7320
caaaaggaat caggagagtt tgaagagagg ctgaactttg atataaactt agagaatcct    7380
agtaggaccc taatatcgat aactcaagcc aaacctgaat ctgagtcctc attttttgtgt    7440 gccagctctg atgggatcct atggaacctg gccaaatgca gccagaagg agaatggacc    7500 acaggtaaca tgtggcagaa aaaagcaaac actccagaaa cccaaactcc agggacagac    7560
ccatctacct gcagggaatc tgatgccagc atggatagtg atgccagcat ggatagtgag    7620
ccaacaccac atctaaagac acggcagcgt agaaagattc actcgggctc tgtcacagcc    7680
ctccatgtgc tacctgagtt gctggtgaca gcttcgaagg acagagatgt taagctatgg    7740
```

```
gagagaccca gtatgcagct gctgggcctg ttccgatgcg aagggtcagt gagctgcctg    7800
gaaccttggc tgggcgctaa ctccaccctg cagcttgccg tgggagacgt gcagggcaat    7860
gtgtactttc tgaattggga atga                                          7884
```

<210> SEQ ID NO 23
<211> LENGTH: 98
<212> TYPE: RNA
<213> ORGANISM: Homo sapiens

<400> SEQUENCE: 23

```
ggcuggcuuu agcucagcgg uuacuucgac aguucuuuaa uugaaacaag caaccugucu    60
ggguuguucg agacccgcgg gcgcucucca guccuuuu                            98
```

<210> SEQ ID NO 24
<211> LENGTH: 88
<212> TYPE: RNA
<213> ORGANISM: Homo sapiens

<400> SEQUENCE: 24

```
ggcuggcuuu agcucagcgg uuacuucgag uacauuguaa ccaccucucu gggugguucg    60
agacccgcgg gugcuuucca gcucuuuu                                       88
```

<210> SEQ ID NO 25
<211> LENGTH: 88
<212> TYPE: RNA
<213> ORGANISM: Homo sapiens

<400> SEQUENCE: 25

```
ggcuggcuuu agcucagcgg uuacuucgcg ugucaucaaa ccaccucucu ggguuguucg    60
agacccgcgg gcgcucucca gcccucuu                                       88
```

<210> SEQ ID NO 26
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg cccctgccc    180 ttcgcctggg acatcctgtc ccctcagttc atgtacggct ccaaggccta cgtgaagcac    240
cccgccgaca tccccgacta cttgaagctg tccttccccg agggcttcaa gtgggagcgc    300
gtgatgaact tcgaggacgg cggcgtggtg accgtgaccc aggactcctc cctgcaggac    360
ggcgagttca tctacaaggt gaagctgcgc ggcaccaact tcccctccga cggccccgta    420
atgcagaaga gaccatgggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaagta a             711
```

<210> SEQ ID NO 27
<211> LENGTH: 237
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (237)..(237)
<223> OTHER INFORMATION: Any amino acid

<400> SEQUENCE: 27

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Xaa
225                 230                 235

<210> SEQ ID NO 28
<211> LENGTH: 1200
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
atggtgagca agggcgagga ggataacatg gccatcatca aggagttcat gcgcttcaag     60
gtgcacatgg agggctccgt gaacggccac gagttcgaga tcgagggcga gggcgagggc    120
cgcccctacg agggcaccca gaccgccaag ctgaaggtga ccaagggtgg ccccctgccc    180
ttcgcctggg acatcctgtc ccctcagttc atgtacggct ccaaggccta cgtgaagcac    240
cccgccgaca tccccgacta cttgaagctg tccttccccg agggcttcaa gtgggagcgc    300

-continued

```
gtgatgaact tcgaggacgg cggcgtggtg accgtgaccc aggactcctc cctgcaggac    360
ggcgagttca tctacaaggt gaagctgcgc ggcaccaact tccctccga cggcccgta     420 atgcagaaga agaccatggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg ccgccactc accggcggc atggacgagc tgtacaagta atgcacacaa      720
cactggcagg atgctgtgcc ttggacagaa ctcctcagtc tacagacaga ggatggcttc    780
tggaaactta caccagaact gggacttata ttaaatctta atacaaatgg tttgcacagc    840
tttcttaaac aaaaaggcat tcaatctcta ggtgtaaaag gaagagaatg tctcctggac    900
ctaattgcca caatgctggt actacagttt attcgcacca ggttggaaaa agagggaata    960
gtgttcaaat cactgatgaa atggatgac ccttctattt ccaggaatat tccctgggct    1020
tttgaggcaa taaagcaagc aagtgaatgg gtaagaagaa ctgaaggaca gtacccatct    1080
atctgcccac ggcttgaact ggggaacgac tgggactctg ccaccaagca gttgctggga    1140
ctccagccca taagcactgt gtcccctctt catagagtcc tccattacag tcaaggctaa    1200
```

<210> SEQ ID NO 29
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (237)..(237)
<223> OTHER INFORMATION: Any amino acid

<400> SEQUENCE: 29

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175
```

His Tyr Asp Ala Glu Val Lys Thr Thr Tyr Lys Ala Lys Lys Pro Val
                            180                 185                 190

Gln Leu Pro Gly Ala Tyr Asn Val Asn Ile Lys Leu Asp Ile Thr Ser
                            195                 200                 205

His Asn Glu Asp Tyr Thr Ile Val Glu Gln Tyr Glu Arg Ala Glu Gly
                            210                 215                 220

Arg His Ser Thr Gly Gly Met Asp Glu Leu Tyr Lys Xaa Cys Thr Gln
                225                 230                 235                 240

His Trp Gln Asp Ala Val Pro Trp Thr Glu Leu Leu Ser Leu Gln Thr
                            245                 250                 255

Glu Asp Gly Phe Trp Lys Leu Thr Pro Glu Leu Gly Leu Ile Leu Asn
                            260                 265                 270

Leu Asn Thr Asn Gly Leu His Ser Phe Leu Lys Gln Lys Gly Ile Gln
                            275                 280                 285

Ser Leu Gly Val Lys Gly Arg Glu Cys Leu Leu Asp Leu Ile Ala Thr
                            290                 295                 300

Met Leu Val Leu Gln Phe Ile Arg Thr Arg Leu Glu Lys Glu Gly Ile
                305                 310                 315                 320

Val Phe Lys Ser Leu Met Lys Met Asp Asp Pro Ser Ile Ser Arg Asn
                            325                 330                 335

Ile Pro Trp Ala Phe Glu Ala Ile Lys Gln Ala Ser Glu Trp Val Arg
                            340                 345                 350

Arg Thr Glu Gly Gln Tyr Pro Ser Ile Cys Pro Arg Leu Glu Leu Gly
                            355                 360                 365

Asn Asp Trp Asp Ser Ala Thr Lys Gln Leu Leu Gly Leu Gln Pro Ile
                            370                 375                 380

Ser Thr Val Ser Pro Leu His Arg Val Leu His Tyr Ser Gln Gly
                385                 390                 395

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer <400> SEQUENCE: 30
cgggatccgc cttcagctgg ggctcgctct ggagc                                    35

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer <400> SEQUENCE: 31
cgggaattct tacagaccca cgatgctgtt cag                                      33

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer <400> SEQUENCE: 32
cgggatccgc cttcagctgg ggctcgctct ggagc                                    35

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgggaattct tactctcggg agggcgggga tc                                       32

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aaaggatcct atggcagcaa ggc                                                 23

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaagaattct tacagaccca cgatgctgtt                                          30

<210> SEQ ID NO 36
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgggatccgc cttcagctgg ggctcgctgt ggagcggcat taaaaatttc ggttccaccg         60
ttaagaacta tgaattccgg                                                     80

<210> SEQ ID NO 37
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccggaattca tagttcttaa cggtggaacc gaaattttta atgccgctcc acagcgagcc         60
ccagctgaag gcggatcccg                                                     80

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgggattcgg cggcgaattc gatttacgat atcccaacga ccgaa                45

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cccctcgagt tagccttgac tgtaatggag gactctatg                       39

<210> SEQ ID NO 40
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctctgctagc caccatggcc ttcagctggg gctcg                           35

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggggccatgg cgctgccgcg cggcaccagg ccgttcttaa cggtggaacc g         51

<210> SEQ ID NO 42
<211> LENGTH: 252
<212> TYPE: PRT
<213> ORGANISM: Homo sapiens

<400> SEQUENCE: 42

Ala Asn Leu Arg Leu Pro Met Ala Ser Ala Leu Pro Glu Ala Leu Cys
1               5                   10                  15

Ser Gln Ser Arg Thr Thr Pro Val Asp Leu Cys Leu Leu Glu Glu Ser
            20                  25                  30

Val Gly Ser Leu Glu Gly Ser Arg Cys Pro Val Phe Ala Phe Gln Ser
        35                  40                  45

Ser Asp Thr Glu Ser Asp Glu Leu Ser Glu Val Leu Gln Asp Ser Cys
    50                  55                  60

Phe Leu Gln Ile Lys Cys Asp Thr Lys Asp Ser Ile Pro Cys Phe
65                  70                  75                  80

Leu Glu Leu Lys Glu Glu Asp Glu Ile Val Cys Thr Gln His Trp Gln
                85                  90                  95

Asp Ala Val Pro Trp Thr Glu Leu Leu Ser Leu Gln Thr Glu Asp Gly
            100                 105                 110

Phe Trp Lys Leu Thr Pro Glu Leu Gly Leu Ile Leu Asn Leu Asn Thr
        115                 120                 125

Asn Gly Leu His Ser Phe Leu Lys Gln Lys Gly Ile Gln Ser Leu Gly
    130                 135                 140

```
Val Lys Gly Arg Glu Cys Leu Leu Asp Leu Ile Ala Thr Met Leu Val
145                 150                 155                 160

Leu Gln Phe Ile Arg Thr Arg Leu Glu Lys Glu Gly Ile Val Phe Lys
                165                 170                 175

Ser Leu Met Lys Met Asp Asp Pro Ser Ile Ser Arg Asn Ile Pro Trp
            180                 185                 190

Ala Phe Glu Ala Ile Lys Gln Ala Ser Glu Trp Val Arg Arg Thr Glu
        195                 200                 205

Gly Gln Tyr Pro Ser Ile Cys Pro Arg Leu Glu Leu Gly Asn Asp Trp
    210                 215                 220

Asp Ser Ala Thr Lys Gln Leu Leu Gly Leu Gln Pro Ile Ser Thr Val
225                 230                 235                 240

Ser Pro Leu His Arg Val Leu His Tyr Ser Gln Gly
                245                 250
```

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
cgggatccgc cttcagctgg ggctcgctct ggagc                     35

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
cgggaattct tacagaccca cgatgctgtt cag                       33

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
cgggatccgc cttcagctgg ggctcgctct ggagc                     35

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
cgggaattct tactctcggg agggcgggga tc                        32

<210> SEQ ID NO 47
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 47
aaaggatcct atggcagcaa ggc                                              23

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aaagaattct tacagaccca cgatgctgtt                                       30

<210> SEQ ID NO 49
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgggatccgc cttcagctgg ggctcgctgt ggagcggcat taaaaatttc ggttccaccg      60
ttaagaacta tgaattccgg                                                  80

<210> SEQ ID NO 50
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccggaattca tagttcttaa cggtggaacc gaaatttttta atgccgctcc acagcgagcc     60
ccagctgaag gcggatcccg                                                  80

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgggattcgg cggcgaattc gatttacgat atcccaacga ccgaa                      45

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52 ccccctcgagt tagccttgac tgtaatggag gactctatg                            39

<210> SEQ ID NO 53
<211> LENGTH: 51
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggggccatgg cgctgccgcg cggcaccagg ccgttcttaa cggtggaacc g            51

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctctgctagc caccatggcc ttcagctggg gctcg                              35

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 55

His His His His His His
1               5
```

VAULT COMPLEXES

CROSS REFERENCE TO RELATED APPLICATIONS

This application is a Continuation of U.S. Ser. No. 14/018,325, filed Sep. 4, 2013, which is a Division of U.S. Ser. No. 12/950,994, filed Nov. 19, 2010, granted as U.S. Pat. No. 8,551,781, which claims the benefit of U.S. 61/291,081, filed Dec. 30, 2009 and U.S. 61/262,667, filed Nov. 19, 2009, all of which are herein incorporated by reference in their entirety.

STATEMENT REGARDING FEDERALLY SPONSORED RESEARCH OR DEVELOPMENT

This invention was made with Government support under EB004553, EY011431, and HL054352, awarded by the National Institutes of Health, and MCB0210690, awarded by the National Science Foundation. The Government has certain rights in the invention.

SEQUENCE LISTING

The content of the ASCII text file of the sequence listing named "20150924_034044_134CON1_seq" which is 126 kb in size was created on Sep. 24, 2015 and electronically submitted via EFS-Web herewith the application is incorporated herein by reference in its entirety.

BACKGROUND OF THE INVENTION

Field of the invention

The present invention relates generally to non-viral compositions and methods useful for the cellular delivery of one or more molecules of interest. In various embodiments, modified recombinant vault particles are described which comprise a peptide domain that enhances the permeability of the particles across the cell membranes of cells targeted for delivery. Also included in the invention is the use of the compositions as cellular delivery agents for selected molecules of interest, such as nucleic acid.

Description of the Related Art

Vaults are cytoplasmic ubiquitous ribonucleoprotein particles first described in 1986 that are found in all eukaryotic cells [1]. Native vaults are 12.9±1 MDa ovoid spheres with overall dimensions of approximately 40 nm in width and 70 nm in length [2,3], present in nearly all-eukaryotic organisms with between $10^4$ and $10^7$ particles per cell [4]. Despite their cellular abundance, vault function remains elusive although they have been linked to many cellular processes, including the innate immune response, multidrug resistance in cancer cells, multifaceted signaling pathways, and intracellular transport [5].

Vaults are highly stable structures in vitro, and a number of studies indicate that the particles are non-immunogenic [6]. Vaults can be engineered and expressed using a baculovirus expression system and heterologous proteins can be encapsulated inside of these recombinant particles using a protein-targeting domain termed INT for vault INTeraction. Several heterologous proteins have been fused to the INT domain (e.g. fluorescent and enzymatic proteins) and these fusion proteins are expressed in the recombinant vaults and retain their native characteristics, thus conferring new properties onto these vaults [7,8].

Vaults are generally described in U.S. Pat. No. 7,482,319, filed on Mar. 10, 2004; U.S. application Ser. No. 12/252,200, filed on Oct. 15, 2008; International Application No. PCT/US2004/007434, filed on Mar. 10, 2004; U.S. Provisional Application No. 60/453,800, filed on Mar. 20, 2003; U.S. Pat. No. 6,156,879, filed on Jun. 3, 1998; U.S. Pat. No. 6,555,347, filed on Jun. 28, 2000; U.S. Pat. No. 6,110,740, filed on Mar. 26, 1999; International Application No. PCT/US1999/06683, filed on Mar. 26, 1999; U.S. Provisional App. No. 60/079,634, filed on Mar. 27, 1998; and International Application No. PCT/US1998/011348, filed on Jun. 3, 1998. Vault compositions for immunization against chlamydia genital infection are described in U.S. application Ser. No. 12/467,255, filed on May 15, 2009. The entire contents of these applications are incorporated by reference in their entirety for all purposes.

SUMMARY OF THE INVENTION

One embodiment of the present invention provides a vault-like particle comprising a modified MVP where the modified MVP comprises a membrane lytic peptide sequence. In one aspect of this embodiment, the vault-like particle has a membrane lytic peptide sequence added to the N-terminus of the modified MVP. In a further aspect, the membrane lytic peptide sequence comprises the membrane lytic domain of adenovirus VI (pVI) (SEQ ID NO:1). In some further aspects, the membrane lytic domain of adenovirus VI (pVI) comprises SEQ ID NO:3 or SEQ ID NO:4. In a yet further aspect, the modified MVP comprises an EGF domain, which can be added to the C-terminus of the modified MVP. In another further aspect, the modified MVP comprises an antibody binding domain, which can be a Z-domain. In some aspects, the Z-domain is added to the C-terminus of the modified MVP. In some aspects, the vault-like particle further comprises a vault poly ADP-ribose polymerase (VPARP), a telomerase vault associated protein 1 (TEP1), or an untranslated RNA molecule (vRNA).

Another embodiment provides a vault-like particle comprising a membrane lytic domain comprising the amino acid sequence of SEQ ID NO:3, a major vault protein comprising the amino acid sequence of SEQ ID NO:16, and an antibody binding Z domain. In one aspect of this embodiment, the membrane lytic domain is fused to the C-terminus of the major vault protein, and the antibody binding Z domain is fused to the N-terminus of the major vault protein., thereby forming a fusion protein. In some aspects, the fusion protein comprises the amino acid sequence of SEQ ID NO:11.

An additional embodiment provides a method of delivering a substance to a cell, comprising introducing the vault-like particle of the above embodiments to the cell.

Yet another embodiment provides an isolated nucleic acid encoding a pVI-MVP fusion protein comprising an adenovirus protein VI membrane lytic domain sequence and an MVP encoding sequence. In some aspects, the MVP encoding sequence comprises the nucleic acid sequence of SEQ ID NO:17 or SEQ ID NO:2. In further aspects, the pVI-MVP fusion protein comprises the nucleic acid sequence of SEQ ID NO:8.

A further embodiment provides an isolated nucleic acid encoding a pVI-MVP-Z fusion protein comprising an adenovirus protein VI membrane lytic domain, an MVP encoding sequence, and a Z domain sequence. In some aspects of this embodiment, the pVI-MVP-Z fusion protein consists of SEQ ID NO:11. In some aspects, the nucleic acids are contained in a vector, which can be a baculovirus expression vector. In other aspects, the nucleic acids or the vectors are contained within a cell.

A further embodiment provides a method of delivering one or more than one substance to an organism, to a tissue, to a cell, or to an environmental medium by providing a composition comprising a pVI membrane lytic domain consisting of SEQ ID NO:3, and administering the composition to the organism, tissue, cell, or environmental medium. In some aspects, the substance is selected from the group consisting of; a therapeutic nucleic acid, a therapeutic compound, or a toxin. In further aspects, the composition is delivered or targeted to a cell.

A yet further embodiment proves a method of delivering one or more than one substance to an organism, to a tissue, to a cell, or to an environmental medium by providing a composition comprising a vault-like particle comprising a modified MVP, where the modified MVP comprises a membrane lytic peptide sequence, administering the composition comprising the one or more than one substance, or in the presence of the one or more than one substance, to the organism, tissue, cell, or environmental medium. In some aspects, the substance is a therapeutic nucleic acid sequence, where the therapeutic nucleic acid sequence can be a calcium phosphate precipitated cDNA plasmid. In other aspects, the vault-like particle facilitates entry of the one or more than one substance into the cell. In some aspects, the cell can be a RAW 264.7 macrophage or a human A549 epithelial cell.

Another embodiment provides a method of delivering one or more than one substance to a targeted organism, a targeted tissue, or a targeted cell, comprising providing a composition comprising a vault-like particle comprising a modified MVP, where the modified MVP comprises a membrane lytic peptide sequence and a Z-domain, functionally incorporating a selected antibody into the vault-like particle via Z-domain binding, administering the composition comprising the one or more than one substance, or in the presence of the one or more than one substance, to the organism, tissue, cells, or environmental medium. In some aspects, the substance is a therapeutic nucleic acid sequence, which can be a calcium phosphate precipitated cDNA plasmid. In further aspects, the vault-like particle facilitates entry of the one or more than one substance into the targeted cell.

A further embodiment provides a vault-like particle comprising a modified INT where the modified INT comprises a membrane lytic peptide sequence.

In one aspect of this embodiment, the vault-like particle has a membrane lytic peptide sequence added to the N-terminus of the modified INT. In a further aspect, the membrane lytic peptide sequence comprises the membrane lytic domain of adenovirus VI (pVI) (SEQ ID NO:1). In some further aspects, the membrane lytic domain of adenovirus VI (pVI) comprises SEQ ID NO:3 or SEQ ID NO:4.

In a yet further aspect, the modified INT comprises an EGF domain, which can be added to the C-terminus of the modified INT. In another further aspect, the modified INT comprises an antibody binding domain, which can be a Z-domain. In some aspects, the Z-domain is added to the C-terminus of the modified INT. In some aspects, the vault-like particle further comprises a MVP, a telomerase vault associated protein 1 (TEP1), or an untranslated RNA molecule (vRNA).

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1, Panel A: Schematic diagram of Ad pVI-INT fusion protein used for vault studies. The N-terminal domain of pVI comprised of residues alanine 34 to glutamic acid 114 were fused to a TEV cleavage site followed by the VPARP INT domain (residues 1563 to 1724). The N-terminal 6His (SEQ ID NO: 55) and thrombin cleavage are derived from the pET28 expression vector. FIG. 1, Panel B: SDS-PAGE and immunoblot of purified pVI-INT vaults. SDS-PAGE (4-15%) and Coomassie blue stain of molecular weight standards (lane 1) and the pVI-INT vaults (lane 2). Immunoblots of pVI-INT vaults probed with anti-MVP monoclonal antibody 1023 (lane 3) or with rabbit polyclonal antisera directed against adenovirus pVI (lane 4).

FIG. 2, Panel A: Negative stain TEM image of vaults containing pVI-INT. Note the presence of additional protein mass in the waist region of the vault barrel (arrow), which based on earlier structural studies, is the expected location of pVI-INT as depicted in FIG. 2, Panel B. FIG. 2, Panel C: Immunoblot using anti-His tag antibody (upper panel) or anti-INT antibody (lower panel) of pVI-INT protein (lane 1), pVI-vaults (lane 2), thrombin-treated pVI-INT (lane 3) or thrombin-treated pVI-vaults (lane 4). Note that since only 17 amino acids are cleaved off of pVI-INT, digestion with thrombin would cause only a minor change in the apparent molecular weight of the fragment observed in the gel.

FIG. 5, Panel A: Internalization of Cy3.5-labeled fluorescent vaults into different cell types at 37° C. was measured by flow cytometry. The cells were incubated with labeled vaults for various times at 37° C. prior to measuring uptake by flow cytometry in the presence of trypan blue dye to quench the fluorescence of uninternalized particles. FIG. 5, Panel B: Internalization of Cy3.5-labeled vaults into RAW 264.7 cells was measured at 4° C. or 37° C.

FIG. 6A: RAW 264.7 cells were incubated with 1 µg of the indicated amounts of pVI INT proteins or 137 µg of pVI-vault particles (4.310×10$^9$/cell) in the presence (black bars) or absence (stripped bars) of 1.65×10-7 M saporin and cell viability was measured 48 hours later using the XTT assay. All values were normalized to untreated cells. FIG. 6B: Dose response of cell killing by pVI-vaults (4.310×10$^9$/cell) in the presence of saporin (open symbols) or with saporin only (closed symbols). Cytoxicity of RAW 264.7 cells was determined by XTT assay at 48 hours following addition of these reagents. FIG. 6C: Dose response induction of cytotoxicity in RAW 264.7 cells. Cells were incubated with varying amounts of pVI-vaults (solid circles) or INT-vaults (open triangles) in the presence of 1.65×10$^{-7}$ M saporin for 4 hours prior to measuring viability by XTT.

FIG. 8, Panels A and B: Targeted co-delivery of calcium phosphate precipitated plasmid DNA (CaPi DNA) by EGF/pVI-INT vaults. FIG. 8, Panel A: Delivery of CaPi DNA to A431 cells expressing more than 10$_6$ of EGFR on the cell surfaces. FIG. 8, Panel B: Delivery of CaPi DNA to HeLa cells expressing low numbers of EGFR. Control included: plasmid DNA only, CaPi DNA only, CaPi DNA with 10×10$^5$ CP- or pVI-MVP vaults/cell (0.8 µg of CaPi DNA/well), Lipofectamine 2000, and EGF/pVI-INT vaults with plasmid DNA.

FIG. 9, Panel A: Purified pVI-MVP vaults (lanes 1, 3 and 5) and CP-MVP vaults (lanes 2, 4 and 6) were fractionated by SDS-PAGE and analyzed by Western blot (lanes 1-4) or stained with Coomassie (lanes 5 and 6). The blot from lanes 1 and 2 was probed with an anti-MVP polyclonal antibody, and the blot from lanes 3 and 4 was probed with an anti-pVI polyclonal antibody to confirm the presence of the pVI tag. FIG. 9, Panel B: Negative stain TEM image of pVI-MVP FIG. 10, Panels A and B: Enhanced delivery of saporin to the cytosol of RAW 264.7 cells with pVI-MVP vaults. Cell viability was examined using an MTT assay. FIG. 10, Panel A: Effect of pVI-MVP (800×10$^6$ particles/cell) on cell viability in the presence and absence of saporin (1.65×10$^-$7M). Control included: Saporin only, Saporin with CP-MVP (800×10$^6$ particles/cell), and pVI-MVP (800×10$^6$ particles/cell) only. FIG. 10, Panel B: pVI-MVP vault concentration dependence of the cell viability. Increasing concentration of vaults, as indicated, was added to cells in the presence of saporin (1.65×10$^{-7}$M) and the viability was examined.

FIG. 11, Panels A-C: Facilitated co-delivery of CaPi DNA by pVI-MVP vaults. FIG. 11, Panel A: Transfection by various amounts of pVI-MVP vaults to RAW cells (2 µg of CaPi DNA/well). Controls included: CaPi DNA alone, CaPi DNA with CP-MVP vaults (250×10$^5$ vaults/cell), and Lipofectamine 2000. FIG. 11, Panel B: Expression of GL proteins (green) in RAW cells by pVI-MVP vaults (4×10$^5$ pVI-MVP vaults/cell, 2 µg of CaPi DNA), Lipofectamine 2000 and CP-MVP (250×10$^5$ CP-MVP/cell, 2 µg of CaPi DNA). The nuclei were stained with Hoechst (blue). FIG. 11, Panel C: Enhanced transfection efficiency of pVI-MVP particles with high amount of CaPi DNA.

DETAILED DESCRIPTION OF THE INVENTION

Figure 1:
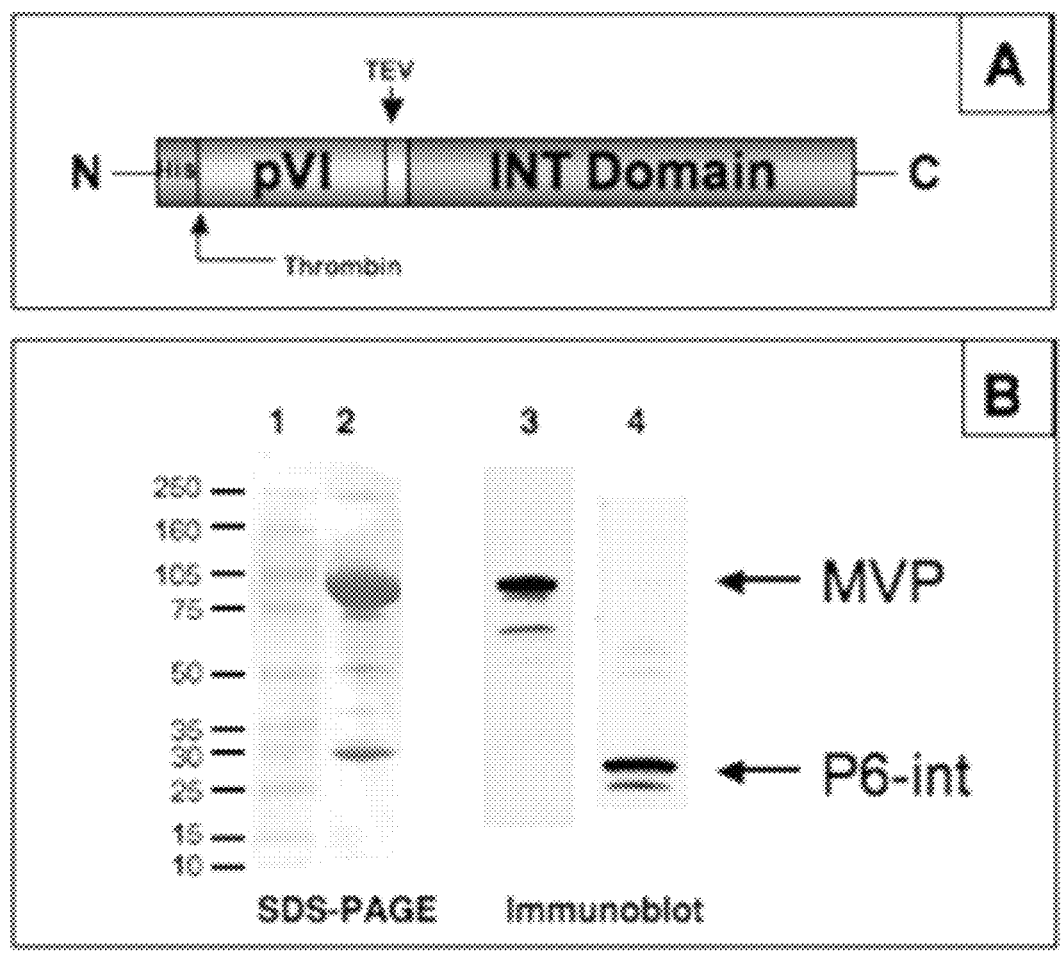
FIG. 1, Panels A and B: Incorporation of Ad pVI into recombinant vault particles.

The descriptions of various aspects of the invention are presented for purposes of illustration, and are not intended to be exhaustive or to limit the invention to the forms disclosed. Persons skilled in the relevant art can appreciate that many modifications and variations are possible in light of the embodiment teachings.

It should be noted that the language used herein has been principally selected for readability and instructional purposes, and it may not have been selected to delineate or circumscribe the inventive subject matter. Accordingly, the disclosure is intended to be illustrative, but not limiting, of the scope of invention.

It must be noted that, as used in the specification, the singular forms "a", "an", and "the" include plural referents unless the context clearly dictates otherwise.

Any terms not directly defined herein shall be understood to have the meanings commonly associated with them as understood within the art of the invention. Certain terms are discussed herein to provide additional guidance to the practitioner in describing the compositions, devices, methods and the like of embodiments of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the invention herein.

Definitions

Terms used in the claims and specification are defined as set forth below unless otherwise specified.

As used herein, the term "vault" or "vault particle" refers to a large cytoplasmic ribonucleoprotein (RNP) particle found in eukaryotic cells. The vault or vault particle is composed of MVP, VPARP, and/or TEP1 proteins and one or more untranslated vRNA molecules.

As used herein, the term "vault complex" refers to a recombinant vault that encapsulates a small molecule or protein of interest. A vault complex of the invention includes a fusion protein, e.g., an adenovirus protein VI (pVI).

As used herein, the term "vault targeting domain" or "vault interaction domain" is a domain that is responsible for interaction or binding of a heterologous fusion protein with a vault protein, or interaction of a VPARP with a vault protein, such as a MVP. As used herein, the term "mINT domain" is a vault interaction domain from a vault poly ADP-ribose polymerase (VPARP) that is responsible for the interaction of VPARP with a major vault protein (MVP). The term "mINT domain" refers to a major vault protein (MVP) interaction domain.

As used herein, the term "MVP" is major vault protein. The term "cp-MVP" is a cysteine-rich peptide major vault protein.

The term "VPARP" refers to a vault poly ADP-ribose polymerase.

As used herein, the term "TEP-1" is a telomerase/vault associated protein 1.

As used herein, the term "vRNA" is an untranslated RNA molecule found in vaults.

As used herein, the term "fluorescent protein" is a protein that has the property of forming a visible wavelength chromophore from within its polypeptide sequence. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalamal), cyan fluorescent protein (ECFP, Cerulean, CyPet) and yellow fluorescent protein derivatives (YFP, Citrine, Venus, YPet).

As used herein, the term "vector" is a DNA or RNA molecule used as a vehicle to transfer foreign genetic material into a cell. The four major types of vectors are plasmids, bacteriophages and other viruses, cosmids, and artificial chromosomes. Vectors can include an origin of replication, a multi-cloning site, and a selectable marker.

As used herein, a "cell" includes eukaryotic and prokaryotic cells.

As used herein, the terms "organism", "tissue" and "cell" include naturally occurring organisms, tissues and cells, genetically modified organisms, tissues and cells, and pathological tissues and cells, such as tumor cell lines in vitro and tumors in vivo.

As used herein, the term "extracellular environment" is the environment external to the cell.

As used herein, the term "in vivo" refers to processes that occur in a living organism.

A "subject" referred to herein can be any animal, including a mammal (e.g., a laboratory animal such as a rat, mouse, guinea pig, rabbit, primates, etc.), a farm or commercial animal (e.g., a cow, horse, goat, donkey, sheep, etc.), a domestic animal (e.g., cat, dog, ferret, etc.), an avian species, or a human.

The term "mammal" as used herein includes both humans and non-humans and include but is not limited to humans, non-human primates, canines, felines, murines, bovines, equines, and porcines.

As used herein, the term "human" refers to "*Homo sapiens*."

As used herein, the term "sufficient amount" is an amount sufficient to produce a desired effect, e.g., an amount sufficient to modulate protein aggregation in a cell.

As used herein, the term "therapeutically effective amount" is an amount that is effective to ameliorate a symptom of a disease, such as cancer.

A "prophylactically effective amount" refers to an amount that is effective for prophylaxis.

As used herein, the term "stimulating" refers to activating, increasing, or triggering a molecular, cellular or enzymatic activity or response from within a cell or organism.

As used herein, the term "administering" includes any suitable route of administration, as will be appreciated by one of ordinary skill in the art with reference to this disclosure, including direct injection into a solid organ, direct injection into a cell mass such as a tumor, inhalation, intraperitoneal injection, intravenous injection, topical application on a mucous membrane, or application to or dispersion within an environmental medium, and a combination of the preceding.

As used in this disclosure, the term "modified" and variations of the term, such as "modification," means one or more than one change to the naturally occurring sequence of MVP, VPARP or TEP1 selected from the group consisting of addition of a polypeptide sequence to the C-terminal, addition of a polypeptide sequence to the N-terminal, deletion of between about 1 and 100 amino acid residues from the C-terminal, deletion of between about 1 and 100 amino acid residues from the N-terminal, substitution of one or more than one amino acid residue that does not change the function of the polypeptide, as will be appreciated by one of ordinary skill in the art with reference to this disclosure, such as for example, an alanine to glycine substitution, and a combination of the preceding.

As used herein, the term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra)

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

As used in this disclosure, the term "comprise" and variations of the term, such as "comprising" and "comprises," are not intended to exclude other additives, components, integers or steps.

It must be noted that, as used in the specification and the appended claims, the singular forms "a," "an" and "the" include plural referents unless the context clearly dictates otherwise.

Compositions of the Invention

As described in more detail below, the invention includes compositions and methods of using vault particles. An embodiment of the invention has recombinant particles having a MVP and a fusion protein, e.g., an adenovirus protein VI (pVI). The vault particle can be used for delivery of a biomolecule, e.g., a vector, to a cell or tumor or subject.

Vaults and Vault Complexes

The compositions of the invention comprise a vault complex. A vault complex is a recombinant particle that encapsulates a small molecule (drug, sensor, toxin, etc.), or a protein of interest, e.g., a peptide, or a protein, including an endogenous protein, a heterologous protein, a recombinant protein, or recombinant fusion protein. Vault complexes are of the invention include an adenovirus protein VI membrane lytic domain. Vault complexes are derived from vault particles.

Vaults, e.g., vault particles are ubiquitous, highly conserved ribonucleoprotein particles found in nearly all eukaryotic tissues and cells, including dendritic cells (DCs), endometrium, and lung, and in phylogeny as diverse as mammals, avians, amphibians, the slime mold *Dictyostelium discoideum*, and the protozoan *Trypanosoma brucei* (Izquierdo et al., *Am. J. Pathol.*, 148(3):877-87 (1996)). Vaults have a hollow, barrel-like structure with two protruding end caps, an invaginated waist, and regular small openings surround the vault cap. These openings are large enough to allow small molecules and ions to enter the interior of the vault. Vaults have a mass of about 12.9±1 MDa (Kedersha et al., *J. Cell Biol.*, 112(2):225-35 (1991)) and overall dimensions of about 42×42×75 nm (Kong et al., *Structure*, 7(4):371-9 (1999)). The volume of the internal vault cavity is approximately $50 \times 10^3$ nm$^3$, which is large enough to enclose an entire ribosomal protein.

Vaults comprise three different proteins, designated MVP, VPARP and TEP1, and comprise one or more different untranslated RNA molecules, designated vRNAs. The number of vRNA can vary. For example, the rat *Rattus norvegicus* has only one form of vRNA per vault, while humans have three forms of vRNA per vault. The most abundant protein, major vault protein (MVP), is a 95.8 kDa protein in *Rattus norvegicus* and a 99.3 kDa protein in humans which is present in 96 copies per vault and accounts for about 75% of the total protein mass of the vault particle. The two other proteins, the vault poly-ADP ribose polymerase, VPARP, a 193.3 kDa protein in humans, and the telomerase/vault associated protein 1, TEP1, a 292 kDa protein in *Rattus norvegicus* and a 290 kDa protein in humans, are each present in between about 2 and 16 copies per vault.

VPARP, mINT Domain, and mINT Fusion Proteins

A vault poly ADP-ribose polymerase (VPARP) includes a region of about 350 amino acids that shares 28% identity with the catalytic domain of poly ADP-ribosyl polymerase, PARP, a nuclear protein that catalyzes the formation of ADP-ribose polymers in response to DNA damage. VPARP catalyzes an NAD-dependent poly ADP-ribosylation reaction, and purified vaults have poly ADP-ribosylation activity that targets MVP, as well as VPARP itself VPARP includes a mINT domain (major vault protein (MVP) interaction domain). The mINT domain is responsible for the interaction of VPARP with a major vault protein (MVP).

A vault complex of the invention includes a mINT domain. The mINT domain is responsible for interaction of a protein of interest with a vault protein such as a MVP. In general, the mINT domain is expressed as a fusion protein with a protein of interest. The mINT of the vault complexes of the invention are derived from VPARP sequences. Exemplary VPARP sequences and mINT sequences can be found in Table 1. One of skill in the art understands that the mINT can have the entire naturally occurring sequence or portions of the sequence or fragments thereof. In other embodiments, the mINT has at least 50%, 60%, 70%, 80%, 90%, 95%, 96%, 97%, 98% or 99% sequence identity to any of the VPARP and/or mINT sequences disclosed in Table 1.

In one embodiment, the mINT is derived from a human VPARP, SEQ ID NO:14, GenBank accession number AAD47250, encoded by the cDNA, SEQ ID NO:15, GenBank accession number AF158255. In some embodiments, the vault targeting domain comprises or consists of the INT domain corresponding to residues 1473-1724 of human VPARP protein sequence (full human VPARP amino acid sequence is SEQ ID NO:14). In other embodiments, the vault targeting domain comprises or consists of the mINT domain comprising residues 1563-1724 (SEQ ID NO: 6) of the human VPARP protein sequence. In certain embodiments, the vault targeting domain is at least 90%, 91%, 92%, 93%, 94%, 95%, 96%, 97%, 98%, or 99% identical to SEQ ID NO: 6 or 14.

In alternative embodiments, the mINT domain is derived from TEP1 sequences. One of skill in the art understands that the mINT can have the entire naturally occurring sequence of the vault interaction domain in TEP1 or portions of the sequence or fragments thereof.

MVP

A vault complex of the invention generally includes an MVP. Exemplary MVP sequences can be found in Table 1. One of skill in the art understands that the MVP can have the entire naturally occurring sequence or portions of the sequence or fragments thereof. In other embodiments, the MVP has at least 50%, 60%, 70%, 80%, 90%, 95%, 96%, 97%, 98% or 99% sequence identity to any of the MVP sequences disclosed in Table 1.

In one embodiment, the MVP is human MVP, SEQ ID NO:16, GenBank accession number CAA56256, encoded by the cDNA, SEQ ID NO:17, GenBank accession number X79882. In other embodiments, the MVP is at least 90%, 91%, 92%, 93%, 94%, 95%, 96%, 97%, 98%, or 99% identical to the MVP sequences described herein.

In one embodiment, there is provided a vault complex comprising, consisting essentially of, or consisting of an MVP modified by adding a peptide to the N-terminal to create a one or more than one of heavy metal binding domains. In a preferred embodiment, the heavy metal binding domains bind a heavy metal selected from the group consisting of cadmium, copper, gold and mercury. In a preferred embodiment, the peptide added to the N-terminal is a cysteine-rich peptide (CP), such as for example, SEQ ID NO:18, the MVP is human MVP, SEQ ID NO:16, and the modification results in CP-MVP, SEQ ID NO:19, encoded by the cDNA, SEQ ID NO:20. These embodiments are particularly useful because vault particles consisting of CP-MVP are stable without the presence of other vault proteins.

Any of the vault complexes described herein can include MVPs or modified MVPs disclosed herein.

TEP1

In some embodiments, a vault particle of the invention includes a TEP1 protein. Exemplary TEP1 sequences can be found in Table 1. One of skill in the art understands that the TEP1 can have the entire naturally occurring sequence or portions of the sequence or fragments thereof. In other embodiments, the TEP1 has at least 50%, 60%, 70%, 80%, 90%, 95%, 96%, 97%, 98% or 99% sequence identity to any of the TEP1 sequences disclosed in Table 1.

The TEP1 can be human TEP1, SEQ ID NO:21, GenBank accession number AAC51107, encoded by the cDNA, SEQ ID NO:26, GenBank accession number U86136. Any of the vault complexes described herein can include TEP1 or modifications thereof.

vRNA

A vault complex of the invention can include a vRNA. Exemplary vRNA sequences can be found in Table 1. One of skill in the art understands that the vRNA can have the entire naturally occurring sequence or portions of the sequence or fragments thereof. In other embodiments, the vRNA has at least 50%, 60%, 70%, 80%, 90%, 95%, 96%, 97%, 98% or 99% sequence identity to any of the vRNA sequences disclosed in Table 1.

In one embodiment, the vRNA can be a human vRNA, SEQ ID NO:23, GenBank accession number AF045143, SEQ ID NO:24, GenBank accession number AF045144, or SEQ ID NO:25, GenBank accession number AF045145, or a combination of the preceding.

As will be appreciated by one of ordinary skill in the art with reference to this disclosure, the actual sequence of any of MVP, VPARP, TEP1 and vRNAs can be from any species suitable for the purposes disclosed in this disclosure, even though reference or examples are made to sequences from specific species. Further, as will be appreciated by one of ordinary skill in the art with reference to this disclosure, there are some intraspecies variations in the sequences of MVP, VPARP, TEP1 and vRNAs that are not relevant to the purposes of the present invention. Therefore, references to MVP, VPARP, TEP1 and vRNAs are intended to include such intraspecies variants.

Adenovirus Protein VI

The compositions of the invention include a vault complex including a membrane lytic domain, i.e. the membrane lytic domain of Adenovirus protein VI. In some embodiments, the membrane lytic domain of adenovirus protein VI is fused to an MVP or mINT. [In general, the vault complex includes a membrane lytic domain.]

Biomolecules or Bioactive Agents

As used herein, "biomolecule" or "bioactive agent" refers to any compound or composition having biological, including therapeutic or diagnostic, activity. A bioactive agent may be a pharmaceutical agent, drug, compound, or composition that is useful in medical treatment, diagnosis, or prophylaxis.

The biomolecule or bioactive agent may be any molecule, material, substance, or construct that may be transported into a cell by association with a membrane lytic peptide. The biomolecule or bioactive agent may be, for example, a pharmaceutical agent, a fluorescent moiety, a radioactive moiety, a radiopaque moiety, a paramagnetic moiety, a nanoparticle, a vesicle, a molecular beacon, a marker, a marker enzyme (e.g., horse-radish peroxidase (HRP), beta-galactosidase, or other enzyme suitable for marking a cell), a contrast agent (e.g., for diagnostic imaging), a chemotherapeutic agent, a radiation-sensitizer (e.g., for radiation therapy), a peptide or protein that affects the cell cycle, a protein toxin, or any other other biomolecule suitable for transport into a cell.

Examples of active agents useful as the bioactive agent or biomolecule component of the composition according to the invention include, but are not limited to, .alpha.-adrenergic agonists, .beta.-adrenergic agonists, .alpha.-adrenergic blockers, .beta.-adrenergic blockers, aldose reductase inhibitors, anabolics, analgesics (narcotic and non-narcotic), androgens, anesthetics, anorexics, anthelmintics (e.g., cestode, nematode, onchocerca, schistosoma, and the like), anti-allergics, anti-ameboics, anti-androgens, anti-anginals, anti-arrhythmics, anti-arteriosclerotics, anti-arthritics, anti-biotics and other antibacterials, anti-cholinergics, anti-convulsants, anti-depressants, anti-diabetics agents, anti-diarrheals, anti-diuretics, anti-estrogens, antifungals, anti-yeast agents, anti-glaucomas, anti-gonadotropins, anti-gout agents, anti-histaminics, anti-hyperlipoproteinemics, anti-hypertensives, anti-hyperthyroid agents, anti-hypertrophy agents, anti-hypotensives, anti-hypothyroid agents, antiinflammatories, anti-malarials, antimicrobials, anti-migraine agents, anti-nausea agents, anti-neoplastics, antioxidants, antiparasitic agents, anti-parkinsonian agents, anti-pheochromocytoma agents, anti-pneumocytis agents, anti-proliferative agents, anti-protozoals (e.g., leishmania, trichomonas, trypansoma, and the like), anti-pruritic agents, anti-psoratic agents, anti-psychotic agents, anti-pyretics, anti-rheumatics, anti ricketts agents, anti-seborrheic agents, antiseptics, anti-spasmodic agents, anti-thrombotic agents, antitussives, anti-ulcer agents, anti-urolithic agents, anti-venins, antivirals, anxiolytics, benzodiazepine antagonists, bronchodilators, calcium channel blockers, calcium regulators, cardiotonics, chelating agents, chemotherapeutics, cholecystokinin antagonists, cholelitholytic agents, choleretics, cholinergics, cholinesterase inhibitors, cholinesterase reactivators, central nervous system stimulants and agents, decongestants, diuretics, dopamine receptor agonists, drugs for treating or preventing pain, ectoparasiticides, enzymes, enzyme inducers, estrogens, gastric secretion inhibitors, glucocorticoids, gonad-stimulating principles, gonadotropic hormones, growth hormones, growth hormone releasing factors, growth stimulants, hemolytics, heparin agonists, hepatoprotectants, hypnotics, immune system boosters, immunomodulators, immunosuppressants, lactation stimulating hormones, LH-RH stimulating agonists, lipotropics, lupus erythmatosus suppressants, mineral corticoids, miotics, monoamine oxidase inhibitors, mucolytics, muscle relaxants, narcotic antagonists, neuroprotectives, neotropics, ovarian hormones, oxytocics, pepsin inhibitors, peristaltic stimulators, progestrogens, prolactin inhibitors, protoglandins, prostoglandin analogs, protease inhibitors, respiratory stimulants, sclerosing agents, sedatives, steroids, thrombolytics, thyrotropic hormones, transdermal penetration enhancers, uricosurics, vasoconstrictors, vasodilators (e.g., cerebral, coronary, peropheral, and the like), vasoprotectants, vitamins, vitamin source extracts, vulneraries (including, but not limited to, those listed in U.S. Pat. No. 5,719,197, the entire disclosure of which is incorporated herein by reference), and combinations thereof. Other additionally or alternately acceptable pharmaceutically active agents can be found, e.g., in U.S. Pat. No. 6,221,383, the entire disclosure of which is incorporated herein by reference.

Fluorescent Proteins

In certain embodiments, the vault complex of the invention includes a fluorescent protein. In some embodiments, the fusion protein comprises a fluorescent protein. Fluorescent proteins can be engineered to be expressed with other proteins, and include, but are not limited to, green fluorescent protein (GFP), red fluorescent protein (mCherry), blue fluorescent protein (EBFP, EBFP2, Azurite, mKalamal), cyan fluorescent protein (ECFP, Cerulean, CyPet) and yellow fluorescent protein derivatives (YFP, Citrine, Venus, YPet). In one embodiment, the fusion protein comprises a mCherry fluorescent protein or a portion of a mCherry fluorescent protein.

Isolated Nucleic Acids and Vectors

Suitable expression vectors generally include DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of expression vectors can be systemic, such as by intravenous or intramuscular administration, by administration to target cells ex-planted from the patient followed by reintroduction into the patient, or by any other means that allows for introduction into a desired target cell.

Plasmids expressing a nucleic acid sequence can be transfected into target cells as a complex with cationic lipid carriers (e.g., Oligofectamine) or non-cationic lipid-based carriers (e.g., Transit-TKO™). Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g., EPV and EBV vectors. Constructs for the recombinant expression of a nucleic acid encoding a fusion protein will generally require regulatory elements, e.g., promoters, enhancers, etc., to ensure the expression of the fusion nucleic acid in target cells. Other aspects to consider for vectors and constructs are further described below.

Vectors useful for the delivery of a nucleic acid can include regulatory elements (promoter, enhancer, etc.) sufficient for expression of the nucleic acid in the desired target cell or tissue. The regulatory elements can be chosen to provide either constitutive or regulated/inducible expression. A person skilled in the art would be able to choose the appropriate regulatory/promoter sequence based on the intended use of the transgene.

In a specific embodiment, viral vectors that contain the recombinant gene can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding a fusion protein are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of isolated nucleic acids encoding fusion proteins into a cell. Adenoviruses are especially attractive vehicles for delivering genes to respiratory epithelia or for use in adenovirus-based delivery systems such as delivery to the liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing a nucleic acid molecule featured in the invention, a method for constructing the recombinant AV vector, and a method for delivering the vector into target cells, are described in Xia H et al. (2002), Nat. Biotech. 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Examples of additional expression vectors that can be used in the invention include pFASTBAC expression vectors and *E. coli* pET28a expression vectors.

Generally, recombinant vectors capable of expressing genes for recombinant fusion proteins are delivered into and persist in target cells. The vectors or plasmids can be transfected into target cells by a transfection agent, such as Lipofectamine. Examples of cells useful for expressing the nucleic acids encoding the fusion proteins of the invention include Sf9 cells or insect larvae cells. Recombinant vaults based on expression of the MVP protein alone can be produced in insect cells. Stephen, A. G. et al. (2001). *J. Biol. Chem.* 276:23217:23220; Poderycki, M. J., et al. (2006). *Biochemistry* (Mosc). 45: 12184-12193.

Pharmaceutical Compositions of the Invention

In one embodiment, the invention provides methods using pharmaceutical compositions comprising the vault complexes of the invention. These compositions can comprise, in addition to one or more of the vault complexes, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

In certain embodiments, the pharmaceutical compositions that are injected intra-tumorally comprise an isotonic or other suitable carrier fluid or solution.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In other embodiments, pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

In some embodiments, administration of the pharmaceutical compositions may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration. Formulations for parenteral administration may include sterile aqueous solutions which may also contain buffers, diluents and other suitable additives. For intravenous use, the total concentration of solutes should be controlled to render the preparation isotonic.

Methods of Use

Vault complexes described herein can be used to deliver a protein of interest to a cell, a tissue, an environment outside a cell, a tumor, an organism or a subject. In one embodiment, the vault complex comprises an adenovirus pVI domain, and the vault complex is introduced to the cell, tissue, or tumor. In some embodiments, the vault complex is introduced into the extracellular environment surrounding the cell. In other embodiments, the vault complex is introduced into an organism or subject. Delivery of the vault complex of the invention can include administering the vault complex to a specific tissue, specific cells, an environmental medium, or to the organism. In some embodiments, delivery of the vault complex can be detected by a sensor within the cell, tissue, or organism. For example, detection can be performed using standard techniques, such as fluorometry or spectrophotometry. This method can be used, for example, to determine the pH within cells, where the sensor is a pH dependent fluorescent sensor, as will be appreciated by one of ordinary skill in the art with reference to this disclosure.

The methods of the invention comprise delivering a biomolecule to a cell by contacting the cell with any of the vault complexes described herein. Cells of the invention can include, but are not limited to, any eukaryotic cell, mammalian cell, or human cells, including tumor cells. In some embodiments, contacting the cell with a vault complex induces migration of T cells and/or dendritic cells to the cell.

Methods of the invention include delivery of the vault complex to a subject. The delivery of a vault complex to a subject in need thereof can be achieved in a number of different ways. In vivo delivery can be performed directly by administering a vault complex to a subject. Alternatively, delivery can be performed indirectly by administering one or more vectors that encode and direct the expression of the vault complex or components of the vault complex. In one embodiment, the vault complex is administered to a mammal, such as a mouse or rat. In another embodiment, the vault complex is administered to a human.

In one embodiment, the methods of delivery of the invention include systemic injection of vault complexes to tumors, producing the enhanced permeability and retention (EPR) effect. See Maeda et al., *J. of Controlled Release* 2000, 65: 271-284; Griesh, K., *J. of Drug Targeting* 2007, 15(7-8): 457-464; Allen et al., *Science* 2004, 303:1818-1822. Solid tumors possess extensive angiogenesis and hence hypervasculature, defective vascular architecture, impaired lymphatic drainage/recovery systems, and greatly increased production of a number of permeability mediators. Due to the biology of solid tumors, macromolecular anticancer drugs and agents, including vault complexes, administered intravenously can accumulate and are retained in the tumor due to the lack of efficient lymphatic drainage in the solid tumor. The invention includes methods of systemic or targeted delivery of vault complexes described herein to solid tumors, such as those found in lung cancer.

Other methods of the invention include stimulating an immune response in a subject. The method comprises administering the vault complex to a subject. Administering can include intra-tumoral injection of the vault complex in a subject, which is described in detail herein.

Methods of Treatment

The invention features a method of treating or managing disease, such as cancer, by administering the vault complex of the invention to a subject (e.g., patient). In some embodiments, the method of the invention comprises treating or managing cancer in a subject in need of such treatment or management, comprising administering to the subject a therapeutically effective amount of the vault complexes described herein.

The data obtained from cell culture assays and animal studies can be used in formulating a range of dosage for use in humans. For any compound used in the methods featured in the invention, the therapeutically effective dose can be estimated initially from cell culture assays. A dose may be formulated in animal models to achieve a circulating plasma concentration range of the vault complex. Such information can be used to more accurately determine useful doses in humans. Analysis of tumor cell samples of mice administered a vault complex can also indicate a therapeutically effective dose.

The pharmaceutical composition according to the present invention to be given to a subject, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. A composition can be administered alone or in combination with other treatments, either simultaneously or sequentially dependent upon the condition to be treated.

In certain embodiments, the dosage of vault complexes is between about 0.1 and 10,000 micrograms per kilogram of body weight or environmental medium. In another embodiment, the dosage of vault complexes is between about 1 and 1,000 micrograms per kilogram of body weight or environmental medium. In another embodiment, the dosage of vault complexes is between about 10 and 1,000 micrograms per kilogram of body weight or environmental medium. For intravenous injection and intraperitoneal injection, the dosage is preferably administered in a final volume of between about 0.1 and 10 ml. For inhalation the dosage is preferably administered in a final volume of between about 0.01 and 1 ml. As will be appreciated by one of ordinary skill in the art with reference to this disclosure, the dose can be repeated a one or multiple times as needed using the same parameters to effect the purposes disclosed in this disclosure.

For instance, the pharmaceutical composition may be administered once for each tumor in a subject, or the vault complex may be administered as two, three, or more sub-doses or injections at appropriate intervals. In that case, the vault complexes can be injected in sub-doses in order to achieve the total required dosage.

The vault complexes featured in the invention can be administered in combination with other known agents effective in treatment of cancers, including lung cancer. An administering physician can adjust the amount and timing of vault complex administration or injection on the basis of results observed using standard measures of efficacy known in the art or described herein. The skilled artisan will also appreciate that certain factors may influence the dosage and timing required to effectively treat a subject, including but not limited to the severity of the disease or disorder, previous treatments, the general health and/or age of the subject, and other diseases present.

Methods of Preparing Vault Complexes

The methods of the invention include preparing the vault complexes described herein.

In one embodiment, the vault complexes are derived or purified from natural sources, such as mammalian liver or spleen tissue, using methods known to those with skill in the art, such as for example tissue homogenization, differential centrifugation, discontinuous sucrose gradient fractionation and cesium chloride gradient fractionation. In another embodiment, the vault complexes are made using recombinant technology. Details about the methods for recombinant vault complexes are described below.

In some embodiments, a target of interest, i.e., protein of interest, is selected for packaging in the vault complexes. The target of interest may be selected from the group consisting of an enzyme, a pharmaceutical agent, a plasmid, a polynucleotide, a polypeptide, a sensor and a combination of the preceding. In a preferred embodiment, the target of interest is a recombinant protein, e.g., a membrane lytic protein, e.g., an adenovirus protein VI.

Preferably, if the target of interest is a recombinant protein, the polynucleotide sequences encoding the recombinant protein are used to generate a bacmid DNA, which is used to generate a baculovirus comprising the sequence. The baculovirus is then used to infect insect cells for protein production using an in situ assembly system, such as the baculovirus protein expression system, according to standard techniques, as will be appreciated by one of ordinary skill in the art with reference to this disclosure. Advantageously, the baculovirus protein expression system can be used to produce milligram quantities of vault complexes, and this system can be scaled up to allow production of gram quantities of vault complexes according to the present invention.

In another embodiment, the target of interest is incorporated into the provided vaults. In a preferred embodiment, incorporation is accomplished by incubating the vaults with the target of interest at an appropriate temperature and for an appropriate time, as will be appreciated by one of ordinary skill in the art with reference to this disclosure. The vaults containing the protein of interest are then purified, such as, for example sucrose gradient fractionation, as will be appreciated by one of ordinary skill in the art with reference to this disclosure.

In other embodiments, the vaults comprising the target of interest are administered to an organism, to a specific tissue, to specific cells, or to an environmental medium. Administration is accomplished using any suitable route, as will be appreciated by one of ordinary skill in the art with reference to this disclosure.

In one embodiment, the method comprises preparing the composition of the invention by a) mixing a fusion protein comprising a pVI fused to a mINT generated in Sf9 cells with a rat MVP generated in Sf9 cells to generate a mixture; b) incubating the mixture for a sufficient period of time to allow packaging of the fusion protein inside of vault complexes, thereby generating the composition. Sf9 cells are infected with pVI-MVP encoding recombinant baculoviruses. Lysates containing recombinant pVI-INT and rat MVP generated in Sf-9 cells can be mixed to allow the formation of a macromolecular vault complex containing the pVI-INT fusion protein.

In another embodiment, the composition is prepared by a) mixing a fusion protein comprising a pVI fused to a mINT generated in insect larvae cells with a rat MVP generated in insect larvae cells to generate a mixture; b) incubating the mixture for a sufficient period of time to allow packaging of the fusion protein inside of vault complexes.

Details about methods of preparing vault complexes are further described in the Examples.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* 3$^{rd}$ Ed. (Plenum Press) Vols A and B(1992).

Methods cDNA Constructs for the Expression of Recombinant pVI Proteins cDNA plasmid constructs encoding the mature, full length protein VI (pVI), designated p6, or the N-terminal region of protein VI (NT) corresponding to residues ala-34 to glu-114, designated nt, were cloned into the BamHI and EcoRI sites of the *Escherichia coli* expression vector pET28a (Novagen, Madison, Wis.). The constructs also included an N-terminal 6His tag (SEQ ID NO: 55) followed by a thrombin cleavage site. The 5' and 3' primers, containing a BamHI restriction site (underlined) in the 5' primers and a TTA stop codon site (italics) and an EcoRI restriction site (underlined) in the 3' primers were used as indicated:

```
for pVI
                                       (SEQ ID NO: 43)
5'-CGGGATCCGCCTTCAGCTGGGGCTCGCTCTGGAGC-3'
and
                                       (SEQ ID NO: 44)
5'-CGGGAATTCTTACAGACCCACGATGCTGTTCAG-3' for NT
                                       (SEQ ID NO: 45)
5'-CGGGATCCGCCTTCAGCTGGGGCTCGCTCTGGAGC-3'
and
                                       (SEQ ID NO: 46)
5'-CGGGAATTCTTACTCTCGGGAGGGCGGGGATC-3'
and for TR
                                       (SEQ ID NO: 47)
5'-AAAGGATCCTATGGCAGCAAGGC-3'
and
                                       (SEQ ID NO: 48)
5'-AAAGAATTCTTACAGACCCACGATGCTGTT-3'.
```

For vault incorporation experiments, we also expressed pVI (amino acid residues 34-53) in *E. Coli.* using 5'CG GGATCCGCCTTCAGCTGGGGCTCGCTGTGGAGCG-GCATTAAAAATTTCGGTT CCACCGTTAAGAACTAT GAATTCCGG-3' (SEQ ID NO:49) and 5'-CCGGAATTCATAGTTCTTAACGGTGGAACCGAA-ATTTTTAATGCCGCTCCACAGC GAGCCCCAGCT-GAAGGCGGATCCCG-3' (SEQ ID NO:50) primers. After endonuclease restriction digests with BamHI and EcoRI, the resulting 60 by cDNA fragment was inserted into pET 28a vector containing His tag at the N terminus. All plasmid constructs were confirmed by sequencing.

Cloning, Expression, and Purification of Vault Complexes

The cDNA constructs encoding the INT and MVP were previously described [9, 10, 11, 12]. The INT domain corresponds to the 162-aa C-terminal region of VPARP (amino acids 1563-1724) and is the smallest region identified for interaction with MVP. The INT domain coding region was PCR cloned into the Bam H1 and Xho1 sites of the *E. coli* expression vector pET28a using the sense primer, 5'-CGGGATCCGGCGGC GAATTCGATTTACGATATCCCAACGACCGAA-3' (SEQ ID NO:51), with BamHI site (underlined) and EcoRI site (underlined italics). The sense primer contains a dipeptide flexible linker, Gly-Gly, and an added EcoRI site designed for further insertion of recombinant pVI-NT. The antisense primer, 5'-CCCCTCGAGTTAGCCTTGA-CTGTAATGGAGGACTCTATG-3' (SEQ ID NO:52) contains an XhoI site (underlined) and a stop codon (italics).

The interaction domain chosen for pVI constructs encompassed amino acids 1563-1724 of VPARP. These pVI-INT fusion molecules were expressed in bacteria and purified as described above. Recombinant vaults based on expression of the MVP protein alone were produced in insect cells as previously described [10, 13]. Purified vaults were also analyzed by immunoblot using polyclonal antibodies to MVP, INT, or pVI. The identity of CP-MVP-Z monomer present in vault particles was also confirmed by MALDI-TOF-M8, which is within the error range of expected molecular masses of CP-MCP-Z monomers [12].

Protease Sensitivity and Transmission Electron Microscopy

To examine the protease sensitivity of purified vault particles, 30 μL of purified pVI-vaults (150 μg/ml) were incubated with 6 μL of 10× thrombin cleavage buffer, 3 μL of thrombin (1 U/μL, Novagen, Madison, Wis.) and 21 μL of water to a total volume of 60 μL. The reaction mixture was incubated at 25° C. Aliquots (10 μL) of this mixture were collected after 24 h and analyzed by immunoblot as described above. Purified vault particle morphology was assessed by negative stain transmission electron microscope as previously described [10]. EM grids were examined on a JEOL 1200 EX elecron microscope and micrographs were captured with a BIOScan 600W digital camera (Gatan Inc., Pleasanton, Calif.).

Liposome Disruption Assay

To assess the ability of pVI or pVI-vaults to mediate membrane disruption, we used model membranes (liposomes) containing an entrapped fluorescent dye. Unilamellar liposomes having an average diameter of 500 μm were prepared using bovine liver phosphatidylcholine (PC), and bovine brain phosphatidylserine (PS) (Avanti Polar Lipids) and sulforhodamine B (SulfoS) (Molecular Probes, Invitrogen) as previously described [14] with slight modifications. Lipid vesicles were prepared by mixing lipids in a molar ratio of PC to PS of 4:1 in a total amount of 5.0 μmole) in 1 ml of chloroform. The solution was then evaporated under argon to generate a lipid film which was vacuum-dried for 12 hrs to remove residual chloroform. The dried lipid film was then hydrated for 1 hr in 1 ml solution of sulforhodamine B (100 mM) in HBS buffer (20 mM HEPES/NaOH buffer, 100 mM NaCl, 0.02% sodium azide pH 7.5). Small unilamellar vesicles (SUVs) were prepared by vortexing the reaction tube vigorously to completely resuspend the lipid mixture followed by sonication for 1 hr in a bath sonicator (Laboratory Supplies Inc). This final solution was then gel-filtered on a Sephadex G-25 column and eluted with HBS buffer. The liposomes, which eluted as a pink band, were collected and used within 24 hours. The final lipid concentration was determined by using an inorganic phosphorus assay [15, 16] and then adjusted to 0.15 mM for the vault and pVI-INT assays as described below.

Time-dependent fluorescence was used to analyze liposome disruption using an Aminco Bowman Series Luminescence Spectrometer equipped with 535/20 nm excitation and 585/20 nm emission filters, respectively. Briefly, 12.5 µl of liposome solution was added to HBS buffer (1 ml) in a fluorescence cuvette equipped with a stir bar and fluorescence measurements were taken at 1 second intervals under stirring conditions for a total time of approximately 7 minutes. After 60 seconds to record background fluorescence, 10 µl of the pVI-INT proteins (1 µg total) or vault-pVI complexes at 13.7 mg/mJ (137 µg total) in 50 mM Tris, 300 mM NaCl, pH 8 were added to the liposome solutions. After reaching a plateau in the fluorescence signal, 25 µl of a 10% aqueous solution of TRITON-X-100® was added and the percentage of SulfoS release was calculated using the following formula: % SulfoS released=$100\times[(F-F_o)/(F_t-F_o)]$, where $F_o$ and F are the fluorescence before and after the addition of protein, respectively, and $F_t$ is the total fluorescence intensity in the presence of TRITON-X-100®.

Preparation of Fluorescent Vault Nanoparticles

Recombinant vaults were fluorescently labeled using the NHS-Ester Cy3.5 bis reactive dye (Amersham Biosciences). Briefly, 1.0 mg of the free bisfunctional NHS-Ester Cy3.5 dye was dissolved in 1 ml of 0.1M carbonate buffer, pH 8.5 and then mixed with 0.65 ml of 13.7 mg/ml purified vaults resulting in the conjugation at a molar ratio of 1.1 dye molecules per 1 MVP molecules. The conjugation mixture was incubated at 4° C. for 40 minutes with occasional rocking and the remaining non-conjugated dye was removed by filtration on a PD-10 column (Amersham Biosciences) pre-equilibrated with buffer A (see above) that was also used for elution of the conjugation product. The colored (pink) fraction containing the dye-conjugated vault nanoparticles was collected and loaded onto a discontinuous 20-60% sucrose density gradient and ultracentrifuged as described above. The pink band corresponding to the 45% fraction was pelleted by centrifugation using a Beckman Ti70 rotor (39,000 rpm for 2 hr at 4° C.) and resuspended in 20 mM MES buffer pH 6.5. The yield of labeled vault particles was estimated by linear regression analyses of the UV absorbance of the labeled vaults assuming Cy3.5 dye $\lambda_{ex}$=581 nm and $\lambda_{ex}$ of proteins at 280 nm resulting in a ratio of 1 Cy3.5 dye molecules per MVP protein subunit.

Vault Interactions with Mammalian Cells

RAW 264.7 mouse macrophages and A549 human epithelial cells were maintained in Dulbecco's complete modified Eagle's medium (DMEM) supplemented with 10 mM HEPES, 2 mM glutamine, 1 mM pyruvate, 0.1 mM nonessential amino acids, 100 U of penicillin G/ml, 0.3 mg of gentamicin/ml, and 10% fetal bovine serum (D-10). U937 human monocytic cells, maintained in RPMI-1640 modified medium, were supplemented with 10 mM HEPES, 2 mM glutamine, and 10% fetal bovine serum.

To measure vault-host cell interactions, cells were cultured 6-well tissue culture plates at a density of $2\times10^5$ cells/well 24 hours prior to measuring vault internalization. The cells were then incubated with varying amounts of Cy3.5-labeled vault nanoparticles in MES buffer for varying times at 37° C. or 4° C. Internalized vaults were then quantified by flow cytometry following the detachment of cells by trypsinization and resuspension in 1 ml of cold $Ca^{2+}$ and $Mg^{2+}$ free PBS buffer, pH 7.0, containing 1 mM EDTA, 25 mM HEPES and 1% heat inactivated fetal bovine serum. Trypan blue dye was then added to each cell sample at a final concentration of 200 µg/ml in cold FACS sort buffer in order to quench the fluorescence of non-internalized Cy3.5-labeled vault particles as previously described [17]. The cell suspensions were analyzed by flow cytometry with a Becton-Dickinson FACSCan cytometer using a 488 nm laser for red emitting fluorochromes excitation. Cy3.5 fluorescence was detected using PL2 channel in conjunction with a 585 nm band-pass filter. An electronic gate was set around cells based on the forward and side scatter properties of the population and a minimum of 10,000 gated events per sample were collected. Data analysis was performed with CellQuest software (BO Bioscience, San Jose, Calif.).

Cell Membrane Penetration Assay

To examine vault mediated endosome penetration we used an assay that measures the co-delivery of a ribotoxin (saporin) into the cytosol of host cells via a membrane lytic virus [18]. RAW 264.7 cells were seeded at a density of 3000 cells per well and allowed to attach for 4 hr in 96-well tissue culture plate. One microgram of vaults alone, or vault-PVI complexes, or pVI protein were incubated with cells in the presence or absence of the ribotoxin saporin [19] in D-1 0 medium for 4 hrs. The saporin concentration was varied from $1.65\times10^{-7}$ M to $8.25\times10^{-9}$ M in two-fold dilutions. The cultured cells were then washed two times with PBS buffer and media and then cultured in medium for 48 hours before measuring cell metabolic activity using the colorimetric XTT assay [22-25] (Promega, Madison, Wis). The absorbance was measured at 485 nm on a Molecular Devices SpectraMAX 250 microplate reader. All experiments were performed in triplicate.

Vault-Mediated Delivery of CaPi:DNA Complexes

The murine macrophage RAW 264.7 cells were cultured in 60-mm dishes in D-10 medium (DMEM+10% FCS medium and antibiotics) and seeded onto 96-well plates ($6\times10^3$ cells per well, in 0.2 ml growth medium) 24 hrs prior to performing transfection experiments. A plasmid encoding a redshifted variant of GFP (pEGFP-N1—Clontech, Palo Alto, Calif.) was amplified in the *E. coli* (DH5α) and purified according to the manufacturer's protocol (Qiagen, USA). The isolated DNA was resuspended in Tris-EDTA (pH 8.0) at a concentration of 0.5 µg/µl and used for the preparation of calcium phosphate precipitates for transfection experiments as previously described [22-25]. Briefly, 1.5 µl of DNA plasmid encoding GFP (0.75 µg) along with calculated volumes of pVI-Vault solution ($5.39\times10^{-7}$ M, $5.68\times10^6$ particles Icell) and 1.00 µl of a 2 M $CaCl_2$ (Profection®, Calcium-Phosphate mammalian transfection system; Promega, Madison, Wis.) aqueous solution were mixed with of EMEM (11 090-81,GIBCO) in a final volume of 50 µl. The mixtures were allowed to incubate for 30 min at 4° C. The cell culture medium was replaced by 150 µl of fresh EMEM medium and 50 µl of the complex was then applied to cells with gentle agitation. After incubation for 1 hr at 37° C., the transfection mixture was removed by washing the cells with 0.15 M NaCl and cultured with D-10 medium. pEGFP gene expression was measured by FACS after 1 day post-transfection.

Recombinant pVI-MVP Vault Protein Constructs

The pVI lytic peptide (aa 34-53, AFSWGSLWSGIKNF-GSTVKN (SEQ ID NO:3)) was fused to the N-terminus of MVP. The following PCR primers were used: pVI reverse: GGG GCC ATG GCG CTG CCG CGC GGC ACC AGG CCG TTC TTA ACG GTG GAA CCG (SEQ ID NO:53) and pVI forward: CTC TGC TAG CCA CCA TGG CCT TCA GCT GGG GCT CG (SEQ ID NO:54) and the template was pVI-mINT in pFastBac. All the primers used in this study were purchased from Invitrogen. The PCR product was gel purified on a column, ligated to PCR 2.1 vector followed by the amplification and purification by Qiagen miniprep kit. The insert was NcoI digested, gel purified, and ligated to NcoI and phosphatase treated rat MVP cDNA inserted in pFastBAC to form pVI-MVP pFastBac. All constructs were confirmed by DNA sequence analysis carried out by Laragen. The constructs encoding EGF vaults, CP-MVP vaults, CP-MVP-Z vaults, pVI-mINT, and mCherry-mINT were described previously. (refs 26-28). The Z domain was subcloned from CP-MVP-Z using Xho I and KpnI and the gel purified 1 kb fragment was inserted into the same sites in pVI-MVP in pFastBac to form pVI-MVP-Z in pFastBac.

Co-Delivery of CaPi DNA via Recombinant pVI-MVP Vault Protein Constructs

The pVI-MVP and pVI-MVP-Z recombinant vaults were expressed in Sf9 insect cells. The vaults were purified as described previously. In order to eliminate the aggregation into vaultimers, buffer A with 25 mM NaCl was used for the purification. In case of EGF+pVI-INT vault purification, buffer A with 150 mM NaCl was used. pVI pellets were resuspended in Bugbuster (Novagen, USA) protein extraction reagent supplemented with Benzonase (20 U/mL, Novagen, USA), 1.0 mg/mL of lysozyme (Sigma, USA), and one tablet of EDTA-free protease inhibitor cocktail (Roche, Switzerland). In order to incorporate different pV1 molecules into the interior of the vaults, ~2 mg of purified pVI-INT proteins in 10 mL of Bugbuster buffer was added to 10 mL of recombinant vault containing Sf9 cell lysates, and the mixture was incubated on ice for 30 min before performing vault purification as previously [29, 30]. The purified vaults were stored at 4° C. in 20 mM MES at pH 6.5 until used.

Expression and Purification of Recombinant pVI-MVP Vault Protein Constructs

The pVIA431 and HeLa cells were grown and maintained in DMEM supplemented with 10% fetal bovine serum. For the transfection with EGF vaults, the cells ($5\times10^4$ cell/well) were seeded on the 24-well culture plates and incubated for 16 h under serum starvation. The determined amounts of EGF vaults were added to the cell culture followed by 1 h incubation at 4° C. with 300 µL of the medium containing 0.2% serum. Then the unbound vaults were washed out with PBS (−) three times and CaPi DNA were added to each well with 400 µL of the medium containing 10% serum. The $CaPO^4$ precipitation of pDNA was followed by the recommended protocol of maker (Mammalian Transfection Kit, Stratagene, USA). Briefly 0.96 µL of 2.5M $CaCl_2$ solution was mixed with 0.8 µg of pDNA. The mixture was incubated for 30 min at RT and then applied to each well for the transfection. After 24 h of incubation (4 h incubation for Lipofectamine as recommended from maker), the medium was replaced with 400 µL of the medium containing 10% serum, followed by an additional 48 h of incubation. For the transfection with pVI-MVP-z vaults, the cells were serum starved for 1 h and the vaults were pre-incubated with anti-EGFR, clone LA22 monoclonal antibody (Millipore, USA) for 16 h before added to cell culture. For the CaPi DNA preparation, 1.8 µL of 2.5M CaCl2 solution was mixed with 1.5 µg of pDNA. The mixture was incubated for 30 min at RT and then applied to each well for the transfection. For non-targeted transfection with pVI-MVP vault, the mouse macrophage RAW 264.7 cells ($5\times104$ cell/well) were seeded on 24-well culture plates and incubated for 16 h in 400 µL of DMEM containing 10% FBS before transfection. The recombinant vaults and CaPi DNA were added to the cell culture and co-incubated for 24 h followed by the 48 h of post-incubation. The luciferase gene expression was then evaluated using the Luciferase Assay System (Promega, USA) and a Lumat LB9507 luminometer (Berthold Technologies, Germany). The amount of protein in each well was concomitantly determined using a Micro BCA Protein Assay Reagent Kit. A plasmid encoding luciferase was amplified in the E. coli and purified using Maxiprep kit (Qiagen, USA).

Vault-Mediated Endosome Penetration of Ribotoxin

To evaluate cell membrane penetration, we measured the delivery of a saporin (sigma, USA) into the cytosol of the murine macrophage RAW 264.7 cells via pVI-MVP. The cells (3,000 cells/well) were seeded on 96-well tissue culture plate and incubated overnight in DMEM containing 10% FBS. The calculated amount of vaults was applied to each well in the presence or absence of the saporin in DMEM for 4 h. The cultured cells were washed three times with PBS buffer and cultured in medium for 48 h before measuring cell viability using MTT assay kit (Roche, Switzerland). The absorbance was measured at 560 nm on a Victor3 1420 multilabel counter (PerkinElmer, USA). All experiments were performed in triplicate.

Endocytosis of Recombinant Vaults

A431 or HeLa cells ($4\times10^4$/well) were plated onto 12 mm glass coverslips coated with poly-L-lysine in 4-well Petri dishes and incubated at 37° C. (with 5% $CO_2$) for 16 h. Purified pVI-MVP-Z/mCherry-INT vaults (100 µg) were incubated with anti-EGFR antibody LA22 (1 µg) in PBS containing 0.05% TWEEN 20® (Fisher Scientific, USA) at 4° C. for 16 h with tumbling. The cells were serum-starved for 1 h before the addition of antibody-bound vaults, followed by 1 h incubation at 4° C. in DMEM (0.25 mL containing 0.2% FBS per well) for specific membrane binding studies. They were washed three times with PBS and incubated with Lysotracker Green DND-26 (Invitrogen, USA) at 37° C. Then the cells were washed three times with cold PBS and fixed in 4% paraformaldehyde and nucleus stained with Hoechst 33342 (Invitrogen, USA). Cells were mounted in Vinol 205 and visualized using fluorescent microscopy (Axio Imager Z1 microscope, Carl Zeiss, Germany).

Example 1

Incorporation of pVI into Recombinant Vault Particles

Despite the potential utility of vaults as gene transfer carriers, these nanoparticles have not been reported to display cell membrane penetrating activity, thus potentially limiting their cell transducing capacity. To overcome this deficiency, we have incorporated the membrane lytic domain of adenovirus protein VI into recombinant vault particles. Adenovirus internalization via endocytosis leads to the partial disassembly of the viral capsid concomitant with the release of protein VI [18]. The N-terminal region of pVI contains a putative amphipathic a-helical domain (amino acid residues 34-53) that exhibits potent membrane lytic activity as measured by the disruption of artificial lipid membranes (liposomes) [18]. The studies reported herein demonstrate that incorporation of the N-terminal domain of pVI into vault particles increases membrane penetration as well as the co-delivery of reporter molecules.

Figure 2:
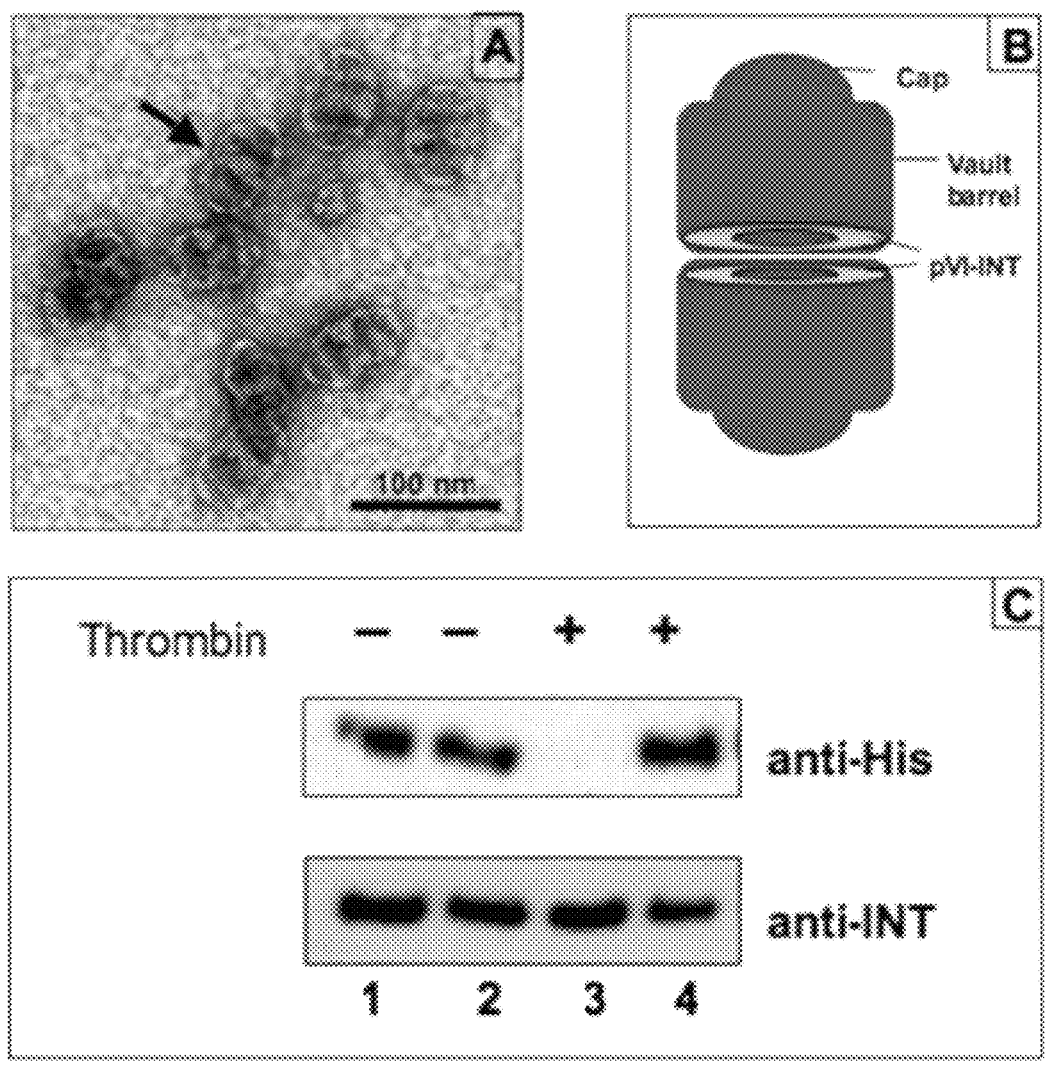
FIG. 2, Panels A-C: Transmission electron microscopy and biochemical analysis of vault particles.

Previous biochemical studies demonstrated that the interior surface of vaults could be targeted to bind exogenous proteins engineered to contain an MVP interaction domain (INT) derived from the VPARP protein (amino acid residues 1532-1724) [9]. Therefore, we examined whether the membrane lytic domain of adenovirus protein VI (amino acid residues 34-114) [18] could be incorporated into the interior of recombinant vault particles via fusion to the VPARP INT domain (FIG. 1, Panel A). Incubation of recombinant MVP and pVI-INT proteins allowed the formation of a macromolecular vault complex that could be isolated by density gradient ultracentrifugation. The purified vaults contained both MVP as well as pVI-INT as indicated by immunoblot analyses (FIG. 1, Panel B). Based on densitometric analysis of stained SDS-PAGE, we estimate that on average, each vault particle contains approximately two molecules of protein VI-INT. The pVI-vault complex also exhibited a very similar sedimentation profile on sucrose gradients as empty vaults or vault particles containing the INT domain fused to eGFP (data not shown) suggesting that incorporation of pVI-INT did not impact the normal structure of recombinant vault particles. To verify this, we examined purified vault-pVI complexes by negative stain transmission electron microscopy (FIG. 2, Panel A). Vault-pVI complexes exhibited the characteristic barrel shaped morphology with additional density observed near the "waist" of some of these particles (FIG. 2, Panels A and B), consistent with the previously established binding site for recombinant-INT fusion proteins.

We next examined whether the pVI-INT protein was located inside vault particles or non-specifically associated with the exterior of the vault. Vault-pVI particles (FIG. 2, Panel C, lanes 2 and 4) or the purified pVI-INT protein (FIG. 2, Panel C, lanes 1 and 3) were subjected to digestion with thrombin to determine if specific sites within the pVI-INT fusion protein were accessible to this protease, and the protease-treated samples were then analyzed by immunoblot. Vault-pVI complexes were resistant to thrombin digestion as detected with an anti-His tag MAb (FIG. 2, Panel C, lane 4). In contrast, soluble recombinant pVI-INT alone that had not been incorporated into vaults was susceptible to thrombin cleavage (FIG. 2, Panel C, lane 3). Control samples treated with thrombin and analyzed with an anti-INT polyclonal antibody did not reveal protease susceptibility, consistent with the retention of the C-terminal INT domain. These findings indicated that pVI-INT could be incorporated into the interior of recombinant vaults, however a concern was that the membrane lytic activity of this Ad-derived protein might not be retained upon fusion to the relatively large VPARP INT domain.

Example 2

Membrane Lytic Activity of Recombinant Vault Particles

Figure 3:
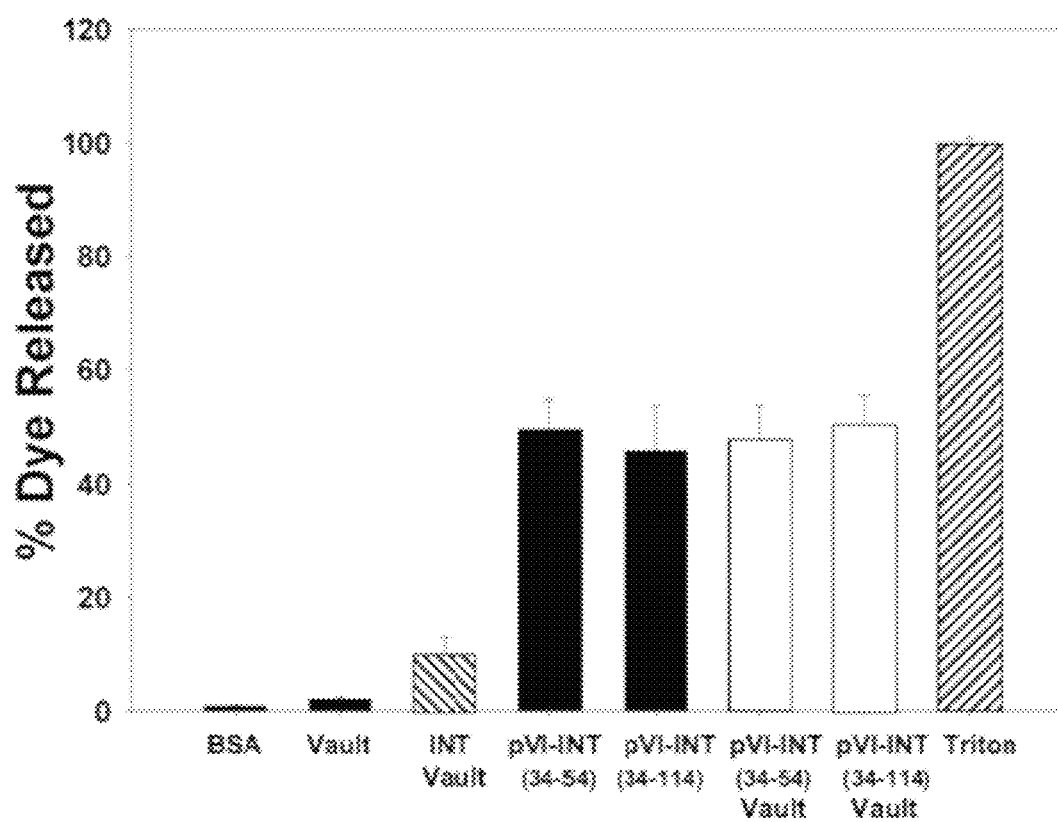
FIG. 3: Disruption of liposomes by recombinant pVI-INT or pVI-INT incorporated into vaults. Unilamellar liposomes containing sulforhodamine B were used to measure fluorescence (dye release) at 585 nm in a cuvette with constant stirring. Background fluorescence was recorded for 60 sec and then the liposomes were incubated at 37° C. with 1 µg of different recombinant pVI-INT proteins (black bars) or 137 µg of vault-INT (grey bar) or 137 µg of different vault-pVI complexes (red bars) was recorded for an interval of 7 minutes. All measurements were performed in triplicate. The membrane lytic activity mediated by the proteins or complexes was expressed as the percentage of dye release relative to that achieved with TRITON-X-100®. Disruption by bovine serum albumin (BSA) or empty vault particles alone were included as a negative control. The data shown is representative of three different experiments.

We measured the membrane lytic activity of pVI-INT fusion proteins alone or pVI-INT fusion proteins incorporated into vault particles using artificial membranes (liposomes) containing an entrapped fluorophore (sulforhodamine B) (FIG. 3). The fluorescence emission of this dye is quenched at the high local concentrations of the liposome but upon membrane disruption and subsequent dilution, it strongly emits fluorescence at 585 nm. The INT domain fused to the N-terminal 34-114 or just the N-terminal 34-53 residues of pVI exhibited substantial membrane lytic activity over a time interval of seven minutes relative to complete release mediated by TRITON-X-100®.The lytic activity of these pVI-INT fusion proteins was also similar to a purified synthetic peptide derived from pVI (pVI-syn, residues 34-54) that lacked the INT domain as well as the full length pVI molecule fused to INT (data not shown). These findings are consistent with previous pVI mutagenesis studies that show the predicted amphipathic α-helical domain (residues 34-53) of pVI is largely responsible for membrane insertion/disruption [18]. The current findings indicate that the membrane lytic domain of pVI retains membrane lytic activity even after fusion to the VPARP INT domain.

Example 3

Liposome Disruption with pVI-INT Vault Particles

Figure 4:
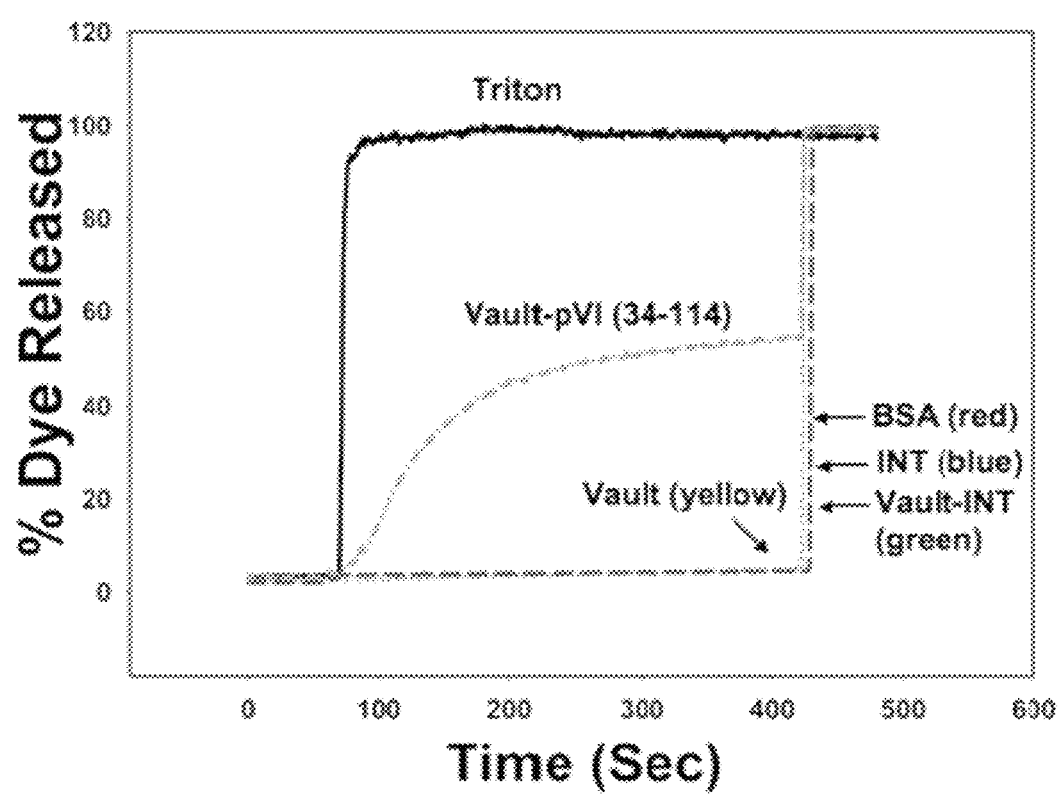
FIG. 4: Time course of liposome disruption by pVI-vaults. Liposomes were incubated for varying lengths of time at 37° C. with 137 µg of empty vault particles (yellow line), vaults containing INT alone (green), or pVI-INT (34-114) (magenta) to disrupt liposomes at 37° C. and the fluorescence emission was recorded as described above. For maximum dye release, TRITON-X-100® was added at the same time (at 420 sec to each sample). Disruption by BSA (red) or INT (blue) alone were included as negative controls.

We sought to determine whether pVI-INT fusion proteins incorporated into recombinant vault particles were capable of mediating liposome disruption (FIG. 3). Vault particles alone showed negligible membrane lytic activity while vaults containing the INT domain exhibited a low level of membrane lysis that was not observed in every experiment. In contrast, vaults containing both the smaller pVI-INT (pVI residues 34-53) and the larger pVI (residues 34-114) fusion proteins caused substantial and consistent membrane disruption. These findings indicate that association of the membrane lytic domain of pVI with vault particles can facilitate membrane disruption. Unexpectedly however, we found that the smaller version of pVI (residues 34-53) was not as efficiently incorporated into vaults (data not shown) as the larger pVI domain (34-114) and therefore we employed the latter construct for additional kinetic and functional analyses. Vaults containing pVI (34-114) caused a rapid and progressive disruption of liposomes as a function of time with 50% maximum disruption occurring at ~2 minutes (FIG. 4). In contrast, empty vaults, the purified INT protein alone, vault-INT, or BSA caused little dye release over this time interval.

Example 4

Cellular Entry of pVI-INT Vault Particles

Figure 5:
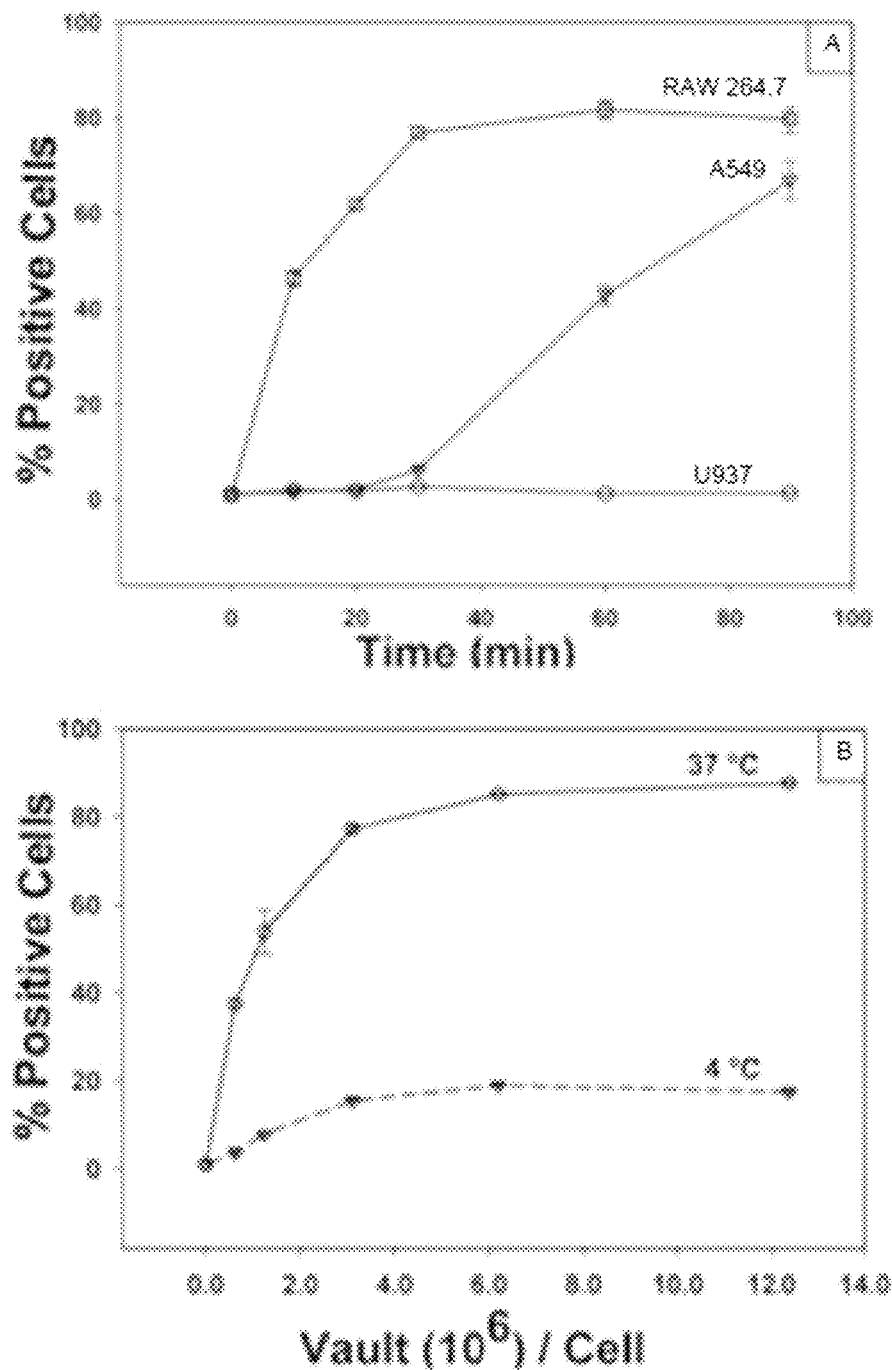
FIG. 5, Panels A and B: Analysis of vault internalization into different mammalian cells.

We examined whether different cell types could support entry of Cy3-labeled vault (empty) particles (FIG. 5, Panel A). These studies used trypan blue dye to quench the fluorescence of externally bound vault particles while allowing detection of internalized vault particles. Murine macrophage RAW 264.7 cells exhibited rapid and substantial internalization of labeled vaults whereas human U937 monocytic cells did not readily support vault internalization. Human A549 epithelial cells also supported significant vault uptake; however, this occurred with slower kinetics than that of RAW 264.7 cells. Vault association with RAW 264.7 cells was also substantially greater at 37° C. than at 4° C. (FIG. 5, Panel B), indicating that the labeled vaults were undergoing internalization into cells rather than simply being bound to the cell surface.

Example 5 pVI-INT Assisted Entry of Selected Biomolecules into RAW 264.7 Macrophages

Figure 6A:
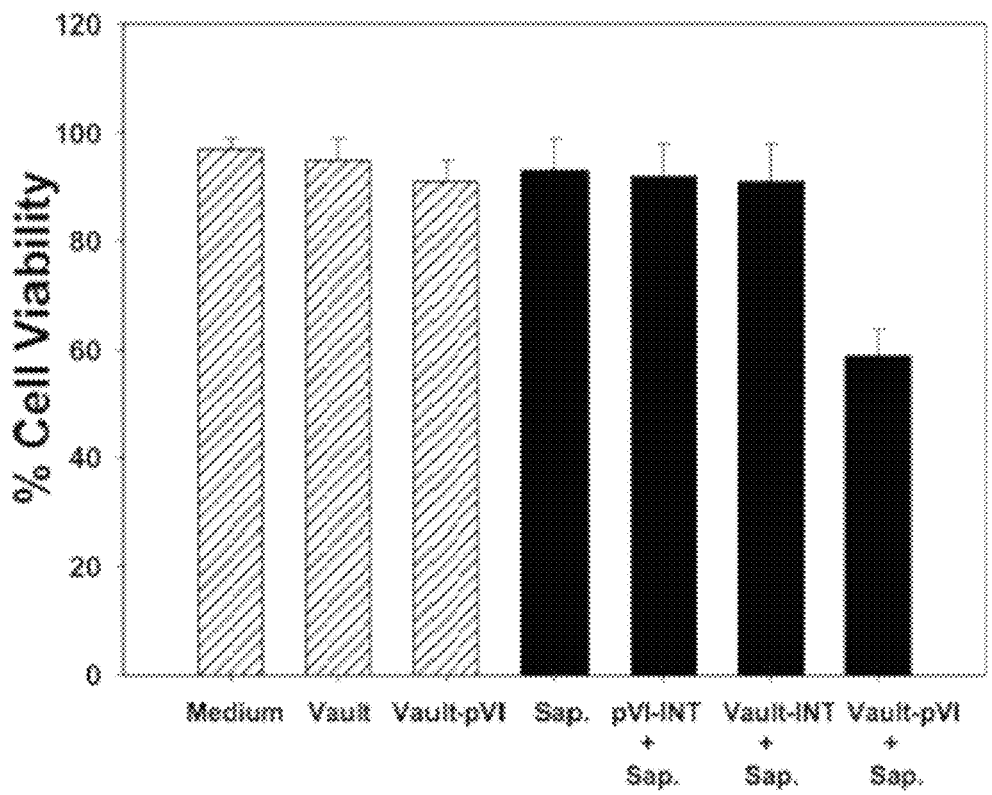
FIGS. 6A-6C: Co-delivery of a ribotoxin (saporin) into cells via pVI-vault particles.

We determined whether pVI-containing vault particles were capable of facilitating entry of selected biomolecules into RAW 264.7 macrophages (FIG. 6A). For these studies we assessed vault-mediated delivery of a soluble ribotoxin (saporin), that blocks host cell protein synthesis and therefore decreases cell viability upon entry into the cytoplasm. Saporin alone in the absence of membrane penetrating agents had little effect on cell viability, consistent with its inability to cross cell membranes. Cell viability was also unaffected by vault particles or vault-pVI complexes in the absence of saporin.

Figure 6B:
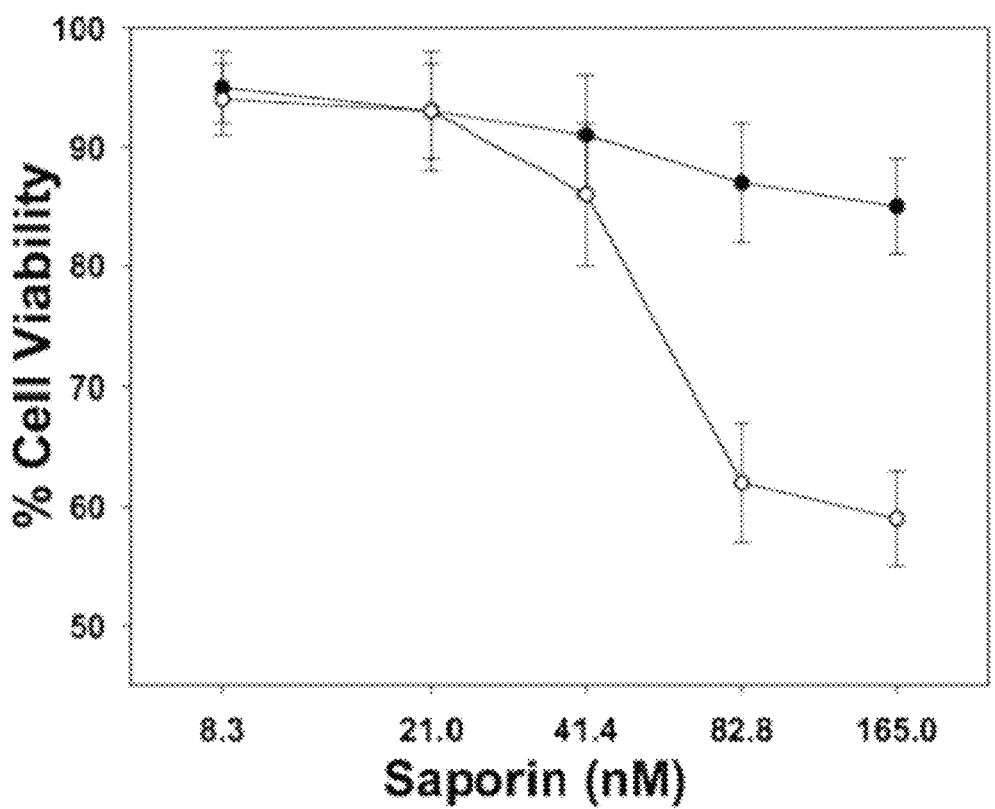
Figure 6C:
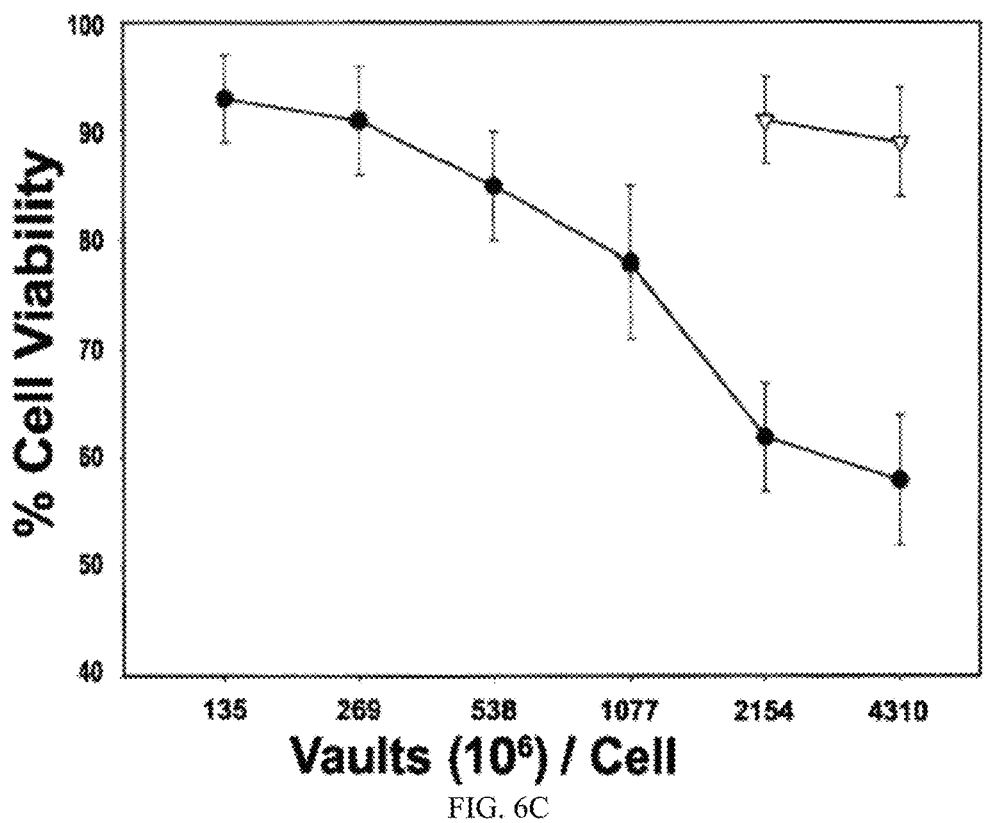

In contrast, vault-pVI (residues 34-114) in the presence of saporin caused a ~40% decrease in cell viability, consistent with significant endosomal membrane disruption by internalized particles. The decrease in cell viability mediated by vault-pVI particles was also directly proportional to the amount of saporin, with a threshold of 21 nM required to reveal RAW 264.7 cell toxicity (FIG. 6B). Cytotoxicity was also directly proportional to the amount of vault-pVI particles added per cell (FIG. 6C).

Example 6 pVI-INT Assisted Gene Transfer into RAW 264.7 Macrophages

Figure 7A:
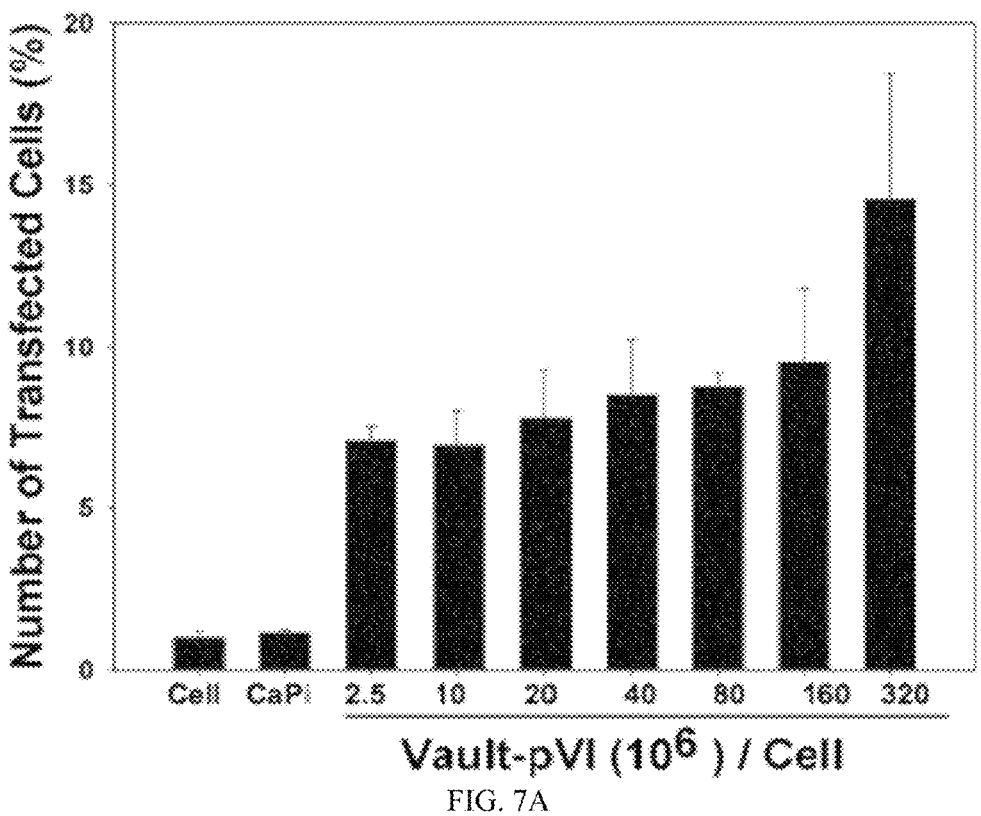
FIGS. 7A and 7B: Enhancement of DNA delivery via pVI-vault particles. Raw 264.7 cells were cultured in the presence of increasing numbers of pVI-vaults (FIG. 7A) or vault-INT particles (FIG. 7B) for 24 hours prior to measuring transgene expression by flow cytometry. For comparison, untransfected cells or cells incubated with calcium phosphate precipitated DNA (CaPi) alone were analyzed in parallel. The data shown are the average of triplicate samples and is representative of at least three experiments.
Figure 7B:
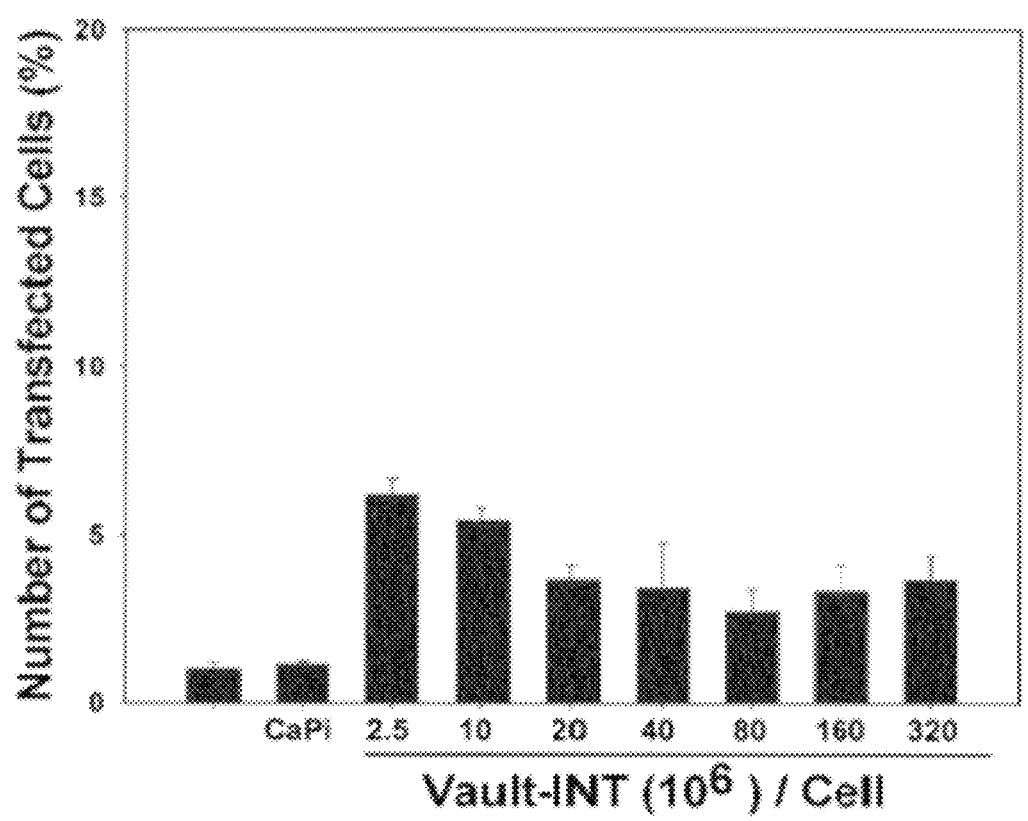

We examined whether pVI-vaults were capable of enhancing gene transfer to RAW 264.7 cells. For these studies, we assessed co-delivery of calcium phosphate precipitated eDNA plasmids encoding GFP (CaPi DNA) in the presence or absence of vaults (FIGS. 7A-7B). Vault particles containing pVI enhanced delivery of GFP plasmid DNA, achieving a ~7-fold higher level of delivery at the highest dose than that observed with calcium phosphate precipitated DNA alone (FIG. 7A). In contrast, vaults containing INT alone conferred relatively low levels (~2-3 fold increase over CaPi alone) of gene transfer and this was independent of input dose (FIG. 7B). These findings indicate that vault-pVI particles are capable of stimulating the transfer of calcium-phosphate precipitated DNA into target cells.

Example 7

Co-Delivery of CaPi DNA by EGF/pVI-INT Vaults

As reported previously, vault particles packaged with pVI-INT were able to facilitate delivery of calcium phosphate precipitated plasmid DNA (CaPi DNA) to RAW cells.[35] We also have shown that vaults engineered to display EGF (MVP-EGF vaults) on their external surface can specifically bind to EGFR on A431 cells.[30] To determine whether targeting the vaults would enhance plasmid transfection, the pVI-INT fusion protein was packaged into the lumen of MVP-EGF vaults pVI-INT/MVP-EGF vaults). We used HeLa and A431 epithelial cell lines expressing different numbers of EGFR on their cell surfaces to evaluate the ability of these vaults to facilitate plasmid transfection (FIG. 1, Panels A and B). These vault particles showed an increase in transfection activity that exceeded that of Lipofectamine 2000 and CaPi DNA when targeted to EGFR (compare FIG. 8, Panels A and B). The highest level of targeted transfection efficiency was seen with 0.1-1×10[5] vaults/cell in A431 cells (FIG. 1, Panel A). Higher numbers of pVI-INT/MVP-EGF vaults induced lower transfection efficiencies probably due to the toxicity of the pVI protein. When HeLa cells were examined, the transfection efficiency of this vault structure was lower than Lipofectamine 2000 (FIG. 1, Panel B). As HeLa cells display many fewer copies of EGFR than A431 cells, this result indicates that the high transfection efficiency of pVI-INT/MVP-EGF vaults in A431 cells resulted from facilitated co-delivery of CaPi DNA to the cells mediated through the ligand-receptor protein interaction.

Example 8

An Alternative pVI Vault Design

Although packaging pVI-INT inside of vaults has been shown to co-deliver various biomolecules, it would be advantageous to develop a particle where the pVI domain is directly attached to the vault particle, leaving the lumen of the particle empty so that additional biomolecules can be packaged inside of these vaults. Towards that goal, we fused a 20 aa lytic peptide derived from pVI (aa 34 to 54) directly onto the N-terminus of MVP (to form pVI-MVP vaults). In these vaults, the pVI would be localized at the waist of the vault particle where other N-terminal tags have been previously shown to localize. [26] Importantly, the INT binding domain on MVP, located above and below the waist of the vault, would be available for binding of additional cargo into these vaults, to add another functional dimension.

Figure 9:
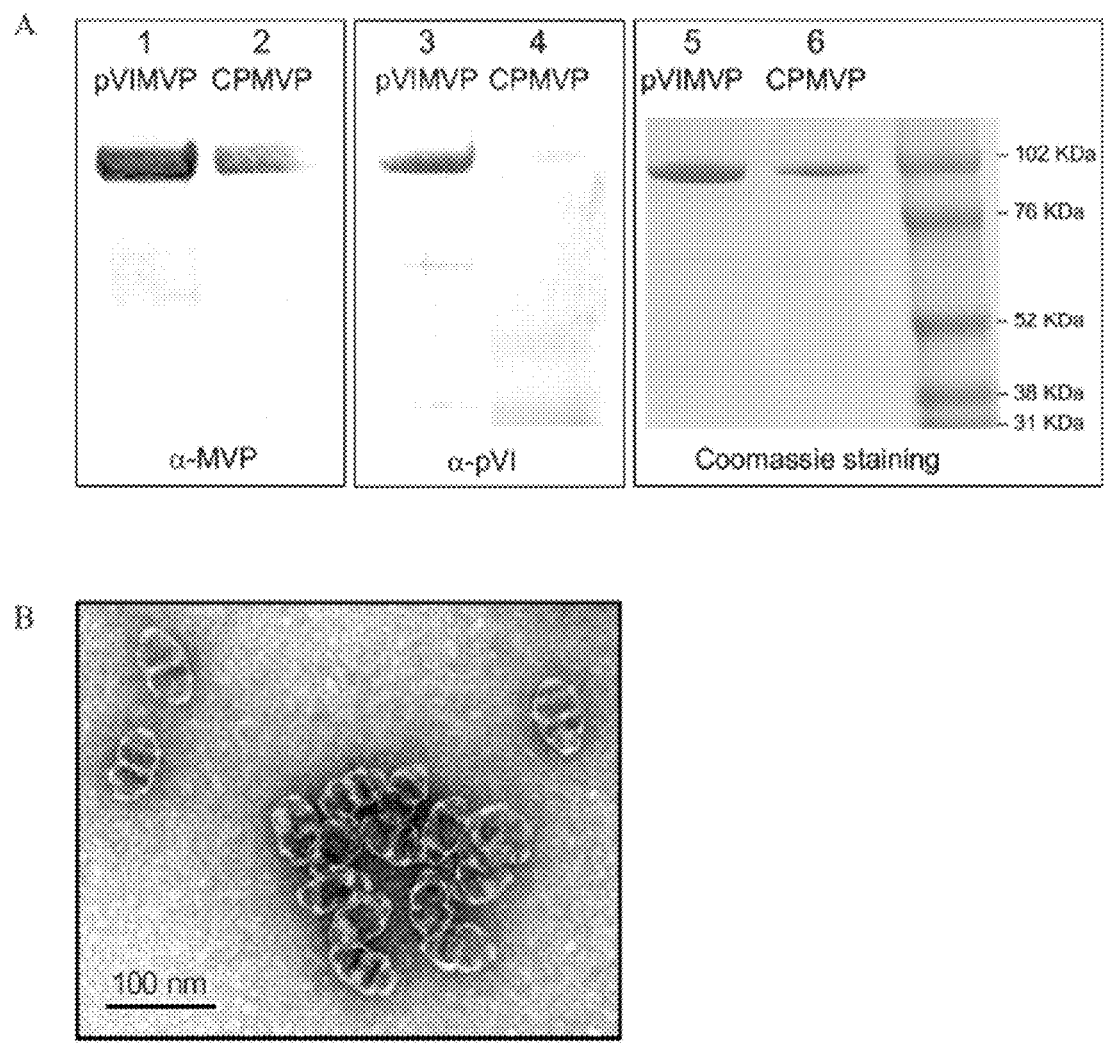
FIG. 9, Panels A and B: Analysis of pVI-MVP recombinant vaults.

Expression of pVI-MVP vaults was compared with CP-MVP vaults in Sf9 insect cells. Vaults which self-assembled from these expressed proteins were purified and analyzed by SDS PAGE (FIG. 9, Panel A). Gels were either stained with Coomassie (FIG. 9, Panel A, lanes 5 and 6) or immunoblotted with an anti-MVP antibody (FIG. 9, Panel A, lanes 1 and 2) or with an anti-pVI antibody (FIG. 9, Panel A, lanes 3 and 4). The results of the Coomassie stained SDS-PAGE confirmed that pVI-MVP vaults were formed in Sf9 insect cells. The presence of the pVI fused to the N-terminus of MVP (~99 KDa) is clearly shown by immunoblotting with an anti-MVP antibody (FIG. 9, Panel A, lane 1) and an anti-pVI antibody (FIG. 9, Panel A, lane 3). Most vault purifications are carried out using 75 mM NaCl, however the pVI-MVP vault structure was sensitive to salt concentration resulting in formation of some half vault aggregates, previously described as vaultimers. [31] These aggregates could be mostly eliminated when vaults were purified using a salt concentration of 25 mM. These purified pVI-MVP vaults were examined by negative stain transmission electron microscopy (FIG. 9, Panel B). The particles observed had the typical morphology of previously published intact mono-dispersed vault particles. [31]

Example 9

Co-Delivery of Ribotoxin by pVI-MVP Vaults

We tested whether pVI-MVP vault particles were able to facilitate the delivery of co-internalized biomolecules into the cytosol of mouse macrophage RAW 264.7 cells (FIG. 10, Panels A and B). For this study, we used a soluble ribotoxin, saporin. Entry of saporin into the cytoplasm results in inhibition of protein synthesis and decrease in cell viability. Saporin alone has low cell toxicity due to its inability to cross the cell membrane (FIG. 10, Panel A). Control vaults (CP-MVP) are also non-toxic, while pVI-MVP vaults at high concentrations decreased cell viability by up to 30%. When pVI-MVP vaults were added to cells in the presence of saporin, a substantially greater cytotoxicity (70% decrease) was observed due to a bystander effect explained by the pVI-mediated lysis of the endosomal membrane and subsequent release of co-internalized saporin. Co-delivery of the ribotoxin by pVI-MVP vaults was also dose-dependent as indicated by studies shown in FIG. 10, Panel B.

Example 10

Co-Delivery of CaPi by pVI-MVP Vaults to RAW Cells

The co-delivery of CaPi DNA by pVI-MVP vaults into 264.7 RAW cells was evaluated as shown in FIG. 11, Panels A-C. For these studies, we assessed delivery of CaPi DNA encoding luciferase in the presence or absence of pVI-MVP vaults. The vault particles containing pVI enhanced delivery of CaPi DNA compared to the addition of CaPi DNA alone or vault particles that did not contain the pVI (FIG. 11, Panel A). Optimal delivery occurred using $4-10\times10^5$ pVI-MVP vaults per cell. When higher numbers of pVI-MVP vaults and/or CaPi DNA were used, lower transfection efficiencies were observed probably due to pVI toxicity. However, pVI-MVP vaults still showed improved transfection efficiencies over CaPi DNA in the range of less than $2\times10^5$ vaults per cell. To visualize the functionality of pVI-MVP vaults, we examined RAW 264.7 cells transfected with Lipofectamine 2000, CP-MVP vaults, and pVI-MVP vaults (FIG. 11, Panel B). Using a higher DNA concentration (10 µg vs 2 µg) pVI-MVP vaults displayed higher transfection efficiencies than CaPi DNA or Lipofectamine 2000 (FIG. 11, Panel C). Here the lower transfection efficiency of Lipofectamine was due to the increased cytotoxicity, while pVI-MVP vaults still showed high transfection efficiencies even considering the toxicity induced by CaPi DNA. Overall we observed lower cytotoxicity of pVI-MVP vaults compared to the commercial Lipofectamine transfection agent under optimized conditions. The enhanced delivery of biomolecules by pVI-MVP vaults is likely due to the high numbers of pVI fused to MVPs. We estimated that only 20 to 30 pVI were conjugated to one vault particle when the INT targeting domain was used [35] while the conjugation of pVI directly to the N-terminus of MVP provided 78 or more pVI-peptides per vault.

Example 11

Disruption of Endosomes by pVI-MVP in RAW Cells

Figure 12:
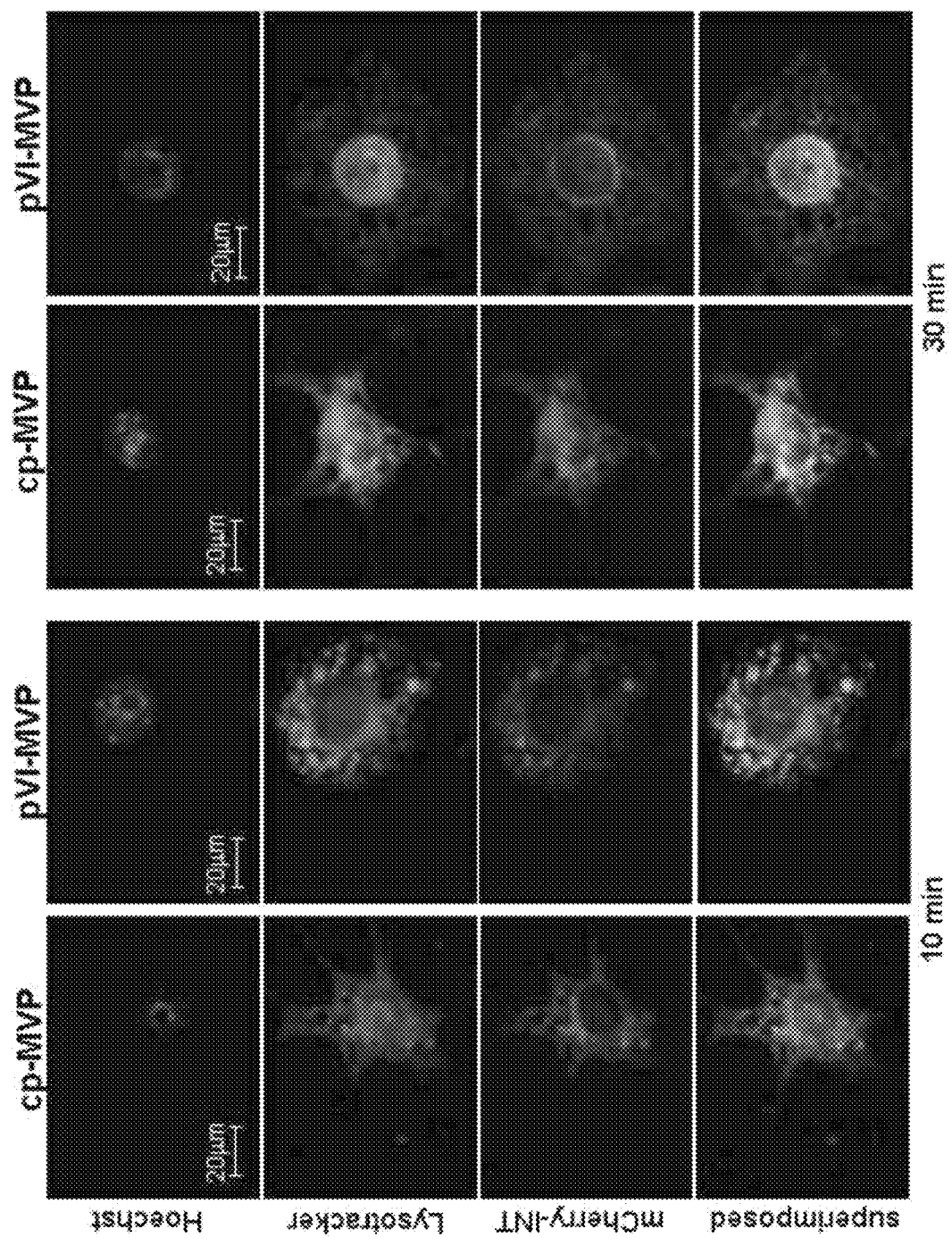
FIG. 12: Swelling and disruption of endosomal/lysosomal membrane by pVI-MVP vaults in RAW cells. Endocytosis of CP-MVP at the identical time points was shown as controls. The nuclei were stained with Hoechst (blue). The lysosomes were stained with Lysotracker (green). The observed red fluorescence is the intrinsic fluorescence from the mCherry protein packaged inside of the vaults.

We examined internalization of pVI-MVP vaults in RAW 264.7 cells by packaging the particles with the red fluorescent, mCherry-INT fusion protein (FIG. 12). Vault particles without pVI (CP-MVP/mCherry-INT vaults) were colocalized with Lysotracker (green) as indicated by punctuate fluorescence at 10 and 30 minutes following cellular uptake. This pattern was quite different when vaults containing the pVI were examined. A distinct endosomal/lysosomal swelling occurred as early as 10 min after pVI-MVP vaults were added (FIG. 12). Strikingly, thirty minutes after uptake of pVI vaults, the Lysotracker staining revealed few if any punctuate vesicles which indicated severe disruption of endosome/lysosomes by the pVI proteins which is consistent with their likely disruption via the established membrane lytic activity of pVI. [33] In addition, cells incubated with pVI vaults showed morphological changes including swelling and spread of cytosol as observed many during the macrophage's response to bacterial infection. [34, 35] Although quite dramatic, the cells recovered from these morphological changes and remained viable as indicated by the transfection results (FIG. 11, Panel B) which were evaluated after 72 h.

Example 12

Multifunctional Recombinant Vaults

With the goal of developing a bifunctional vector that can both target surface receptors and enhance cytosomal release, we designed vault particles combining two functional motifs. Despite the enhanced co-delivery of CaPi DNA facilitated by EGF vaults, those vaults have been shown to stimulate receptor phosphorylation and downstream events such as proliferation. [36,37] To evaluate targeting and facilitated delivery without affecting cell division, we turned to vaults engineered to display the IgG binding, Z domain, on their external surface. [29] Rather than packaging these vaults with the pVI-INT protein, we utilized the strategy described above where a 20 aa lytic peptide derived from pVI is fused to the N-terminus of MVP (to form pVI-MVP-Z vaults)

Figure 13:
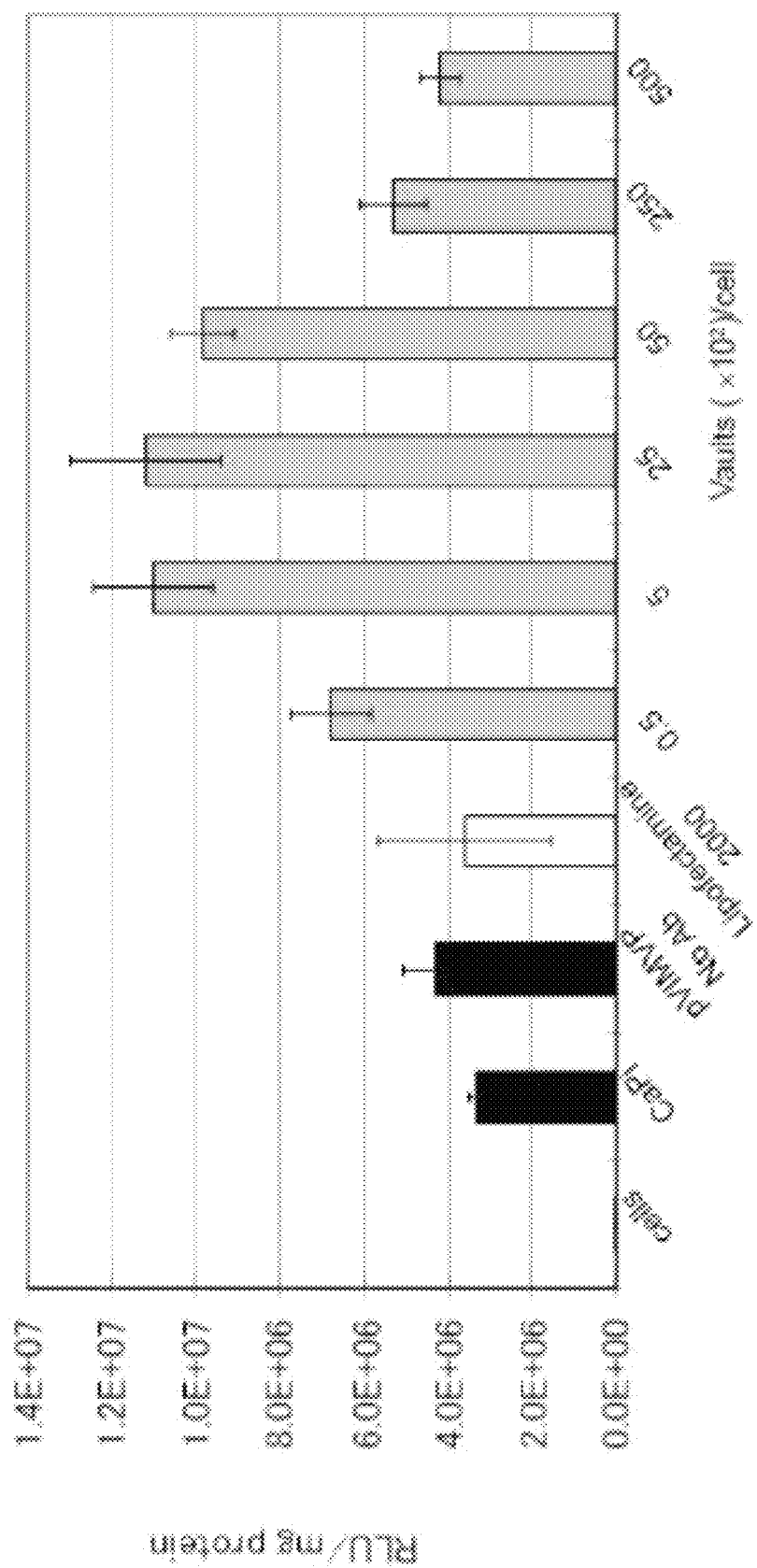
FIG. 13: Transfection efficiencies of pVI-MVP-z and anti-EGFR antibody complexes to A431 cells (1.5 µg of CaPi DNA/well). Control included: CaPi DNA only, pVI-MVP (500×10$_2$ vaults/cell) without antibody, and Lipofectamine 2000.

As shown previously, [29] CP-MVP-Z vaults incubated with anti-EGFR showed high specific binding to A431 cells. We next tested the transfection efficiency of pVI-MVP-Z vaults (FIG. 13). The pVI-MVP-Z vaults were incubated with anti-EGFR antibody overnight at 4° C. to allow binding of antibodies to the Z domain. Antibody bound vaults were incubated with serum starved A431 cells at 4° C. for 1 h to allow surface binding, and the cells were washed to remove unbound complexes prior to the addition of CaPi DNA to the culture media and warming to 37° C. Interestingly, the highest transfection efficiencies that we observed among all the structures tested in this study (pVI-MVP, EGF/pVI-INT, CP-MVP, and pVI-MVP-z), were seen with this engineered vault. As seen in FIG. 13, only 500 pVI-MVP-z vault particles were required to facilitate plasmid expression per cell. As few as 50 pVI-MVP-Z+EGFR mAb vaults per cell achieved greater transfection than Lipofectamine 2000. Furthermore the Lipofectamine 2000 showed high toxicity in this cell line while little or no toxicity was observed with the pVI-MVP-Z+EGFR mAb vault complexes. This result implies that the targeted vaults are efficiently taken up by the A431 cells where they disrupt endosome/lysosome allowing the co-delivery of CaPi DNA into the cytoplasm where it can presumably be transported to the nucleus for expression. The enhanced uptake of vaults was facilitated by the greater binding between the pVI-MVP-Z+EGFR mAb vaults and the receptors on these cells. The specificity of this process was further demonstrated by pre-incubating A431 cells with free EGFR mAB which significantly blocked the binding of anti EGFR-bound vaults to the cells (not shown).

Example 13

Release of Packaged Protein to Cytosol by pVI-MVP-Z Vaults

Figure 14:
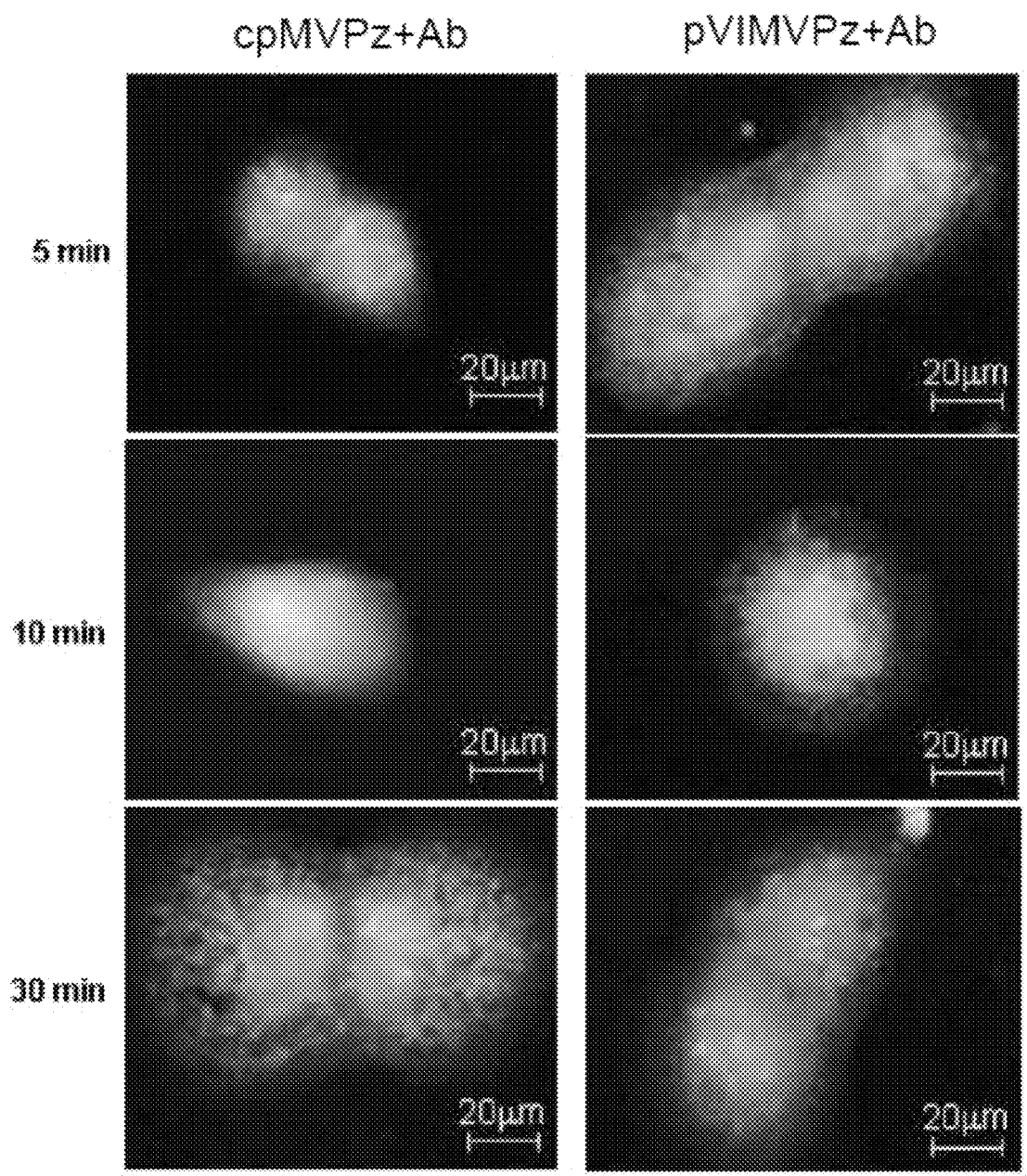
FIG. 14: The enhanced release of vault nanoparticles to cytosol of A431 cells by pVI proteins. The superimposed images were shown. The nuclei were stained with Hoechst (blue). The colocalization of lysosome (Lysotracker with green fluorescence) and vault particles (intrinsic red fluorescence from the mCherry protein packaged inside of the vaults) was shown as yellow.

We observed the endocytosis of antibody bound pVI-MVP-Z vaults in A431 cells by tracking red fluorescent mCherry-INT protein packaged into these particles. The immediate escape of these vaults was observed in areas surrounding the outer rim of cells in less than 5 min after vault addition (FIG. 14). This result is consistent with our previous studies which indicated that vaults containing pVI caused a rapid and progressive disruption of liposomes within ~2 min. [32] We assumed that the instantaneous interaction between pVI and the endosomal membranes occurred shortly after formation of the endosomal/lysosomal compartment. In 30 min, vaults were already released from endosome/lysosomes and located independently within the cytoplasm as shown by the red staining in FIG. 14, while vault particles without pVI proteins were still trapped in Lysotracker-positive compartments.

Taken together these results show that vaults can be engineered as multifunctional non-toxic delivery vehicles that can be targeted to bind cell-specific receptors, enter via endocytosis and efficiently lyse endosomal membranes to deliver a packaged payload to the cell cytoplasm. These particles have the potential to be used for targeted delivery of therapeutics.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 1

Sequences

SEQ ID NO: 1    pVI Protein sequence (Genbank# AAW65513.1)
MEDINFASLAPRHGSRPFMGNWQDIGTSNMSGGAFSWGSLWSGIKNFGSTVKNYGSKAWNSSTGQM
LRDKLKEQNFQQKVVDGLASGISGVVDLANQAVQNKINSKLDPRPPVEEPPPAVETVSPEGRGEKR
PRPDREETLVTQIDEPPSYEEALKQGLPTTRPIAPMATGVLGQHTPVTLDLPPPADTQQKPVLPGP
TAVVVTRPSRASLRRAASGPRSLRPVASGNWQSTLNSIVGLGVQSLKRRRCF SEQ ID NO: 2    pVI lytic peptide (aa 34-53) nucleotide sequence
GCC TTC AGC TGG GGC TCG CTG TGG AGC GGC ATT AAA AAT TTC GGT TCC
ACC GTT AAG AAC SEQ ID NO: 3    pVI lytic peptide (aa 34-53) protein sequence
AFSWGSLWSGIKNFGSTVKN SEQ ID NO: 4    pVI lytic peptide (aa 34-114) nucleotide sequence
AFSWGSLWSGIKNFGSTVKNYGSKAWNSSTGQMLRDKLKEQNFQQKVVDGLASGISGVVDLANQAV
QNKINSKLDPRPPVE SEQ ID NO: 5    mINT DNA sequence
TGC ACA CAA CAC TGG CAG GAT GCT GTG CCT TGG ACA GAA CTC CTC AGT
CTA CAG ACA GAG GAT GGC TTC TGG AAA CTT ACA CCA GAA CTG GGA CTT
ATA TTA AAT CTT AAT ACA AAT GGT TTG CAC AGC TTT CTT AAA CAA AAA
GGC ATT CAA TCT CTA GGT GTA AAA GGA AGA GAA TGT CTC CTG GAC CTA
ATT GCC ACA ATG CTG GTA CTA CAG TTT ATT CGC ACC AGG TTG GAA AAA
GAG GGA ATA GTG TTC AAA TCA CTG ATG AAA ATG GAT GAC CCT TCT ATT
TCC AGG AAT ATT CCC TGG GCT TTT GAG GCA ATA AAG CAA GCA AGT GAA
TGG GTA AGA AGA ACT GAA GGA CAG TAC CCA TCT ATC TGC CCA CGG CTT
GAA CTG GGG AAC GAC TGG GAC TCT GCC ACC AAG CAG TTG CTG GGA CTC
CAG CCC ATA AGC ACT GTG TCC CCT CTT CAT AGA GTC CTC CAT TAC AGT
CAA GGC TAA SEQ ID NO: 6    mINT protein sequence (residues 1563-1724 of
                 the human VPARP protein sequence)
CTQHWQDAVPWTELLSLQTEDGFWKLTPELGLILNLNTNGLHSFLKQKGIQSLGVKGRECLLDLIA
TMLVLQFIRTRLEKEGIVFKSLMKMDDPSISRNIPWAFEAIKQASEWVRRTEGQYPSICPRLELGN
DWDSATKQLLGLQPISTVSPLHRVLHYSQG SEQ ID NO: 8    pVI(aa 34-53)-MVP nucleotide sequence
AANNNGNATTTTACTGTTTTCGTACAGTTTTGTAATAAAAAAACCTATAAATATTCCGGATTATTC
ATACCGTCCCACCATCGGGCGCGGATCCCGGTCCGAAGCGCGCGGAATTCGCGGCCGCGTCGACTG
TGGCTTGCAGCTGCCAGCTACCCTGCTAAATGTTTGGTGGGAAAAGCTTGGGATTCACCATG**GCCT
TCAGCTGGGGCTCGCTGTGGAGCGGCATTAAAAATTTCGGTTCCACCGTTAAGAAC**GGCCTGGTGC
CGCGCGGCAGCGCCATGGCAACTGAAGAGGCCATCATCCGCATCCCCCCATACCACTACATCCATG
TGCTGGACCAGAACAGTAATGTGTCCCGTGTGGAGGTTGGACCAAAGACCTACATCCGGCAGGACA
ATGAGAGGGTACTGTTTGCCCCAGTTCGCATGGTGACCGTCCCCCCACGCCACTACTGCATAGTGG
CCAACCCTGTGTCCCGGGACACCCAGAGTTCTGTGTTATTTGACATCACAGGACAAGTCCGACTCC
GGCACGCTGACCAGGAGATCCGACTAGCCCAGGACCCCTTCCCCCTGTATCCAGGGGAGGTGCTGG
AAAAGGACATCACCCCACTGCAGGTGGTTCTGCCCAACACAGCACTGCATCTTAAGGCGTTGCTGG
ACTTTGAGGATAAGAATGGAGACAAGGTCATGGCAGGAGACGAGTGGCTATTTGAGGGACCTGGCA
CCTACATCCCACAGAAGGAAGTGGAAGTCGTGGAGATCATTCAGGCCACAGTCATCAAACAGAACC
AAGCACTGCGGCTAAGGGCCCGAAAGGAGTGCTTTGACCGGGAGGGCAAGGGGCGCGTGACAGGTG
AGGAGTGGCTGGTCCGATCCGTGGGGGCTTACCTCCCAGCTGTCTTTGAAGAGGTGCTGGATCTGG
TGGATGCTGTGATCCTTACAGAAAAGACTGCCCTGCACCTCCGGGCTCTGCAGAACTTCAGGGACC
TTCGGGGAGTGCTCCACCGCACCGGGGAGGAATGGTTAGTGACAGTGCAGGACACAGAAGCCCATG
TTCCAGATGTCTATGAGGAGGTGCTTGGGGTAGTACCCATCACCACCCTGGGACCTCGACACTACT
GTGTCATTCTTGACCCAATGGGACCAGACGGCAAGAACCAGCTGGGACAAAAGCGTGTTGTCAAGG
GAGAGAAGTCCTTTTTCCTCCAGCCAGGAGAGAGGCTGGAGCGAGGCATCCAGGATGTGTATGTGC
TGTCAGAGCAGCAGGGGCTGCTACTGAAGGCACTGCAGCCCCTGGAGGAGGGAGAGAGCGAGGAGA
AGGTCTCCCATCAGGCCGGAGACTGCTGGCTCATCCGTGGGCCCCTGGAGTATGTGCCATCTGCAA
AAGTGGAGGTGGTGAGGAGCGTCAGGCTATCCCTCTGGACCAAAATGAGGGCATCTATGTGCAGG
ATGTCAAGACGGGGAAGGTGCGGGCTGTGATTGGAAGCACCTACATGCTGACTCAGGATGAAGTCC
TGTGGGAAAAGGAGCTGCCTTCTGGGTGGAGGAGCTGCTGAACTTGGGGCATGACCCTCTGGCAG
ACAGGGGTCAGAAGGGCACAGCCAAGCCCCTTCAGCCCTCAGCTCCAAGGAACAAGACCCGAGTGG TABLE 1-continued Sequences

```
TCAGCTACCGTGTCCCGCACAATGCAGCGGTGCAGGTCTATGACTACAGAGCCAAGAGAGCCCGTG
TGGTCTTTGGGCCCGAGCTAGTGACACTGGATCCTGAGGAGCAGTTCACAGTATTGTCCCTTTCTG
CCGGGCGACCCAAGCGTCCTCATGCCCGCCGTGCACTCTGCCTACTGCTGGGACCTGATTTCTTTA
CTGATGTCATCACCATCGAAACTGCAGATCATGCCAGGTTGCAGCTGCAGCTTGCCTACAACTGGC
ACTTTGAACTGAAGAACCGGAATGACCCTGCAGAGGCAGCCAAGCTTTTCTCCGTGCCTGACTTCG
TGGGTGACGCCTGCAAGGCCATTGCATCCCGAGTCCGGGGGGCTGTAGCCTCTGTCACCTTTGATG
ACTTCCATAAAAACTCAGCCCGGATCATTCGAATGGCTGTTTTTGGCTTTGAGATGTCTGAAGACA
CAGGTCCTGATGGCACACTCCTGCCCAAGGCTCGAGACCAGGCAGTCTTTCCCCAAAACGGGCTGG
TAGTCAGCAGTGTGGATGTGCAGTCAGTGGAGCCCGTGGACCAGAGGACCCGGGATGCCCTTCAGC
GCAGCGTTCAGCTGGCCATCGAAATTACCACCAACTCCCAGGAGGCAGCAGCCAAGCACGAGGCTC
AGAGACTGGAACAGGAAGCCCGTGGTCGGCTTGAGAGGCAGAAGATCTTGGACCAGTCAGAAGCTG
AAAAAGCCCGCAAGGAACTCTTGGAGCTTGAGGCTATGAGCATGGCTGTGGAGAGCACGGGTAATG
CCAAAGCAGAGGCTGAGTCCCGTCAGAGGCAGCGAGGATCGAAGGAGAAGGCTCTGTGCTGCAGG
CCAAGCTCAAGGCACAGGCGCTAGCCATTGAGACGGAGGCTGAGTTGGAGCGAGTAAAGAAAGTAC
GAGAGATGGAACTGATCTATGCCCGGGCCCAGTTGGAGCTGGAGGTGAGCAAGGCGCAGCAGCTTG
CCAATGTGGAGGCAAAGAAGTTCAAGGAGATGACAGAGGCACTGGGCCCCGGCACCATCAGGGACC
TGGCTGTGGCCGGGCCAGAGATGCAGGTGAAACTTCTCCAGTCCCTGGGCCTGAAATCCACTCTCA
TCACCGATGGCTCGTCTCCCATCAACCTCTTCAGCACAGCCTTCGGGTTGCTGGGGCTGGGGTCTG
ATGGTCAGCCGCCAGCACAGAAG
```

SEQ ID NO: 9    pVI(aa 34-53)-MVP amino acid sequence

MAFSWGSLWSGIKNFGSTVKNGLVPRGSAMATEEAIIRIPPYHYIHVLDQNSNVSRVEVGPKTYIR
QDNERVLFAPVRMVTVPPRHYCIVANPVSRDTQSSVLFDITGQVRLRHADQEIRLAQDPFPLYPGE
VLEKDITPLQVVLPNTALHLKALLDFEDKNGDKVMAGDEWLFEGPGTYIPQKEVEVVEIIQATVIK
QNQALRLRARKECFDREGKGRVTGEEWLVRSVGAYLPAVFEEVLDLVDAVILTEKTALHLRALQNF
RDLRGVLHRTGEEWLVTVQDTEAHVPDVYEEVLGVVPITTLGPRHYCVILDPMGPDGKNQLGQKRV
VKGEKSFFLQPGERLERGIQDVYVLSEQQGLLLKALQPLEEGESEEKVSHQAGDCWLIRGPLEYVP
SAKVEVVEERQAIPLDQNEGIYVQDVKTGKVRAVIGSTYMLTQDEVLWEKELPSGVEELLNLGHDP
LADRGQKGTAKPLQPSAPRNKTRVVSYRVPHNAAVQVYDYRAKRARVVFGPELVTLDPEEQFTVLS
LSAGRPKRPHARRALCLLLGPDFFTDVITIETADHARLQLQLAYNWHFELKNRNDPAEAAKLFSVP
DFVGDACKAIASRVRGAVASVTFDDFHKNSARIIRMAVFGFEMSEDTGPDGTLLPKARDQAVFPQN
GLVVSSVDVQSVEPVDQRTRDALQRSVQLAIEITTNSQEAAAKHEAQRLEQEARGRLERQKILDQS
EAEEKARKELLELEAMSMAVESTGNAKAEAESRAEAARIEGEGSVLQAKLKQALAIETEAELERVK
KVREMELIYARAQLELEVSKAQQLANVEAKKFKEMTEALGPGTIRDLAVAGPEMQVKLLQSLGLKS
TLITDGSSPINLFSTAFGLLGLGSDGQPPAQK

SEQ ID NO: 10    pVI(aa 34-53)-MVP-Z nucleotide sequence (pVI domain in bold, Z domain underlined)

```
AANNNGNATTTTACTGTTTTCGTACAGTTTTGTAATAAAAAAACCTATAAATATTCCGGATTATTC
ATACCGTCCCACCATCGGGCGCGGATCCCGGTCCGAAGCGCCGAAGTTCGCGGCCGCGTCGACTG
TGGCTTGCAGCTGCCAGCTACCCTGCTAAATGTTTGGTGGGAAAAGCTTGGGATTCACCATGGCCT
TCAGCTGGGGCTCGCTGTGGAGCGGCATTAAAAATTTCGGTTCCACCGTTAAGAACGGCCTGGTGC
CGCGCGGCAGCGCCATGGCAACTGAAGAGGCCATCATCCGCATCCCCCCATACCACTACATCCATG
TGCTGGACCAGAACAGTAATGTGTCCCGTGTGGAGGTTGGACCAAAGACCTACATCCGGCAGACA
ATGAGAGGGTACTGTTTGCCCCAGTTCGCATGGTGACCGTCCCCCCACGCCACTACTGCATAGTGG
CCAACCCTGTGTCCCGGGACACCCAGAGTTCTGTGTTATTTGACATCACAGGACAAGTCCGACTCC
GGCACGCTGACCAGGAGATCCGACTAGCCCAGGACCCCTTCCCCCTGTATCCAGGGGAGGTGCTGG
AAAAGGACATCACCCCACTGCAGGTGGTTCTGCCCAACACAGCACTCATCTTAAGGCGTTGCTGG
ACTTTGAGGATAAGAATGGAGACAAGGTCATGGCAGGAGACGAGTGGCTATTTGAGGGACCTGGCA
CCTACATCCCACAGAAGGAAGTGGAAGTCGTGGAGATCATTCAGGCCACAGTCATCAAACAGAACC
AAGCACTGCGGCTAAGGGCCCGAAAGGAGTGCTTTGACCGGGAGGGCAAGGGGCGCGTGACAGGTG
AGGAGTGGCTGGTCCGATCCGTGGGGGCTTACCTCCCAGCTGTCTTTGAAGAGGTGCTGGATCTGG
TGGATGCTGTGATCCTTACAGAAAAGACTGCCCTGCACCTCCGGGCTCTGCAGAACTTCAGGGACC
TTCGGGGAGTGCTCCACCGCACCGGGGAGGAATGGTTAGTGACAGTGCAGGACACAGAAGCCCATG
TTCCAGATGTCTATGAGGAGGTGCTTGGGGTAGTACCCATCACCACCCTGGGACCTCGACACTACT
GTGTCATTCTTGACCCAATGGGACCAGACGGCAAGAACCAGCTGGGACAAAAGCGTGTTGTCAAGG
GAGAGAAGTCCTTTTTCCTCCAGCCAGGAGAGAGGCTGGAGCGAGGCATCCAGGATGTGTATGTGC
TGTCAGAGCAGCAGGGGCTGCTACTGAAGGCACTGCAGCCCCTGGAGGAGGGAGAGAGCGAGGAGA
AGGTCTCCCATCAGGCCGGAGACTGCTGGCTCATCCGTGGGCCCCTGGAGTATGTGCCATCTGCAA
AAGTGGAGGTGGTGGAGGAGCGTCAGGCTATCCCTCTGGACCAAAATGAGGGCATCTATGTGCAGG
ATGTCAAGACGGGGAAGGTGCGGGCTGTGATTGGAAGCACCTACATGCTGACTCAGGATGAAGTCC
TGTGGGAAAAGGAGCTGCCTTCTGGGGTGGAGGAGCTGCTGAACTTGGGCATGACCCTCTGGCAG
ACAGGGGTCAGAAGGGCACAGCCAAGCCCCTTCAGCCCTCAGCTCCAAGGAACAAGACCCGAGTGG
TCAGCTACCGTGTCCCGCACAATGCAGCGGTGCAGGTCTATGACTACAGAGCCAAGAGAGCCCGTG
TGGTCTTTGGGCCCGAGCTAGTGACACTGGATCCTGAGGAGCAGTTCACAGTATTGTCCCTTTCTG
CCGGGCGACCCAAGCGTCCTCATGCCCGCCGTGCACTCTGCCTACTGCTGGGACCTGATTTCTTTA
CTGATGTCATCACCATCGAAACTGCAGATCATGCCAGGTTGCAGCTGCAGCTTGCCTACAACTGGC
ACTTTGAACTGAAGAACCGGAATGACCCTGCAGAGGCAGCCAAGCTTTTCTCCGTGCCTGACTTCG
TGGGTGACGCCTGCAAGGCCATTGCATCCCGAGTCCGGGGGGCTGTAGCCTCTGTCACCTTTGATG
ACTTCCATAAAAACTCAGCCCGGATCATTCGAATGGCTGTTTTTGGCTTTGAGATGTCTGAAGACA
CAGGTCCTGATGGCACACTCCTGCCCAAGGCTCGAGACCAGGCAGTCTTTCCCCAAAACGGGCTGG
TAGTCAGCAGTGTGGATGTGCAGTCAGTGGAGCCCGTGGACCAGAGGACCCGGGATGCCCTTCAGC
GCAGCGTTCAGCTGGCCATCGAAATTACCACCAACTCCCAGGAGGCAGCAGCCAAGCACGAGGCTC
AGAGACTGGAACAGGAAGCCCGTGGTCGGCTTGAGAGGCAGAAGATCTTGGACCAGTCAGAAGCTG
AAAAAGCCCGCAAGGAACTCTTGGAGCTTGAGGCTATGAGCATGGCTGTGGAGAGCACGGGTAATG
CCAAAGCAGAGGCTGAGTCCCGTCAGAGGCAGCGAGGATCGAAGGAGAAGGCTCTGTGCTGCAGG
CCAAGCTCAAGGCACAGGCGCTAGCCATTGAGACGGAGGCTGAGTTGGAGCGAGTAAAGAAAGTAC
GAGAGATGGAACTGATCTATGCCCGGGCCCAGTTGGAGCTGGAGGTGAGCAAGGCGCAGCAGCTTG
```

TABLE 1-continued

Sequences

```
CCAATGTGGAGGCAAAGAAGTTCAAGGAGATGACAGAGGCACTGGGCCCCGGCACCATCAGGGACC
TGGCTGTGGCCGGGCCAGAGATGCAGGTGAAACTTCTCCAGTTGCAGCTGAAATCCACTCTCA
TCACCGATGGCTCGTCTCCCATCAACCTCTTCAGCACAGCCTTCGGGTTGCTGGGGCTGGGGTCTG
ATGGTCAGCCGCCAGCACAGAAGTTTAACATGCAGCAGCAGCGCCGCTTTTACGAGGCCCTGCACG
ACCCCAACCTGAACGAGGAGCAGCGCAACGCCAAGATTAAGAGCATTCGCGACGACTAGGGTACCT
CAG
```

SEQ ID NO: 11   pVI-MVP-Z amino acid sequence (pVI domain in bold, Z domain underlined)

MAFSWGSLWSGIKNFGSTVKNGLVPRGSAMATEEAIIRIPPYHYIHVLDQNSNVSRVEVGPKTYIR
QDNERVLFAPVRMVTVPPRHYCIVANPVSRDTQSSVLFDITGQVRLRHADQEIRLAQDPFPLYPGE
VLEKDITPLQVVLPNTALHLKALLDFEDKNGDKVMAGDEWLFEGPGTYIPQKEVEVVEIIQATVIK
QNQALRLRARKECFDREGKGRVTGEEWLVRSVGAYLPAVFEEVLDLVDAVILTEKTALHLRALQNF
RDLRGVLHRTGEEWLVTVQDTEAHVPDVYEEVLGVVPITTLGPRHYCVILDPMGPDGKNQLGQKRV
VKGEKSFFLQPGERLERGIQDVYVLSEQQGLLLKALQPLEEGESEEKVSHQAGDCWLIRGPLEYVP
SAKVEVVEERQAIPLDQNEGIYVQDVKTGKVRAVIGSTYMLTQDEVLWEKELPSGVEELLNLGHDP
LADRGQKGTAKPLQPSAPRNKTRVVSYRVPHNAAVQVYDYRAKRARVVFGPELVTLDPEEQFTVLS
LSAGRPKRPHARRALCLLLGPDFFTDVITIETADHARLQLQLAYNWHFELKNRNDPAEAAKLFSVP
DFVGDACKAIASRVRGAVASVTFDDFHKNSARIIRMAVFGFEMSEDTGPDGTLLPKARDQAVFPQN
GLVVSSVDVQSVEPVDQRTRDALQRSVQLAIEITTNSQEAAAKHEAQRLEQEARGRLERQKILDQS
EAEKARKELLELEAMSMAVESTGNAKAEAESRAEAARIEGEGSVLQAKLKAQALAIETEAELERVK
KVREMELIYARAQLELEVSKAQQLANVEAKKFKEMTEALGPGTIRDLAVAGPEMQVKLLQSLGLKS
TLITDGSSPINLFSTAFGLLGLGSDGQPPAQK<u>FNMQQQRRFYEALHDPNLNEEQRNAKIKSIRDD</u>

SEQ ID NO: 12   pVI-mINT fusion DNA sequence (pVI domain in bold, mINT domain underlined)

**atg gcc ttc agc tgg ggc tcg ctg tgg agc ggc att aaa aat ttc ggt tcc acc
gtt aag aac** tat ggc aag gcc tgg aac agc agc aca ggc cag atg ctg agg
gat aag ttg aaa gag caa aat ttc caa caa aag gtg gta gat ggc ctg gcc tct
ggc att agc ggg gtg gtg gac ctg gcc aac cag gca gtg caa aat aag att aac
agt aag ctt gat ccc cgc cct ccc gta gag gga tcc gaa ttc ggc acg agg cgg
<u>tgc aca caa cac tgg cag gat gct gtg cct tgg aca gaa ctc ctc agt cta cag
aca gag gat ggc ttc tgg aaa ctt aca cca gaa ctg gga ctt ata tta aat ctt
aat aca aat ggt ttg cac agc ttt ctt aaa caa aaa ggc att caa tct cta ggt
gta aaa gga aga gaa tgt ctc ctg gac cta att gcc aca atg ctg gta cta cag
ttt att cgc acc agg ttg gaa aaa gag gga gtg ttc aaa tca ctg atg aaa
atg gat gac cct tct att tcc agg aat att ccc tgg gct ttt gag gca ata aag
caa gca agt gaa tgg gta aga aga act gaa gga cag tac cca tct atc tgc cca
cgg ctt gaa ctg ggg aac gac tgg gac tct gcc acc aag cag ttg ctg gga ctc
cag ccc ata agc act gtg tcc cct ctt cat aga gtc ctc cat tac agt caa ggc
taa</u>

SEQ ID NO: 13   pVI-mINT fusion Protein sequence (pVI domain in bold, mINT domain underlined)

MAFSWGSLWS GIKNFGSTVK NYGSKAWNSS TGQMLRDKLK EQNFQQKVVD GLASGISGVV
DLANQAVQNK INSKLDPRPP VEGSEFGTRR <u>CTQHWQDAVP WTELLSLQTE DGFWKLTPEL
GLILNLNTNG LHSFLKQKGI QSLGVKGREC LLDLIATMLV LQFIRTRLEK EGIVFKSLMK
MDDPSISRNI PWAFEAIKQA SEWVRRTEGQ YPSICPRLEL GNDWDSATKQ LLGLQPISTV
SPLHRVLHYS QG</u>

SEQ ID NO: 14   VPARP protein sequence (Genbank #AAD47250)

Met Val Met Gly Ile Phe Ala Asn Cys Ile Phe Cys Leu Lys Val Lys Tyr Leu
Pro Gln Gln Gln Lys Lys Lys Leu Gln Thr Asp Ile Lys Glu Asn Gly Gly Lys
Phe Ser Phe Ser Leu Asn Pro Gln Cys Thr His Ile Ile Leu Asp Asn Ala Asp
Val Leu Ser Gln Tyr Gln Leu Asn Ser Ile Gln Lys Asn His Val His Ile Ala
Asn Pro Asp Phe Ile Trp Lys Ser Ile Arg Glu Lys Arg Leu Leu Asp Lys Lys
Asn Tyr Asp Pro Tyr Lys Pro Leu Asp Ile Thr Pro Pro Asp Gln Lys Ala
Ser Ser Ser Glu Val Lys Thr Glu Gly Leu Cys Pro Asp Ser Ala Thr Glu Glu
Glu Asp Thr Val Glu Leu Thr Glu Phe Gly Met Gln Asn Val Glu Ile Pro His
Leu Pro Gln Asp Phe Glu Val Ala Lys Tyr Asn Thr Leu Glu Lys Val Gly Met
Gly Gly Gly Gln Glu Ala Val Val Val Glu Gln Leu Cys Ser Arg Asp Ser Arg
Asp Cys Pro Phe Leu Ile Ser Ser His Phe Leu Leu Asp Asp Gly Met Glu Thr
Arg Arg Gln Phe Ala Ile Lys Lys Thr Ser Glu Asp Ala Ser Glu Tyr Phe Glu
Asn Tyr Ile Glu Glu Leu Lys Lys Gln Gly Phe Leu Leu Arg Glu His Phe Thr
Pro Glu Ala Thr Gln Leu Ala Ser Gln Leu Asn Leu Leu Leu Glu Val Gly
Val Met Asn Ser Ser Thr Leu Ser Gln Glu Val Ser Asp Leu Val Glu Met Ile
Trp Ala Glu Ala Leu Gly His Leu Glu His Met Leu Leu Lys Pro Val Asn Arg
Ile Ser Leu Asn Asp Val Ser Lys Ala Glu Gly Ile Leu Leu Leu Val Lys Ala
Ala Leu Lys Asn Gly Glu Thr Ala Glu Gln Leu Lys Lys Met Met Thr Glu Phe
Tyr Arg Leu Ile Pro His Lys Gly Thr Met Pro Lys Glu Val Asn Leu Gly Leu
Leu Ala Lys Lys Ala Asp Leu Cys Gln Leu Ile Arg Asp Met Val Asn Val Cys
Glu Thr Asn Leu Ser Lys Pro Asn Pro Pro Ser Leu Ala Lys Tyr Arg Ala Leu
Arg Cys Lys Ile Glu His Val Glu Gln Asn Thr Val Glu Leu Arg Val Arg
Lys Glu Val Leu Gln Asn His His Ser Lys Ser Pro Val Asp Val Leu Gln Ile
Phe Arg Val Gly Arg Val Asn Glu Thr Thr Glu Phe Leu Ser Lys Leu Gly Asn
Val Arg Pro Leu Leu His Gly Ser Pro Val Gln Asn Ile Val Gly Ile Leu Cys
Arg Gly Leu Leu Leu Pro Lys Val Val Glu Asp Arg Gly Val Gln Arg Thr Asp
Val Gly Asn Leu Gly Ser Gly Ile Tyr Phe Ser Asp Ser Leu Ser Thr Ser Ile

TABLE 1-continued

Sequences

Lys Tyr Ser His Pro Gly Glu Thr Asp Gly Thr Arg Leu Leu Leu Ile Cys Asp
Val Ala Leu Gly Lys Cys Met Asp Leu His Glu Lys Asp Phe Pro Leu Thr Glu
Ala Pro Pro Gly Tyr Asp Ser Val His Gly Val Ser Gln Thr Ala Ser Val Thr
Thr Asp Phe Glu Asp Asp Glu Phe Val Val Tyr Lys Thr Asn Gln Val Lys Met
Lys Tyr Ile Ile Lys Phe Ser Met Pro Gly Asp Gln Ile Lys Asp Phe His Pro
Ser Asp His Thr Glu Leu Glu Glu Tyr Arg Pro Gly Phe Ser Asn Phe Ser Lys
Val Glu Asp Tyr Gln Leu Pro Asp Ala Lys Thr Ser Ser Thr Lys Ala Gly
Leu Gln Asp Ala Ser Gly Asn Leu Val Pro Leu Glu Asp Val His Ile Lys Gly
Arg Ile Ile Asp Thr Val Ala Gln Val Ile Val Phe Gln Thr Tyr Thr Asn Lys
Ser His Val Pro Ile Glu Ala Lys Tyr Ile Phe Pro Leu Asp Asp Lys Ala Ala
Val Cys Gly Phe Glu Ala Phe Ile Asn Gly Lys His Ile Val Gly Val Glu Lys
Glu Lys Glu Glu Ala Gln Gln Glu Tyr Leu Glu Ala Val Thr Gln Gly His Gly
Ala Tyr Leu Met Ser Gln Asp Ala Pro Asp Val Phe Thr Val Ser Val Gly Asn
Leu Pro Pro Lys Ala Lys Val Leu Ile Lys Ile Thr Tyr Ile Thr Glu Leu Ser
Ile Leu Gly Thr Val Gly Val Phe Phe Met Pro Ala Thr Val Ala Pro Trp Gln
Gln Asp Lys Ala Leu Asn Glu Asn Leu Gln Asp Thr Val Glu Lys Ile Cys Ile
Lys Glu Ile Gly Thr Lys Gln Ser Phe Ser Leu Thr Met Ser Ile Glu Met Pro
Tyr Val Ile Glu Phe Ile Phe Ser Asp Thr His Glu Leu Lys Gln Lys Arg Thr
Asp Cys Lys Ala Val Ile Ser Thr Met Glu Gly Ser Leu Asp Ser Ser Gly
Phe Ser Leu His Ile Gly Leu Ser Ala Ala Tyr Leu Pro Arg Met Trp Val Glu
Lys His Pro Glu Lys Glu Ser Glu Ala Cys Met Leu Val Phe Gln Pro Asp Leu
Asp Val Asp Leu Pro Asp Leu Ala Ser Glu Ser Glu Val Ile Ile Cys Leu Asp
Cys Ser Ser Met Glu Gly Val Thr Phe Leu Gln Ala Lys Gln Ile Thr Leu
His Ala Leu Ser Leu Val Gly Glu Lys Gln Lys Val Asn Ile Ile Gln Phe Gly
Thr Gly Tyr Lys Glu Leu Phe Ser Tyr Pro Lys His Ile Thr Ser Asn Thr Thr
Ala Ala Glu Phe Ile Met Ser Ala Thr Pro Thr Met Gly Asn Thr Asp Phe Trp
Lys Thr Leu Arg Tyr Leu Ser Leu Leu Tyr Pro Ala Arg Gly Ser Arg Asn Ile
Leu Leu Val Ser Asp Gly His Leu Gln Asp Glu Ser Leu Thr Leu Gln Leu Val
Lys Arg Ser Arg Pro His Thr Arg Leu Phe Ala Cys Gly Ile Gly Ser Thr Ala
Asn Arg His Val Leu Arg Ile Leu Ser Gln Cys Gly Ala Gly Val Phe Glu Tyr
Phe Asn Ala Lys Ser Lys His Ser Trp Arg Lys Gln Ile Glu Asp Gln Met Thr
Arg Leu Cys Ser Pro Ser Cys His Ser Val Ser Val Lys Trp Gln Gln Leu Asn
Pro Asp Ala Pro Glu Ala Leu Gln Ala Pro Ala Gln Val Pro Ser Leu Phe Arg
Asn Asp Arg Leu Leu Val Tyr Gly Phe Ile Pro His Cys Thr Gln Ala Thr Leu
Cys Ala Leu Ile Gln Glu Lys Glu Phe Cys Thr Met Val Ser Thr Thr Glu Leu
Gln Lys Thr Thr Gly Thr Met Ile His Lys Leu Ala Ala Arg Ala Leu Ile Arg
Asp Tyr Glu Asp Gly Ile Leu His Glu Asn Glu Thr Ser His Glu Met Lys Lys
Gln Thr Leu Lys Ser Leu Ile Ile Lys Leu Ser Lys Glu Asn Ser Leu Ile Thr
Gln Phe Thr Ser Phe Val Ala Val Glu Lys Arg Asp Glu Asn Glu Ser Pro Phe
Pro Asp Ile Pro Lys Val Ser Glu Leu Ile Ala Lys Glu Gly Val Asp Phe Leu
Pro Tyr Met Ser Trp Gln Gly Glu Pro Gln Glu Ala Val Arg Asn Gln Ser Leu
Leu Ala Ser Ser Glu Trp Pro Glu Leu Arg Leu Ser Lys Arg Lys His Arg Lys
Ile Pro Phe Ser Lys Arg Lys Met Glu Leu Ser Gln Pro Glu Val Ser Glu Asp
Phe Glu Glu Asp Gly Leu Gly Val Leu Pro Ala Phe Thr Ser Asn Leu Gly Arg
Gly Gly Val Glu Lys Leu Leu Asp Leu Ser Trp Thr Glu Ser Cys Lys Pro Thr
Ala Thr Glu Pro Leu Phe Lys Lys Val Ser Pro Trp Glu Thr Ser Thr Ser Ser
Phe Phe Pro Ile Leu Ala Pro Ala Val Gly Ser Tyr Leu Thr Pro Thr Thr Arg
Ala His Ser Pro Ala Ser Leu Ser Phe Ala Ser Tyr Arg Gln Val Ala Ser Phe
Gly Ser Ala Ala Pro Pro Arg Gln Phe Asp Ala Ser Gln Phe Ser Gln Gly Pro
Val Pro Gly Thr Cys Ala Asp Trp Ile Pro Gln Ser Ala Ser Cys Pro Thr Gly
Pro Pro Gln Asn Pro Ser Ala Pro Tyr Cys Gly Ile Val Phe Ser Gly Ser
Ser Leu Ser Ser Ala Gln Ser Ala Pro Leu His Pro Gly Gly Phe Thr Thr
Arg Pro Ser Ala Gly Thr Phe Pro Glu Leu Asp Ser Pro Gln Leu His Phe Ser
Leu Pro Thr Asp Pro Asp Pro Ile Arg Gly Phe Gly Ser Tyr His Pro Ser Ala
Tyr Ser Pro Phe His Phe Gln Pro Ser Ala Ala Ser Leu Thr Ala Asn Leu Arg
Leu Pro Met Ala Ser Leu Pro Glu Ala Cys Ser Gln Ser Arg Gly Thr Thr
Pro Val Asp Leu Cys Leu Leu Glu Glu Ser Val Gly Ser Leu Glu Gly Ser Arg
Cys Pro Val Phe Ala Phe Gln Ser Ser Asp Thr Glu Ser Asp Glu Leu Ser Glu
Val Leu Gln Asp Ser Cys Phe Leu Gln Ile Lys Cys Asp Thr Lys Asp Asp Ser
Ile Pro Cys Phe Leu Glu Leu Lys Glu Glu Asp Glu Ile Val Cys Thr Gln His
Trp Gln Asp Ala Val Pro Trp Thr Glu Leu Leu Ser Leu Thr Arg Thr Glu Gly
Phe Trp Lys Leu Thr Pro Glu Leu Gly Leu Ile Leu Asn Leu Asn Thr Asn Gly
Leu His Ser Phe Leu Lys Gln Lys Gly Ile Gln Ser Leu Gly Val Lys Gly Arg
Glu Cys Leu Leu Asp Leu Ile Ala Thr Met Leu Val Leu Gln Phe Ile Arg Thr
Arg Leu Glu Leu Lys Glu Gly Ile Val Phe Lys Ser Leu Val Met Asp Pro Met
Ser Ile Ser Arg Asn Ile Pro Trp Ala Phe Glu Ala Ile Lys Gln Ala Ser Glu
Trp Val Arg Arg Thr Glu Gly Gln Tyr Pro Ser Ile Cys Pro Arg Leu Glu Leu
Gly Asn Asp Trp Asp Ser Ala Thr Lys Gln Leu Leu Gly Leu Gln Pro Ile Ser
Thr Val Ser Pro Leu His Arg Val Leu His Tyr Ser Gln Gly

SEQ ID NO: 15    VPARP cDNA, Genbank #AF158255
atggtgatgg gaatctttgc aaattgtatc ttctgtttga aagtgaagta cttacctcag
cagcagaaga aaaagctaca aactgacatt aaggaaaatg gcggaaagtt ttccttttcg
ttaaatcctc agtgcacaca tataatctta gataatgctg atgttctgag tcagtaccaa
ctgaattcta tccaaaagaa ccacgttcat attgcaaacc agattttat atggaaatct
atcagagaaa agagactctt ggatgtaaag aattatgatc cttataagcc cctggacatc
acaccaccte ctgatcagaa ggcgagcagt tctgaagtga aaacagaagg tctatgcccg
gacagtgcca cagaggagga agacactgtg gaactcactg agtttggtat gcagaatgtt TABLE 1-continued Sequences

```
gaaattcctc atcttcctca agattttgaa gttgcaaaat ataacacctt ggagaaagtg
ggaatggagg gaggccagga agctgtggtg gtggagcttc agtgttcgcg ggactccagg
gactgtcctt tcctgatatc ctcacacttc ctcctggatg atggcatgga gactagaaga
cagtttgcta taaagaaaac ctctgaagat gcaagtgaat actttgaaaa ttacattgaa
gaactgaaga aacaaggatt tctactaaga gaacatttca cacctgaagc aacccaatta
gcatctgaac aattgcaagc attgcttttg gaggaagtca tgaattcaag cactctgagc
caagaggtga gcgatttagt agagatgatt tgggcagagg ccctgggcca cctggaacac
atgcttctca agccagtgaa caggattagc ctcaacgatg tgagcaaggc agaggggatt
ctccttctag taaaggcagc actgaaaaat ggagaaacag cagagcaatt gcaaaagatg
atgacagagt tttacagact gataccttac aaaggcacaa tgcccaaaga agtgaacctg
ggactattgg ctaagaaagc agacctctgc cagctaataa gagacatggt taatgtctgt
gaaactaatt tgtccaaacc caacccacca tccctggcca aataccgagc tttgaggtgc
aaaattgagc atgttgaaca gaatactgaa gaatttctca gggttagaaa agaggttttg
cagaatcatc acagtaagag cccagtggat gtcttgcaga tatttagagt tggcagagtg
aatgaaacca cagagttttt gagcaaactt ggtaatgtga ggcccttgtt gcatggttct
cctgtacaaa acatcgtggg aatcttgtgt cgagggttgc ttttacccaa agtagtggaa
gatcgtggtg tgcaaagaac agacgtcgga aaccttggaa gtgggattta tttcagtgat
tcgctcagta caagtatcaa gtactcacac ccggagagaa cagatggcac cagactcctg
ctcatttgtg acgtagccct cggaaagtgt atggacttac atgagaagga ctttccctta
actgaagcac caccaggcta cgacagtgtg catggagttt cacaaacagc ctctgtcacc
acagactttg aggatgatga atttgttgtc tataaaacca atcaggttaa aatgaaatat
attattaaat tttccatgcc tggagatcag ataaaggact ttcatcctag tgatcatact
gaattagagg aatacagacc tgagtttca aatttttcaa aggttgaaga ttaccagtta
ccagatgcca aaacttccag cagcaccaag gccggcctcc aggatgcctc tgggaacttg
gttcctctgg aggatgtcca catcaaaggg agaatcatag acactgtagc ccaggtcatt
gtttttcaga catacacaaa taaaagtcac gtgcccattg aggcaaaata tatctttcct
ttggatgaca aggccgctgt gtgtggcttc gaagccttca tcaatgggaa gcacatagtt
ggagagatta agagaaggaa gaagcccag caagagtacc tagaagccgt gacccagggc
catgcgcctt acctgatgag tcaggatgct ccggacgttt ttactgtaag tgttggaaac
ttaccccta aggctaaggt tctttataaaa attacctaca tcacagaact cagcatcctg
ggcactgttg gtgtctttt catgcccgcc accgtagcac cctggcaaca ggacaaggct
ttgaatgaaa accttcagga tacagtagag aagatttgta taaagaaat aggaacaaag
caaagcttct ctttgactat gtctattgag atgccgtatg tgattgaatt catttcagt
gatacacatg aactgaaaca aaagcgcaca gactgcaaag ctgtcattag caccatggaa
ggcagctcct tagacagcag tggattttct ctccacatcg gtttgtctgc tgcctatctc
ccaagaatgt gggttgaaaa acatccagaa aaagaaagcg aggcttgcat gcttgtcttt
caacccgatc tcgatgtcga cctccctgac ctagccagtg agagcgaagt gattatttgt
cttgactgct ccagttccat ggagggtgtg acattcttgc aagccaagca aatcaccttg
catgcgctgt ccttggtggg tgagaagcag aaagtaaata ttatccagtt cggcacaggt
tacaaggagc tattttcgta tcctaagcat atcacaagca ataccacggc agcagagttc
atcatgtctg ccacacctac catggggaac acagacttct ggaaaacact ccgatatctt
agcttattgt accctgctcg agggtcacgg aacatcctcc tggtgtctga tgggcacctc
caggatgaga gcctgacatt acagctcgtg aagaggagcc gcccgcacac caggttattc
gcctgcggta tcggttctac agcaaatcgt cacgtcttaa ggattttgtc ccagtgtggt
gccggagtat ttgaatattt taatgcaaaa tccaagcata gttggagaaa acagatagaa
gaccaaatga ccaggctatg ttctccgagt tgccactctg tctccgtcaa atggcagcaa
ctcaatccag atgcgcccga ggccctgcag gccccagccc aggtgccatc cttgtttcgc
aatgatcgac tccttgtcta tggattcatt cctcactgca cacaagcaac tctgtgtgca
ctaattcaag agaaagaatt ttgtacaatg gtgtcgacta ctgagcttca gaagacaact
ggaactatga tccacaagct ggcagcccga gctctaatca gagattatga agatggcatt
cttcacgaaa atgaaaccag tcatgagatg aaaaaacaaa ccttgaaatc tctgattatt
aaactcagta aagaaaactc tctcataaca caatttacaa gctttgtggc agttgagaaa
agggatgaga atgagtcgcc ttttcctgat attccaaaag tttctgaact tattgccaaa
gaagatgtag acttcctgcc ctacatgagc tggcagggg agcccaaga agccgtcagg
aaccagtctc ttttagcatc ctctgagtgg ccagaattac gtttatccaa acgaaaacat
aggaaaattc cattttccaa aagaaaaatg gaattatctc agccagaagt ttctgaagat
tttgaagagg atggcttagg tgtactacca gctttcacat caaatttgga acgtggaggt
gtggaaaagc tattggattt aagttggaca gagtcatgta aaccaacagc aactgaacca
ctatttaaga agtcagtcc atgggaaaca tctacttcta gctttttcc tattttggct
ccggccgttg gttcctatct taccccgact acccgcgctc acagtcctgc ttccttgtct
tttgcctcat atcgtcaggt agctagtttc ggttcagctg ctcctcccag acagtttgat
gcatctcaat tcagccaagg ccctgtgcct ggcacttgtg ctgactggat cccacagtcg
gcgtcttgtc ccacaggacc tccccagaac ccaccttctg cacccattg tggcattgtt
ttttcaggga gctcattaag ctctgcacag tctgctccac tgcaacatcc tggaggcttt
actaccaggc cttctgctgg caccttccct gagctggatt ctccccagct tcatttctct
cttcctacag accctgatcc catcagaggt tttgggtctt atcatccctc tgcttactct
ccttttcatt ttcaaccttc cgcagcctct ttgactgcca accttaggct gccaatggcc
tctgctttac ctgaggctct ttgcagtcag tcccggacta ccccagtaga tctctgtctt
ctagaagaat cagtaggcag tctgaagga agtcgatgtc ctgtctttgc ttttcaaagt
tctgacacag aaagtgatga gctatcagaa gtacttcaag acagctgctt tttacaaata
aagtgtgata caaaagatga cagtatcccg tgctttctgg aattaaaaga agaggatgaa
atagtgtgca cacaacactg gcaggatgct gtgccttgga cagaactcct cagtctacag
acagaggatg gcttctggaa acttacacca gaactgggac ttatattaaa tcttaataca
```

TABLE 1-continued

Sequences aatggtttgc acagctttct taaacaaaaa ggcattcaat ctctaggtgt aaaaggaaga
gaatgtctcc tggacctaat tgccacaatg ctggtactac agtttattcg caccaggttg
gaaaaagagg gaatagtgtt caaatcactg atgaaaatgg atgaccctc tatttccagg
aatattccct gggctttga ggcaataaag caagcaagtg aatgggtaag aagaactgaa
ggacagtacc catctatctg cccacggctt gaactgggga acgactggga ctctgccacc
aagcagttgc tgggactcca gcccataagc actgtgtccc ctcttcatag agtcctccat
tacagtcaag gctaa SEQ ID NO: 16   MVP (Genbank #CAA56256)
Met Ala Thr Glu Glu Phe Ile Ile Arg Ile Pro Pro Tyr His Tyr Ile His Val
Leu Asp Gln Asn Ser Asn Val Ser Arg Val Glu Val Gly Pro Lys Thr Tyr Ile
Arg Gln Asp Asn Glu Arg Val Leu Phe Ala Pro Met Arg Met Val Thr Val Pro
Pro Arg His Tyr Cys Thr Val Ala Asn Pro Val Ser Arg Asp Ala Gln Gly Leu
Val Leu Phe Asp Val Thr Gly Gln Val Arg Leu Arg His Ala Asp Leu Glu Ile
Arg Leu Ala Gln Asp Pro Phe Pro Leu Tyr Pro Gly Glu Val Leu Glu Lys Asp
Ile Thr Pro Leu Gln Val Val Leu Pro Asn Thr Ala Leu His Leu Lys Ala Leu
Leu Asp Phe Glu Asp Lys Asp Gly Asp Lys Val Val Ala Gly Asp Glu Trp Leu
Phe Glu Gly Pro Gly Thr Tyr Ile Pro Arg Lys Glu Val Glu Val Val Glu Ile
Ile Glu Ala Thr Ile Ile Arg Gln Asn Gln Ala Leu Arg Leu Arg Ala Arg Lys
Glu Cys Trp Asp Arg Asp Gly Lys Glu Arg Val Thr Gly Glu Glu Trp Leu Val
Thr Thr Val Gly Ala Tyr Leu Pro Ala Val Phe Glu Glu Val Leu Asp Leu Val
Asp Ala Val Ile Leu Thr Glu Lys Thr Ala Leu His Leu Arg Ala Arg Arg Asn
Phe Arg Asp Phe Arg Gly Val Ser Arg Arg Thr Gly Glu Glu Trp Leu Val Thr
Val Gln Asp Thr Glu Ala His Val Pro Asp Val His Glu Glu Val Leu Gly Val
Val Pro Ile Thr Thr Leu Gly Pro His Asn Tyr Cys Val Ile Leu Asp Pro Val
Gly Pro Asp Gly Lys Asn Gln Leu Gly Gln Lys Arg Val Val Lys Gly Glu Lys
Ser Phe Phe Leu Gln Pro Gly Glu Gln Leu Glu Gln Gly Ile Gln Asp Val Tyr
Val Leu Ser Glu Gln Gln Gly Leu Leu Leu Arg Ala Leu Gln Pro Leu Glu Glu
Gly Glu Asp Glu Glu Lys Val Ser His Gln Ala Gly Asp His Trp Leu Ile Arg
Gly Pro Leu Glu Tyr Val Pro Ser Ala Lys Val Glu Val Val Glu Glu Arg Gln
Ala Ile Pro Leu Asp Glu Asn Gly Ile Tyr Val Gln Asp Val Lys Thr Gly
Lys Val Arg Ala Val Ile Gly Ser Thr Tyr Met Leu Thr Gln Asp Glu Val Leu
Trp Glu Lys Glu Leu Pro Pro Gly Val Glu Glu Leu Leu Asn Lys Gly Gln Asp
Pro Leu Ala Asp Arg Gly Glu Lys Asp Thr Ala Lys Ser Leu Gln Pro Leu Ala
Pro Arg Asn Lys Thr Arg Val Val Ser Tyr Arg Val Pro His Asn Ala Ala Val
Gln Val Tyr Asp Tyr Arg Glu Lys Arg Ala Arg Val Val Phe Gly Pro Glu Leu
Val Ser Leu Gly Pro Glu Glu Gln Phe Thr Val Leu Ser Leu Ser Ala Gly Arg
Pro Lys Arg Pro His Ala Arg Arg Ala Leu Cys Leu Leu Leu Gly Pro Asp Phe
Phe Thr Asp Val Ile Thr Ile Glu Thr Ala Asp His Ala Arg Leu Gln Leu Gln
Leu Ala Tyr Asn Trp His Phe Glu Val Asn Asp Arg Lys Asp Pro Gln Glu Thr
Ala Lys Leu Phe Ser Val Pro Asp Phe Val Gly Asp Ala Cys Lys Ala Ile Ala
Ser Arg Val Arg Gly Ala Val Ala Ser Val Thr Phe Asp Asp Phe His Lys Asn
Ser Ala Arg Ile Ile Arg Thr Ala Val Phe Gly Phe Glu Thr Ser Glu Ala Lys
Gly Pro Asp Gly Met Ala Leu Pro Arg Pro Arg Gly Gln Ala Val Phe Pro Gln
Asn Gly Leu Val Val Ser Ser Val Asp Val Gln Ser Val Glu Pro Val Asp Gln
Arg Thr Arg Asp Ala Leu Gln Arg Ser Val Gln Leu Ala Ile Glu Ile Thr Thr
Asn Ser Gln Glu Ala Ala Ala Lys His Glu Ala Gln Arg Leu Glu Gln Glu Ala
Arg Gly Arg Leu Glu Arg Gln Lys Ile Leu Asp Gln Ser Glu Ala Glu Lys Ala
Arg Lys Glu Leu Leu Glu Leu Glu Ala Leu Ser Met Ala Val Glu Ser Thr Gly
Thr Ala Lys Ala Glu Ala Glu Ser Arg Ala Glu Ala Ala Arg Ile Glu Gly Glu
Gly Ser Val Leu Gln Ala Lys Leu Lys Ala Gln Ala Leu Ala Ile Glu Thr Glu
Ala Glu Leu Gln Arg Val Gln Lys Val Arg Glu Leu Glu Leu Val Tyr Ala Arg
Ala Gln Leu Glu Leu Glu Val Ser Lys Ala Gln Gln Leu Ala Glu Val Glu Val
Lys Lys Phe Lys Gln Met Thr Glu Ala Ile Gly Pro Ser Thr Ile Arg Asp Leu
Ala Val Ala Gly Pro Glu Met Gln Val Lys Leu Leu Gln Ser Leu Gly Leu Lys
Ser Thr Leu Ile Thr Asp Gly Ser Thr Pro Ile Asn Leu Phe Asn Thr Ala Phe
Gly Leu Leu Gly Met Gly Pro Glu Gly Gln Pro Leu Gly Arg Arg Val Ala Ser
Gly Pro Ser Pro Gly Glu Gly Ile Ser Pro Gln Ser Ala Gln Ala Pro Gln Ala
Pro Gly Asp Asn His Val Val Pro Val Leu Arg SEQ ID NO: 17   MVP cDNA, Genbank #X79882
atggcaactg aagagttcat catccgcatc cccccatacc actatatcca tgtgctggac
cagaacagca acgtgtcccg tgtggaggtc gggccaaaga cctacatccg caggacaat
gagagggtac tgtttgcccc catgcgcatg gtgaccgtcc ccccacgtca ctactgcaca
gtgccaaacc ctgtgtctcg ggatgccag ggcttggtgc tgtttgatgt cacaggcaa
gttcggcttc gccacgctga cctcgagatc cggctggccc aggacccctt ccccctgtac
ccaggggagg tgctggaaaa ggacatcaca ccctgcagg tggttctgcc caacactgcc
ctccatctaa aggcgctgct tgattttgag gataaagatg gagacaaggt ggtggcagga
gatgagtggc ttttcgaggg acctggcacg tacatccccc ggaaggaagt ggaggtcgtg
gagatcattc aggccaccat catcaggcag aaccaggctc tgcggctcag ggcccgcaag
gagtgctggg accggacgg caaggagagg gtgacagggg aagaatggct ggtcaccaca
gtaggggcgt acctcccagc ggtgtttgag gaggttctgg atttggtgga cgccgtcatc
cttacggaaa agacagccct gcacctccgg gctcggcgga acttccggga cttcagggga
gtgtcccgcc gcactgggga ggagtggctg gtaacagtgc aggacacaga ggcccacgtg
ccagatgtcc acgaggaggt gctggggtt gtgcccatca ccaccctggg cccccacacc
tactgcgtga ttctcgaccc tgtcggaccg gatggcaaga atcagctggg gcagaagcgc
gtggtcaagg gagagaagtc tttttcctc cagccaggag agcagctgga acaaggcatc
caggatgtgt atgtgctgtc ggagcagcag gggctgctgc tgagggccct gcagcccctg

TABLE 1-continued

Sequences

```
gaggaggggg aggatgagga gaaggtctca caccaggctg gggaccactg gctcatccgc
ggacccctgg agtatgtgcc atctgccaaa gtggaggtgg tggaggagcg ccaggccatc
cctctagacg agaacgaggg catctatgtg caggatgtca agaccggaaa ggtgcgcgct
gtgattggaa gcacctacat gctgacccag gacgaagtcc tgtgggagaa agagctgcct
cccgggtgg aggagctgct gaacaagggg caggaccctc tggcagacag gggtgagaat
gacacagcta agagcctcca gcccttggcg ccccggaaca agacccgtgt ggtcagctac
cgcgtgcccc acaacgctgc ggtgcaggtg tacgactacg gagagaagcg agcccgcgtg
gtcttcgggc ctgagctggt gtcgctgggt cctgaggagc agttcacagt gttgtccctc
tcagctgggc ggcccaagcg tcccatgcc cgccgtgcgc tctgcctgct gctgggcct
gacttcttca cagacgtcat caccatcgaa acggcggatc atgccaggct gcaactgcag
ctggcctaca actggcactt tgaggtgaat gaccggaagg accccaaga gacggccaag
ctcttttcag tgccagactt tgtaggtgat gcctgcaaag ccatcgcatc ccgggtgcgg
ggggccgtgg cctctgtcac tttcgatgac ttccataaga actcagcccg catcattcgc
actgctgtct ttggctttga gacctcgaa gcgaagggcc ccgatggcat ggccctgccc
aggcccggg accaggctgt cttcccccaa aacgggctgg tggtcagcag tgtggacgtg
cagtcagtgg agcctgtgga tcagaggacc cgggacgccc tgcaacgcag cgtccagctg
gccatcgaga tcaccaccaa ctcccaggaa gcggcggcca agcatgaggc tcagagactg
gagcaggaag cccgcggccg gcttgagcgg cagaagatcc tggaccagtc agaagccgag
aaagctcgca aggaacttt ggagctggag gctctgagca tggccgtgga gagcaccggg
actgccaagg cggaggccga gtcccgtgcg gaggcagccc ggattgaggg agaagggtcc
gtgctgcagg ccaagctaaa agcacaggcc ttggccattg aaacggaggc tgagctccag
agggtccaga aggtccgaga gctggaactg gtctatgccc gggcccagct ggagctggag
gtgagcaagg ctcagcagct ggctgaggtg gaggtgaaga agttcaagca gatgacagag
gccataggcc ccagcaccat cagggacctt gctgtggctg ggcctgagat gcaggtaaaa
ctgctccagt ccctgggcct gaaatcaacc ctcatcaccg atggctccac tcccatcaac
ctcttcaaca cagcctttgg gctgctgggg atggggcccg agggtcagcc cctgggcaga
agggtggcca gtgggcccag ccctggggag gggatatccc cccagtctgc tcaggcccct
caagctcctg gagacaacca cgtggtgcct gtactgcgct aa
```

SEQ ID NO: 18    CP Peptide  
Met Ala Gly Cys Gly Cys Pro Cys Gly Cys Gly Ala

SEQ ID NO: 19    CP-MVP  
Met Ala Gly Cys Gly Cys Pro Cys Gly Cys Gly Ala Met Ala Thr Glu Glu Phe  
Ile Ile Arg Ile Pro Pro Tyr His Tyr Ile His Val Leu Asp Gln Asn Ser Asn  
Val Ser Arg Val Glu Val Gly Pro Lys Thr Tyr Ile Arg Gln Asp Asn Glu Arg  
Val Leu Phe Ala Pro Met Arg Met Val Thr Val Pro Pro Arg His Tyr Cys Thr  
Val Ala Asn Pro Val Ser Arg Asp Ala Gln Gly Leu Val Leu Phe Asp Val Thr  
Gly Gln Val Arg Leu Arg His Ala Asp Leu Glu Ile Arg Leu Ala Gln Asp Pro  
Phe Pro Leu Tyr Pro Gly Glu Val Leu Glu Lys Asp Ile Thr Pro Leu Gln Val  
Val Leu Pro Asn Thr Ala Leu His Leu Lys Ala Leu Leu Asp Phe Glu Asp Lys  
Asp Gly Asp Lys Val Val Ala Gly Asp Glu Trp Leu Phe Glu Gly Pro Gly Thr  
Tyr Ile Pro Arg Lys Glu Val Glu Val Val Glu Ile Ile Gln Ala Thr Ile Ile  
Arg Gln Asn Gln Ala Leu Arg Leu Arg Ala Arg Lys Glu Cys Trp Asp Arg Asp  
Gly Lys Glu Arg Val Thr Gly Glu Glu Trp Leu Val Thr Thr Val Gly Ala Tyr  
Leu Pro Ala Val Phe Glu Glu Val Leu Asp Leu Val Asp Ala Val Ile Leu Thr  
Glu Lys Thr Ala Leu His Leu Arg Ala Arg Arg Asn Phe Arg Asp Phe Arg Gly  
Val Ser Arg Arg Thr Gly Glu Glu Trp Leu Val Thr Val Gln Asp Thr Glu Ala  
His Val Pro Asp Val His Glu Glu Val Leu Gly Val Val Pro Ile Thr Thr Leu  
Gly Pro His Asn Tyr Cys Val Ile Leu Asp Pro Val Gly Pro Asp Gly Lys Asn  
Gln Leu Gly Gln Lys Arg Val Val Lys Gly Glu Lys Ser Phe Phe Leu Gln Pro  
Gly Glu Gln Leu Glu Gln Gly Ile Gln Asp Val Tyr Val Leu Ser Glu Gln Gln  
Gly Leu Leu Leu Arg Ala Leu Gln Pro Leu Glu Glu Gly Glu Asp Glu Glu Lys  
Val Ser His Gln Ala Gly Asp His Trp Leu Ile Arg Gly Pro Leu Glu Tyr Val  
Pro Ser Ala Lys Val Glu Val Val Glu Glu Arg Gln Ala Ile Pro Leu Asp Glu  
Asn Glu Gly Ile Tyr Val Gln Asp Val Lys Thr Gly Lys Val Arg Ala Val Ile  
Gly Ser Thr Tyr Met Leu Thr Gln Asp Glu Val Leu Trp Glu Lys Glu Leu Pro  
Pro Gly Val Glu Glu Leu Leu Asn Lys Gly Gln Asp Pro Leu Ala Asp Arg Gly  
Glu Lys Asp Thr Ala Lys Ser Leu Gln Pro Leu Ala Pro Arg Asn Lys Thr Arg  
Val Val Ser Tyr Arg Val Pro His Asn Ala Ala Val Gln Val Tyr Asp Tyr Arg  
Glu Lys Arg Ala Arg Val Val Phe Gly Pro Glu Leu Val Ser Leu Gly Pro Glu  
Glu Gln Phe Thr Val Leu Ser Leu Ser Ala Gly Arg Pro Lys Arg Pro His Ala  
Arg Arg Ala Leu Cys Leu Leu Leu Gly Pro Asp Phe Phe Thr Asp Val Ile Thr  
Ile Glu Thr Ala Asp His Ala Arg Leu Gln Leu Gln Leu Ala Tyr Asn Trp His  
Phe Glu Val Asn Asp Arg Lys Asp Pro Gln Glu Thr Ala Lys Leu Phe Ser Val  
Pro Asp Phe Val Gly Asp Ala Cys Lys Ala Ile Ala Ser Arg Val Arg Gly Ala  
Val Ala Ser Val Thr Phe Asp Asp Phe His Lys Asn Ser Ala Arg Ile Ile Arg  
Thr Ala Val Phe Gly Phe Glu Thr Ser Glu Ala Lys Gly Pro Asp Gly Met Ala  
Leu Pro Arg Pro Arg Asp Gln Ala Val Phe Pro Gln Asn Gly Leu Val Val Ser  
Ser Val Asp Val Gln Ser Val Glu Pro Val Asp Gln Arg Thr Arg Asp Ala Leu  
Gln Arg Ser Val Gln Leu Ala Ile Glu Ile Thr Thr Asn Ser Gln Glu Ala Ala  
Ala Lys His Glu Ala Gln Arg Leu Glu Gln Glu Ala Arg Gly Arg Leu Glu Arg  
Gln Lys Ile Leu Asp Gln Ser Glu Ala Glu Lys Ala Arg Lys Glu Leu Val Glu  
Leu Glu Ala Leu Ser Met Ala Val Glu Ser Thr Gly Thr Ala Lys Ala Glu Ala  
Glu Ser Arg Ala Glu Ala Ala Arg Ile Glu Gly Glu Gly Ser Val Leu Gln Ala  
Lys Leu Lys Ala Gln Ala Leu Ala Ile Glu Thr Glu Ala Glu Leu Gln Arg Val  
Gln Lys Val Arg Glu Leu Glu Leu Val Tyr Ala Arg Ala Gln Leu Glu Leu Glu  
Val Ser Lys Ala Gln Gln Leu Ala Glu Val Glu Val Lys Lys Phe Lys Gln Met

TABLE 1-continued

Sequences

Thr Glu Ala Ile Gly Pro Ser Thr Ile Arg Asp Leu Ala Val Ala Gly Pro Glu
Met Gln Val Lys Leu Leu Gln Ser Leu Gly Leu Lys Ser Thr Leu Ile Thr Asp
Gly Ser Thr Pro Ile Asn Leu Phe Asn Thr Ala Phe Gly Leu Leu Gly Met Gly
Pro Glu Gly Gln Pro Leu Gly Arg Arg Val Ala Ser Gly Pro Ser Pro Gly Glu
Gly Ile Ser Pro Gln Ser Ala Gln Ala Pro Gln Ala Pro Gly Asp Asn His Val
Val Pro Val Leu Arg

SEQ ID NO: 20   CP-MVP cDNA
atggcaggct gcggttgtcc atgcggttgt ggcgccatgg caactgaaga gttcatcatc
cgcatcccc cataccacta tatccatgtg ctggaccaga acagcaacgt gtcccgtgtg
gaggtcgggc aaaagaccta catccggcag acaatgagag gggtactgtt tgccccccatg
cgcatggtga ccgtcccccc acgtcactac tgcacagtgg ccaaccctgt gtctcgggat
gcccagggct tggtgctgtt tgatgtcaca gggcaagttc ggcttcgcca cgctgacctc
gagatccggc tggcccagga ccccttcccc ctgtacccag ggaggtgct ggaaaaggac
atcacacccc tgcaggtggt tctgcccaac actgccctcc atctaaaggc gctgcttgat
tttgaggata agatggaga caaggtggtg gcaggagatg agtggctttt cgagggacct
ggcacgtaca tcccccggaa ggaagtggag gtcgtggaga tcattcaggc caccatcatc
aggcagaacc aggctctgcg gctcagggcc cgcaaggagt gctgggaccg ggacggcaag
gagagggtga caggggaaga atggctggtc accacagtga gggcgtacct cccagcggtg
tttgaggagg ttctggattt ggtgacgcc gtcatcctta cggaaaagac agccctgcac
ctccgggctc ggcggaactt ccgggacttc aggggagtgt cccgccgcac tgggagggag
tggctggtaa cagtgcagga cacagaggcc acgtgccag atgtccacga ggaggtgctg
ggggttgtgc ccatccaccac cctgggcccc cacaactact gcgtgattct cgaccctgtc
ggaccggatg gcaagaatca gctggggcag aagcgcgtgg tcaagggaga gaagtcttt
ttcctccagc caggagagca gctggaacaa ggcatccagg atgtgtatgt gctgtcggag
cagcagggc tgctgctgag ggccctgcag cccctggagg aggggagga tgaggagaag
gtctcacacc aggctgggga ccactggctc atccgcggac ccctggagta tgtgccatct
gccaaagtgg aggtggtgga ggagcgccag gccatccctc tagacgagaa cgagggcatc
tatgtgcagg atgtcaagac cggaaaggtg cgcgctgtga ttggaagcac ctacatgctg
acccaggacg aagtcctgtg ggagaaagag ctgcctcccg gggtgaggga gctgctgaac
aaggggcagg accctctggc agacaggggt gagaaggaca cagctaagag cctccagccc
ttggcgcccc ggaacaagac ccgtgtggtc agctaccgcg tgccccacaa cgctgcggtg
caggtgtacg actaccgaga gaagcgagcc cgcgtggtct cgggcctga gctggtgtcg
ctgggtcctg aggagcagtt cacagtgttg tccctctcag ctgggcggcc caagcgtccc
catgcccgcc gtgcgctctg cctgctgctg gggcctgact tcttcacaga cgtcatcacc
atcgaaacgg cggatcatgc caggctgcaa ctgcagctgg cctacaactg gcactttgag
gtgaatgacc ggaaggaccc ccaagagacg gccaagctct tttcagtgcc agactttgta
ggtgatgcct gcaaagccat cgcatcccgg gtgcgggggg ccgtggcctc tgtcactttc
gatgacttcc ataagaactc agcccgcatc attcgcactg ctgtctttgg ctttgagacc
tcggaagcga agggccccga tggcatggcc ctgcccaggc ccgggaccca ggctgtcttc
ccccaaaacg ggctggtggt cagcagtgtg gacgtcagt cagtggagcc tgtggatcag
aggaccgggg acgccctgca acgcagcgtc cagctggcca tcgagatcac caccaactcc
caggaagcgg cggccaagca tgaggctcag agactggagc aggaagcccg cggccggctt
gagcggcaga agatcctgga ccagtcagaa gccgagaaga ctcgcaagga acttttggag
ctggaggctc tgagcatggc cgtggagagc accgggactg ccaaggcgga ggccgagtcc
cgtgcggagg cagcccggat tgagggagaa gggtccgtgc tgcaggccaa gctaaaagca
caggccttgg ccattgaaac ggaggctgag ctccagaggg tccagaaggt ccgagagctg
gaactggtct atgcccgggc ccagctggag ctggaggtga gcaaggctca gcagctgagt
gaggtggagg tgaagaagtt caagcagatg acagaggcca taggcccccag caccatcagg
gaccttgctg tggctgggcc tgagatgcag gtaaaactgc tccagtccct gggcctgaaa
tcaaccctca tcaccgatgg ctccactccc atcaacctct tcaacacagc ctttgggctg
ctggggatgg ggcccgaggg tcagcccctg gcagaaggg tggccagtgg gcccagccct
ggggagggga tatccccca gtctgctcag gcccctcaag ctcctggaga caaccacgtg
gtgcctgtac tgcgctaa SEQ ID NO: 21   TEP1, Genbank #AAC51107
Met Glu Lys Leu His Gly His Val Ser Ala His Pro Asp Ile Leu Ser Leu Glu
Asn Arg Cys Leu Ala Met Leu Pro Asp Leu Gln Pro Leu Glu Lys Leu His Gln
His Val Ser Thr His Ser Asp Ile Leu Ser Leu Lys Asn Gln Cys Leu Ala Thr
Leu Pro Asp Leu Lys Thr Met Glu Lys Pro His Gly Tyr Val Ser Ala His Pro
Asp Ile Leu Ser Leu Glu Asn Gln Cys Leu Ala Thr Leu Pro Ser Leu Lys Thr
Met Glu Lys Pro His Gly His Val Ser Ala His Pro Asp Ile Leu Ser Leu Glu
Asn Arg Cys Leu Ala Thr Leu Pro Ser Leu Lys Ser Thr Val Ser Ala Ser Pro
Leu Phe Gln Ser Leu Gln Ile Ser His Met Thr Gln Ala Asp Leu Tyr Arg Val
Asn Asn Ser Asn Cys Leu Leu Ser Glu Pro Pro Ser Trp Arg Ala Gln His Phe
Ser Lys Gly Leu Asp Leu Ser Thr Cys Pro Ile Ala Leu Lys Ser Ile Ser Ala
Thr Glu Thr Ala Gln Glu Ala Thr Leu Gly Arg Trp Phe Asp Ser Glu Glu Lys
Lys Gly Ala Glu Thr Gln Met Pro Ser Tyr Ser Leu Ser Leu Gly Glu Glu Glu
Glu Val Glu Asp Leu Ala Val Lys Leu Thr Ser Gly Asp Ser Glu Ser His Pro
Glu Pro Thr Asp His Val Leu Gln Glu Lys Lys Met Ala Leu Leu Ser Leu Leu
Cys Ser Thr Leu Val Ser Glu Val Asn Met Asn Asn Thr Ser Asp Pro Thr Leu
Ala Ala Ile Phe Glu Ile Cys Arg Glu Leu Ala Leu Leu Glu Pro Glu Phe Ile
Leu Lys Ala Ser Leu Tyr Ala Arg Gln Gln Leu Asn Val Arg Asn Val Ala Asn
Asn Ile Leu Ala Ile Ala Ala Phe Leu Pro Ala Cys Arg Pro His Leu Arg Arg
Tyr Phe Cys Ala Ile Val Gln Leu Pro Ser Asp Trp Ile Gln Val Ala Glu Leu
Tyr Gln Ser Leu Ala Glu Gly Asp Lys Asn Lys Leu Val Pro Leu Pro Ala Cys
Leu Arg Thr Ala Met Thr Asp Lys Phe Ala Gln Phe Asp Glu Tyr Gln Leu Ala
Lys Tyr Asn Pro Arg Lys His Arg Ala Lys Arg His Pro Arg Arg Pro Pro Arg TABLE 1-continued Sequences Ser Pro Gly Met Glu Pro Pro Phe Ser His Arg Cys Phe Pro Arg Tyr Ile Gly
Phe Leu Arg Glu Glu Gln Arg Lys Phe Glu Val Ala Gly Asp Thr Val Ser Glu
Lys Lys Asn Pro Pro Arg Phe Thr Leu Lys Lys Leu Val Gln Arg Leu His Ile
His Lys Pro Ala Gln His Val Gln Ala Leu Leu Gly Tyr Arg Tyr Pro Ser Asn
Leu Gln Leu Phe Ser Arg Ser Arg Leu Pro Gly Pro Trp Asp Ser Ser Arg Ala
Gly Lys Arg Met Lys Leu Ser Arg Pro Glu Thr Trp Glu Arg Glu Leu Ser Leu
Arg Gly Asn Lys Ala Ser Val Trp Glu Glu Leu Ile Glu Asn Gly Lys Leu Pro
Phe Met Ala Met Leu Arg Asn Leu Cys Asn Leu Leu Arg Val Gly Ile Ser Ser
Arg His His Glu Leu Ile Leu Gln Arg Leu Gln His Gly Lys Ser Val Ile His
Ser Arg Gln Phe Pro Phe Arg Phe Leu Asn Ala His Asp Ala Ile Asp Ala Leu
Glu Ala Gln Leu Arg Asn Gln Ala Leu Pro Phe Pro Ser Asn Ile Thr Leu Met
Arg Arg Ile Leu Thr Arg Asn Glu Lys Asn Arg Pro Arg Arg Phe Leu Cys
His Leu Ser Arg Gln Gln Leu Arg Met Ala Met Arg Ile Pro Val Leu Tyr Glu
Gln Leu Lys Arg Glu Lys Leu Arg Val His Lys Ala Arg Gln Trp Lys Tyr Asp
Gly Glu Met Leu Asn Arg Tyr Arg Gln Ala Leu Val Ala Val Asn Leu Ser
Val Lys His Ser Leu Pro Leu Leu Pro Gly Arg Thr Val Leu Val Tyr Leu Thr
Asp Ala Asn Ala Asp Arg Leu Cys Pro Lys Ser Asn Pro Gln Gly Pro Pro Leu
Asn Tyr Ala Leu Leu Ile Gly Met Met Ile Thr Arg Ala Glu Gln Val Asp
Val Leu Cys Gly Gly Asp Thr Leu Lys Thr Ala Val Leu Lys Ala Glu Glu
Gly Ile Leu Lys Thr Ala Ile Lys Leu Gln Ala Gln Val Gln Glu Phe Asp Glu
Asn Asp Gly Trp Ser Leu Asn Thr Phe Gly Lys Tyr Leu Leu Ser Leu Ala Gly
Gln Arg Val Pro Val Asp Arg Val Ile Leu Leu Gly Gln Ser Met Asp Asp Gly
Met Ile Asn Val Ala Lys Gln Leu Tyr Trp Gln Arg Val Asn Ser Lys Cys Leu
Phe Val Gly Ile Leu Arg Arg Val Gln Tyr Leu Ser Thr Asp Leu Asn Pro
Asn Asp Val Thr Leu Ser Gly Cys Thr Asp Ala Ile Leu Lys Phe Ile Ala Glu
His Gly Ala Ser His Leu Leu Glu His Val Gly Gln Met Asp Lys Ile Phe Lys
Ile Pro Pro Pro Gly Lys Thr Gly Val Gln Ser Leu Arg Pro Leu Gly Glu
Asp Thr Pro Ser Pro Leu Ala Pro Val Ser Gln Gln Gly Trp Arg Ser Ile Arg
Leu Phe Ile Ser Ser Thr Phe Arg Asp Met His Gly Glu Arg Asp Leu Leu Leu
Arg Ser Val Leu Pro Ala Leu Gln Ala Arg Ala Ala Pro His Arg Ile Ser Leu
His Gly Ile Asp Leu Arg Trp Gly Val Thr Glu Gln Thr Arg Val Arg Asn Arg
Gln Leu Glu Val Cys Leu Gly Val Glu Asn Ala Gln Leu Phe Val Gly Ile
Leu Gly Ser Arg Tyr Gly Tyr Ile Pro Pro Ser Tyr Asn Leu Pro Asp His Pro
His Phe His Trp Ala Gln Gln Tyr Pro Ser Gly Arg Ser Val Thr Glu Met Glu
Val Met Gln Phe Leu Asn Arg Asn Gln Arg Leu Gln Pro Ser Ala Gln Ala Leu
Ile Tyr Phe Arg Asp Ser Ser Phe Leu Ser Ser Arg Pro Asp Ala Trp Lys Ser
Asp Phe Val Ser Glu Ser Glu Glu Ala Ala Cys Arg Ile Ser Glu Leu Lys Ser
Tyr Leu Ser Arg Gln Lys Gly Ile Thr Cys Arg Arg Tyr Pro Cys Glu Trp Gly
Gly Val Ala Ala Gly Arg Pro Tyr Val Gly Gly Leu Glu Glu Phe Gly Gln Leu
Val Leu Gln Asp Val Trp Asn Met Ile Gln Lys Leu Tyr Leu Gln Pro Ala
Leu Leu Glu Gln Pro Val Ser Ile Pro Asp Asp Leu Val Gln Ala Thr Phe
Gln Gln Leu Gln Lys Pro Pro Ser Pro Ala Arg Pro Arg Leu Leu Gln Asp Thr
Val Gln Gln Leu Met Leu Pro His Gly Arg Leu Ser Leu Val Thr Gly Gln Ser
Gly Gly Lys Thr Ala Phe Leu Ala Ser Leu Val Ala Ser Leu Ala Leu Ala Pro
Asp Gly Ala Lys Val Ala Pro Leu Val Phe Phe His Phe Ser Gly Ala Arg Pro
Asp Gln Gly Leu Ala Leu Thr Leu Leu Arg Arg Leu Cys Thr Tyr Leu Arg Gly
Gln Leu Lys Glu Pro Gly Ala Leu Pro Ser Thr Tyr Arg Ser Leu Val Trp Glu
Leu Gln Gln Arg Leu Leu Pro Lys Ser Ala Glu Ser Leu His Pro Gly Gln Thr
Gln Val Leu Ile Ile Asp Gly Ala Asp Arg Leu Val Asp Gln Asn Gly Gln Leu
Ile Ser Asp Trp Ile Pro Lys Lys Leu Pro Arg Cys Val His Leu Val Leu Ser
Val Ser Ser Asp Ala Gly Leu Gly Glu Thr Leu Glu Gln Ser Gln Gly Ala His
Val Ala Leu Gly Pro Leu Glu Ala Ser Ala Arg Ala Arg Leu Val Arg Gly
Glu Leu Ala Leu Tyr Gly Lys Arg Leu Glu Glu Ser Pro Phe Asn Asn Gln Met
Arg Leu Leu Val Lys Arg Glu Ser Gly Arg Pro Leu Tyr Leu Arg Leu Val
Thr Asp His Leu Arg Leu Phe Thr Leu Tyr Glu Gln Val Ser Glu Arg Leu Arg
Thr Leu Pro Ala Thr Val Pro Leu Leu Leu Gln His Ile Leu Ser Thr Leu Glu
Lys Glu His Gly Pro Asp Val Leu Pro Gln Ala Leu Thr Ala Leu Glu Val Thr
Arg Ser Gly Leu Thr Val Asp Gln Leu His Gly Val Leu Ser Val Trp Arg Thr
Leu Pro Lys Gly Thr Lys Ser Trp Glu Glu Ala Val Ala Ala Gly Asn Ser Gly
Asp Pro Tyr Pro Met Gly Pro Phe Ala Cys Leu Val Gln Ser Leu Arg Ser Leu
Leu Gly Glu Gly Pro Leu Glu Arg Pro Gly Ala Arg Leu Cys Leu Pro Asp Gly
Pro Leu Arg Thr Ala Ala Lys Arg Cys Tyr Gly Lys Arg Pro Gly Leu Glu Asp
Thr Ala His Ile Leu Ile Ala Ala Gln Leu Trp Lys Thr Cys Asp Ala Asp Ala
Ser Gly Thr Phe Arg Ser Cys Pro Pro Glu Ala Leu Gly Asp Leu Pro Tyr His
Leu Gln Ser Gly Asn Arg Gly Leu Leu Ser Lys Phe Leu Thr Asn Leu His
Val Val Ala Ala His Leu Glu Leu Gly Leu Val Ser Arg Leu Leu Glu Ala His
Ala Leu Tyr Ala Ser Ser Val Pro Lys Glu Glu Gln Lys Leu Pro Glu Ala Asp
Val Ala Val Phe Arg Thr Phe Leu Arg Gln Gln Ala Ser Ile Leu Ser Gln Tyr
Pro Arg Leu Leu Pro Gln Gin Ala Ala Asn Gln Pro Arg Leu Asp Ser Pro Leu Cys
His Gln Ala Ser Leu Leu Ser Arg Arg Trp His Leu Gln His Thr Leu Arg Trp
Leu Asn Lys Pro Arg Thr Met Lys Asn Gln Ser Ser Ser Leu Ser Leu Ala
Val Ser Ser Ser Pro Thr Ala Val Ala Phe Ser Thr Asn Gly Gln Arg Ala Ala
Val Gly Thr Ala Asn Gly Thr Val Tyr Leu Leu Asp Leu Arg Thr Trp Gln Glu
Glu Lys Ser Val Val Ser Gly Cys Asp Gly Ile Ser Ala Cys Leu Phe Leu Ser
Asp Asp Thr Leu Phe Leu Thr Ala Phe Asp Gly Leu Leu Glu Leu Trp Asp Leu
Gln His Gly Cys Arg Val Leu Gln Thr Lys Ala His Gln Tyr Gln Ile Thr Gly
Cys Cys Leu Ser Pro Asp Cys Arg Leu Leu Ala Thr Val Cys Leu Gly Gly Cys
Leu Lys Leu Trp Asp Thr Val Arg Gly Gln Leu Ala Phe Gln His Thr Tyr Pro TABLE 1-continued Sequences Lys Ser Leu Asn Cys Val Ala Phe His Pro Glu Gly Gln Val Ile Ala Thr Gly
Ser Trp Ala Gly Ser Ile Ser Phe Phe Gln Val Asp Gly Leu Lys Val Thr Lys
Asp Leu Gly Ala Pro Gly Ala Ser Ile Arg Thr Leu Ala Phe Asn Val Pro Gly
Gly Val Val Ala Val Gly Arg Leu Asp Ser Met Val Glu Leu Trp Ala Trp Arg
Glu Gly Ala Arg Leu Ala Ala Phe Pro Ala His His Gly Phe Val Ala Ala Ala
Leu Phe Leu His Ala Gly Cys Gln Leu Leu Thr Thr Ala Gly Glu Gly Lys Val
Gln Val Trp Ser Gly Ser Leu Gly Arg Pro Arg Gly His Leu Gly Ser Leu Ser
Leu Ser Pro Ala Leu Ser Val Ala Leu Ser Pro Asp Gly Asp Arg Val Ala Val
Gly Tyr Arg Ala Asp Gly Ile Arg Ile Tyr Lys Ile Ser Ser Gly Ser Gln Gly
Ala Gln Gly Gln Ala Leu Asp Val Ala Val Ser Ala Leu Ala Trp Leu Ser Pro
Lys Val Leu Val Ser Gly Ala Glu Asp Gly Ser Leu Gln Gly Trp Ala Leu Lys
Glu Cys Ser Leu Gln Ser Leu Trp Leu Leu Ser Arg Phe Gln Lys Pro Val Leu
Gly Leu Ala Thr Ser Gln Glu Leu Leu Ala Ser Ala Ser Glu Asp Phe Thr Val
Gln Leu Trp Pro Arg Gln Leu Leu Thr Arg Pro His Lys Ala Glu Asp Phe Pro
Cys Gly Thr Glu Leu Arg Gly His Glu Gly Pro Val Ser Cys Cys Ser Phe Ser
Thr Asp Gly Gly Ser Leu Ala Thr Gly Gly Arg Asp Arg Ser Leu Leu Cys Trp
Asp Val Arg Thr Pro Lys Thr Pro Val Leu Ile His Ser Phe Pro Ala Cys His
Arg Asp Trp Val Thr Gly Cys Ala Trp Thr Lys Asp Asn Leu Leu Ile Ser Cys
Ser Ser Asp Gly Ser Val Gly Leu Trp Asp Pro Ser Gly Gln Arg Gly Leu Gly
Gln Phe Leu Gly His Gln Ser Ala Val Ser Ala Val Ala Ala Val Glu Glu His
Val Val Ser Val Ser Arg Asp Gly Thr Leu Lys Val Trp Asp His Gln Gly Val
Glu Leu Thr Ser Ile Pro Ala His Ser Gly Pro Ile Ser His Cys Ala Ala Ala
Met Glu Pro Arg Ala Ala Gly Gln Pro Gly Ser Gln Leu Leu Val Val Thr Val
Gly Leu Asp Gly Ala Thr Arg Leu Trp His Pro Leu Leu Val Cys Gln Thr His
Thr Leu Leu Gly His Ser Gly Pro Val Arg Ala Ala Val Ser Glu Thr Ser
Gly Leu Met Leu Thr Ala Ser Glu Asp Gly Ser Val Arg Leu Trp Gln Val Pro
Lys Glu Ala Asp Asp Thr Cys Ile Pro Arg Ser Ser Ala Ala Val Thr Ala Val
Ala Trp Ala Pro Asp Gly Ser Met Ala Val Ser Gly Asn Gln Ala Gly Glu Leu
Ile Leu Trp Gln Glu Ala Lys Ala Val Ala Thr Ala Gln Ala Pro Gly His Ile
Gly Ala Leu Ile Trp Ser Ser Ala His Thr Phe Phe Val Leu Ser Ala Asp Glu
Lys Ile Ser Glu Trp Gln Val Lys Leu Arg Lys Gly Ser Ala Pro Gly Asn Leu
Ser Leu His Leu Asn Arg Ile Leu Gln Glu Gly Val Leu Pro Val Leu Ser Leu
Asp Trp Ala Pro Asp Gly His Phe Leu Ile Leu Ala Lys Ala Asp Leu Lys Leu
Leu Cys Met Lys Pro Gly Asp Ala Pro Ser Glu Ile Trp Ser Ser Tyr Thr Glu
Asn Pro Met Ile Leu Ser Thr His Lys Glu Tyr Gly Ile Phe Val Leu Gln Pro
Lys Asp Pro Gly Val Leu Ser Phe Leu Arg Gln Leu Lys Gly Glu Gly Phe Glu
Glu Arg Leu Asn Phe Asp Ile Asn Leu Glu Asn Pro Ser Arg Thr Leu Ile Ser
Ile Thr Gln Ala Lys Pro Glu Ser Glu Ser Ser Phe Leu Cys Ala Ser Ser Asp
Gly Ile Leu Trp Asn Leu Ala Lys Cys Ser Pro Glu Gly Glu Trp Thr Thr Gly
Asn Met Trp Gln Lys Lys Ala Asn Thr Pro Glu Thr Gln Thr Pro Gly Thr Asp
Pro Ser Thr Cys Arg Glu Ser Asp Ala Ser Met Asp Ser Asp Ala Ser Met Asp
Ser Glu Pro Thr Pro His Leu Lys Thr Arg Gln Arg Arg Lys Ile His Ser Gly
Ser Val Thr Ala Leu His Val Leu Pro Glu Leu Leu Val Thr Ala Ser Lys Asp
Arg Asp Val Lys Leu Trp Glu Arg Pro Ser Met Gln Leu Leu Gly Leu Phe Arg
Cys Glu Gly Ser Val Ser Cys Leu Glu Pro Trp Leu Gly Ala Asn Ser Thr Leu
Gln Leu Ala Val Gly Asp Val Gln Gly Asn Val Tyr Phe Leu Asn Trp Glu SEQ ID NO: 22    TEP1 cDNA, Genbank #U86136
atggaaaaac tccatgggca tgtgtctgcc catccagaca tcctctcctt ggagaaccgg
tgcctggcta tgctccctga cttacagccc ttggagaaac tacatcagca tgtatcctacc
cactcagata tcctctcctt gaagaaccag tgcctagcca cgcttcctga cctgaagacc
atggaaaaac cacatggata tgtgtctgcc cacccagaca tcctctcctt ggagaaccag
tgcctggcca cactttctga cctgaagacc atggagaaac cacatggaca tgtttctgcc
cacccagaca tcctctcctt ggagaaccgg tgcctggcca cctcccctag tctaaaagagc
actgtgtctg ccagcccctt gttccagagt ctacagatat ctcacatgac gcaagctgat
ttgtaccgtg tgaacaacag caattgcctg ctctctgagc ctccaagttg gagggctcag
catttctcta agggactaga ccttttcaacc tgccctatag ccctgaaatc catctctgcc
acagagacag ctcaggaagc aactttgggt cgttggtttg attcagaaga gaagaaaggg
gcagagaccc aaatgccttc ttatagtctg agcttgggag aggaggagga ggtgaggat
ctggccgtga agctcacctc tggagactct gaatctcatc cagagcctac tgaccatgtc
cttcaggaaa agaagatggc tctactgagc ttgctgtgct ctactctggt ctcagaagta
aacatgaaca atacatctga ccccaccctg gctgccattt ttgaaatctg tcgtgaactt
gccctcctgg agcctgagtt tatcctcaag gcatctttgt atgccaggca gcagctgaac
gtccggaatg tggccaataa catcttggcc attgctgctt tcttgccggc gtgtcgcccc
cacctgcgac gatatttctg tgccattgtc cagctgcctt ctgactggat ccaggtggct
gagctttacc agagcctggc tgagggagat aagaataagc tggtgcccct gcccgcctgt
ctccgtactg ccatgacgga caaatttgcc cagtttgacg agtaccagct ggctaagtac
aaccctcgga agcaccgggc caagagacac ccccgccggc caccccgctc tccagggatg
gagcctccat tttctcacag atgttttcca aggtacatag ggtttctcag agaagagcag
agaaagtttg agaaggccgg tgatacagtg tcagagaaaa agaatcctcc aaggttcacc
ctgaagaagc tggttcagcg actgcacatc cacaagcctg cccagcacgt tcaagccctg
ctgggttaca gataccctc caacctacag ctctttttctc gaagtcgcct tcctgggcct
tgggattcta gcagagctgg gaagaggatg aagtcgtcta ggccagagac ctgggagcgg
gagctgagcc tacgggggaa caaagcgtcg gtctgggagg aactcattga aaatgggaag
cttccctcca tggccatgct tcggaacctg tgcaacctgc tgcgggttgg aatcagttcc
cgccaccatg agctcattct ccagagactc cagcatggga gtcggtgat ccacagtcgg
cagtttccat tcagatttct taacgcccat gatgccattg atgccctcga ggctcaactc
agaaatcaag cattgcccctt tccttcgaat ataacactga tgaggcggat actaactaga TABLE 1-continued Sequences

```
aatgaaaaga accgtcccag gcggaggttt ctttgccacc taagccgtca gcagcttcgt
atggcaatga ggatacctgt gttgtatgag cagctcaaga gggagaagct gagagtacac
aaggccagac agtggaaata tgatggtgag atgctgaaca ggtaccgaca ggccctagag
acagctgtga acctctctgt gaagcacagc ctgcccctgc tgccaggccg cactgtcttg
gtctatctga cagatgctaa tgcagacagg ctctgtccaa agagcaaccc acaagggccc
ccgctgaact atgcactgct gttgattggg atgatgatca cgagggcgga gcaggtggac
gtcgtgctgt gtggaggtga cactctgaag actgcagtgc ttaaggcaga agaaggcatc
ctgaagactg ccatcaagct ccaggctcaa gtccaggagt ttgatgaaaa tgatggatgg
tccctgaata cttttgggaa atacctgctg tctctggctg gccaaagggt tcctgtggac
agggtcatcc tccttggcca aagcatggat gatggaatga taaatgtggc caaacagctt
tactggcagc gtgtgaattc caagtgcctc tttgttggta tcctcctaag aagggtacaa
tacctgtcaa cagatttgaa tcccaatgat gtgacactct caggctgtac tgatgcgata
ctgaagttca ttgcagagca tggggcctcc catcttctgg aacatgtggg ccaaatggac
aaaatattca agattccacc accccagga aagacagggg tccagtctct ccggccactg
gaagaggaca ctccaagccc cttggctcct gtttcccagc aaggatggcg cagcatccgg
cttttcattt catccacttt ccgagacatg cacggggagc gggacctgct gctgaggtct
gtgctgccag cactgcaggc ccgagcggcc cctcaccgta tcagccttca cggaatcgac
ctccgctggg gcgtcactga ggaggagacc cgtaggaaca gacaactgga agtgtgcctt
ggggaggtgg agaacgcaca gctgtttgtg gggattctgg gctcccgtta tggatacatt
ccccccagct acaaccttcc tgaccatcca cacttccact gggcccagca gtacccttca
gggcgctctg tgacagagat ggaggtgatg cagttcctga accggaacca acgtctgcag
ccctctgccc aagctctcat ctacttccgg gattccagct tcctcagctc tgtgccagat
gcctggaaat ctgactttgt ttctgagtct gaagaggccg catgtcggat ctcagaactg
aagagctacc taagcagaca gaaagggata acctgccgca gataccccctg tgagtggggg
ggtgtggcag ctggccggcc ctatgttggc gggctggagg agtttgggca gttggttctg
caggatgtat ggaatatgat ccagaagctc tacctgcagc ctggggccct gctggagcag
ccagtgtcca tcccagacga tgacttggtc caggccacct tccagcagct gcagaagcca
ccgagtcctg cccggccacg ccttcttcag gacacagtgc aacagctgat gctgccccac
ggaaggctga gcctggtgac ggggcagtca ggacagggca agacagcctt cctggcatct
cttgtgtcag ccctgcaggc tcctgatggg gccaaggtgg caccattagt cttcttccac
ttttctgggg ctcgtcctga ccagggtctt gccctcactc tgctcagacg cctctgtacc
tatctgcgtg gccaactaaa agagccaggt gccctcccca gcacctaccg aagcctggtg
tgggagctgc agcagaggct gctgcccaag tctgctgagt ccctgcatcc tggccagacc
caggtcctga tcatcgatgg ggctgatagg ttagtggacc agaatgggca gctgatttca
gactggatcc caaagaagct tccccggtgt gtacacctgg tgctgagtgt gtctagtgat
gcaggcctag gggagaccct tgagcagagc cagggtgccc acgtgctggc cttggggcct
ctggaggcct ctgctcgggc ccggctggtg agagaggagc tggccctgta cgggaagcgg
ctggaggagt caccatttaa caaccagatg cgactgctgc tggtgaagcg ggaatcaggc
cggccgctct acctgcgctt ggtcaccgat cacctgaggc tcttcacgct gtatgagcag
gtgtctgaga gactccggac cctgcctgcc actgtccccc tgctgctgca gcacatcctg
agcacactgg agaaggagca cgggcctgat gtccttcccc aggccttgac tgccctagaa
gtcacacgga gtggtttgac tgtggaccag ctgcacggag tgctgagtgt gtggcggaca
ctaccgaagg ggactaagag ctgggaagaa gcagtggctg ctggtaacag tggagacccc
taccccatgg gcccgtttgc ctgcctcgtc cagagtctgc gcagtttgct aggggagggc
cctctggagc gccctggtgc ccggctgtgc ctccctgatg ggcccctgag aacagcagct
aaacgttgct atgggaagag gccagggcta gaggacacgg cacacatcct cattgcagct
cagctctgga agacatgtga cgctgatgcc tcaggcacct tccgaagttg ccctcctgag
gctctgggag acctgcctta ccacctgctc cagagcggga accgtggact tctttcgaag
ttccttacca acctccatgt ggtggctgca cacttggaat tgggtctggt ctctcggctc
ttggaggccc atgccctcta tgcttcttca gtccccaaag aggaacaaaa gctcccgag
gctgacgttg cagtgtttcg caccttcctg aggcagcagg cttcaatcct cagccagtac
ccccggctcc tgccccagca ggcagccaac cagcccctgg actcacctct ttgccaccaa
gcctcgctgc tctcccggag atggcacctc caacacacac tacgatggct taataaaccc
cggaccatga aaaatcagca aagctccagc ctgtctctgg cagtttcctc atcccctact
gctgtgcct tctccaccaa tgggcaaaga gcagctgtgg gcactgccaa tgggacagtt
tacctgttgg acctgagaac ttggcaggag gagaagtctg tggtgagtgg ctgtgatgga
atctctgctt gtttgttcct ctccgatgat acactctttc ttactgcctt cgacgggctc
ctggagctct gggacctgca gcatggttgt cgggtgctgc agactaaggc tcaccagtac
caaatcactg gctgctgcct gagcccagac tgccggctgc tagccaccgt gtgcttggga
ggatgcctaa agctgtggga cacagtccgt gggcagctgg ccttccagca cacctacccc
aagtccctga actgtgttgc cttccaccca gaggggcagg taatagccac aggcagctgg
gctggcagca tcagcttctt ccaggtggat gggctcaaag tcaccaagga cctgggggca
cccgagcct ctatccgtac cttggccttc aatgtgcctg ggggggttgt ggctgtgggc
cggctggaca gtatggtgga gctgtgggcc tggcagaaag gggcacggct ggctgccttc
cctgcccacc atggctttgt tgctgctgcg cctttcctgc atgcgggttg cagttactg
acggctggag aggatggcaa ggttcaggtg tggtcagggt ctctgggtcg gcccccgtggg
cacctggtt cccttctct ctctcctgcc ctctctgtgg cactcagccc agatggtgat
cgggtggctg ttgatatcg agcggatggc attaggatct acaaaatctc ttcaggttcc
caggggctc aggtcaggc actgatgtg gcagtgtccg ccctggcctg gctaagcccc
aaggtattgg tgagtggtgc agaagatggg tccttgcagg gctgggcact caaggaatgc
tcccttcagt ccctctggct cctgtccaga ttccagaagc ctgtgctagg actgccact
tcccaggagc tcttggcttc tgcctcagag gatttcacag tgcagctgtg gccaaggcag
ctgctgacgc ggccacacaa ggcagaagac tttccctgcg cactgagct gcggggacat
gagggccctc tgagctgctg tagtttcagc actgatggag gcagcctggc caccgggctg
cgggatcgga gtctcctctg ctgggacgtg aggacaccca aaaccctgt tttgatccac
tccttccctg cctgtcaccg tgactgggtc actggctgtg cctggaccaa agataaccta
ctgatatcct gctccagtga tggctctgtg gggctctggg acccagagtc aggacagcgg
cttggtcagt tcctgggtca tcagagtgct gtgagcgctg tggcagctgt ggaggagcac
```

TABLE 1-continued

Sequences

```
gtggtgtctg tgagccggga tgggaccttg aaagtgtggg accatcaagg cgtggagctg
accagcatcc ctgctcactc aggacccatt agccactgtg cagctgccat ggagccccgt
gcagctggac agcctgggtc agagcttctg gtggtaaccg tcgggctaga tggggccaca
cggttatggc atccactctt ggtgtgccaa acccacaccc tcctgggaca cagcggccca
gtccgtgctg ctgctgtttc agaaacctca ggcctcatgc tgaccgcctc tgaggatggt
tctgtacggc tctggcaggt tcctaaggaa gcagatgaca catgtatacc aaggagttct
gcagccgtca ctgctgtggc ttgggcacca gatggttcca tggcagtatc tggaaatcaa
gctggggaac taatcttgtg gcaggaagct aaggctgtgg ccacagcaca ggctccaggc
cacattggtg ctctgatctg gtcctcggca cacaccttt ttgtcctcag tgctgatgag
aaaatcagcg agtggcaagt gaaactgcgg aagggttcgg cacccggaaa tttgagtctt
cacctgaacc gaattctaca ggaggactta ggggtgctga caagtctgga ttgggctcct
gatggtcact ttctcatctt ggccaaagca gatttgaagt tactttgcat gaagccaggg
gatgctccat ctgaaatctg gagcagctat acagaaaatc ctatgatatt gtccacccac
aaggagtatg gcatatttgt cctgcagccc aaggatcctg gagttctttc tttcttgagg
caaaaggaat caggagagtt tgaagagagg ctgaactttg atataaactt agagaatcct
agtaggaccc taatatcgat aactcaagcc aaacctgaat ctgagtcctc attttttgtgt
gccagctctg atgggatcct atggaacctg ccaaatgca gcccagaagg agaatggacc
acaggtaaca tgtggcagaa aaaagcaaac actccagaaa cccaaactcc agggacagac
ccatctacct gcagggaatc tgatgccagc atggatagtg atgccagcat ggatagtgag
ccaacaccac atctaaagac acggcagcgt agaaagattc actcgggctc tgtcacagcc
ctccatgtgc tacctgagtt gctggtgaca gcttcgaagg acagagatgt taagctatgg
gagagaccca gtatgcagct gctgggcctg ttccgatgcg aagggtcagt gagctgcctg
gaaccttggc tgggcgctaa ctccaccctg cagcttgccg tgggagacgt gcagggcaat
gtgtactttc tgaattggga atga SEQ ID NO: 23      vRNA, Genbank #AF045143
ggcuggcuuu agcucagcgg uuacuucgac aguucuuuaa uugaaacaag caaccugucu
ggguuguucg agacccgcgg gcgcucucca guccuuuu SEQ ID NO: 24      vRNA, Genbank #AF045144
ggcuggcuuu agcucagcgg uuacuucgag uacauuguaa ccaccucucu gggugguucg
agacccgcgg gugcuuucca gcucuuuu SEQ ID NO: 25      vRNA, Genbank #AF045145
ggcuggcuuu agcucagcgg uuacuucgcg ugucaucaaa ccaccucucu ggguuguucg
agacccgcgg gcgcucucca gcccucuu SEQ ID NO: 26      mCherry nucleotide sequence
ATGGTGAGCA AGGGCGAGGA GGATAACATG GCCATCATCA AGGAGTTCAT GCGCTTCAAG
GTGCACATGG AGGGCTCCGT GAACGGCCAC GAGTTCGAGA TCGAGGGCGA GGGCGAGGGC
CGCCCCTACG AGGGCACCCA GACCGCCAAG CTGAAGGTGA CCAAGGGTGG CCCCCTGCCC
TTCGCCTGGG ACATCCTGTC CCCTCAGTTC ATGTACGGCT CCAAGGCCTA CGTGAAGCAC
CCCGCCGACA TCCCCGACTA CTTGAAGCTG TCCTTCCCCG AGGGCTTCAA GTGGGAGCGC
GTGATGAACT TCGAGGACGG CGGCGTGGTG ACCGTGACCC AGGACTCCTC CCTGCAGGAC
GGCGAGTTCA TCTACAAGGT GAAGCTGCGC GGCACCAACT TCCCCTCCGA CGGCCCCGTA
ATGCAGAAGA AGACCATGGG CTGGGAGGCC TCCTCCGAGC GGATGTACCC CGAGGACGGC
GCCCTGAAGG GCGAGATCAA GCAGAGGCTG AAGCTGAAGG ACGGCGGCCA CTACGACGCT
GAGGTCAAGA CCACCTACAA GGCCAAGAAG CCCGTGCAGC TGCCCGGCGC CTACAACGTC
AACATCAAGT TGGACATCAC CTCCCACAAC GAGGACTACA CCATCGTGGA ACAGTACGAA
CGCGCCGAGG GCCGCCACTC CACCGGCGGC ATGGACGAGC TGTACAAGTA A SEQ ID NO: 27      mCherry amino acid sequence
MVSKGEEDNMAIIKEFMRFKVHMEGSVNGHEFEIEGEGEGRPYEGTQTAKLKVTKGGPLPFAWDILSPQFMYG
SKAYVKHPADIPDYLKLSFPEGFKWERVMNFEDGGVVTVTQDSSLQDGEFIYKVKLRGTNFPSDGPVMQKKTM
GWEASSERMYPEDGALKGEIKQRLKLKDGGHYDAEVKTTYKAKKPVQLPGAYNVNIKLDITSHNEDYTIVEQY
ERAEGRHSTGGMDELYKX SEQ ID NO: 28      mCherry-mINT fusion DNA sequence
ATGGTGAGCA AGGGCGAGGA GGATAACATG GCCATCATCA AGGAGTTCAT GCGCTTCAAG
GTGCACATGG AGGGCTCCGT GAACGGCCAC GAGTTCGAGA TCGAGGGCGA GGGCGAGGGC
CGCCCCTACG AGGGCACCCA GACCGCCAAG CTGAAGGTGA CCAAGGGTGG CCCCCTGCCC
TTCGCCTGGG ACATCCTGTC CCCTCAGTTC ATGTACGGCT CCAAGGCCTA CGTGAAGCAC
CCCGCCGACA TCCCCGACTA CTTGAAGCTG TCCTTCCCCG AGGGCTTCAA GTGGGAGCGC
GTGATGAACT TCGAGGACGG CGGCGTGGTG ACCGTGACCC AGGACTCCTC CCTGCAGGAC
GGCGAGTTCA TCTACAAGGT GAAGCTGCGC GGCACCAACT TCCCCTCCGA CGGCCCCGTA
ATGCAGAAGA AGACCATGGG CTGGGAGGCC TCCTCCGAGC GGATGTACCC CGAGGACGGC
GCCCTGAAGG GCGAGATCAA GCAGAGGCTG AAGCTGAAGG ACGGCGGCCA CTACGACGCT
GAGGTCAAGA CCACCTACAA GGCCAAGAAG CCCGTGCAGC TGCCCGGCGC CTACAACGTC
AACATCAAGT TGGACATCAC CTCCCACAAC GAGGACTACA CCATCGTGGA ACAGTACGAA
CGCGCCGAGG GCCGCCACTC CACCGGCGGC ATGGACGAGC TGTACAAGTA ATGC ACA CAA CAC
TGG CAG GAT GCT GTG CCT TGG ACA GAA CTC CTC AGT CTA CAG ACA GAG GAT GGC
TTC TGG AAA CTT ACA CCA GAA CTG GGA CTT ATA TTA AAT CTT AAT ACA AAT GGT
TTG CAC AGC TTT CTT AAA CAA AAA GGC ATT CAA TCT CTA GGT GTA AAA GGA AGA
GAA TGT CTC CTG GAC CTA ATT GCC ACA ATG CTG GTA CTA CAG TTT ATT CGC ACC
AGG TTG GAA AAA GAG GGA ATA GTG TTC AAA TCA CTG ATG AAA ATG GAT GAC CCT
TCT ATT TCC AGG AAT ATT CCC TGG GCT TTT GAG GCA ATA AAG CAA GCA GTT GAA
```

TABLE 1-continued

Sequences

TGG GTA AGA AGA ACT GAA GGA CAG TAC CCA TCT ATC TGC CCA CGG CTT GAA CTG
GGG AAC GAC TGG GAC TCT GCC ACC AAG CAG TTG CTG GGA CTC CAG CCC ATA AGC
ACT GTG TCC CCT CTT CAT AGA GTC CTC CAT TAC AGT CAA GGC TAA

SEQ ID NO: 29   mCherry-mINT fusion amino acid sequence
MVSKGEEDNMAIIKEFMRFKVHMEGSVNGHEFEIEGEGEGRPYEGTQTAKLKVTKGGPLPFAWDILSPQFMYG
SKAYVKHPADIPDYLKLSFPEGFKWERVMNFEDGGVVTVTQDSSLQDGEFIYKVKLRGTNFPSDGPVMQKKTM
GWEASSERMYPEDGALKGEIKQRLKLKDGGHYDAEVKTTYKAKKPVQLPGAYNVNIKLDITSHNEDYTIVEQY
ERAEGRHSTGGMDELYKXCTQHWQDAVPWTELLSLQTEDGFWKLTPELGLILNLNTNGLHSFLKQKGIQSLGV
KGRECLLDLIATMLVLQFIRTRLEKEGIVFKSLMKMDDPSISRNIPWAFEAIKQASEWVRRTEGQYPSICPRL
ELGNDWDSATKQLLGLQPISTVSPLHRVLHYSQG SEQ ID NO: 30   Full length protein VI (pVI) primer
CGGGATCCGCCTTCAGCTGGGGCTCGCTCTGGAGC SEQ ID NO: 31   Full length protein VI (pVI) primer
CGGGAATTCTTACAGACCCACGATGCTGTTCAG SEQ ID NO: 32   N-Term region of protein VI (NT) (aa 34-114) primer
CGGGATCCGCCTTCAGCTGGGGCTCGCTCTGGAGC SEQ ID NO: 33   N-Term region of protein VI (NT) (aa 34-114) primer
CGGGAATTCTTACTCTCGGGAGGGCGGGGATC SEQ ID NO: 34   TR primer
AAAGGATCCTATGGCAGCAAGGC SEQ ID NO: 35   TR primer
AAAGAATTCTTACAGACCCACGATGCTGTT SEQ ID NO: 36   pVI (aa 34-53) primer
CGGGATCCGCCTTCAGCTGGGGCTCGCTGTGGAGCGGCATTAAAAATTTCGGTTCCACCGTTAAGA
ACTATGAATTCCGG SEQ ID NO: 37   pVI (aa 34-53) primer
CCGGAATTCATAGTTCTTAACGGTGGAACCGAAATTTTTAATGCCGCTCCACAGCGAGCCCCAGCT
GAAGGCGGATCCCG SEQ ID NO: 38   INT domain (aa 1563-1724) primer
CGGGATTCGGCGGCGAATTCGATTTACGATATCCCAACGACCGAA SEQ ID NO: 39   INT domain (aa 1563-1724) primer
CCCCTCGAGTTAGCCTTGACTGTAATGGAGGACTCTATG SEQ ID NO: 40   pVI lytic peptide (aa 34-53) Forward primer
CTC TGC TAG CCA CCA TGG CCT TCA GCT GGG GCT CG SEQ ID NO: 41   pVI lytic peptide (aa 34-53) Reverse primer
GGG GCC ATG GCG CTG CCG CGC GGC ACC AGG CCG TTC TTA ACG GTG AAC
CCG SEQ ID NO: 42   mINT protein sequence (residues 1473-1724 of human
                VPARP protein sequence)
Ala Asn Leu Arg Leu Pro Met Ala Ser Ala Leu Pro Glu Ala Leu Cys Ser Gln
Ser Arg Thr Thr Pro Val Asp Leu Cys Leu Leu Glu Glu Ser Val Gly Ser Leu
Glu Gly Ser Arg Cys Pro Val Phe Ala Phe Gln Ser Ser Asp Thr Glu Ser Asp
Glu Leu Ser Glu Val Leu Gln Asp Ser Cys Phe Leu Gln Ile Lys Cys Asp Thr
Lys Asp Asp Ser Ile Pro Cys Phe Leu Glu Leu Lys Glu Glu Asp Glu Ile Val
Cys Thr Gln His Trp Gln Asp Ala Val Pro Trp Thr Glu Leu Leu Ser Leu Gln
Thr Glu Asp Gly Phe Trp Lys Leu Thr Pro Glu Leu Gly Leu Ile Leu Asn Leu
Asn Thr Asn Gly Leu His Ser Phe Leu Lys Gln Lys Gly Ile Gln Ser Leu Gly
Val Lys Gly Arg Glu Cys Leu Leu Asp Leu Ile Ala Thr Met Leu Val Leu Gln
Phe Ile Arg Thr Arg Leu Glu Lys Glu Gly Ile Val Phe Lys Ser Leu Met Lys
Met Asp Asp Pro Ser Ile Ser Arg Asn Ile Pro Trp Ala Phe Glu Ala Ile Lys
Gln Ala Ser Glu Trp Val Arg Arg Thr Glu Gly Gln Tyr Pro Ser Ile Cys Pro
Arg Leu Glu Leu Gly Asn Asp Trp Asp Ser Ala Thr Lys Gln Leu Leu Gly Leu
Gln Pro Ile Ser Thr Val Ser Pro Leu His Arg Val Leu His Tyr Ser Gln Gly

REFERENCES CITED

1. Kedersha N L, Rome L H: *Isolation and characterization of a novel ribonucleoprotein particle: large structures contain a single species of small RNA. J Cell Biol* 1986, 103(3):699-709.
2. Kong L B, Siva A C, Rome L H, Stewart P L: *Structure of the vault, a ubiquitous celular component. Structure* 1999, 7(4):371-379.
3. Kedersha N L, Heuser J E, Chugani D C, Rome L H: Vaults. III. *Vault ribonucleoprotein particles open into flower-like structures with octagonal symmetry. J Cell Biol* 1991, 112(2):225-235.
4. Suprenant K A: *Vault ribonucleoprotein particles: sarcophagi, gondolas, or safety deposit boxes? Biochemistry* 2002, 41(49):14447-14454.
5. Berger W, Steiner E, Grusch M, Elbling L, Micksche M: *Vaults and the major vault protein: novel roles in signal pathway regulation and immunity. Cell Mol Life Sci* 2009, 66(1):43-61.
6. Champion C I, Kickhoefer V A, Liu G, Moniz R J, Freed A S, Bergmann L L, Vaccari D, Raval-Fernandes S, Chan A M, Rome L H et al: *A vault nanoparticle vaccine induces protective mucosal immunity. PLoS One* 2009, 4(4): e5409. Epub 2009 April 5430.
7. Stephen A G, Raval-Fernandes S, Huynh T, Tones M, Kickhoefer V A, Rome L H: *Assembly of vault-like particles in insect cells expressing only the major vault protein. J Biol Chem* 2001, 276(26):23217-23220. Epub 22001 May 23210.
8. Kickhoefer V A, Garcia Y, Mikyas Y, Johansson E, Zhou J C, Raval-Fernandes S, Minoofar P, Zink J I, Dunn B, Stewart P L et al: *Engineering of vault nanocapsules with enzymatic and fluorescent properties. Proc Natl Acad Sci USA* 2005, 102(12):4348-4352. Epub 2005 March 4347.
9. Kickhoefer, V. A., et al. (2005). Engineering of vault nanocapsules with enzymatic and fluorescent properties. *Proc. Natl. Acad. Sci. U.S.A.* 102: 4328-4352.
10. Poderycki, M. J., et al. (2006). The vault exterior shell is a dynamic structure that allows incorporation of vault-associated proteins into its interior. *Biochemistry (Mosc)*.45: 12184-12193.
11. Goldsmith, L. E., Yu, M., Rome, L. H., and Monbouquette, H. G. (2007). Vault nanocapsule dissociation into halves triggered at low pH. *Biochemistry (Mose)*. 46:2865-2875.
12. Kaddis, C. S., et al. (2007). Sizing large proteins and protein complexes by electrospray ionization mass spectrometry and ion mobility. *J. Am. Soe. Mass. Speetmm.* 18: 1206-1216.
13. Stephen, A G., Raval-Fernandes, S., Huynh, T., Torres, M., Kickhoefer, V. A, and Rome, L. H. (2001). Assembly of vault-like particles in insect cells expressing only the major vault protein. *J. Biol. Chem.* 276: 23217-23220.
14. Blumenthal, R., Seth, P., Willingham, M. C., and Pastan, I. (1986). PH-dependent lysis of liposomes by adenovirus biochemistry. *Biochemistry (Mose)*. 25: 2231-2237.
15. Haidar, M. A (1976). Tobacco rattle virus RNA-protein interactions. *Philosophical transactions of the Royal Society of London* 276: 165-172.
16. Goodman, R. M., McDonald, J. G., Home, R. W., and Bancroft, J. B. (1976). Assembly of flexuous plant viruses and their proteins. *Philosophical transactions of the Royal Society of London* 276: 173-179.
17. Hed, J., Hallden, G., Johansson, S. G., and Larsson, P. (1987). The use of fluorescence quencing in flow cytofluorometry to measure the attachment and ingestion phases in phagocytosis in peripheral blood without prior cell separation. *J. Immunol. Methods* 101: 119-125.
18. Wiethoff. C. M., Wodrich, H., Gerace. L., and Nemerow, G. R. (2005). Adenovirus protein VI mediates membrane disruption following capsid disassembly. *J. Viral.* 79: 1992-2000.
19. Barbiei, L., Battelli, M. G., and Stirpe, F. (1993). Ribosome-inactivating proteins from plants. *Biochima et Biophysica Acta* 1154: 237-282.
20. Weyergang, A, Selbo, P. K., and Berg, K. (2006). Photochemically stimulated drug delivery increases the cytotoxicity and specificity of EGF-saporin. *J. Controlled Release* 111: 165-173.
21. Yip, W. L., Weyergang, A, Berg, K., Tennesen, H. H" and Selbo, P. K. (2007).Targeted delivery and enhanced cytotoxicity of cetuximab-saporin by photochemical internalization in EGFR-positive cancer cells. *Mol. Pharmacol.* 4: 241-251.
22. Walters, R., and Welsh, M. (1999). Mechanism by which calcium phosphate coprecipitation enhances adenovirus-mediated gene transfer. *Gene Ther.* 6: 1845-1850.
23. Lee, J. H., Zabner, J., and Welsh, M. J. (1999). Delivery of an adenovirus vector in a calcium phosphate coprecipitate enhances the therapeutic index of gene transfer to airway epithelia. *Hum. Gene Ther.* 10: 603-613.
24. Toyoda, K., Andresen, J. J., Zabner, J., Faraci, F. M., and Heistad, D. D. (2007) Calcium phosphate precipitates augment adenovirus-mediated gene transfer to blood vessels in vitro and in vivo. *Gene Ther.* 10: 603-613.
25. Seiler, M. P., et al. (2007). Dendritic cell function after gene transfer with adenovirus-calcium phosphate co-precipitates. Mol. Ther. 15: 386-392.
26. Mikyas, Y.; Makabi, M.; Raval-Fernandes, S.; Harrington, L.; Kickhoefer, V. A.; Rome, L. H.; Stewart, P. L., Cryoelectron microscopy imaging of recombinant and tissue derived vaults: localization of the MVP N termini and VPARP. *J Mol Biol* 2004, 344, (1), 91-105.
27. Champion, C. I.; Kickhoefer, V. A.; Liu, G.; Moniz, R. J.; Freed, A. S.; Bergmann, L. L.; Vaccari, D.; Raval-Fernandes, S.; Chan, A. M.; Rome, L. H.; Kelly, K. A., A vault nanoparticle vaccine induces protective mucosal immunity. *PLoS One* 2009, 4, (4), e5409.
28. Esfandiary, R.; Kickhoefer, V. A.; Rome, L. H.; Joshi, S. B.; Middaugh, C. R., Structural stability of vault particles. *J Pharm Sci* 2009, 98, (4), 1376-86.
29. Kickhoefer, V. A.; Han, M.; Raval-Fernandes, S.; Poderycki, M. J.; Moniz, R. J.; Vaccari, D.; Silvestry, M.; Stewart, P. L.; Kelly, K. A.; Rome, L. H., Targeting vault nanoparticles to specific cell surface receptors. *ACS Nano* 2009, 3, (1), 27-36.
30. Goldsmith, L. E.; Yu, M.; Rome, L. H.; Monbouquette, H. G., Vault nanocapsule dissociation into halves triggered at low pH. *Biochemistry* 2007, 46, (10), 2865-75.
31. Stephen, A. G.; Raval-Fernandes, S.; Huynh, T.; Torres, M.; Kickhoefer, V. A.; Rome, L. H., Assembly of vault-like particles in insect cells expressing only the major vault protein. *J Biol Chem* 2001, 276, (26), 23217-20.
32. Lai, C. Y.; Wiethoff, C. M.; Kickhoefer, V. A.; Rome, L. H.; Nemerow, G. R., Vault nanoparticles containing an adenovirus-derived membrane lytic protein facilitate toxin and gene transfer. *ACS Nano* 2009, 3, (3), 691-9.
33. Wiethoff, C. M.; Wodrich, H.; Gerace, L.; Nemerow, G. R., Adenovirus protein VI mediates membrane disruption following capsid disassembly. *J Virol* 2005, 79, (4), 1992-2000.
34. Shaughnessy, L. M.; Hoppe, A. D.; Christensen, K. A.; Swanson, J. A., Membrane perforations inhibit lysosome fusion by altering pH and calcium in Listeria monocytogenes vacuoles. *Cell Microbiol* 2006, 8, (5), 781-92.

35. Kingdon, G. C.; Sword, C. P., Effects of Listeria monocytogenes Hemolysin on Phagocytic Cells and Lysosomes. *Infect Immun* 1970, 1, (4), 356-62.

36. Xie, H.; Pallero, M. A.; Gupta, K.; Chang, P.; Ware, M. F.; Witke, W.; Kwiatkowski, D. J.; Lauffenburger, D. A.; Murphy-Ullrich, J. E.; Wells, A., EGF receptor regulation of cell motility: EGF induces disassembly of focal adhesions independently of the motility-associated PLCgamma signaling pathway. *J Cell Sci* 1998, 111 (Pt 5), 615-24.

37. Wells, A., EGF receptor. *Int J Biochem Cell Biol* 1999, 31, (6), 637-43

---

The invention claimed is:

1. A vault complex comprising a major vault protein (MVP) having at least 90% sequence identity to SEQ ID NO: 16 and a membrane lytic peptide sequence fused to the N-terminus of the major vault protein (MVP).

2. The vault complex of claim 1, wherein said membrane lytic peptide sequence comprises a membrane lytic domain of adenovirus VI (pVI).

3. The vault complex of claim 2, wherein the membrane lytic domain comprises SEQ ID NO:3.

4. The vault complex of claim 2, wherein the membrane lytic domain comprises SEQ ID NO:4.

5. The vault complex of claim 1, further comprising an epidermal growth factor (EGF) domain.

6. The vault complex of claim 5, wherein the epidermal growth factor (EGF) domain is added to the C-terminus of the major vault protein (MVP).

7. The vault complex of claim 1, further comprising an antibody binding domain.

8. The vault complex of claim 7, wherein the antibody binding domain is a Z-domain.

9. The vault complex of claim 1, further comprising a vault poly ADP-ribose polymerase (VPARP), a telomerase vault associated protein 1 (TEP1), or an untranslated RNA molecule (vRNA).

10. The vault complex of claim 2, wherein the membrane lytic domain comprises SEQ ID NO:1.

11. The vault complex of claim 7, wherein the antibody binding domain is fused to the C-terminus of the major vault protein (MVP).

12. The vault complex of claim 8, wherein the antibody binding domain is fused to the C-terminus of the major vault protein (MVP).

* * * * *

UNITED STATES PATENT AND TRADEMARK OFFICE
CERTIFICATE OF CORRECTION

| | | |
|---|---|---|
| PATENT NO. | : 9,951,107 B2 | Page 1 of 1 |
| APPLICATION NO. | : 14/863750 | |
| DATED | : April 24, 2018 | |
| INVENTOR(S) | : Rome et al. | |

It is certified that error appears in the above-identified patent and that said Letters Patent is hereby corrected as shown below:

In the Specification

Column 1, Lines 14-21, the text of STATEMENT REGARDING FEDERALLY SPONSORED RESEARCH OR DEVELOPMENT should be changed to:
-- This invention was made with government support under grant numbers HL054352 and EB004553 awarded by the National Institutes of Health and under grant number MCB0210690 awarded by the National Science Foundation. The government has certain rights in the invention. --

Signed and Sealed this
Twenty-eighth Day of April, 2020

Andrei Iancu
*Director of the United States Patent and Trademark Office*